(12) United States Patent
Lyons et al.

(10) Patent No.: US 8,809,001 B2
(45) Date of Patent: Aug. 19, 2014

(54) HIGH THROUGHPUT ASSAYS FOR INHIBITORS AND ACTIVATORS OF PAQR RECEPTORS

(75) Inventors: Thomas Lyons, Gainesville, FL (US); Brian R. Kupchak, Gainesville, FL (US); Jessica L. Smith, Frederick, MD (US); Ibon Garitaonandia, San Diego, CA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 732 days.

(21) Appl. No.: 12/679,753

(22) PCT Filed: Sep. 23, 2008

(86) PCT No.: PCT/US2008/077304
§ 371 (c)(1),
(2), (4) Date: Jun. 17, 2010

(87) PCT Pub. No.: WO2009/042561
PCT Pub. Date: Apr. 2, 2009

(65) Prior Publication Data
US 2010/0261178 A1    Oct. 14, 2010

Related U.S. Application Data

(60) Provisional application No. 60/974,657, filed on Sep. 24, 2007, provisional application No. 61/042,537, filed on Apr. 4, 2008.

(51) Int. Cl.
*G01N 33/53* (2006.01)
*C12Q 1/54* (2006.01)
*C12Q 1/02* (2006.01)
*G01N 33/566* (2006.01)
*C07K 14/72* (2006.01)

(52) U.S. Cl.
CPC .......... *G01N 33/566* (2013.01); *G01N 2500/10* (2013.01); *G01N 2333/723* (2013.01); *C07K 14/72* (2013.01)
USPC ................................ 435/7.31; 435/14; 435/29

(58) Field of Classification Search
CPC . A61K 36/06; A61K 49/008; C12N 15/8209; C12N 2503/02; C12N 2510/00; C12Q 2600/136; C12Q 1/6895; C07K 14/72
See application file for complete search history.

(56) References Cited

U.S. PATENT DOCUMENTS

7,501,490 B2 * 3/2009 Kadowaki et al. ............. 530/350
2010/0227802 A1 * 9/2010 Tang et al. ....................... 514/12

OTHER PUBLICATIONS

Tang et al. 2005. J. Mol. Evol. 61:372-380.*
Eide, D. et al. "Increased dosage of a transcriptional activator gene enhances iron-limited growth of *Saccharomyces cerevisiae*" *J. Gen. Microbiol.*, 1992, pp. 347-354, vol. 138.
Kupchak, B. R. et al. "Probing the mechanism of *FET3* repression by lzh2p overexpression" *Biochimica et Biophysica Acta*, 2007, pp. 1124-1132, vol. 1773, No. 7.
Lyons, T. J. et al. "Genome-wide characterization of the Zap1p zinc-responsive regulon in yeast" *Proc. Natl. Acad. Sci. U.S.A.*, Jul. 5, 2000, pp. 7957-7962, vol. 97, No. 14.
Lyons, T. J. et al. "Metalloregulation of yeast membrane steroid receptor homologs" *Proc. Natl. Acad. Sci. U.S.A.*, Apr. 13, 2004, pp. 5506-5511, vol. 101, No. 15.
Narasimhan, M. L. et al. "Osmotin is a Homolog of Mammalian Adiponectin and Controls Apoptosis in Yeast through a Homolog of Mammalian Adiponectin Receptor" *Mol. Cell*, Jan. 21, 2005, pp. 171-180, vol. 17.
Singh, A. et al. "Assembly, Activation, and Trafficking of the Fet3p Ftr1p High Affinity Iron Permease Complex in *Saccharomyces cerevisiae*" *J. Biol. Chem.*, May 12, 2006, pp. 13355-13364, vol. 281, No. 19.
Waters, B. M. et al. "Combinatorial Control of Yeast FET4 Gene Expression by Iron, Zinc, and Oxygen" *J. Biol. Chem.*, Sep. 13, 2002, pp. 33749-33757, vol. 277, No. 37.
Yun, D.-Y. et al. "Osmotin, a Plant Antifungal Protein, Subverts Signal Transduction to Enhance Fungal Cell Susceptibility" *Molecular Cell*, May 1998, pp. 807-817, vol. 1.
Fashena, S. J. et al. "The continued evolution of two-hybrid screening approaches in yeast: how to outwit different preys with different baits" *Gene*, 2000, pp. 1-14, vol. 250.

* cited by examiner

*Primary Examiner* — Shulamith H Shafer
(74) *Attorney, Agent, or Firm* — Saliwanchik, Lloyd & Eisenschenk

(57) ABSTRACT

The subject invention provides methods of screening compounds or ligands that interact with human and/or non-human PAQR receptors or fungal osmotin receptors. These methods utilize a colorimetric assay to ascertain whether a compound binds to and activates a PAQR receptor or the osmotin receptor.

20 Claims, 17 Drawing Sheets

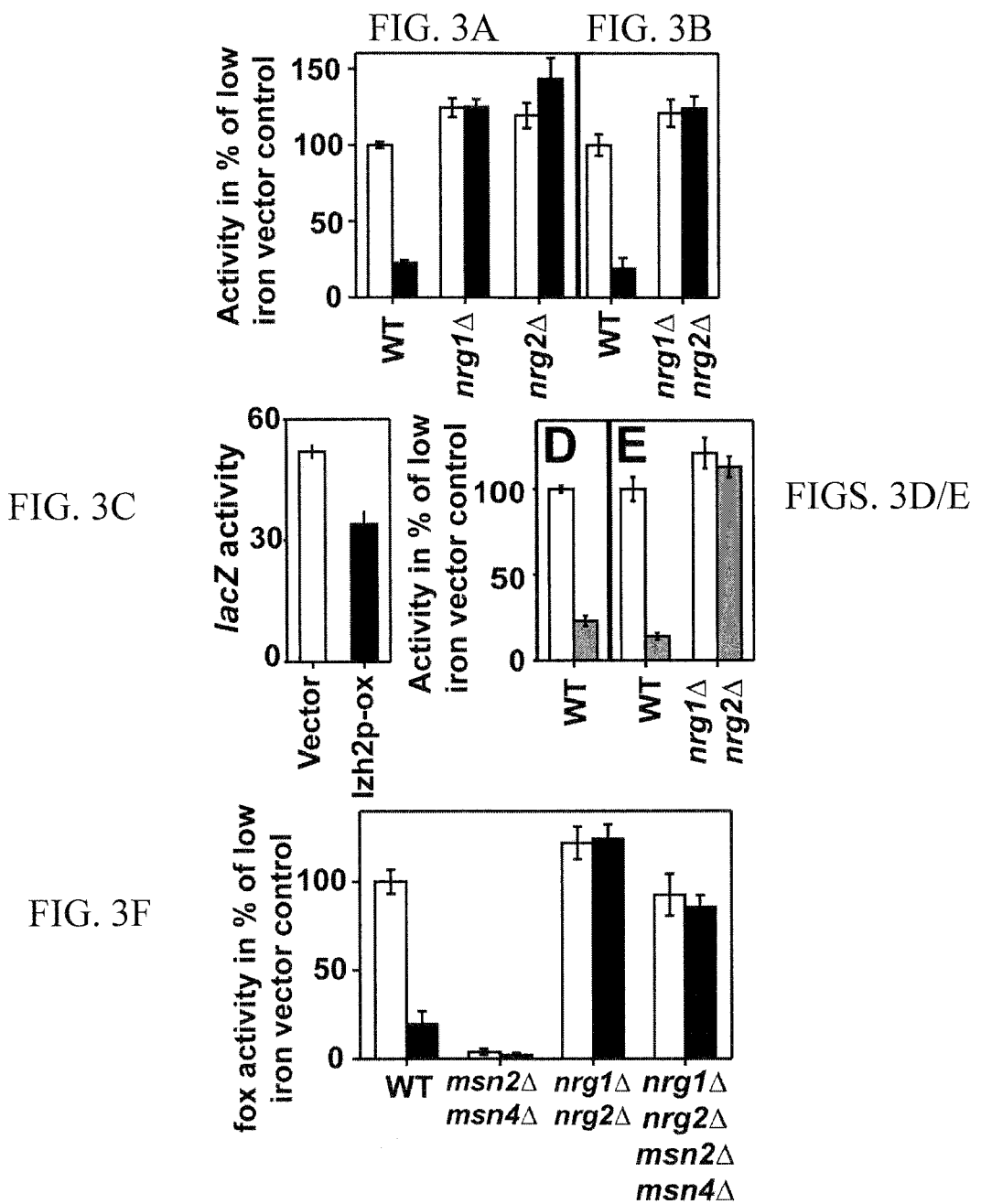

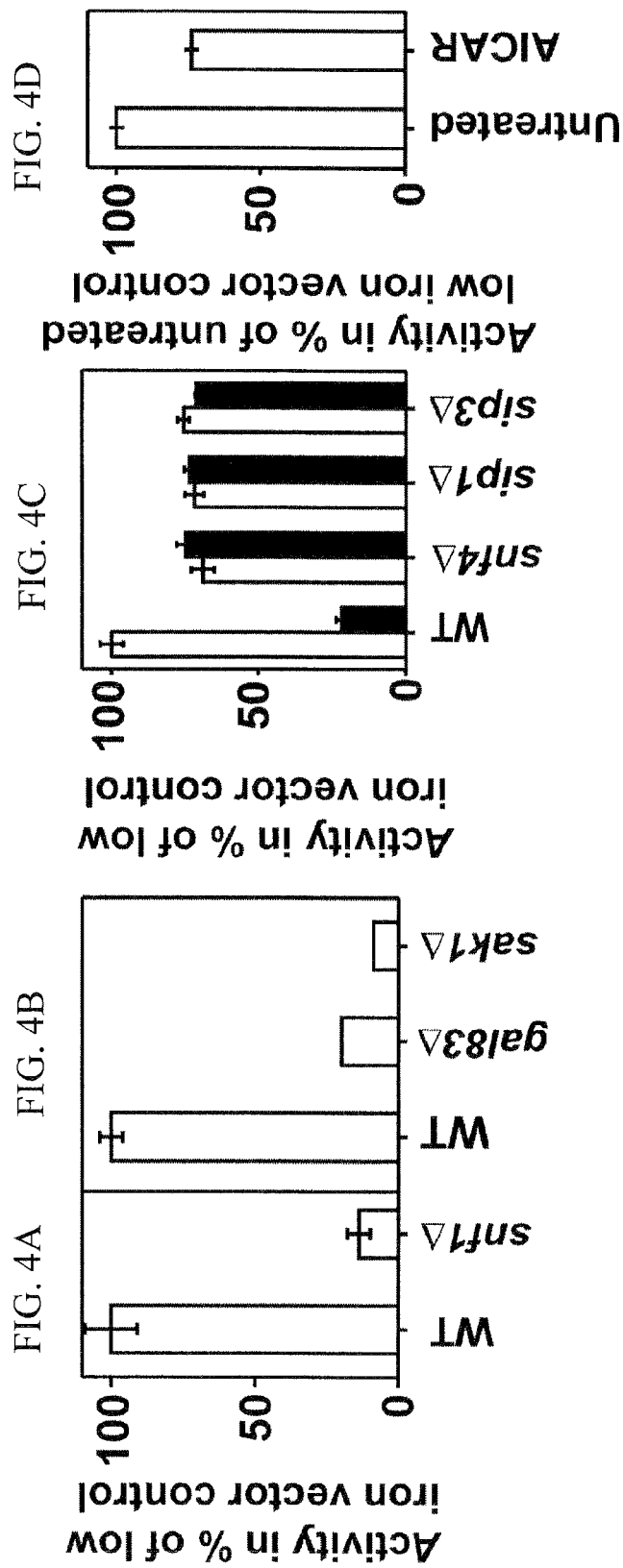

```
   1 GTCTGTGTTCTCTGTGTGAGACATTACTGCTGTGTAAAAAGGAAAAATAGAAAAGAATAACAGATACGAGAATCTGTGCTGCCTTCTTTGCGATAATGCCTTG         100
 101 GCTTGCCTATTTCACGGTTACAGGAATAACATGTTCATACCGTTTCAGGACCAATAAATGGTCTTCTGCGAGAGAAAAGACACTCTCCGTCCGAC              200
 201 AGAAATAAGCTTTACTTTCCGGGTGCGAATCAGCCGCCAAGGCCCATCAGCCCTGGTGCCCTACAGGTACGCTCAGGTGCCTCTTATTCTCGCCAATTGCGACAGAAAATGAA 300
 301 GGCGAGGCTGACTTAGGCAGGCCCAACAGGCAAGGCCCATCTTCAAAAGTGCACCCATTGCAGGTGCTCTTATCTCGCCAATTGCGACAGAAATGAA              400
 401 GGATGCACTCAAACAGTGCGATCCTTCGAGGGAGTATGCCAAGGCCTCGTGCATGTAGTGCATAGGAAGAGAACCCCAGTGTAAGGAAGAGTAGCAAAAAATTAGAACTAG   500
 501 GCAGGCCATGCCCTATAGCTCTGCTTCTAATAAGCGATGGAAACGGAGACCGCACACGTTAATTGGACCACTGGCTGGGACT                             600
 601 ATGACTAACGCTTTGATGGGCTAAAAGAGCCGTCCCGTGATCACCTGTAATGCCAGTTCCCATGGCCAGTGTCAACAAAGGTGACCGTGCAGAT                 700
 701 ACAGGAACGTTGATGGGCTAAAAGAGCCGTCCCGTGATCACCTGTAATGCCAGTTCCCATGGCCAGTGTCAACAAAGGTGACCGTGCAGAT                   800
 801 TTACTTGACCAACGGAATGAACAACACCAATACTTCTATGCATTTCACGGTCGACTGGACTACCATTCACACACGGACGGTCAATATG                     900
 901 CAATGTCCAATTGCGCCAGGCAGTACTATGCTTTACAATTCACGGTGGACTACAGCTTGGACTACCATTCACACACGGACGGTCAATATG                   1000
1001 AAGACGGGATGAAAGGTCTTTTCATCAACAAGGATGATTAGCTTCCCCTACAGTGCTGAGCCATCCGAGCCCCTACGATTAGCTAGGAACTTTCTTTATCGCTTAGTGAGTGGTACCACGACTT 1100
1101 GGTCACGGGACTTCAGCCCGATACGACGTATCTTTTGAGAAGTGTCAACGTAACGGTATCTTTTGAGAAGAACGTAACGGTAACAACGATGAATCTGACA         1200
1201 TGGGAAGTCCAGCCCGATACGACGTATCTTTTGAGAAGTGTCAACGTAACGGATATGCTTTACATCACTGTCGCTCAGAGATATACAGTCCTGTTCACTATCAAAAACGACAC 1300
1301 TCGAAATCGACGGTATCACTACCGAGAAGAACGTAACGGATATGCTTTACATCACTGTCGCTCAGAGATATACAGTCCTGTTCACTATCAAAAACGACAC         1400
1401 GGACAAAAATTCGCCATCATGCAGAAATTTGATGACAGTGATGACCATGTTGGATGTCATTCCAAGTGATTCTCCTGACGATTTCTACTTGCAACCGTACAACCGTACAACCGTATGCCTATATGGTCTACAAC 1500
1501 AAAACCGCTGCGCTGCCCACACAATGTTACCGTTGACGTTGTTATGGATAATCACTCGAATTACGGCCTTCTCAATAATATCACTTTCATCCTAGAGAAGGATGAAATC 1600
1601 AGCCAGATCATGTGATTACCGTTGTCTTCAGTGATCAAGCAACACCAGGTACCCATCCGAAATCTACGGTTCAAACATGGTTCATCCTAGAGAAGGATGAAATC       1700
1701 TCCTACTTTGATGACCGTTTGTCTTCAGTGATCAAGCAACACCAGGTACCCATCCGAAATCTACGGTTCAAACATGGTACATATGTCATAATATG              1800
1801 GTGGAGATTGTGCTAAATAACCAGGACACAGGTACCCATCCGAAATCTACGGTTCAAACATGGTACATATGTCATATATGATG                           1900
1901 CCCTAGGTGAAGTTCCTCACAGTTCGATCCGGAATAACCCAGTTGGTTCTTCCATTGTCATATACCAGATAACTTATACGTTAGACCACAATCCAA             2000
2001 TTTCGTCATCAGTTTGGTATCCAAGATGCTCATTCTCAACAACTCAGTGAAAAAACCACTTGGTCTGGCCATTCGTTGCAACTTGGGTTCTTCTGTGGAG          2100
2101 GATCCTTTCATCAGTTTGGTATCCAAGATGCTCATTCTCAACAACTCAGTGAAAAACCACTTAGTGTATGCAGCATCCTGTGGCCATGACATTCTC              2200
2201 CCAATACACTGGATTCTTGGTATCTGATTAACTGCTAATTAACTGGTGAAAAATGTTCAGCAGTTGCAATTTATGGTGATATGCGACCCGAAAAAGGTATTATTGCGAGACTTGGAC 2300
2301 CTGCTTGCCGTGATTCTGCTAAATGAGGTTGATGAAAAATGCAAGAGCGTCAGGTAACGCGTCAGGTAACGCGTCATTCCACTGGAAGCATCCAAAC             2400
2401 CCTGAGTCTTGCTAATAAAGGAAGATCATGTATTTCGGTGGTTAACCTGTTTTTTTTTTCGGTCAAGGTTCCAAATGCATTTGCATGTAAAGTGAATGCCCT        2500
2501 GGTTCTTCTAATAAAGGAAGATCATGTATTTCGGTGGTTAACCTGTTTTTTTTTCGGTCAAGGTTCCAAATGCATTTGCATGTAAAGTGAATGCCCT             2600
2601 TGTCTTACTTAAATATTACATAGACATATTAATAATCTACCACGTTTCAAATTCAATAATGCATGCGGTTTCTTGGCGGTTCTTTTGACATGAGATCCATC        2700
2701 TGTCACGAGGCTGATGTGCATATGCATCTTTAATCGATGACATGATCAGTTTCTTTGAAAAAAAGCCGTTATGGGTTGAAAAAAAGTGAAAATGAA              2800
2801 AAAGTCATCAGAAAATAATTACTCTATTTCAAAATATGAAGATAATAAATTGTCGAAGAATATTACGTCGAGGAGGTTGAGGAAAATAAGCAACGACAGATATCATATC 2900
2901 TCTAGTAAAAATAATTATTACTCTATTTCCAAAATGTGGACGGAAGTTACAAGACGATTTATCATGGAAGGGAAATAGCCTGAGATTACTGAGA                3000
3001 GGTCGTCCGCCTCACAAGCTTGTCATGCAACGATGTAGACACAGAGCATGAAAATAGCTTCATATTACCCATCAATATGT                              3100
3101 CACAGTACAAA                                                                                                   3111
```

FIG. 6

FIG. 9A
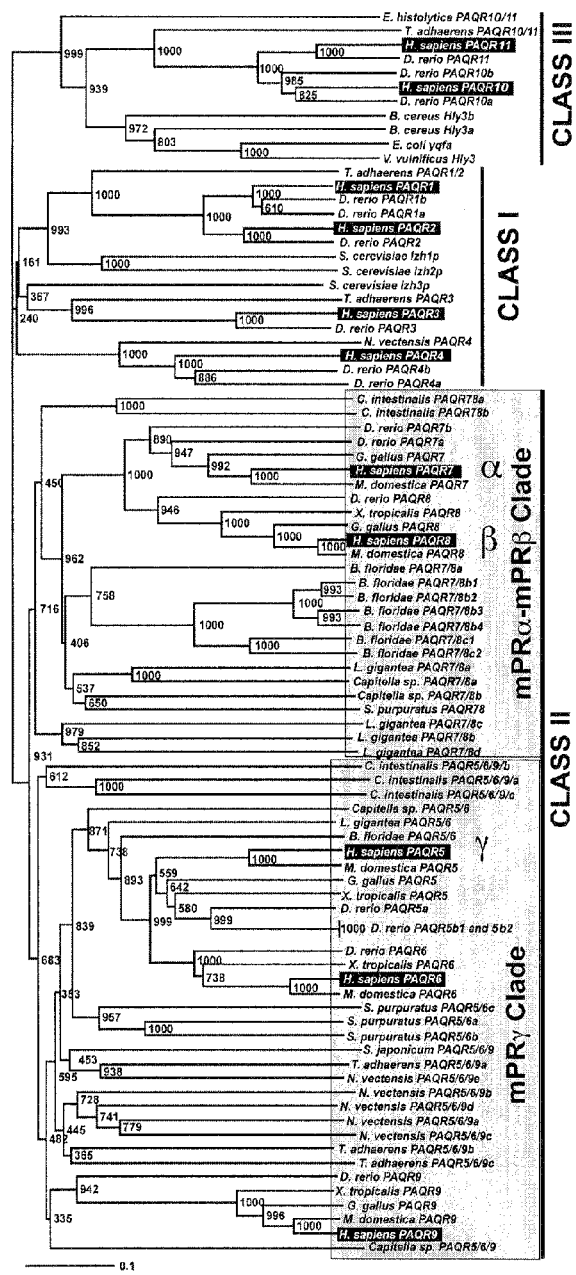
FIG. 9B
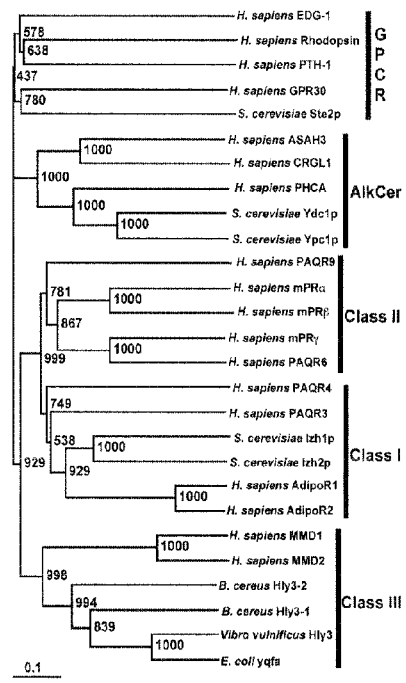
FIG. 9C

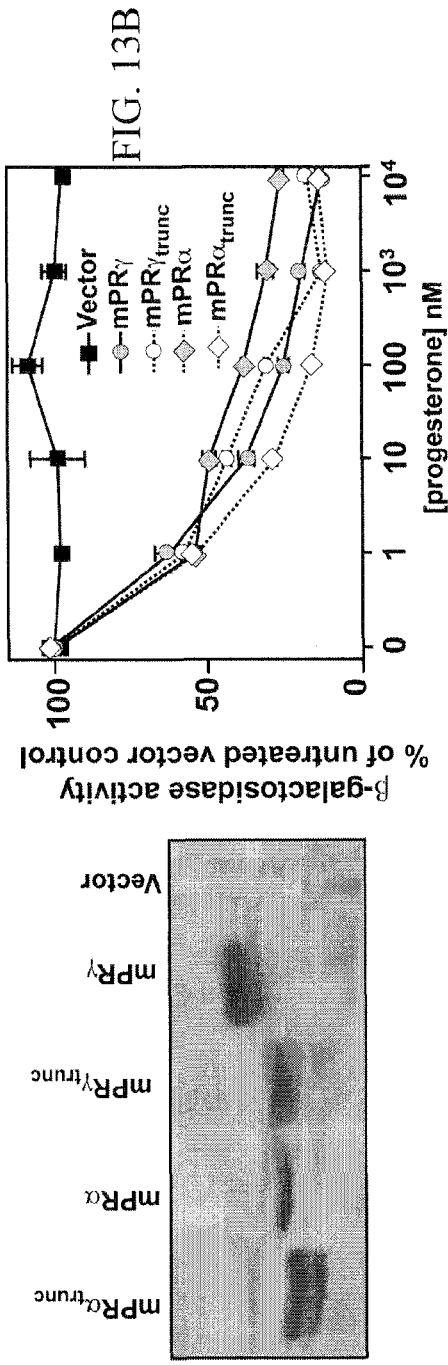
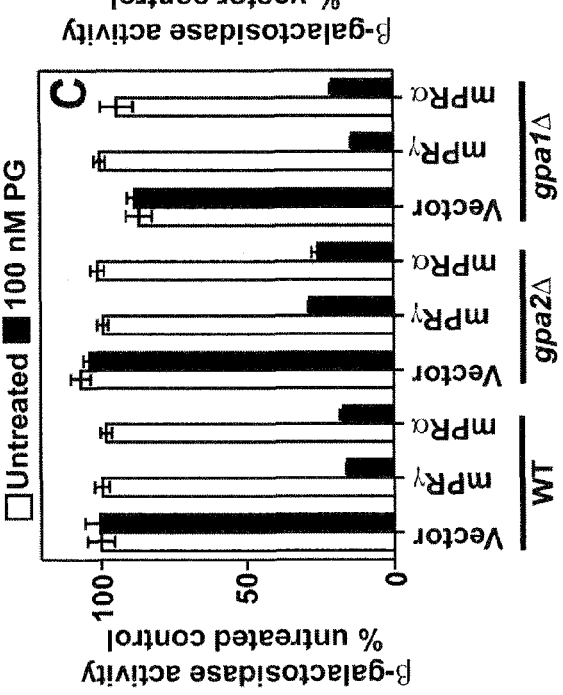
FIG. 13A
FIG. 13B
FIG. 13C
FIG. 13D
FIG. 13E

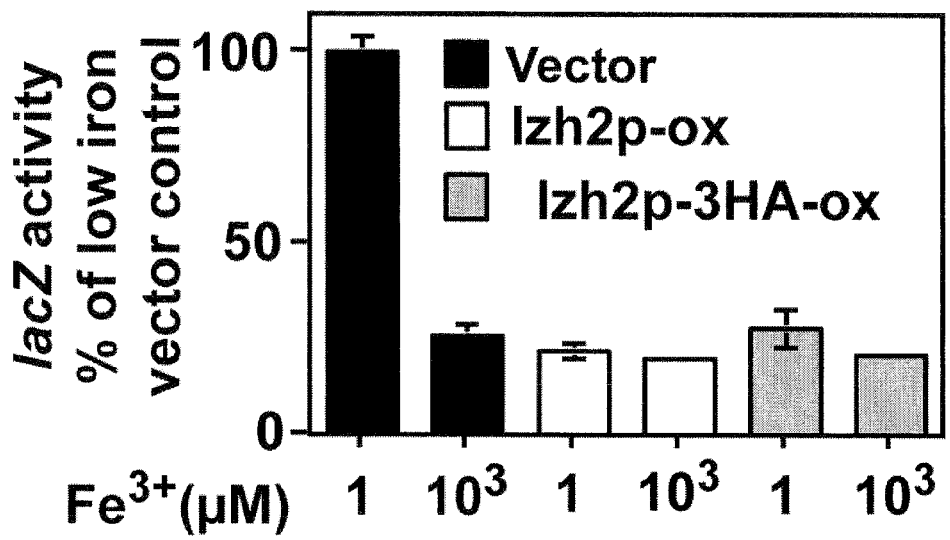
FIG. 14A
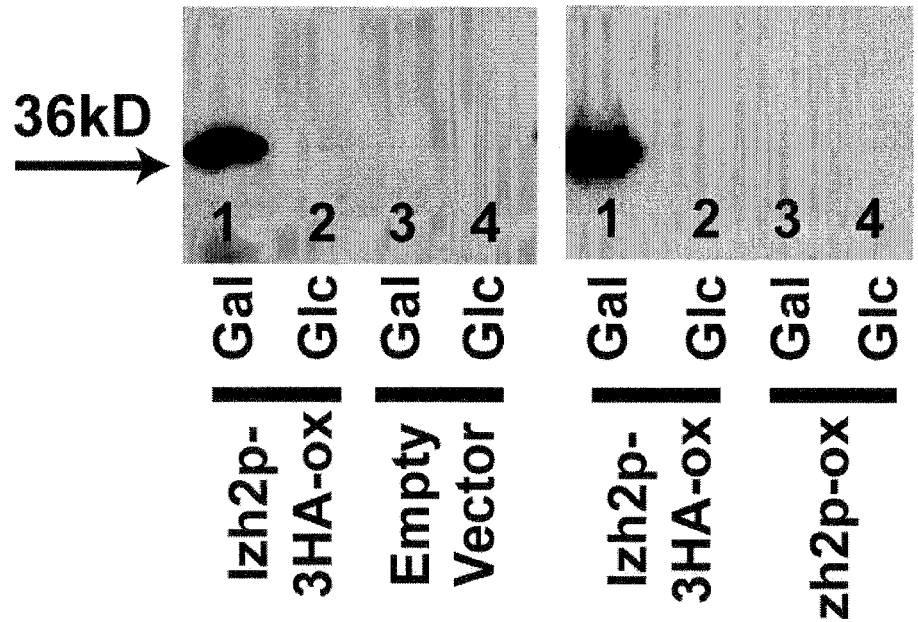
FIG. 14B
FIG. 14C

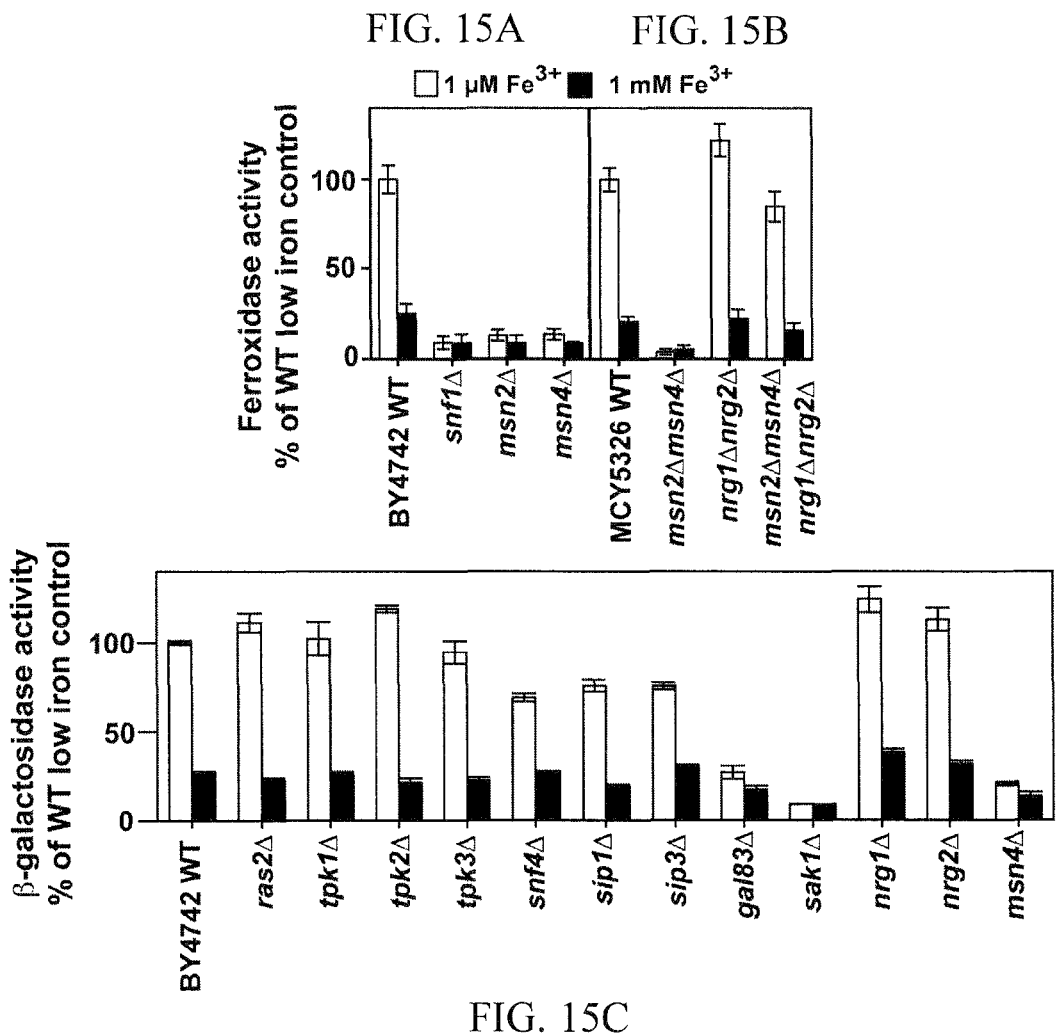

HIGH THROUGHPUT ASSAYS FOR INHIBITORS AND ACTIVATORS OF PAQR RECEPTORS

This invention was made with government support under National Institutes of Health grant number R21 DK074812. The government has certain rights in the invention.

CROSS-REFERENCE TO RELATED APPLICATIONS

This application is the U.S. national stage application of International Patent Application No. PCT/US2008/077304, filed Sep. 23, 2008, which claims the benefit of U.S. Provisional Application Ser. No. 60/974,657, filed Sep. 24, 2007 and Ser. No. 61/042,537, filed Apr. 4, 2008, the disclosures of which are hereby incorporated by reference in their entirety, including all figures, tables and amino acid or nucleic acid sequences.

The Sequence Listing for this application is labeled "Seq-List-replace.txt" which was created on Mar. 18, 2011 and is 454 KB. The entire contents of the sequence listing is incorporated herein by reference in its entirety.

BACKGROUND OF THE INVENTION

Iron and zinc are cofactors for hundreds of proteins making them essential for viability. When grown in metal-limiting environments, microorganisms must increase their ability to scavenge these metals to maintain maximal growth rates. As a result, intricate regulatory systems have evolved to up-regulate metal ion acquisition in response to nutritional depletion (Rutherford et al., 2004). In *Saccharomyces cerevisiae*, iron- and zinc-acquisition are controlled by Aft1p and Zap1p, respectively. These transcriptional activators sense the nutritional status of their respective micronutrients and, in response to deficiency, induce genes involved in uptake. However, some studies indicate that iron- and zinc-uptake systems are inducible under metal replete conditions when Aft1p and Zap1p are believed to be silent. For example, the expression of genes involved in high-affinity iron- and zinc-uptake fluctuate with the phase of the cell cycle (Cho et al., 1998) and seem to be regulated by carbon starvation (Haurie et al., 2003). These studies suggest that iron and zinc bioavailability are not the only environmental stimuli that affect metal accumulation and that Aft1p and Zap1p are not the only regulators of iron and zinc uptake. Therefore, identification of novel genes involved in the regulation of iron and zinc homeostasis is of critical importance for a proper understanding of metal metabolism.

IZH2 expression is induced by both zinc-deficiency via the Zap1p zinc-sensor and zinc-toxicity via the Mga2p hypoxia-sensing transcription factor (Lyons et al., 2004). We present evidence suggesting that Izh2p exerts its effects on FET3 by regulating the activities of four transcription factors with previously unrecognized roles in iron homeostasis—Msn2p, Msn4p, Nrg1p and Nrg2p. Msn2p and Msn4p are stress-responsive transcriptional activators (Smith et al., 1998) while Nrg1p and Nrg2p are carbon source-dependent transcriptional repressors (Berkey et al., 2004). We demonstrate that the Msn2p/Msn4p activators and the Nrg1p/Nrg2p repressors are epistatic with respect to the expression of FET3. Furthermore, we demonstrate that Izh2p dependent-repression requires both cAMP-dependent protein kinase (protein kinase A, PKA) and AMP-dependent protein kinase (AMPK). Since PKA inhibits Msn2p/Msn4p (Smith et al., 1998) and AMPK inhibits Nrg1p/Nrg2p (Kuchin et al., 2002), our findings fit a model in which Izh2p regulates FET3 expression via negative regulation of AMPK, positive regulation PKA or both. It remains to be seen how Izh2p affects PKA and AMPK and whether these transcription factors affect FET3 expression through binding to cis-regulatory elements.

The physiological importance of FET3 regulation by Izh2p is still a mystery. However, Izh2p was recently identified as a cell surface receptor for the plant protein osmotin (Narasimhan et al., 2005). While the exact function of osmotin remains a matter of debate, the fact that it is induced by plants as part of the innate immune response and possesses potent antifungal activity suggests that it functions as a primary line of defense against fungal pathogens (Linthorst, 1993). Therefore, from a pharmacological standpoint, there is significant interest in understanding how osmotin affects fungal physiology. Since yeast with defects in high-affinity iron-uptake show decreased virulence (Eck et al., 1999; Ramanan et al., 2000), the regulation of high affinity iron-uptake represents a reasonable mechanism by which osmotin, via Izh2p, may exert an antifungal effect.

Izh2p belongs to a newly discovered family of receptors known as PAQRs (Progesterone and AdipoQ Receptors) that are ubiquitous in eukaryotes (Tang et al., 2005). The first members of this family to be characterized as receptors were the membrane progesterone receptors from seatrout (Zhu et al., 2003a) and the adiponectin (AdipoQ) receptors from human (Yamauchi et al., 2003). Adiponectin is an insulin-sensitizing hormone and the human adiponectin receptors are believed to play an important role in the etiology of type II diabetes. Despite the medical importance of adiponectin receptors, little is known about how they convert extracellular signals into physiological changes inside cells. Indeed, all that seems to be known is that they somehow transmit signals to AMPK (Kadowaki et al., 2006). In this report, we show heterologous expression of two human adiponectin receptors in yeast. Not only do these receptors repress FET3 in response to adiponectin, this effect requires the same signaling proteins as Izh2p overexpression, including AMPK. The functional expression of these receptors in yeast demonstrates mechanistic conservation in the PAQR receptor family and establishes a valuable model system for the investigation of a pair of receptors that are critical for human health.

BRIEF SUMMARY OF THE INVENTION

The subject invention provides methods of screening compounds or ligands that interact with human and/or non-human PAQR receptors or fungal osmotin receptors. These methods utilize a signaling system to ascertain whether a compound binds to and activates a PAQR receptor or the osmotin receptor.

BRIEF DESCRIPTION OF THE DRAWINGS

(FIG. 1A) β-galactosidase activity (lacZ) of the pFET3-397 reporter and cell surface ferroxidase activity (fox) are induced by low iron in wild type yeast carrying empty overexpression vector, but not in yeast carrying a plasmid that overexpresses Izh2p. (FIG. 1B) The effect of Izh2p on pFET3-397 decreases as the % galactose in iron-deficient LIM is decreased. Activities for each galactose concentration are normalized to % of activity in a strain carrying empty overexpression vector grown at the same galactose concentration. (FIG. 1C) Overexpression of Izh2p in a wild type strain causes a growth defect in plates containing synthetic media supplemented with 1 mM ferrozine and 20 μM $Fe^{3+}$. (FIG. 1D) lacZ activity is induced by growth in iron-deficient LIM carrying pFET3-397, pFET3-297 or pCYC1-FeRE. Overexpression of Izh2p in low iron represses only the pFET3-397 construct.

(FIGS. 2A and 2B) Cell surface ferroxidase activity (fox) is constitutively repressed in msn2Δ and msn4Δ strains when compared to the isogenic BY4742 wild type and in the msn2Δmsn4Δ mutant when compared to the isogenic MCY5326 wild type. Overexpression of Izh2p in any of the msn mutant strains had no effect on fox activity. (FIG. 2C) β-galactosidase activity (lacZ) in BY4742 carrying pCYC1-STRE reporter is repressed when Izh2p is overproduced in early log phase ($OD_{600}$=0.04) but not in mid-log phase ($OD_{600}$=1.60). (FIG. 2D) pFET3-397 repression by Izh2p overexpression seen in the BY4742 wild type strain is alleviated in ras2Δ, tpk1Δ, tpk2Δ and tpk3Δ strains. (FIG. 2E) Insensitivity of pFET3-397 to Izh2p overexpression in the ras2Δ strain can be overcome by cAMP addition to the growth medium prior to assay. (1) BY4742 WT strain carrying pFET3-397, empty overexpression vector and treated with 3 mM cAMP; (2) ras2Δ carrying pFET3-397, empty overexpression vector and treated with 3 mM cAMP; (3) ras2Δ carrying pFET3-397, Izh2p overexpression vector and treated with 3 mM cAMP.

FIGS. 3A-3F: Nrg1p, Nrg2p, Msn2p and Msn4p in Izh2p-dependent FET3 repression. For panels A, B, C and F, white bars show strains carrying empty expression vector and black bars show strains carrying Izh2p overexpression vector. For panels D and E, white bars show strains carrying empty expression vector and grey bars show strains carrying Nrg2p-TAP overexpression vector. For all panels except C, activities are shown as a percentage of fully induced activity in the isogenic wild type strain grown in iron-deficient LIM. (FIGS. 3A and 3B) The repression of pFET3-397 lacZ activity by Izh2p overexpression in the BY4742 wild type strain is absent in the nrg1Δ and nrg2Δ mutant strains. Similarly the repression of activity seen in MCY5326 is not seen in the nrg1Δnrg2Δ strain. (FIG. 3C) Overexpression of Izh2p represses a FLO11-lacZ construct in the Σ1278b wild type strain. lacZ activities are shown in Miller Units (FIGS. 3D and 3E) Overexpression of TAP-tagged Nrg2p resulted in repression of pFET3-397 in BY4742 wild type. Similarly Nrg2p-TAP repressed ferroxidase activity in MCY5326 wild type but not in the isogenic nrg1Δnrg2Δ strain. (FIG. 3F) The constitutive repression of ferroxidase activity in low iron medium seen in an msn2Δmsn4Δ strain relative to the MCY5326 isogenic wild type strain can be partially alleviated by concomitant deletion of nrg1Δ and nrg2Δ to generate the quadruple mutant. Izh2p overexpression has no effect on ferroxidase activity in strains lacking Nrg1p/Nrg2p.

FIGS. 4A-4D: The role of AMPK in FET3 repression. For all panels, β-galactosidase or ferroxidase activities are shown as a percentage of activity produced in the isogenic wild type strain carrying an empty overexpression vector and grown in iron-deficient LIM. (FIG. 4A) In a strain lacking Snf1p, cell surface ferroxidase activity is repressed relative to the isogenic BY4742 wild type. (FIG. 4B) In gal83Δ and sak1Δ strains, pFET3-397 is similarly constitutively repressed. (FIG. 4C) In strains lacking various AMPK interacting proteins, there is a slight, but significant reduction in pFET3-397. In addition, Izh2p overexpression (black bars) in these strains has no effect on lacZ activity when compared to activity in strains carrying empty overexpression vector (white bars). (FIG. 4D) Addition of 500 μM AICAR to the growth medium results in a small but reproducible repression of pFET3-397.

(FIG. 5A) Overexpression of three homologous yeast receptors (Izh1p, Izh3p and Izh4p) and one homologous human receptor (AdipoR1) has similar effects on pFET3-397 and ferroxidase activity. Overexpression of a second human homologue (AdipoR2) has no effect. (FIG. 5B) Decreased expression of AdipoR1 by lowering the % galactose diminishes its effect on pFET3-397. Activities for each galactose concentration are normalized to % of activity in a strain carrying empty overexpression vector grown at the same galactose concentration. (FIG. 5C) Expression of AdipoR2 in 2% galactose fully has no effect on pFET3-397 unless adiponectin is added to the medium (black squares). Adiponectin has no effect on pFET3-397 in a strain carrying empty vector control (white squares). Expression of AdipoR1 in 1.98% raffinose/0.02% galactose has no effect on pFET3-397 unless adiponectin is added (black circles) while adiponectin alone has no effect (white circles). For cells grown with 0.02% galactose, activities are normalized to activity in a strain carrying the empty overexpression vector and grown in iron-deficient LIM with the same concentration of galactose. (FIG. 5D) Dose dependent pFET3-397 repression by either AdipoR1 overexpression in the absence of adiponectin or AdipoR2 activation in the presence of adiponectin is alleviated in strains lacking RAS2, TPK1, TPK2, TPK3, SIP1, SNF4, SIP3, NRG1 or NRG2.

FIG. 6: The sequence of the FET3 gene is provided (SEQ ID NO: 181). As discussed within this application, the full promoter region of the gene or truncated promoter regions thereof can be used to drive lacZ expression in transformed yeast cells. In this regard, the specification refers to a truncated FET3 promoter comprising nucleotides −397 to +3 or −297 to +3 of the sequence. This numbering is relative to the ATG codon starting at position 601 of the FET3 sequence (having a double underline) with nucleotides 601, 602 and 603 constituting positions +1, +2 and +3 of the truncated FET3 promoter sequence.

FIGS. 9A-9C: Phylogenetic analysis of the PAQR family. For each tree, the length of the tree branches is proportional to the calculated distance between sequences with the scale bar indicating 0.1 substitutions per site. Numbers at the nodes are confidence values that refer to the number times per 1000 trees drawn a particular grouping is made (FIG. 9A). A bootstrapped phylogenetic tree showing the relationship between PAQR receptors from a variety of eukaryotic and prokaryotic sources. Lines delineate the three Classes of PAQR and grey shading indicates the distinct clades within Class II. The tree is rooted using the sequences in Class III as an outgroup (FIG. 9B). A bootstrapped phylogenetic tree containing human, yeast and bacterial PAQRs as well as several sequences belonging to two other groups of proteins with a characteristic seven TM structure. One group includes five G-protein coupled receptor (GPCR) sequences and the other group includes five proteins in the alkaline ceramidase (AlkCer) family of enzymes. The tree is rooted with the clade containing the GPCRs (FIG. 9C). Taxonomic grouping of the organisms from which the sequences in these trees were derived.

(FIGS. 12A-D) Hydropathy plots for the individual proteins analyzed in FIG. 3 were generated and aligned (dotted lines). An average hydropathy plot for all members of each clade were generated (solid lines). The core PAQR motif is shaded in grey and the predicted TMs are numbered. All vertebrate members of the AdipoR1 and AdipoR2 clade (A), the mPRγ/PAQR6 clade (FIG. 12B), the mPRα/mPRβ clade (FIG. 12C) and the PAQR9 homologs (FIG. 12D). (FIG. 12E) Predicted topology of the core PAQR motif with the locations of the three highly conserved motifs shaded in black in FIG. 10. The predicted eighth TM in the mPRs is shown with a dotted line. FIG. 12(F) The structure of the dual topology reporter tag. (FIG. 12G) DTR-tagged PAQR6 and mPRα expressed in the pJK90 plasmid repress FET3-lacZ in response to 100 nM progesterone in cells grown in medium containing 0.05% galactose/1.95% raffinose. (FIG. 12H) Rescue of the histidine auxotrophy of the STY50 strain by DTR-tagged PAQR6 and mPRα on plates containing histidinol. Plasmids expressing untagged versions of PAQR6 and mPRa are shown as negative controls. A plasmid expressing DTR-tagged Ost4p is shown as a positive control. (FIG. 12I) Membrane extracts from cells expressing DTR-tagged PAQR6 or mPRα are either left untreated (−) or treated with the endoglycosidase EndoH (+) and subsequently run on protein gels and transferred to nitrocellulose membranes for Western blot. anti-HA antibodies were used to detect the DTR tag. (left) Coomassie stained gel of EndoH treated RNase B under the same conditions as those used to treat the cell membrane extracts is shown on the right as a positive control.

FIGS. 13A-13E: Truncation mutations and G-protein signaling. In all cases, FET3 expression is measured using the FET3-lacZ reporter. (FIG. 13A) Full length and truncated mPRγ and mPRα were expressed in wild type cells grown in 2% galactose from the pGREG536 vector. The location of the C-terminal truncations is shown in FIG. 10. All proteins possess an N-terminal 7x-HA tag. Proteins were detected by Western blot using an anti-HA antibody. (FIG. 13B) The dose response of FET3 to progesterone in cells expressing the full length or truncated mPRγ and mPRα and grown in 0.05% galactose/1.95% raffinose. (FIG. 13C) The ability of mPRα and mPRγ to respond to progesterone and repress FET3 is not impaired in either gpa2Δ or gpa1Δ cells (gpa1Δ cells also lack the STE7 gene, see text) (FIG. 13D) Overexpression of the Ste2p GPCR using the GAL1 promoter does not repress FET3 in wild type cells (mat a) grown in 2% galactose. Activation of overexpressed Ste2p via the addition of 1 μM of its agonist, α-factor, also has no effect on FET3 under these conditions. (FIG. 13E) Expression of constitutively active alleles of Gpa1p (Gpa1p$^{Q323L}$) and Gpa2p (Gpa2p$^{Q300L}$) from the GAL1 promoter had no effect on FET3 in cells grown in 2% galactose.

FIGS. 14A-C: Functional expression of Izh2p-3HA. (FIG. 14A) Izh2p or Izh2p-3HA overexpression represses the induction of pFET3-397 in low iron. (FIG. 14B) Western blot showing that the Izh2p-3HA tagged protein is expressed in cells grown in galactose but not in cells grown in glucose. (FIG. 14C) Western blot showing that the Izh2p-3HA tagged protein is induced in cells carrying the Izh2p-3HA overexpression construct but not in those carrying the untagged Izh2p construct. Protein samples in B and C were heated to 37° C. rather than boiled prior to loading.

FIGS. 15A-C: Aft1p responds normally to iron-deficiency in most mutant strains. (FIG. 15A) Ferroxidase activity is induced by iron-deficiency in the BY4742 wild type strain. Fet3p activity is not induced in isogenic strains lacking SNF1, MSN2 or MSN4. (FIG. 15B) Ferroxidase activity is inducible by iron-deficiency in the MCY5326 wild type strain, the isogenic nrg1Δnrg2Δ double mutant and the isogenic nrg1Δnrg2Δmsn2Δmsn4Δ quadruple mutant but not in the isogenic msn2Δmsn4Δ double mutant. (FIG. 15C) b-galactosidase activity of the pFET3-397 construct is inducible by iron-deficiency in the BY4742 wild type strain and in all isogenic mutants tested except for the gal83Δ, sak1Δ and msn4Δ mutants. For all panels, activities are shown as a % of isogenic wild type control grown in low iron media. The legend above FIG. 15A applies to FIGS. 15A-C.

DETAILED DISCLOSURE OF THE INVENTION

Figure 1A:
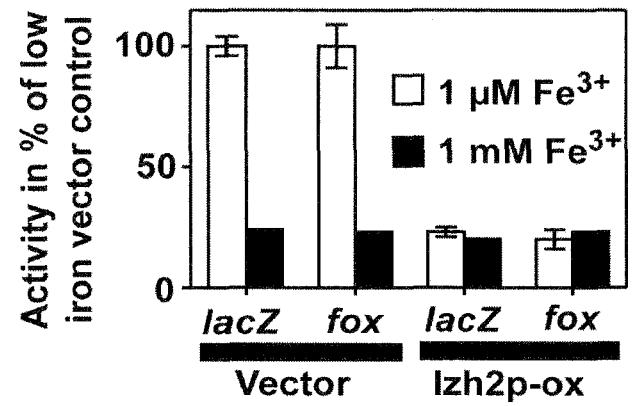
FIGS. 1A-1D: Izh2p represses FET3 transcription and Fet3p activity. BY4742 wild type strain is used in all panels. Activities in panels A and D are shown as a percentage of fully induced activity in a strain carrying empty overexpression vector grown in iron-deficient LIM.

The subject application provides various methods of screening compounds (ligands) that bind to PAQR receptors or the fungal osmotin receptor. Thus, one aspect of the invention provides methods of identifying candidate ligands of PAQR receptors, comprising:
a) providing a yeast cell expressing one or more PAQR receptor and a reporter molecule, said reporter molecule providing a signal in response to activation of said one or more PAQR receptor;
b) contacting said yeast cell with a candidate ligand;
c) detecting the activation of said one or more PAQR receptor by the development of a signal within the cell or in medium in which the cell is cultured, the detection of a signal indicating the activation of said one or more PAQR receptor.

Each of the methods disclosed herein can be used to screen for both agonists and antagonists of PAQR receptors or the osmotin receptor. Where one wishes to determine if a candidate ligand is an antagonist of a PAQR or osmotin receptor, one contacts the cell with the candidate ligand, adds a known agonist of a PAQR or osmotin receptor and evaluates the ability of the agonist to activate the receptor as evidenced by the development of a signal. The assays disclosed herein can also be used to identify "inverse antagonists" of the receptors disclosed herein. An "inverse antagonist" is any compound or ligand that antagonizes the activity of the receptor without antagonizing the binding of an agonist to the receptor. Non-limiting examples of agonists useful in the context of this invention include thaumatin for the osmotin receptor, adiponectin for AdipoR1 and AdipoR2 and progesterone or 10α-hydroxyprogesterone for mPRa, mPRb, mPRGg, PAQR6 and PAQR9. Where reduced signal is observed, as compared to control cells that have not been contacted with a candidate ligand, the candidate compound can be designated as an antagonist of the receptor. Antagonists include those ligands or compounds that cause a 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% reduction in signal within the screening protocols disclosed herein. Conversely, those candidate ligands that result in production of a signal by a cell contacted with a candidate ligand, as compared to cells not contacted with a candidate ligand, are agonists of the receptor being tested.

With respect to this aspect of the invention, human and non-human PAQR receptors can be used in identifying ligands or compounds that activate a PAQR receptor. Human PAQR receptors can be selected from human PAQR1 (GenBank Accession No. NM_015999), PAQR2 (GenBank Accession No. NM_024551), PAQR3 (GenBank Accession No. BC047510), PAQR4 (GenBank Accession No. NM_152341), PAQR5 (mPRγ; GenBank Accession No. NM_017705), PAQR6 (GenBank Accession No. NM_024897), PAQR7 (mPRα; GenBank Accession No. BC034015), PAQR8 (mPRβ; GenBank Accession No. NM_133367), PAQR9 (GenBank Accession No. NM_198504), PAQR10 (GenBank Accession No. NM_198403), PAQR11 (GenBank Accession No. NM_012329) and/or various combinations thereof. The sequences of the human PAQR receptors are provided in the appendix attached to this application and the designation, with respect to the PAQR receptor, can be found in either the "Symbol" section of the pages presented within the appendix or in the "Synonyms" section of the pages provided in the appendix. Additionally, each of the sequences (both nucleic acid and polypeptide) associated with each GenBank Accession numbers recited within this paragraph is hereby incorporated by reference in their entireties. Additionally, PAQR receptors disclosed at pages A-53 through A-64 of the attached appendix can be expressed in yeast cells (and these pages disclose both human and non-human PAQR receptors). As would be apparent to those skilled in the art, any nucleic acid sequence encoding the PAQR receptors disclosed at pages A-53 through A64 can be used to transform yeast cells.

In some aspects of the invention, the human and/or non-human PAQR receptors expressed by the transformed yeast cells are overexpressed in the yeast cells. Other embodiments provide for the control of PAQR receptor expression via culture conditions (e.g., via the control of galactose concentrations used in medium in which the yeast cells are cultured).

The subject invention also provides a method of identifying antifungal agents comprising:
a) providing a yeast cell expressing the osmotin receptor and a reporter molecule, said reporter molecule providing a signal in response to activation of said osmotin receptor;
b) contacting said yeast cell with a candidate antifungal agent;
c) detecting the activation of said osmotin receptor by the development of a signal within the cell or in medium in which the cell is cultured, the detection of a said signal indicating the activation of said osmotin receptor and identifying the agent as a potential antifungal agent.

With respect to the detection of PAQR or osmotin receptor activation, the subject invention can utilize a colorimetric system for identifying cells activated by a candidate compound/ligand/agent or a phenotypic change in the cell (e.g., fluorescence or resistance to an antibiotic). In certain aspects of the invention, the colorimetric system utilizes a reporter molecule. A reporter molecule in the context of this application can be any protein that provides for the development of a colorimetric or optically measurable response where the osmotin receptor or a PAQR receptor is activated. Non-limiting examples of such reporter molecules include enzymes and fluorescent proteins (e.g., green fluorescent protein, Certain aspects of the invention use a reporter molecule that is β-galactosidase (lacZ). The lacZ gene can be driven by the FET3 promoter or truncations thereof. Promoters that can be used for driving the expression of reporter molecules discussed herein are those that include the element/motif (subsequence) CCCTC. Non-limiting examples of promoters containing this element/motif include FET3, ZRT1, OLE1, ZRC1 and ZPS1. Thus, any promoter or truncated promoter that contains the CCCTC motif can be used to drive the expression of reporter molecules to which they are operably linked. The sequence of the FET3 gene is provided below (see FIG. 6). As discussed within this application, the full promoter region of the gene or truncated promoter regions thereof can be used to drive lacZ expression (or the expression of any other reporter molecule) in transformed yeast cells. In this regard, the specification refers to a truncated FET3 promoter comprising nucleotides −397 to +3 or of the sequence. This numbering is relative to the ATG codon found at nucleotide positions 601-603 of the FET3 sequence (as presented in FIG. 6) with nucleotides 601, 602 and 603 constituting positions +1, +2 and +3 of the truncated FET3 promoter sequence referred to within the claims and specification.

The signal detected in the above identified methods can be a detectable phenotype or colorimetric response that allows for the differentiation of a cell as activated by the candidate compound. As discussed above, the signal is caused by a "reporter molecule" that allows one to detect a cell in which the receptor is activated. A reporter molecule can be encoded by those genes that cause a detectable change in phenotype (the development of a change in color (e.g., fluorescent markers) growth under certain culture conditions or antibiotic resistance). For example, reporter molecules can be those proteins encoded by antibiotic resistance genes that are well known to those skilled in the art. Alternatively auxotrophic markers, such as those provided at the website: yeastgenome.org/alleletable.shtml, can be operably linked to promoters disclosed herein and used to identify agonists and antagonists of the receptors on the basis of cell growth in suitable selective medium. Other commonly used auxotrophic markers that can be operably linked to promoters disclosed herein for yeast include URA3, HIS3, LEU2, TRP1 and LYS2, which complement specific auxotrophic mutations in yeast, such as ura3-52, his3-Δ1, leu2-Δ1, trp1-Δ1 and lys2-201.

Other examples of reporter molecules include as fluorescent proteins. As recognized in the art, fluorescent proteins can be used in a variety of applications and have particular utility as a tool in molecular biology (see, e.g., Irie, M. & Mori, M. J. Org. Chem. 53:803 (1988); Parthenopoulos, D. A. & Rentzepis, P. M. Science 245:843 (1989); Hanazawa, M., et al. J. Chem. Soc. Chem. Commun. 206 (1992); Dvornikov, A. S., et al. J. Phys. Chem. 98:6746-6752 (1994); Dvornikov, A. S. & Rentzepis, P. M. Opt. Mem. Neur. Netw. 3:75-86 (1994); U.S. Pat. No. 4,471,470; U.S. Pat. No. 5,325,324; and U.S. Pat. No. 6,900,289, each of these cited documents is hereby incorporated by reference in its entirety for all purposes). Green fluorescent proteins (GFP) have been modified to alter their excitation and emission spectra. Specifically, a variety of GFPs have been constructed by modifying the amino acid sequence of a naturally-occurring (or wild-type) GFP from *Aequorea victoria* (see, e.g., Prasher, D. C., et al., Gene, 111:229-233 (1992); Heim, R., et al., Proc. Natl. Acad. Sci., USA, 91:12501-04 (1994); and U.S. Pat. Nos. 6,124,128 and 5,625,048, each of which is hereby incorporated by reference in its entirety. Further, nucleic acids encoding GFP can be operably linked to nucleic acids encoding other proteins and the resulting fusion polypeptides can be fluorescent and retain the biochemical features of the partner proteins (see, e.g., Cubitt, A. B., et al., Trends in Biochem. Sci. 20:448-455 (1995)). Mutagenesis studies have produced GFP mutants with shifted wavelengths of excitation or emission (see, e.g., Heim, R. & Tsien, R. Y. Current Biol. 6:178-182 (1996); and Tsien, R. Y., et al., Trends Cell Biol. 3:242-245 (1993). In addition, mutations in *Aequorea* fluorescent proteins, referred to as "folding mutations", improve the ability of fluorescent proteins to fold at higher temperatures and to be more fluorescent when expressed in mammalian cells, but have little or no effect on the peak wavelengths of excitation and emission. Such mutations can be combined with mutations that influence the spectral properties of GFP to produce proteins with altered spectral and folding properties. In addition, new fluorescent proteins based on GFP have been identified by random screening of GFPs (see, for example, Heim, R., et al. Proc. Natl. Acad. Sci. USA 91:12501-12504 (1994); Ehrig, et al. FEBS Lett. 367:163-166 (1995); and Delagrave, et al. Bio/Technology 13:151-154 (1995)). Other non-limiting examples of detectable phenotype reporter molecules include: DHFR, luciferase, chloramphenicol acetyltransferase, β-lactamase, adenylate cyclase, alkaline phosphatase, beta-galactosidase, and various other fluorescent proteins (such as red fluorescent protein, blue fluorescent protein and/or yellow fluorescent protein).

The signal produced in the methods described above can also be produced by a signal producing system. Such systems may include, besides reporter molecule(s)/gene(s), additional elements that allow for the production of the signal. Such an element could be, for example, the substrate of a reporter molecule, such as an enzyme. Thus, additional examples of reporter molecules include those genes encoding enzymes that can be operably linked to promoters as disclosed herein and which then act upon a particular substrate (e.g., a chromogenic or fluorogenic substrate). Non-limiting examples of such enzyme/fluorogenic substrate combinations that can be used as the signal include:

a) alpha-D-glucosidase, chymotrypsin or fatty acid esterase: fluorogenic enzyme substrates that may be used include 4-methylumbelliferyl-alpha-D-glucoside, 7-glutarylphenylalanine-7-amido-4-methyl coumarin, or 4-methylumbelliferyl heptanoate, respectively.

b) alpha-L-arabinofuranosidase: a fluorogenic enzyme substrate that may be used is 4-methylumbelliferyl-alpha-L-arabinofuranoside; and c) beta-D-glucosidase: a fluorogenic enzyme substrate that may be used is 4-methylumbelliferyl-beta-D-glucoside. Enzyme/Substrate combinations that may be used in the context of this invention are provided in the following table:

| Enzyme Substrate | Enzyme |
| --- | --- |
| 4-Methylumbelliferyl acetate | Esterase |
| 4-Methylumbelliferyl butyrate | Esterase |
| 4-Methylumbelliferyl elaidate | Lipase |
| 4-Methylumbelliferyl-beta-D-galactopyranoside | beta-D-Galactosidase |
| 4-Methylumbelliferyl-alpha-D-galactopyranoside | alpha-D-Galactosidase |
| 4-Methylumbelliferyl-alpha-D-glucopyranoside | alpha-D-Glucosidase |
| 4-Methylumbelliferyl-beta-D-glucopyranoside | beta-D-Glucosidase |
| 4-Methylumbelliferyl heptanoate | Esterase |
| 4-Methylumbelliferyl oleate | Lipase |
| 4-Methylumbelliferyl phosphate | Acid or Alkaline Phosphatase |
| 4-Methylumbelliferyl propionate | Esterase |
| 4-Methylumbelliferyl-beta-D-galactoside | beta-D-Galactosidase |
| 4-Methylumbelliferyl-beta-D-glucoside | beta-D-Glucosidase |
| 4-Methylumbelliferyl-alpha-D-glucoside | alpha-D-Glucosidase |
| 4-Methylumbelliferyl-alpha-L-arabinofuranoside | alpha-L-Arabinofuranosidase |
| L-Leucine-7-amido-4-methylcoumarin | Leucine aminopeptidase |
| 7-glutaryl-phenylalanine-7-amido-4-methylcoumarin | Chymotrypsin |
| D-Melibiose | alpha-D-Galactosidase |
| p-Nitrophenyl phosphate | Alkaline or Acid phosphatase |
| p-Nitrophenyl acetate | Lipase |
| o-Nitrophenyl-beta-D-galactopyranoside | beta-D-Galactosidase |
| p-Nitrophenyl-alpha-D-galactopyranoside | alpha-D-Galactosidase |
| o-Nitrophenyl-beta-D-glucopyranoside | beta-D-Glucosidase |
| p-Nitrophenyl-alpha-D-glucopyranoside | alpha-D-Glucosidase |
| p-Nitrophenyl-beta-D-glucuronide | beta-D-Glucuronidase |
| p-Nitrophenyl-alpha-L-arabinofuranoside | alpha-L-Arabinofuranosidase |
| p-Nitrophenyl laurate | Esterase |
| p-Nitrophenyl myristate | Esterase |
| p-Nitrophenyl palmitate | Esterase |
| p-Nitrophenyl phosphate disodium salt | Alkaline Phosphatase |
| Phenolphthalein dibutyrate | Esterase |
| Phenolphthalein diphosphate | Acid or Alkaline phosphatase |
| Phenolphthalein diphosphate pentasodium salt | Acid or Alkaline phosphatase |
| Phenolphthalein-beta-D-glucuronide sodium salt | beta-D-Glucuronidase |
| Phenolphthalein-beta-D-glucuronide | beta-D-Glucuronidase |
| L-Phenylalanine ethylester HCl | Chymotrypsin |
| Phenyl-beta-D-galactopyranoside | beta-D-Galactosidase |
| Phenyl-beta-D-glucuronide | beta-D-Glucuronidase |
| Phenyl-beta-D-glucopyranoside | beta-D-Glucosidase |
| Phenyl-beta-D-glucuronide | beta-D-Glucuronidase |

-continued

| Enzyme Substrate | Enzyme |
|---|---|
| Phenyl-alpha-D-glucoside | alpha-D-Glucosidase |
| Sodium beta-glycerophosphate | Acid or Alkaline phosphatase |
| Sodium 1-naphthyl phosphate | Acid or Alkaline phosphatase |
| Sodium 2-naphthyl phosphate | Acid or Alkaline phosphatase |
| 2-Naphthyl-butyrate | Esterase |
| beta-Naphthyl acetate | Lipase |
| 6-Br-2-naphthyl-beta-D-glucoside | beta-D-Glucosidase |
| L-Leucyl-2-naphthylamide | aminopeptidase |
| Leucine L-Valyl-2-naphthylamide | aminopeptidase |
| Valine N-glutaryl-phenylalanine-2-naphthylamine | Chymotrypsin |
| Naphthyl-AS-BI-Phosphate | Phosphohydralase |
| Indoxyl acetate | Lipase |
| N-Methylinodoxyl acetate | Lipase |
| N-Methylinodoxyl myristate | Lipase |
| 5-Bromoindoxyl acetate | Lipase |
| 3-Indoxyl phosphate | Acid or Alkaline phosphatase |
| Indoxyl-beta-D-glucoside | beta-D-Glucosidase |
| 5-Br-4-Cl-3-Indolyl acetate | Lipase |
| 5-Br-4-Cl-3-Indolyl phosphate | Alkaline or Acid phosphatase |
| 5-Br-4-Cl-3-Indolyl-beta-D-glucuronic acid | beta-D-Glucuronidase |
| Diacetylfluorescein | Lipase/esterase |

Reporter genes are commercially available from a variety of commercial entities, such as Clontech, Invitrogen and Promega and it is not intended that the present invention be limited to any particular detection system or label.

In certain embodiments of the invention, medium used to culture yeast cell can comprise 5%, 4.5%, 4%, 3.5%, 3%, 2.5%, 2%, 1.5%, 1%, 0.5%, 0.25%, 0.10%, 0.05% or 0.025% galactose (w/v). Some assays utilize medium comprising about 2% galactose (w/v) for the identification of antagonists (e.g., inverse antagonists) of the receptors disclosed herein. Other aspects of the invention provide for the use of culture medium that contains galactose at a concentration less than or equal to 0.10% galactose (w/v). Other aspects of the invention provide culture medium that contains galactose at a concentration less than or equal to 0.05% galactose (w/v) and greater than or equal to 0.005% galactose (w/v) (preferably greater than or equal to 0.01% galactose (w/v). Culture medium containing no galactose is not within the scope of the instant invention.

The osmotin receptor comprises the amino acid sequence:

```
                                              (SEQ ID NO: 56)
    mstllertks vgelkkraag ktsanpaeva kakkvlrrly swdeipewqr dndfilhgyv ketssfietf kslfylhnes vniyshlipa lgfftvllld kstikvfatt twldhmvidl fysgafacli lsssfhclks hslriatlgn kldylgicil ivtsmvsily ygyfekfslf clfalitvsf giacsivslk dkfrkrewrp yraglfvcfg lssiipifsg lycysfseiw tqiqlfwvll ggvlyiigav lygmrfpeki cpgkfdiwgh shqlfhflvv iaalchlrgl lnsyelvhik mengivs.
```

Thus cells can be transformed by any nucleic acid sequence encoding this receptor in methods of screening antifungal agents as set forth herein (e.g., the nucleic acid sequence associated with GenBank Accession No. NC_001147, which is hereby incorporated by reference in its entirety).

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Materials and Methods

Yeast Strains

Genotypes for strains referred to herein are listed in Table 1. The strains are: MCY5326 wild type, MCY5338 (msn2Δmsn4Δ), MCY5378 (nrg1Δnrg2Δ) and MCY5385 (msn2Δmsn4Δnrg1Δnrg2), generously provided by Dr. Marian Carlson at Columbia University (Vyas et al., 2005) and the pFLO11-lacZ strain, in which the lacZ ORF has replaced the FLO11 ORF in the genome of Σ1278b, generously provided by Dr. Florian Bauer at the University of Stellenbosch, Matieland, South Africa (van Dyk et al., 2005). All other yeast strains used in this study were purchased from Euroscarf (See Worldwide Website: web.uni-frankfurt.de/fb15/mikro/euroscarf/) and are in the BY4742 (MATα his3 leu2 ura3 lys2) background.

lacZ Reporters and Plasmids pFET3-397 and pFET3-297 are episomal reporter plasmids (provided by Dr. Andrew Dancis at the University of Pennsylvania) in which lacZ is driven by different truncations of the FET3 promoter (−397 to +3 and −297 to +3, respectively) (Yamaguchi-Iwai et al., 1996). Several different reporters were obtained that have the lacZ gene driven by a minimal CYC1 promoter in which the native upstream activating sequence has been replaced with fragments from various other promoters. pCYC1-FeRE (pFL-W, provided by Dr. Andrew Dancis) contains a fragment of the FET3 promoter that includes the Aft1-binding site known as an iron-response element or FeRE (Yamaguchi-Iwai et al., 1996). pCYC1-STRE (pCZ-oligo31/32, provided by Dr. Janet Trager, UCLA) contains a fragment of the DDR2 promoter that includes tandem stress response elements (STRE) to which the Msn2p and Msn4p transcription factors bind (Treger et al., 1998).

IZH1-4 were cloned into pRS316-GAL1 via gap repair as previously described (Lyons et al., 2004). The triple hemagglutinin epitope (3×HA) tagged construct of the IZH2 gene was generated by replacing the ZRC1 promoter and open reading frame in the YCpZRC1-HA plasmid (MacDiarmid et al., 2002) with those of IZH2. This was accomplished by gap repair of Age I-digested YCpZRC1-HA to generate pIZH2-3×HA. This construct has the IZH2 gene driven by its native promoter and retains the ZRC1 terminator sequence. The native IZH2 promoter was then exchanged with the GAL1 promoter using gap repair of pIZH2-3×HA plasmids cut with EcoN I. AdipoR1 and AdipoR2 were amplified from cDNAs obtained from OpenBiosystems (Accession #: BC010743 and BC051858, respectively). PCR products were cloned into NcoI/BamHI digested pYES260 vector (Melcher, 2000) by gap repair allowing for GAL1-driven expression. Primer sequences are reported in Table 2. Plasmids containing GAL1-driven the TAP (Tandem Affinity Purification) tagged NRG1 and NRG2 constructs were purchased from OpenBiosystems.

Biochemical Assays

Most experiments were performed in a defined EDTA-containing medium known as low iron medium (LIM) (Eide et al., 1992). Iron-deficiency and repletion were generated by adding either 1 μM or 1 mM of FeCl$_3$, respectively, to LIM. 2% galactose was used to fully induce GAL1-driven gene overexpression. Total sugar concentration was maintained at 2% by the addition of raffinose in those experiments in which the % galactose was modulated to decrease expression levels. Cells were allowed to grow to mid-log phase in LIM and β-galactosidase assays on permeabilized yeast were performed as previously described (Lyons et al., 2000). Ferroxidase activity assays on intact yeast cells followed published procedures using ferrozine as a colorimetric indicator of iron oxidation state (De Silva et al., 1995). All experiments include triplicate data points and each experiment was performed a minimum of three times. Representative experiments are shown. All error bars represent ±1 standard deviation within a single experiment. Because of the simplicity of β-galactosidase assays and the fact that Izh2p overexpression similarly affects both lacZ and ferroxidase activity, lacZ assays are shown for most experiments. For some strains with significant growth defects, such as snf1Δ, lacZ assays were not performed because of the low efficiency of co-transformation of lacZ reporter and overexpression plasmids. For these strains, only ferroxidase activity is shown. Iron-limited agar plates were made by adding 20 μM FeCl$_3$ to plates containing synthetic media and 1 mM of the iron-specific chelator, ferrozine. Western blots were performed using standard protocol and commercially available anti-HA antibodies.

Results

Effect of Izh2p Dosage on FET3 Expression

Figure 1B:
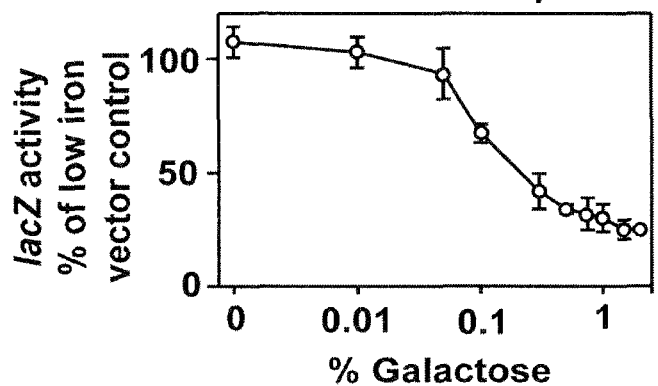
Figure 1C:
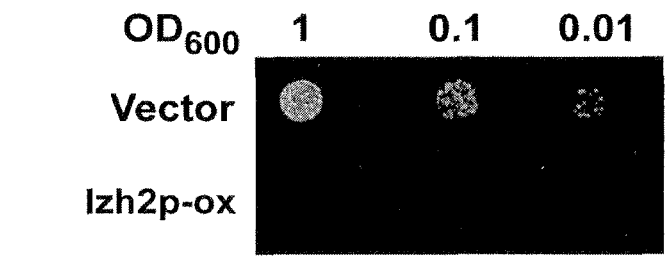

The pFET3-397 lacZ reporter responds reciprocally to the amount of iron added to LIM. (FIG. 1A) The induction during iron-deficiency, which is due to the presence of the FeRE from −250 to −244 to which the Aft1p protein must bind for transcriptional activation (Yamaguchi-Iwai et al., 1996), is repressible by IZH2 gene overexpression. (FIG. 1A) We demonstrate that iron-deficiency and IZH2 gene dosage have the same effect on cell surface ferroxidase activity—the physiological function of Fet3p—as they do on the β-galactosidase activity of pFET3-397. (FIG. 1A) pFET3-397 repression is proportional to the amount of galactose used to induce Izh2p overexpression. (FIG. 1B) Wild type cells carrying an empty overexpression vector are capable of growing on agar plates made iron-limited by the addition of ferrozine, while those carrying an Izh2p overexpression plasmid are not. (FIG. 1C).

To ensure that Izh2p is functionally expressed under the conditions of our experiment, we tagged the IZH2 gene with a 3x-HA epitope at the C-terminus. This construct functionally complements the phenotypes of an izh2Δ strain (Lyons et al., 2004) and is fully capable of repressing pFET3-397. (FIG. 14A; published online in association with B. R. Kupchak et al., Biochimica et Biophysica Acta, 2007, 1773:1124-1132 (the online version of which is hereby incorporated by reference in its entirety). Furthermore, we demonstrate by Western blot that the tagged construct is, indeed, galactose inducible and expressed in iron-deficient LIM. (FIGS. 14B and 14C; published online in association with B. R. Kupchak et al., Biochimica et Biophysica Acta, 2007, 1773:1124-1132 (the online version of which is hereby incorporated by reference in its entirety)).

Izh2p does not Globally Affect the Activity of Aft1p and Specifically Affects a 100 bp Region of the FET3 Promoter.

Figure 1D:
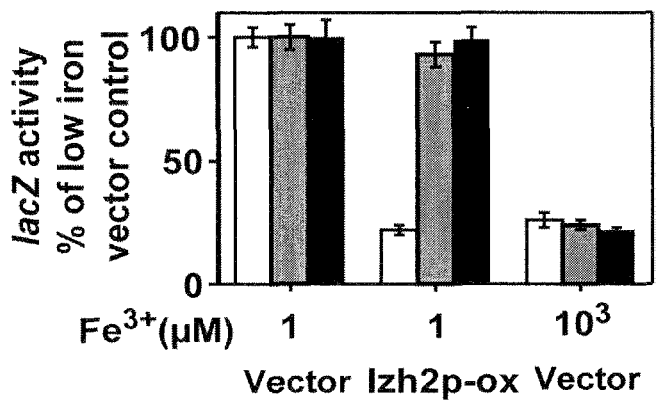

Like pFET3-397, the pFET3-297 and pCYC1-FeRE lacZ reporters are inducible by growth in iron-deficient LIM due to the presence of the FeRE from the FET3 promoter. (FIG. 1D) While pFET3-397 responds to Izh2p overexpression, pFET3-297 and pCYC1-FeRE do not. Furthermore, the Aft1p-dependent induction of pFET3-397 or ferroxidase activity in iron-deficient LIM is unaffected in all the mutant strains we tested with the exception of snf1Δ, msn2Δ, msn4Δ, msn2Δmsn4Δ, gal83Δ and sak1Δ. (FIG. 15; published online in association with B. R. Kupchak et al., Biochimica et Biophysica Acta, 2007, 1773:1124-1132 (the online version of which is hereby incorporated by reference in its entirety).

Msn2p and Msn4p Positively Regulate FET3 Expression

Figures 2A, 2B:
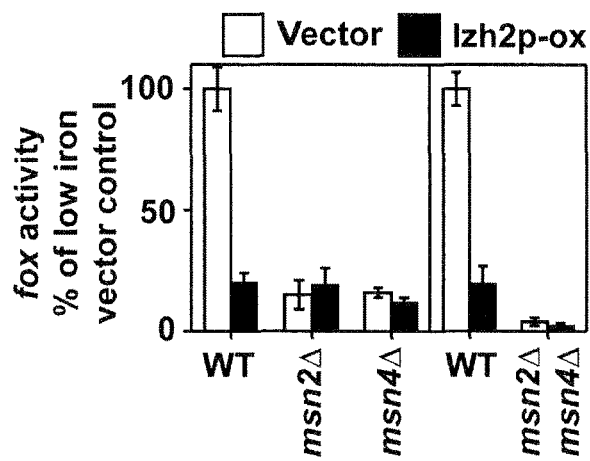
FIGS. 2A-2E: Msn2p, Msn4p and PKA regulate FET3. The legend above panel A applies to panels A-D. Activities in panels A-E are shown as a percentage of fully induced activity in the isogenic wild type strain carrying empty overexpression vector grown in iron-deficient LIM.
Figure 2C:
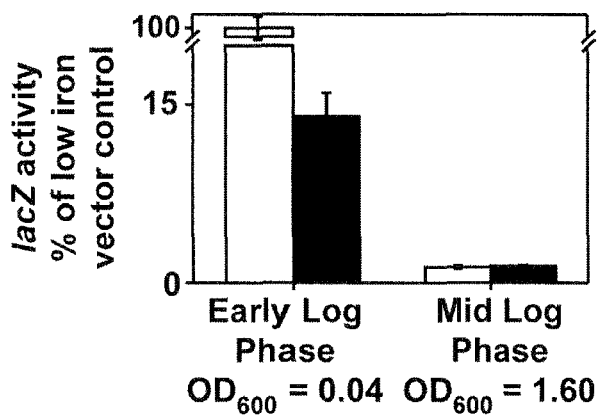

FET3 is significantly induced during the diauxic shift in iron-replete medium (Haurie et al., 2003). Since Msn2p and Msn4p are known to activate gene transcription during this growth phase, we examined their role in FET3 regulation. In msn2Δ and msn4Δ strains, ferroxidase activity is constitutively repressed in iron-deficient LIM. (FIG. 2A) Ferroxidase activity is even more repressed in an msn2Δmsn4Δ double mutant relative to the proper isogenic wild type control. (FIG. 2B) The pCYC1-STRE reporter contains tandem STREs and is conditionally activated by Msn2p/Msn4p (Treger et al., 1998). In keeping with a role for Msn2p/Msn4p in gene activation during carbon depletion, the activity pCYC1-STRE decreases as cells exit stationary phase and enter log phase (FIG. 2C). Izh2p overexpression significantly repressed pCYC1-STRE at low OD$_{600}$ when Msn2p/Msn4p are active but not at higher OD$_{600}$.

Involvement of Ras-cAMP and PKA in IZH2-Dependent FET3 Repression

Figure 2D:
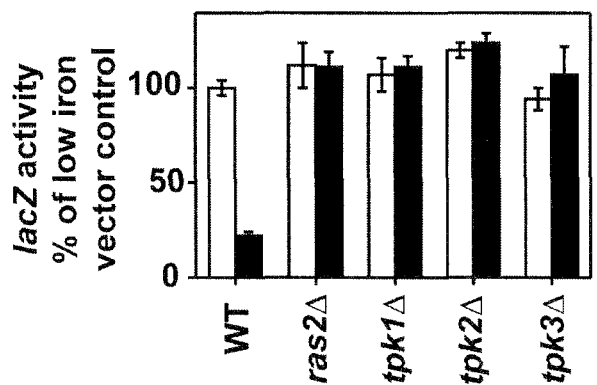
Figure 2E:
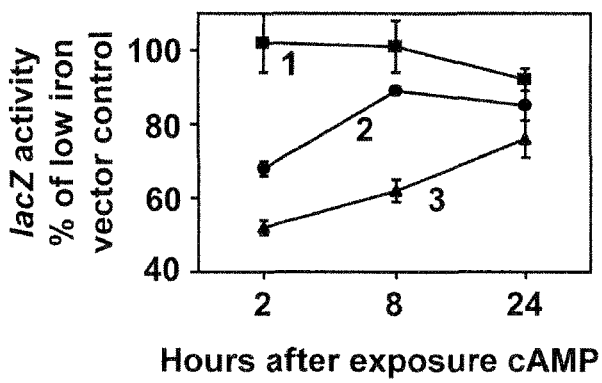

Since PKA negatively regulates the activity of Msn2p/Msn4p and has been implicated in the repression of Aft1-target genes (Robertson et al., 2000), we examined the role of PKA in Izh2p-dependent signal transduction. Deletion of any of the three genes encoding catalytic isoforms of PKA (TPK1, TPK2 and TPK3) results in a complete loss of pFET3-397 repression due to Izh2p overexpression in iron-deficient LIM. (FIG. 2D) PKA is positively controlled by input from the Ras2p-cAMP pathway (Jiang et al., 1998). Deletion of RAS2 results in impaired Izh2p-dependent pFET3-397 repression (FIG. 2D), however, Izh2p overexpression still represses pFET3-397 in the ras2Δ mutant if cAMP is added to the culture medium. (FIG. 2E)

Nrg1p and Nrg2p Negatively Regulate FET3 Expression

Data from *Candida albicans* suggests that iron-uptake genes may be under the control of the CaNrg1 transcriptional repressor (Murad et al., 2001). Thus, we examined the role of the *S. cerevisiae* CaNrg1p homologues, Nrg1p and Nrg2p, in FET3 expression. Izh2p-dependent pFET3-397 repression is lost in nrg1Δ or nrg2Δ strains. (FIG. 3A) The effect of Izh2p on ferroxidase activity is also lost in an nrg1Δnrg2Δ double mutant strain. (FIG. 3B) Nrg1p/Nrg2p negatively regulate the pFLO11-lacZ reporter (van Dyk et al., 2005). Izh2p represses the activity of pFLO11-lacZ in iron-deficient LIM. (FIG. 3C) Furthermore, we obtained GAL1-driven TAP-tagged Nrg1p or Nrg2p constructs and found that Nrg2p-TAP overexpression has the same effect on pFET3-397 as does Izh2p overexpression. (FIG. 3D) Nrg1p-TAP overexpression has no effect, however, the Nrg1p-TAP construct does not restore the effect of Izh2p on pFET3-397 in the nrg1Δ strain (data not shown) suggesting that Nrg1p-TAP may be non-functional or not expressed. Nrg2p-TAP overexpression is not capable of repressing ferroxidase activity in an nrg1Δnrg2Δ strain. (FIG. 3E)

The negative effect of Msn2p/Msn4p deletion on ferroxidase activity is alleviated if Nrg1p and Nrg2p are concomitantly knocked-out. (FIG. 3F) In addition, overexpression of Izh2p has no effect on ferroxidase activity in the quadruple mutant strain.

AMP-Dependent Kinase and the Repression of FET3

AMP-dependent kinase (AMPK) is a known negative regulator of Nrg1p/Nrg2p (Kuchin et al., 2002) and has been implicated in the regulation of iron-regulated genes (Haurie et al., 2003). AMPK has multiple isoforms depending on subunit composition. There is a lone catalytic α-subunit of AMPK (Snf1p) which forms a heterotrimeric complex with a lone stimulatory γ-subunit (Snf4p) and one of three β-subunits (Gal83p, Sip1p or Sip2p) that regulate AMPK cellular localization (Vincent et al., 2001). Its activity is regulated by AMP and by phosphorylation by an upstream activating kinase (AMPKK) of which there are three partially redundant isoforms (Elm1p, Sak1p or Tos3p) (Hedbacker et al., 2004). Complete loss of AMPK activity caused by SNF1 deletion results in constitutive repression of the FET3 gene as measured by basal ferroxidase activity in iron-deficient LIM. (FIG. 4A) Selective inactivation of nuclear AMPK activity by deletion of the β subunit (Gal83p) that targets AMPK to the nucleus or the AMPK activating kinase (AMPKK, Sak1p) responsible for activation of nuclear AMPK also results in constitutive pFET3-397repression. (FIG. 4B) Finally, strains lacking Snf4p also show an approximately 40% decrease in pFET3-397 activity. (FIG. 4C)

Perturbations of a cytoplasmic isoform of AMPK by deletion of Sip1p results in a decrease in pFET3-397 activity similar to that seen in the snf4Δ mutant. (FIG. 4C) Deletion of another cytoplasmic Snf1p-interacting protein, Sip3p, has an identical effect on pFET3-397. (FIG. 4C) In the snf4Δ, sip1Δ and sip3Δ strains, Izh2p overexpression no longer represses pFET3-397. The addition of 500 μM AICAR, an activator of mammalian AMPK (Corton et al., 1995), to the growth medium resulted in a small but reproducible decrease in pFET3-397 activity, suggesting that AMPK activation may play a role in signal transduction. (FIG. 4D)

PAQR Overexpression Mimics Receptor Activation

Figures 5A, 5B, 5C:
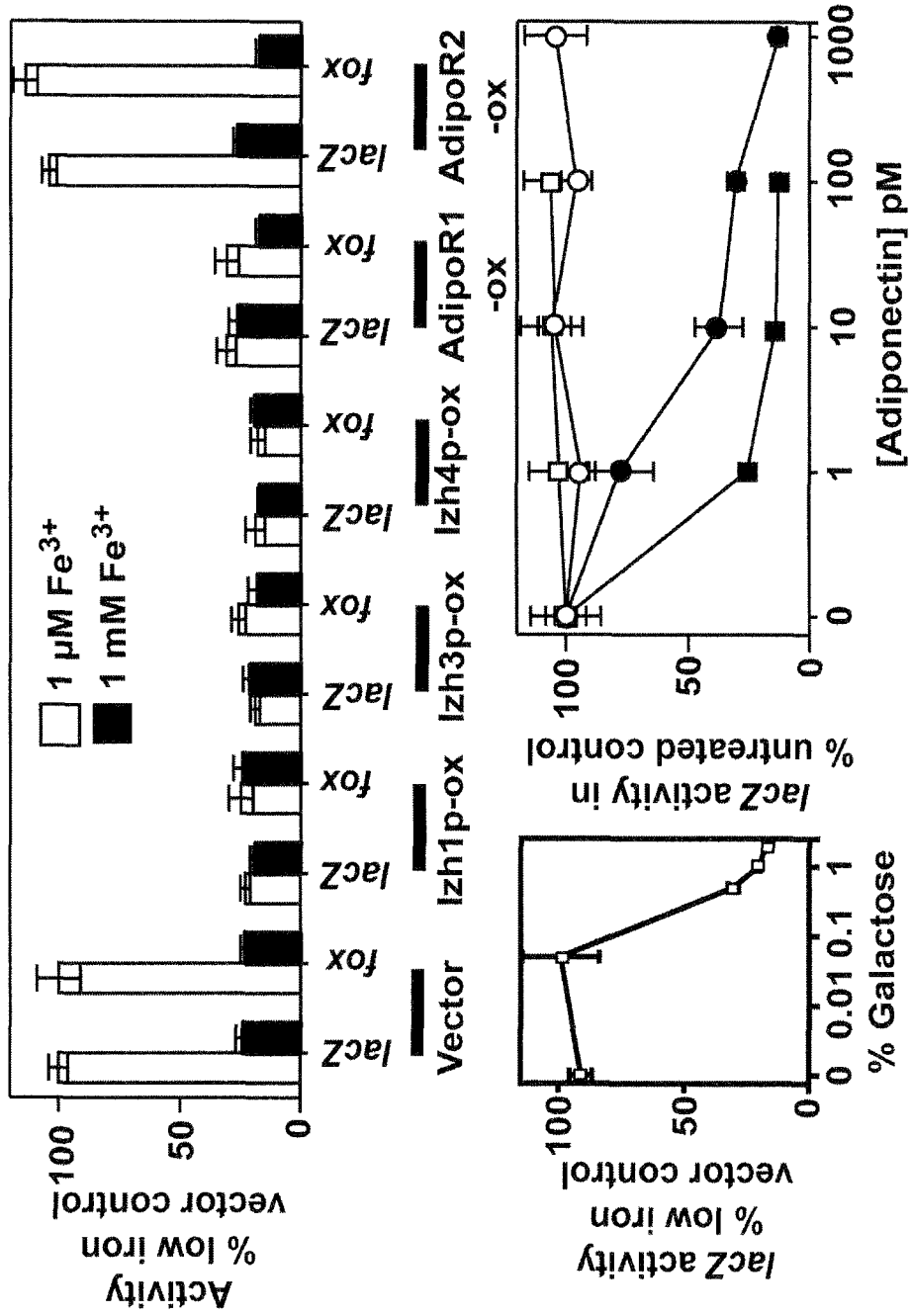
FIGS. 5A-5D: Functional expression of human PAQR receptors in yeast. For panels A and D, β-galactosidase (lacZ) or ferroxidase (fox) activities are shown as a percentage of activity produced in the BY4742 wild type strain carrying an empty overexpression vector and grown in iron-deficient LIM.
Figure 5D:
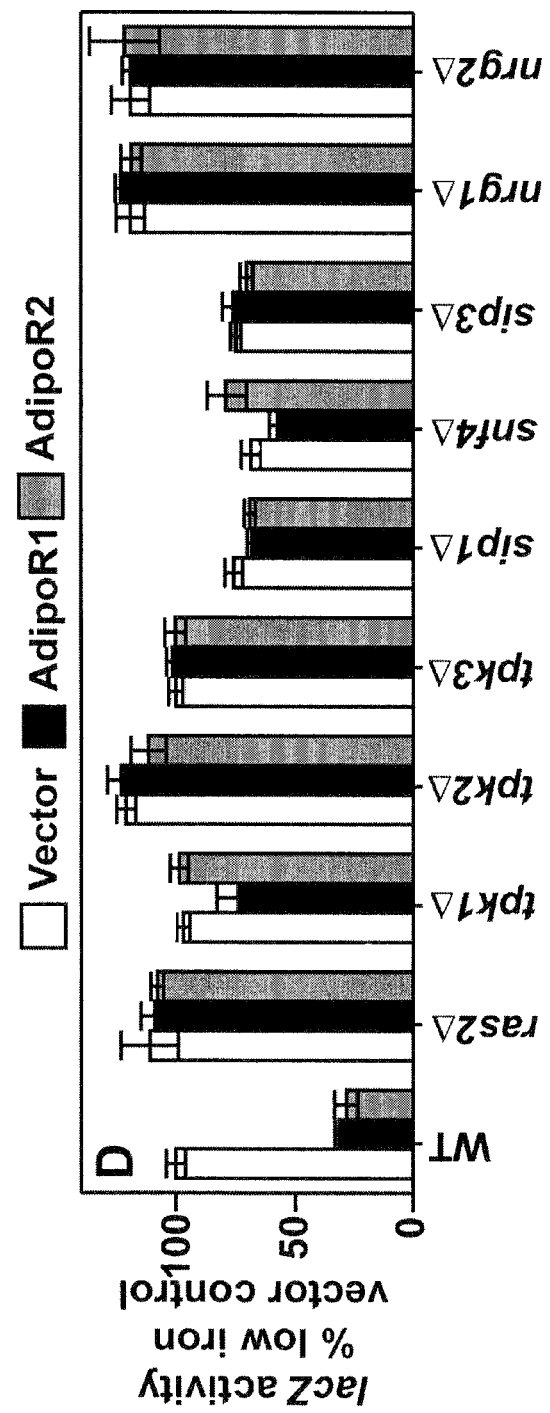
Figure 7A:
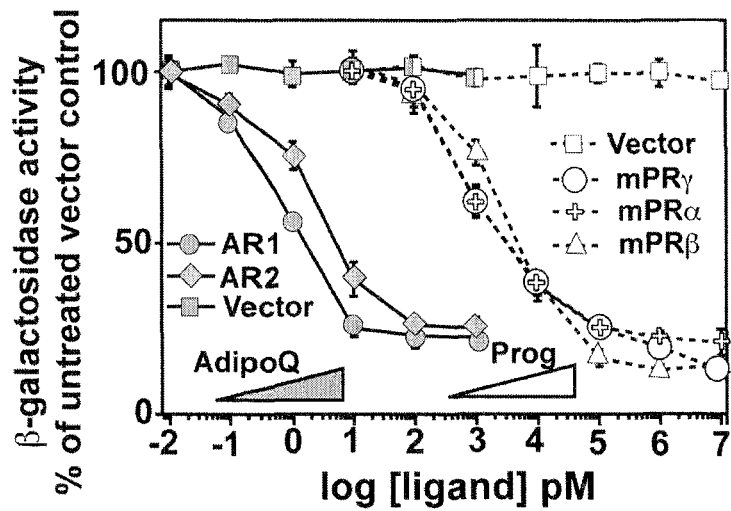
FIGS. 7A-7C: Functional expression of human mPRα, mPRβ and mPRγ in yeast. All cells are wild type and are grown in iron-deficient LIM. Medium in panels (FIG. 7A) and (FIG. 7B) contains 0.05% galactose/1.95% raffinose and medium in panel (FIG. 7C) contains 2% galactose. In all boxes, the activity of the FET3 gene is monitored by measuring β-galactosidase activity produced by the FET3-lacZ reporter (FIG. 7A). All PAQRs are cloned into the pYES260 vector except AdipoR2, which is cloned into pGREG536. White symbols show the effect of progesterone on FET3 in cells carrying either empty expression vector or vectors that express mPRα, mPRβ or mPRγ. Grey symbols show the effect of adiponectin on FET3 in cells carrying either empty expression vector or vectors that express AdipoR1 or AdipoR2 (FIG. 7B). The effect of various steroids on the FET3 gene cells expressing either mPRγ or mPRα from the pYES260 plasmid (FIG. 7C). The effect of various steroids on FET3 in cells expressing mPRα from the pRS316 plasmid.
Figure 7B:
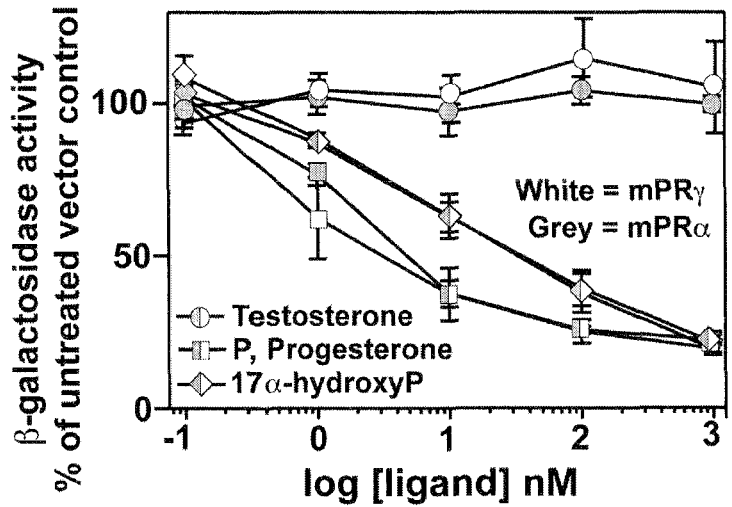
Figure 7C:
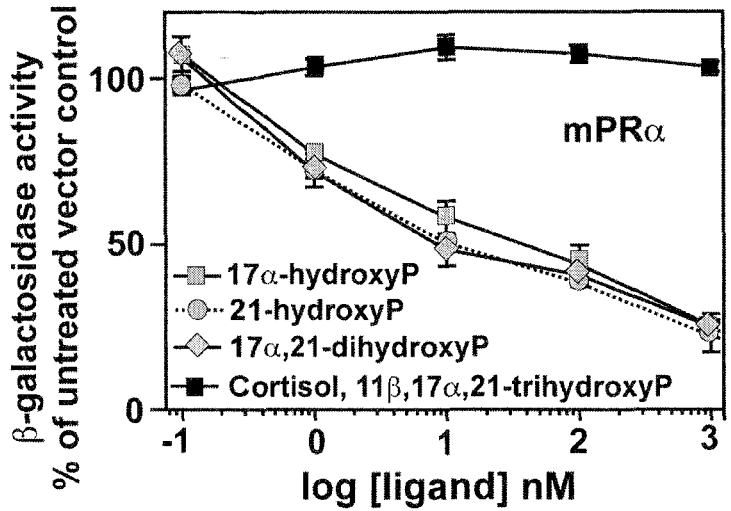

Overexpression of three homologous yeast PAQR receptors (Izh1p, Izh3p and Izh4p) results in pFET3-397 repression and decreased ferroxidase activity in iron-deficient LIM. (FIG. 5A) We also demonstrate that overexpression of the human adiponectin receptor, AdipoR1, but not its functional homologue, AdipoR2, represses pFET3-397 and ferroxidase activity. (FIG. 5A) By decreasing the amount of galactose, the effect of AdipoR1 on pFET3-397 can be incrementally diminished. (FIG. 5B) At first glance it appears as though AdipoR2 does not function in yeast. When adiponectin is added to cells expressing either AdipoR2 (in 2% galactose) or low levels of AdipoR1 (in 0.02% galactose), pFET3-397 is repressed in a dose-dependent manner. (FIG. 5C) As in the case of Izh2p overexpression, pFET3-397 repression by either overexpression of AdipoR1 in the absence of adiponectin or AdipoR2 in the presence of adiponectin required RAS2, TPK1, TPK2, TPK3, SIP1, SNF4, SIP3, NRG1 and NRG2. (FIG. 5F)

Repression of FET3 by Izh2p Overexpression

In this study, we provide genetic evidence that supports a new mechanism for the regulation of the FET3 gene encoding a ferroxidase involved in high-affinity iron-uptake. The first clues to this regulatory mechanism came from a previous study in which we showed Izh2p-dependent repression of a zinc-dependent reporter (Lyons et al., 2004). This effect was not due to a generalized growth defect, aberrant expression of any random membrane protein or a global defect in transcription, translation, or β-galactosidase activity. While investigating the specificity of Izh2p-dependent repression, we discovered—and herein report—the finding that Izh2p also represses the iron-dependent induction of the FET3 gene. More importantly, Izh2p causes a decrease in Fet3p enzymatic activity and cell viability in iron-limited medium, thus confirming that the Izh2p effect is neither an artifact of our reporter constructs nor a physiologically irrelevant phenomenon. The level of repression of both FET3 expression and ferroxidase activity by Izh2p are comparable to repression caused by full iron-repletion (approximately 25% of fully induced levels), suggesting that the loss of ferroxidase activity is mainly caused by decreased gene expression. A generic iron-dependent reporter was unaffected by Izh2p overproduction, indicating that Izh2p modulates FET3 activity in an iron-independent manner. Due to the importance of iron acquisition in host environments, the negative effect of Izh2p on iron-uptake represents a viable mechanism by which osmotin, the proposed ligand for Izh2p, might exert its fungicidal effects.

Msn2p/Msn4p, PKA and Ras-cAMP in the Negative Regulation of FET3

We envision two probable mechanisms by which Izh2p and its homologous receptors may function to repress FET3. In the first scenario, the signaling pathway inactivates an essential co-activator of FET3 expression. We demonstrate that—at least under the conditions of our experiments—the Msn2p and Msn4p stress-responsive transcriptional activators are indeed essential for FET3 induction and that Izh2p may affect FET3 by negatively regulating Msn2p/Msn4p. This possibility is bolstered by several lines of evidence. First, Msn2p/Msn4p are the main transcription factors responsible for inducing genes during the diauxic shift—a growth phase during which FET3 is known to be induced (Haurie et al., 2003). Second, Izh2p-dependent repression requires PKA, a kinase known to negatively regulate Msn2p/Msn4p (Cameroni et al., 2004) and purported to regulate a subset of Aft1p-target genes (Robertson et al., 2000). Third, PKA activity is positively regulated by cAMP produced by the Ras-cAMP module (Cameroni et al., 2004), which is required for Izh2p-dependent repression. Fourth, Izh2p overexpression represses a generic stress responsive reporter that is directly activated by Msn2p/Msn4p. Thus, Izh2p negatively affects the activity of Msn2p/Msn4p and, in turn, these are essential co-activators of FET3.

In this model, Izh2p, through Msn2p/Msn4p, directly or indirectly affect FET3 transcription by altering flux through the Ras-cAMP/PKA pathway. The fact that osmotin signaling in yeast (Narasimhan et al., 2005; Narasimhan et al., 2001) and FET3 repression via Izh2p both require the Ras2p G-protein has led to the supposition that Izh2p is coupled with Ras2p. Since the PAQR family of proteins has been postulated to comprise a novel class of G-protein coupled receptor (GPCR) (Thomas et al., 2006; Thomas et al., 2007), the involvement of Ras-cAMP/PKA would seem to support the conclusion that Izh2p is a Ras2p-coupled GPCR. However, if Izh2p were a Ras2p-coupled GPCR, then the physical presence of the Ras2p polypeptide would be essential for Izh2p-dependent signaling. We have demonstrated that it is not Ras2p, but cAMP that is essential, thus demonstrating that Izh2p is not directly coupled to Ras2p. Our data suggest that the Ras-cAMP module is only required by virtue of the essentiality of cAMP in PKA activation and that it is likely that signals from Izh2p converge on PKA downstream of Ras-cAMP.

Nrg1p/Nrg2p and AMPK in the Negative Regulation of FET3

A second, non-mutually-exclusive, possibility for the mechanism of Izh2p-dependent repression is the activation of a repressor of FET3 transcription. Increased expression of genes involved in high-affinity iron-uptake in C. albicans strains lacking the CaNrg1p repressor has been previously reported (Murad et al., 2001). CaNrg1p has two partially redundant homologues in S. cerevisiae named Nrg1p and Nrg2p. We demonstrate that without these repressors, Izh2p was incapable of repressing FET3. We also show that overexpression of Izh2p represses a generic reporter known to be directly regulated by Nrg1p/Nrg2p. Furthermore, we show that Nrg2p overexpression was sufficient to recapitulate the effect of Izh2p overproduction. Repression by Nrg1p/Nrg2p is believed to be mediated by their binding to a CCCTC motif in the promoters of target genes (Park et al., 1999). A CCCTC motif can be found from −316 to −312 in the FET3 promoter as well as in the zinc-dependent reporter described in the beginning of the discussion. The fact that pFET3-397 construct is Izh2p-regulated, while pFET3-297 is not, strongly suggests that there is an element—possibly the CCCTC motif at −312—directly responsible for repression, however, we cannot yet state unequivocally that Nrg1p/Nrg2p bind the FET3 promoter at a cis-regulatory element.

Nrg1p and Nrg2p physically interact with and are negatively regulated by AMPK (Vyas et al., 2001), thus it is possible that Izh2p activates Nrg1p/Nrg2p by inactivation of AMPK. A possible role for AMPK in Izh2p-dependent signaling is very attractive since human adiponectin receptors are known to function through AMPK (Kadowaki et al., 2006) and yeast AMPK has been shown to positively regulate genes involved in iron homeostasis (Haurie et al., 2003). We present two pieces of evidence that are consistent with an important role for nuclear AMPK in FET3 regulation by inactivation of nuclear Nrg1p/Nrg2p. First, strains completely lacking AMPK or those lacking the nuclear isoform of AMPK show constitutively repressed ferroxidase activity. Second, strains lacking a variety of AMPK subunits show a 40% reduction in FET3 expression. Evidence for an essential role for cytoplasmic AMPK in Izh2p-dependent repression comes from data showing FET3 repression by the addition of an AMPK activator (AICAR) and loss of Izh2p-dependent repression in strains lacking cytoplasmic isoforms of AMPK. Finally, the finding that the Snf1p-interacting protein, Sip3p (Lesage et al., 1994), is required for Izh2p-dependent repression is particularly exciting considering that the human homologue of Sip3p, APPL1, physically interacts with and is required for signal transduction via the human adiponectin receptor, AdipoR1 (Mao et al., 2006).

Epistasis of Msn2p/Msn4p and Nrg1p/Nrg2p

Nrg1p/Nrg2p and Msn2p/Msn4p have opposing effects on FET3 expression. Nrg1p and Nrg2p are predicted to bind the CCCTC motif as well as the CCCCT STRE that functions as a binding site for Msn2p and Msn4p (Park et al., 1999). Due to the similarity of the STRE and CCCTC motifs to which Nrg1p/Nrg2p bind, it is possible that both the Nrg1p/Nrg2p repressors and Msn2p/Msn4p activators recognize the same elements. Indeed, a recent study suggests that Nrg1p/Nrg2p and Msn2p/Msn4p compete with each other for binding to the same regulatory elements in a subset of stress-responsive promoters (Vyas et al., 2005). Our data shows that Nrg1p/Nrg2p are epistatic to Msn2p/Msn4p with respect to FET3 expression, however, we cannot yet conclude if these transcription factors act on FET3 through cis-regulatory elements. Based on our data, we propose that Msn2p/Msn4p function competitively and antagonistically to Nrg1p/Nrg2p in the direct or indirect regulation of FET3 and that Izh2p overexpression may alter this competition by inactivating Msn2p/Msn4p via PKA or activating Nrg1p/Nrg2p via AMPK.

Izh2p Overexpression vs. Receptor Activation

A final point to address is that the Izh2p receptor causes FET3 repression in the absence of its supposed activating ligand osmotin. It is possible that Izh2p is actually a receptor for an, as yet unidentified, endogenous molecule and that this hypothetical ligand is present in high enough concentration to activate Izh2p when it is overexpressed. It is also possible that Izh2p, like many signaling proteins, has an intrinsic basal signaling capability that is amplified by overexpression making the presence of activating ligand unnecessary. In the latter case, overexpression would function equivalently to activation. Due to the fact that osmotin is neither commercially available nor easily produced, we cannot yet directly test the latter model. However, we have functionally expressed two homologous human adiponectin receptors in yeast. In both cases, activation of the receptor with adiponectin represses FET3 expression in a manner that is nearly identical to that of Izh2p overexpression.

Conclusions

Our findings support several important conclusions. First, Izh2p affects iron homeostasis via the Nrg1p/Nrg2p and Msn2p/Msn4p transcription factors. Second, the regulation of Izh2p by zinc suggests cross-talk between the iron- and zinc-dependent regulons, thus adding to the growing body of data indicating a complex relationship between iron and zinc homeostasis in yeast (Courel et al., 2005; Rutherford et al., 2005; Santos et al., 2003; Waters et al., 2002). Third, every PAQR protein tested, regardless of activating ligand and physiological function, activate a similar intracellular signaling cascade, suggesting a conserved mechanism of signal transduction. Specifically, these studies shed light on the physiology of Izh2p and its relation to iron metabolism in yeast. More generally, they provide a simple assay to expedite investigations into the structure/function relationship in human PAQR proteins of biomedical interest.

Example 2

This example evaluates the ability of PAQR receptors to respond to progesterone. In this example, we demonstrate that membrane progesterone receptors, mPRα, mPRβ and mPRγ, can sense and respond to progesterone with $EC_{50}$ values that are physiologically relevant. Agonist profiles also show that mPRα, mPRβ and mPRγ are activated by ligands, such as 17α-hydroxyprogesterone, that are known to activate non-genomic pathways but not the nuclear progesterone receptor (nPR). These results strongly suggest that these receptors may function as the long-sought-after membrane progesterone receptors. Additionally, we show that two uncharacterized PAQRs, PAQR6 and PAQR9, are also capable of responding to progesterone. These mPR-like PAQRs have been renamed mPRδ (PAQR6) and mPRε (PAQR9). Additional characterization of mPRγ and mPRα indicate that their progesterone-dependent signaling in yeast does not require heterotrimeric G-proteins.

A resolution to the debate about whether mPRα, mPRβ and mPRγ can sense and respond to progesterone requires a system with two fundamental properties. First, such a system must be devoid of progesterone binding/sensing proteins so that the mPRs can be studied in isolation. Second, this system must have an intact signaling apparatus that allows for monitoring signal transduction in response to progesterone. The systems provided in this application provide such a system and allows for the heterologous expression of mPRα, mPRβ and mPRγ in the yeast *Saccharomyces cerevisiae*. This model systems is advantageous for several reasons. First, yeast is a eukaryotic system for which simple yet powerful genetic tools exist. Second, yeast possess receptors in the PAQR family suggesting that the machinery required to read second messengers produced by these proteins is present (Lyons et al., 2004). Third, *S. cerevisiae* neither makes nor uses progesterone. In fact, a recent publication showed that massive doses of progesterone (1 mM) did little more than weakly induce the general stress response (Banerjee et al., 2004). *S. cerevisiae* has already been successfully adapted for the biochemical characterization of nuclear progesterone receptors (MeEwan, 2001).

Materials and Methods

Yeast strains. Wild type BY4742 (Mat a), BY4741 (Mat a) and gpa2Δ (Mat a, BY4742 background) mutant yeast strains were obtained from Euroscarf (See Worldwide Website: web.uni-frankfurt.de/fb15/mikro/euroscarf/). gpa1Δ mutants are inviable due to constitutive growth arrest caused by the hyperactivation of the Ste4p/Ste18p $G_{bg}$ subunit in the absence of the Gpa1p $G_\alpha$ subunit. Viability of gpa1Δ mutant strains can be restored by concomitant deletion of the Ste7p MAP kinase that functions downstream of Ste4p/Ste18p. The gpa1Δste7Δ mutant strain (in the BY4741 background) was kindly provided by Dr. Henrik Dohlman (University of North Carolina, Chapel Hill) (Wu et al., 2004). The STY50 strain lacking the HIS4 gene (Sengstag et al., 2004) was kindly provided by Dr. Gunnar von Heijne (Stockholm University).

Plasmids and primers. Human PAQRs were cloned into various vectors by PCR from commercially/publically available cDNAs. PAQRs were cloned into the pYES260 (Melcher, 2000), pRS316 (Liu et al., 1992) or pGREG536 (Jansen et al., 2005) expression vectors using gap repair. The pJK90 plasmid containing a Dual Topology Reporter (DTR)-tagged OST4 gene driven by the constitutive TPI1 promoter was kindly provided by Dr. Gunnar von Heijne (Stockholm University) (Kim et al., 2003). The OST4 open reading frame in pJK90 was replaced with the PAQR6 and mPRα open reading frames by gap repair. Primers for all cloning reactions are listed herein. Proteins expressed in pYES260 have an N-terminal 6×-histidine tag followed by a TEV protease cleavage site. Proteins expressed in pGREG536 have an N-terminal 7×-HA tag. Proteins expressed in the pRS316 vector are untagged. The pYES260, pRS316 and pGREG536 vectors allow for galactose-inducible expression via the GAL1 promoter. We see no vector-dependent difference in the functionality of any PAQR receptor, indicating that receptors in this family seem to be highly tolerant of N-terminal modifications. The FET3-lacZ plasmid was previously described (Kupchak et al., 2007). Plasmids derived from pADM4 carrying hyperactive alleles of Gpa1p (Gpa1p$^{Q323L}$) (Slessareva et al., 2006) and Gpa2p (Gpa2p$^{Q300L}$) (Harashima et al., 2002) driven by the ADH1 promoter were kindly provided by Dr. Henrik Dohlman (UNC Chapel Hill). A pRS316-based plasmid containing the STE2 gene under the control of the GAL1 promoter (Feng et al., 2000) was kindly provided by Dr. Nicholas G. Davis (Wayne State University).

Assays and growth conditions. Strains were maintained using standard protocol and grown in synthetic defined (SD) media with the appropriate amino acids to match the auxotrophies of the individual strains. Low Iron Medium (LIM) contains EDTA to limit iron-bioavailability and its composition has been previously described (Kupchak et al., 2007). When supplemented with only 1 μM $Fe^{3+}$, LIM is considered iron-deficient and the FET3 gene is fully induced under these conditions. b-galactosidase (lacZ) assays were performed as previously described (Kupchak et al., 2007). In brief, overnights of cells grown in SD-glucose media were re-inoculated into iron-deficient LIM to induce the expression of FET3. 2% galactose was used as a carbon source to induce full expression of PAQR genes driven by the GAL1 promoter, while 0.05% galactose/1.95% raffinose was used for reduced PAQR expression. All ligands were added to the growth medium upon re-inoculation into LIM. For experiments in which steroids were added as ligands, steroids were added from ethanol stocks and "untreated" controls are actually treated with an equal volume of ethanol to control for vehicle effects. Cells were allowed to grow to mid-log phase at which time the activity of the FET3 gene was monitored using a FET3-lacZ promoter-reporter construct. lacZ activities are presented as a percentage of activity seen in untreated cells expressing the appropriate empty expression vector control. For individual experiments, each data point has been done in triplicate and the error bars represent +/−1 standard deviation. All experiments were performed at least three times and a representative experiment is shown. $EC_{50}$ values were obtained using the web-based BioDataFit software using sigmoidal curve-fitting. (web site changbioscience.com/stat/ec50.html)

Total membrane protein preparations were prepared as previously described (Kupchak et al., 2007). Protein concentrations were determined and equal amounts were loaded onto SDS-PAGE gels for Western blotting. Western blots were performed using standard protocol using a rabbit polyclonal anti-HA primary antibody (Santa Cruz Biotechnology) and a goat anti-rabbit IgG-HRP conjugate as the secondary antibody (Santa Cruz Biotechnology). Proteins were detected by chemiluminescence. Determination of glycosylation with EndoH treatment was performed as published (Kim et al., 2003a).

Sequence analysis. Multiple sequence alignments and bootstrapped phylogenetic trees were produced using ClustalX with default parameters (Thompson et al., 1997). Trees were visualized using Tree View (Page et al., 1996) and TreeView X (web site: darwin.zoology.gla.ac.uk/~rpage/treeviewx/index.html). Pairwise sequence analysis was performed at the NCBI website by Blast 2 Sequences (Tatusova et al., 1999). Hydropathy plots were first generated with TopPredictII 1.2 (Claros et al., 1994) using the Kyte-Doolittle algorithm and default parameters. Data was downloaded into a spreadsheet and the hydropathy values were aligned based on the multiple sequence alignment produced by ClustalX. Average hydropathy across the entire set of aligned proteins was then calculated. Most sequences were obtained from the NCBI database; however, sequences from *Trichoplax adhaerens*, *Nematostella vectensis*, *Lottia gigantea*, *Capitella* sp., *Branchiostoma floridae* and *Ciona intestinalis* were obtained from the Joint Genome Institute website (See Worldwide Website: genome.jgi-psf.org/euk_home.html).

Results

Heterologous Expression of Human mPRs in Yeast

When grown in iron-deficient medium, the FET3 gene is induced to facilitate the uptake of exogenous iron. We previously demonstrated that the yeast osmotin receptor (Izh2p) activated a pathway that resulted in the constitutive repression of FET3 in iron-deficient conditions (Kupchak et al., 2007). Control experiments demonstrated that this effect was not an artifact of the FET3-lacZ reporter and that the expression of FET3 was, indeed, regulated by Izh2p. We also demonstrated that the human adiponectin receptors (AdipoR1 and AdipoR2) could be functionally expressed in yeast. In these experiments, expression of the FET3 gene responded reciprocally to the amount of adiponectin in the medium in cells expressing AdipoR1 and AdipoR2 (Kupchak et al., 2007). The $EC_{50}$ values for adiponectin were 0.7 and 2.4 pM for AdipoR1 and AdipoR2, respectively. (Table 3) This data is re-plotted in FIG. 13A to demonstrate two important concepts. First, the expression of the FET3 gene can be used as a reporter for the activity of human PAQR receptors. Second, PAQR receptors from diverse sources activate the same pathway in yeast. This led us to predict that this system could be used to address whether mPRα, mPRβ and mPRγ could sense and respond to progesterone. We cloned all three human receptors into GAL1 driven expression plasmids and grew them in iron deficient LIM containing 0.05% galactose. In cells expressing the mPRs the expression of the FET3 gene responded reciprocally to progesterone in a dose dependent manner. (FIG. 13A) The $EC_{50}$ values for progesterone were 1.3, 2.3 and 1.6 nM for mPRγ, mPRα and mPRβ, respectively. (Table 3).

Wild type cells carrying empty expression plasmid did not respond to either adiponectin or progesterone indicating that the effects described above cannot be attributed to an endogenous yeast protein, such as a yeast PAQR receptor. Furthermore, AdipoR1 and AdipoR2 do not respond to progesterone at concentrations as high as 10 μM (FIG. 11A), demonstrating that progesterone specifically affects mPRα, mPRβ and mPRγ and does not generally affect yeast expressing non-native PAQR receptors.

Specificity of mPRα, mPRβ and mPRγ

We also investigated the steroid specificity of mPRα and mPRγ and found that 17α-hydroxyprogesterone was an effective activator of both receptors, albeit with a lower $EC_{50}$. (FIG. 13B, Table 4). A further analysis of mPRα revealed that the receptor was largely permissive of alterations at the 17 and 21 positions of the pregnane ring. 17α-hydroxyprogesterone, 21-hydroxyprogesterone and 17α,21-dihydroxyprogesterone were all similarly effective activators of mPRα. However, 11β,17α,21-trihydroxyprogesterone (cortisol) was an ineffective agonist (FIG. 13C).

Figure 8A:
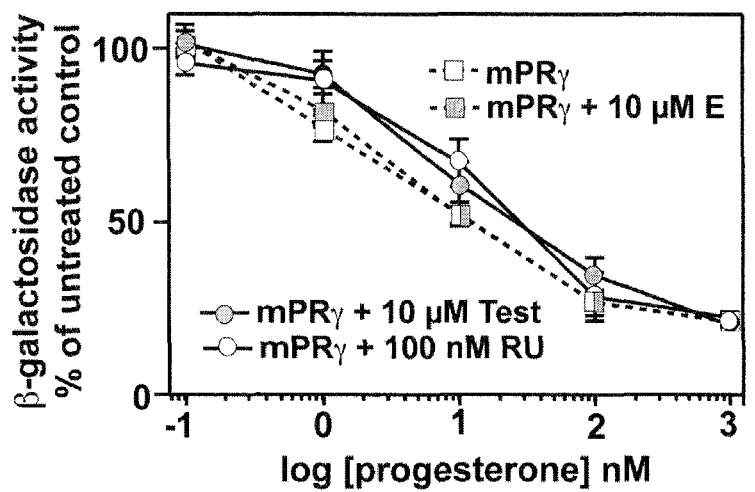
FIGS. 8A-8C: Steroid specificities for mPRγ and mPRα. In all cases, FET3 expression is measured using the FET3-lacZ reporter. All PAQR are cloned into the pGREG536 vector. All cells are wild type and are grown in iron-deficient LIM containing 0.05% galactose/1.95% raffinose (FIG. 8A). The dose response of FET3 in cells expressing mPRγ plasmid to progesterone either alone or in the presence of 10 μM β-estradiol (E), 10 μM testosterone (test) or 100 nM RU-486 (RU) (FIG. 8B). Dose response of FET3 to either progesterone (P) or RU-486 (RU) in cells carrying either empty expression vector or vectors that express mPRγ or mPRα (FIG. 8C). Dose response of FET3 to RU-486 in cells carrying either empty expression vector or a vector that expresses mPRγ. Cells are either treated with RU-486 alone or in the presence of 100 nM progesterone (P).

While testosterone is closely related in structure to progesterone, it is a poor agonist of the non-genomic pathways of progesterone signaling (Blackmore et al., 1990). However, testosterone does seem to competitively inhibit progesterone binding to mPRγ and mPRα in mammalian cells (Thomas et al., 2007; Zhu et al., 2003; Zhu et al., 2003a) and our data suggests that mPRγ and mPRα are tolerant to substitutions at the 17 position of the pregnane ring where testosterone and progesterone differ. This raised the possibility that testosterone might function as an antagonist of the mPRs. FIG. 13B shows that testosterone had no agonist activity against either mPRγ or mPRα in concentrations up to 10 μM. However, when the response of mPRγ to progesterone was measured in the presence of 10 μM testosterone, the $EC_{50}$ of progesterone increased 10-fold (FIG. 8A, Table 4). Exposure of cells to 10 μM estradiol had no effect on the $EC_{50}$ of progesterone, indicating that this effect was specific for testosterone and not a non-specific effect of steroids on the assay system (FIG. 8A).

Figure 8B:
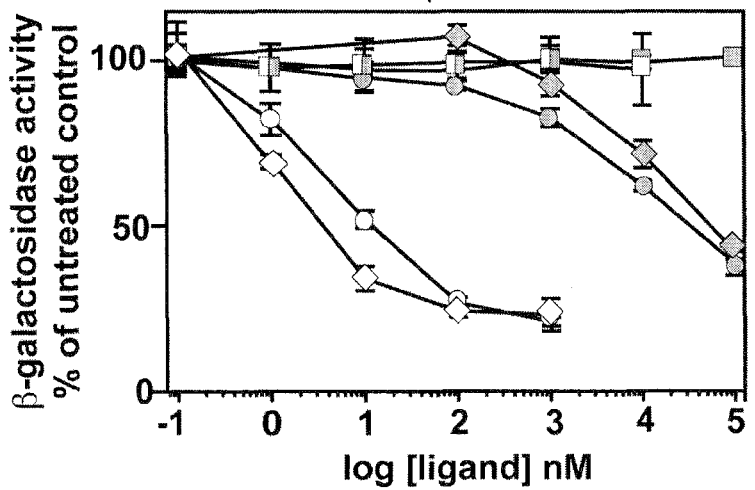
Figure 8C:
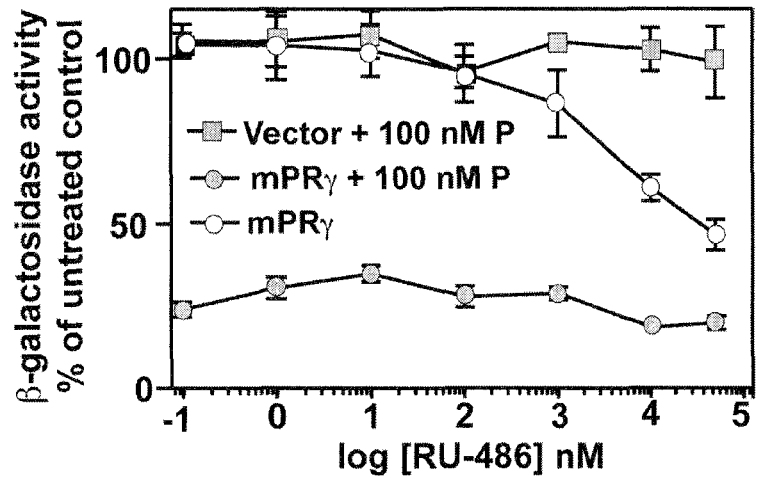

Mifepristone, also known as RU-486, is a clinically important antagonist of the nuclear progesterone receptor (Sarkar, 2002). We examined the ability of this synthetic steroid to antagonize mPRγ and mPRα. Surprisingly, RU-486 functioned as a weak agonist of both receptors with $EC_{50}$ values in the low μM range (FIG. 8B, Table 4). RU-486 had no effect on yeast carrying empty expression vector (FIG. 8B). We also demonstrated that RU-486 functions as a weak antagonist of mPRγ at lower concentrations. FIG. 8C shows that RU-486 weakly antagonizes mPRγ in the presence of 100 nM progesterone and that this effect disappears at higher concentrations of RU-486. Furthermore, exposure of cells to 100 nM RU-486 causes a 15-fold increase in the $EC_{50}$ of progesterone for the activation of mPRγ (FIG. 8A, Table 4).

Sequence Analysis of the mPR Family

The human genome contains 11 genes encoding proteins in the PAQR family (Tang et al., 2005), all of which are highly conserved in the vertebrate lineage. PAQR5, PAQR7 and PAQR8 encode the putative membrane progesterone receptors and their gene products have been named mPRγ, mPRα and mPRβ, respectively. FIG. 9A is a bootstrapped phylogenetic tree showing the relatedness of the mPRs to other receptors in the PAQR family including the human adiponectin receptors and the yeast osmotin receptor homologues, Izh1p, Izh2p and Izh3p. We included sequences from a variety of species to demonstrate conservation throughout the vertebrate lineage. This tree clearly demonstrates that the PAQR family can be grouped into three distinct clades. Human PAQR10 and PAQR11 belong to a highly divergent clade of PAQRs that contains bacterial proteins been previously characterized as hemolysins (Baida et al., 1996). We designated this clade as Class III and used it as an outgroup to root the tree. A second clade includes human PAQR1, PAQR2, PAQR3 and PAQR4 as well as the yeast PAQR homologues. We designated this clade as Class I. Homologs of PAQR1, PAQRQ2 and PAQR3 can be found in fungi. A homolog of PAQR4 can be found in *Nematostella vectensis*, but not *Trichoplax adhaerens*, suggesting that this gene may have originated in eumetazoans. The three mPRs belong to a third clade designated as Class II. This tree indicates that Class II receptors can be subdivided into 2 subgroups—one that contains mPRγ and one that contains mPRα and mPRβ. In addition to mPRγ, the human genome encodes 2 additional PAQRs (PAQR6 and PAQR9) that belong to the mPRγ subgroup. We could not identify a PAQR6 homologue in chicken or an mPRα homologue in frog. The absence of such sequences in the databases may be due to gaps in *G. gallus*, *X. tropicalis* or *X. laevis* genomes, however, we could find neither supporting cDNAs nor ESTs, suggesting that these genes may have been lost in these species. The PAQR9 gene in the *G. gallus* genome is interrupted by an unsequenced gap. While the genomes of higher vertebrates contain only one copy of each of the mPRs, teleost fish genomes (herein represented by zebrafish) encode three distinct mPRγ isoforms, two of which are 100% identical and found in tandem on chromosome 7. The zebrafish genome also encodes multiple paralogs of mPRα, AdipoR1, PAQR4 and PAQR10. The multiple PAQR paralogs in zebrafish fish are consistent with the genome duplication event that is believed to have led to the evolution of teleost fish (Hurley et al., 2005).

The mPRs have been proposed to be a novel class of GPCR. FIG. 9B shows another bootstrapped phylogenetic tree that contains the human and yeast PAQRs as well as several proteins belonging to the GPCR (Surratt et al., 2005) and alkaline ceramidase (Mao et al., 2003) protein families. The tree is rooted with the GPCRs as an outgroup. The PAQRs, GPCRs and alkaline ceramidases are alike in that all three families have a core of seven transmembrane domains (TM). This tree demonstrates that the PAQR family is no more similar to GPCRs than they are to alkaline ceramidases, suggesting that any structural similarity between the PAQR and GPCR families is superficial. It should be noted, however, that the GPCR family is highly divergent and that there are no amino acid motifs that unify the entire family (Surratt et al., 2005). Thus, it is still possible that the PAQRs represent a unique class of highly divergent GPCR.

Figure 10:
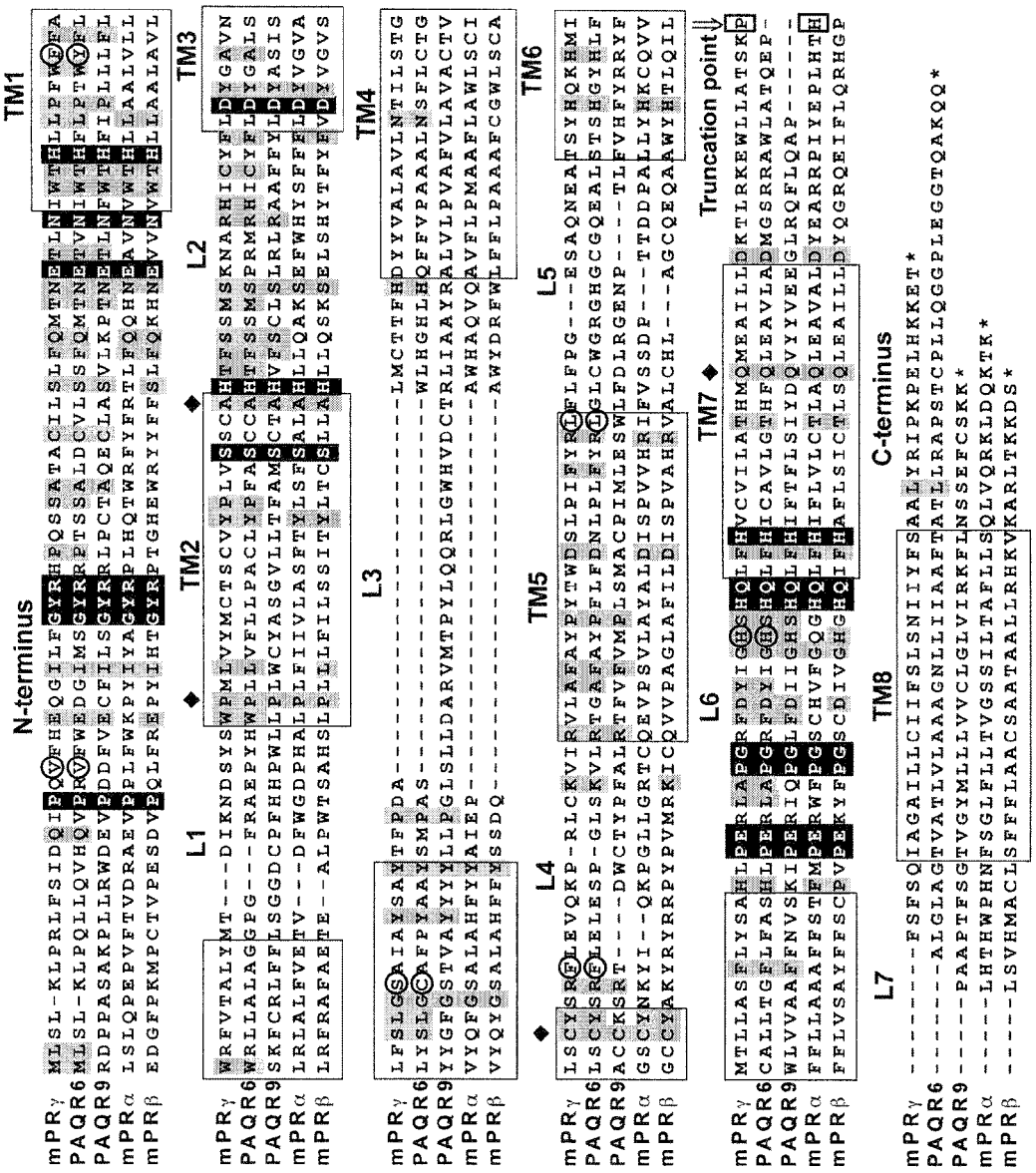
FIG. 10: Multiple sequence alignment of human Class II PAQRs. This alignment was originally performed using ClustalX but was modified manually afterwards. TM and loop regions (L) are numbered. Predicted TMs are also boxed. Black shading shows amino acids that are highly, but not universally, conserved in the entire PAQR family. Grey shading indicates amino acids that are conserved in all vertebrate members of the mPRγ/PAQR6 clade, although only human sequences are shown. Circled amino acids indicate the positions of intron/exon boundaries in the pre-mRNA. Arrow indicates the location of truncations in the mPRγ and mPRα proteins discussed in FIG. 7.

FIG. 10 shows a multiple sequence alignment of the five human Class II PAQRs. The entire PAQR family is unified by the presence of seven predicted TMs and three conserved regions (see alignment in Lyons et al., 2004). First, there is a conserved motif that precedes TM1. This motif has the consensus $Px_nGYRx_nEx_2Nx_3H$, although this motif is truncated to $Ex_{2-3}Nx_3H$ in Class III PAQRs. A second motif spans the end of TM2 and the beginning of TM3 and has the consensus sequence $Sx_3Hx_nD$. A third motif spans the loop preceding TM7 and has the motif $PEx_3PGx_nHQx_2H$, although this is also truncated to $Hx_3H$ in Class III proteins. The seven TM core and these three short motifs are all that unify the entire PAQR family. Class II PAQR receptors are unique in that they contain an eighth predicted hydrophobic motif that is C-terminal to the conserved PAQR core (see FIG. 12 for hydropathy plots).

Figures 11A, 11B, 11C, 11D, 11E:
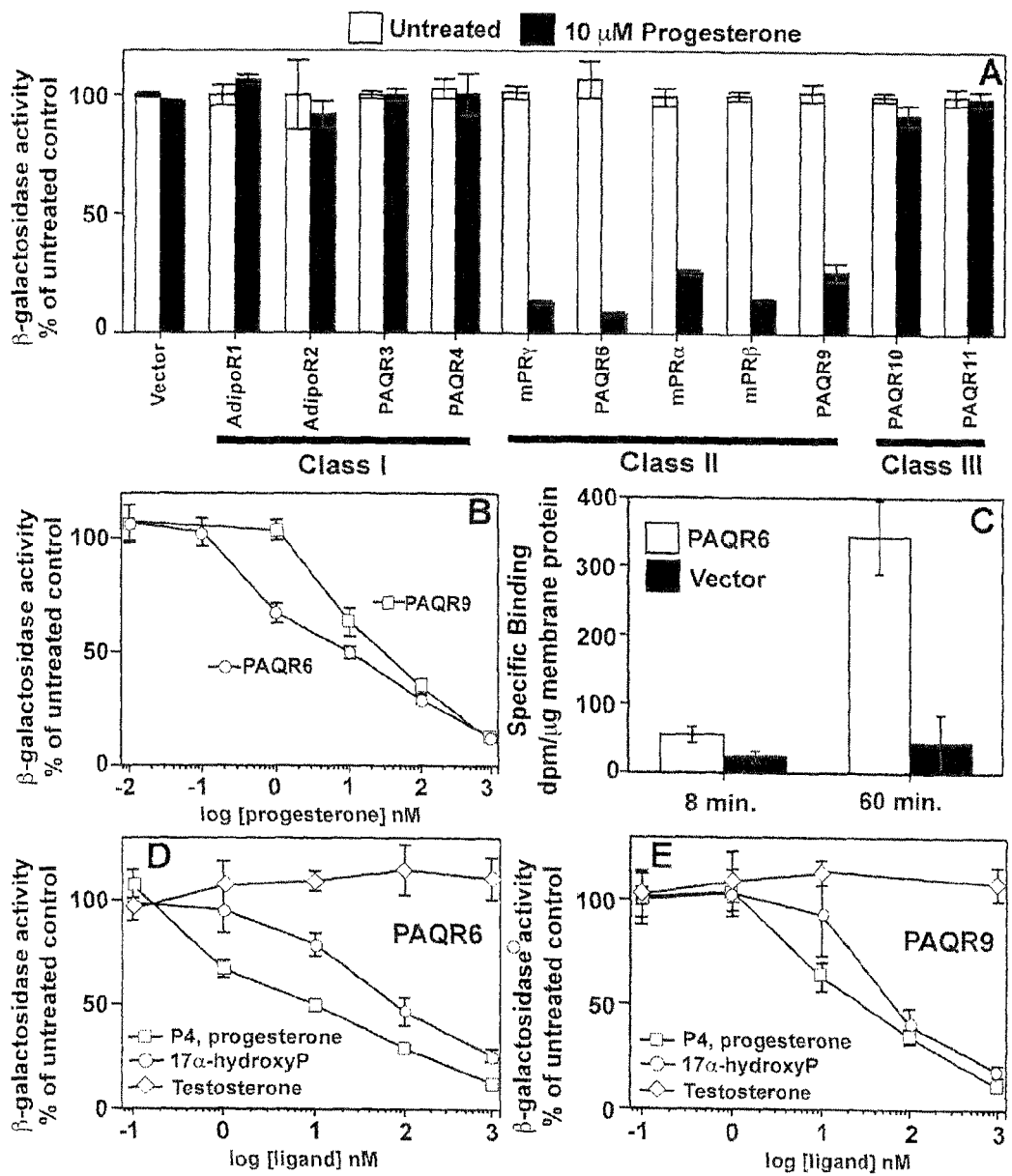
FIGS. 11A-11E: Identification of additional membrane progesterone receptors. In all panels except (FIG. 11C) cells were grown in medium containing 0.05% galactose/1.05% raffinose and FET3 activity is measured using the FET3-lacZ construct as a reporter. All PAQRs are cloned into the pYES260 vector except AdipoR2, which is cloned into pGREG536 (FIG. 11A). Response FET3 in cells expressing all 11 human PAQR proteins to 10 μM progesterone (FIG. 11B). Response of FET3 to various steroids in wild type cells expressing either PAQR6 (white symbols, FIG. 11D) or PAQR9 (grey symbols, FIG. 11E).

Effect of Progesterone on Class II Receptors mPRγ is more similar to PAQR6 and PAQR9 than it is to mPRα and mPRβ. Since mPRγ, mPRα and mPRβ all function as progesterone receptors, it is likely that PAQR6 and PAQR9 do as well. To test this, we cloned all 11 human PAQRs into GAL1-driven yeast expression vectors to determine if they could repress FET3 in response to progesterone treatment. (We have evidence for expression of all human PAQRs except PAQR10, data not shown). FIG. 11A shows that 10 μM progesterone was an effective agonist of all five Class II PAQRs, but was ineffective against receptors in Classes I and III. The dose response of PAQR6 and PAQR9 to progesterone reveals $EC_{50}$ values of 2.6 and 13.8 nM, respectively (FIG. 11B, Table 3). FIG. 11B shows that, like mPRγ and mPRα, PAQR6 and PAQR9 can be activated by 17α-hydroxyprogesterone, but not testosterone.

Structural Analysis of Class II PAQRs

Figure 12A:
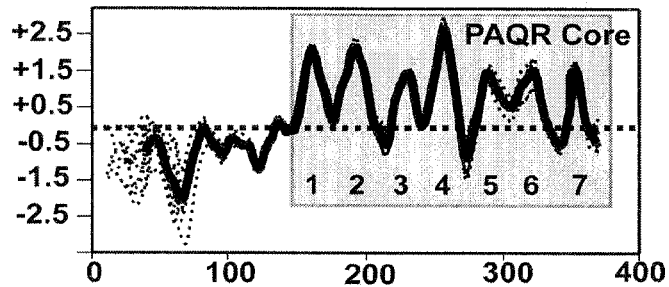
FIGS. 12A-12I: Topological analysis of Class I and Class II PAQRs.
Figure 12B:
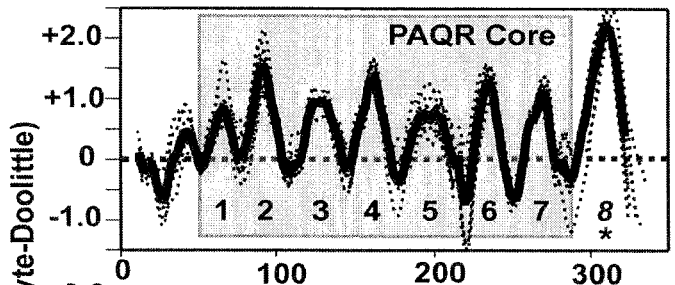
Figure 12C:
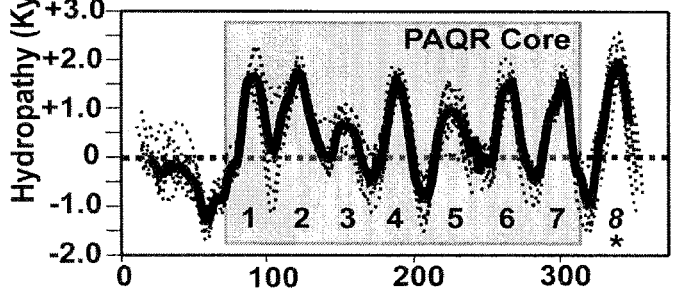
Figure 12D:
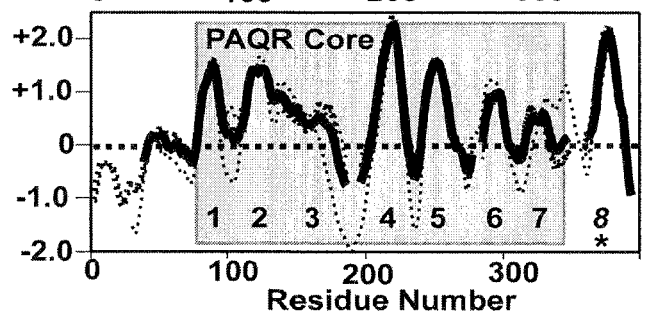
Figure 12E:
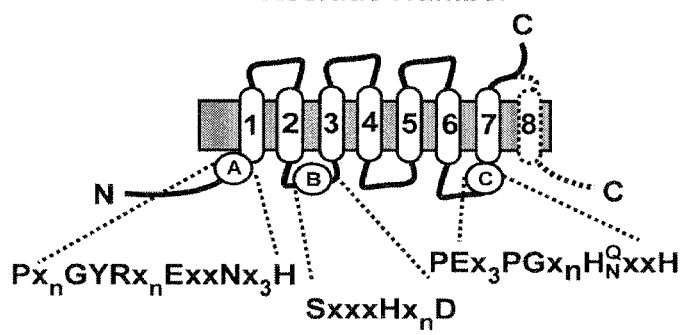

In FIG. 12A overlaid hydropathy plots of various vertebrate homologs of the human adiponectin receptors demonstrate the seven predicted TMs of the conserved PAQR core. The same work up for vertebrate proteins in the mPRα/β clade (FIG. 12B) and the mPRγ clade (FIGS. 12C and 12D) clearly shows that the seven hydrophobic domains of the PAQR core are conserved with varying degrees of hydrophobicity. Topological studies of the yeast and human Class I receptors as well as bacterial Class III receptors indicated that the C-terminus of these receptors is extracellular (Daley et al., 2005; Deckert et al., 2006; Kim et al., 2003a). This led to the topological model shown in FIG. 12E showing the conserved PAQR core and the location of the three highly conserved motifs shown in FIG. 10. If the additional hydrophobic domain at the C-termini of the Class II receptors is, indeed, a TM, then the C-termini of receptors in this class should be intracellular.

Figure 12F:
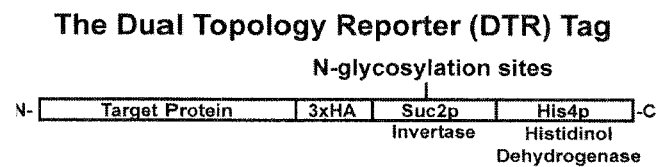

To test this, we used the dual topology reporter method to probe the topology of mPRα and PAQR6 in yeast. This is the same method that was previously used to determine the topology of the yeast Izh2p receptor (Kim et al., 2003a). In this method, an HA-Suc2p-His4p tag is placed at the C-terminus of a protein of interest (FIG. 12F). The HA (hemagglutinin) part of the tag allows for detection of the chimera by Western blot. The His4p part of the tag encodes a functional histidinol dehydrogenase that is required for histidine biosynthesis. This enzyme requires cytosolic NADH as a cofactor and will only rescue the histidine auxotrophy of a his4Δ mutant strain if the tag is cytosolic. In addition, if the C-terminus is extracellular, it must pass through the lumen of the Endoplasmic Reticulum. The Suc2p fragment of the tag contains multiple N-glycosylation sites, which will be glycosylated if it passes through the ER lumen. This modification can be detected by a shift in molecular weight in Western blots after treatment with an endoglycosidase.

Figure 12G:
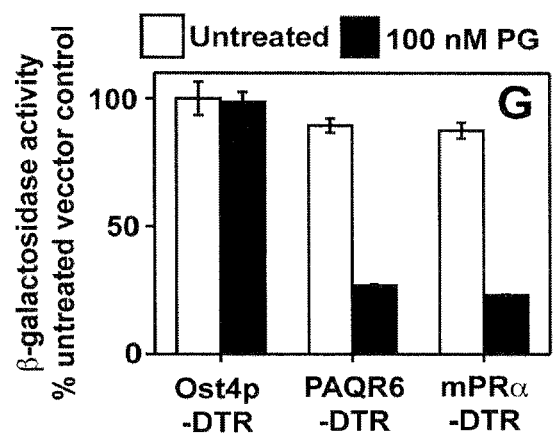
Figure 12H:
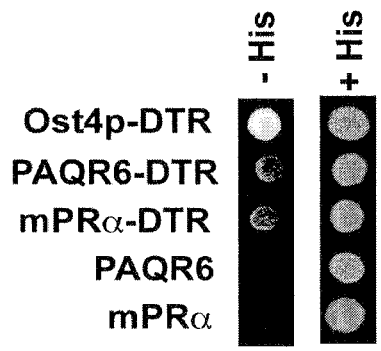
Figure 12I:
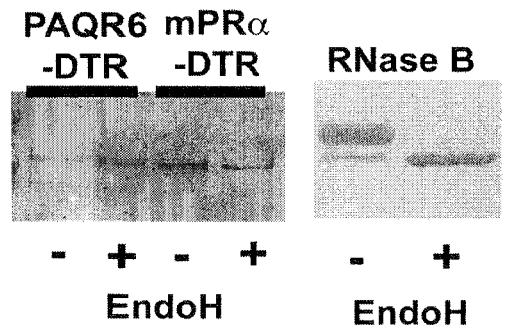

Consistent with the model shown in FIG. 12E, C-terminally tagged Izh2p was previously shown to be unable to confer histidine prototrophy indicating that its C-terminus was extracellular (see Kim et al., 2003a). When this tag was placed at the C-terminus of PAQR6 and mPRα, the resulting chimeras could still respond to progesterone demonstrating that the tag did not affect functionality (FIG. 12G). Moreover, both chimeras could weakly rescue the histidine auxotrophy of a his4Δ strain, indicating that their C-termini are intracellular (FIG. 12H). Treatment of membrane extracts from cells expressing PAQR6 and mPRα with the endoglycosidase, EndoH, does not alter the mobility of either PAQR6 or mPRα in Western blots (FIG. 12I). A change in mobility for RNase B, a protein that is known to be N-glycosylated, is shown as a positive control. These findings indicate that the C-terminus of PAQR6 and mPRα does not pass through the ER lumen and that the C-terminus of Class II PAQRs does, indeed, contain an additional TM.

Thus, human Class II receptors are unified by the presence of an additional TM that is C-terminal to the conserved PAQR core and by the fact that all five respond to progesterone when expressed in yeast. This led us to postulate that this additional hydrophobic domain is responsible for progesterone sensing. Unfortunately, there are no amino acids in this TM that are conserved in all five receptors, (see FIG. 10) hence, we did not undertake site directed mutagenesis to determine if any particular amino acid is involved in sensing. Instead we truncated the entire TM for mPRγ and mPRα. Western blots show that these truncation mutants are stably expressed in yeast (FIG. 13A). Unexpectedly, these truncations had no effect on the ability of these receptors to sense and respond to progesterone (FIG. 13B).

Lack of Involvement of $G_a$-Proteins in mPR-Dependent Signaling

It has been proposed that mPRα, mPRβ and mPRγ function as a novel class of GPCR (Thomas et al., 2006; Thomas et al., 2007; Zhu et al., 2003; Zhu et al., 2003a). If this were true, then heterotrimeric G-proteins would be required as intracellular second messengers downstream of the mPRs. Yeast possess only two heterotrimeric $G_{abg}$-protein complexes. The first includes Gpa1p (α), Ste4p (β) and Ste18p (γ) and is coupled to the Ste2p and mating pheromone-sensing GPCR (Wu et al., 2004). The second is less well characterized and contains Gpa2p (α) and a non-canonical b-subunit, Acs1p. To date, no g-subunit has been identified for Gpa2p. Gpa2p is coupled to the Gpr1p glucose-sensing GPCR (Zeller et al., 2007). Both mPRγ and mPRα were capable of sensing and responding to progesterone in strains lacking either Gpa1p or Gpa2p (FIG. 13C). In addition, we demonstrated that neither overexpression of the Ste2p GPCR from the GAL1 promoter nor its concomitant activation with a-factor pheromone could recapitulate the effect of the PAQRs on the FET3 gene (FIG. 13D). Moreover, expression of constitutively active alleles of Gpa1p (Gpa1p$^{Q323L}$) and Gpa2p (Gpa2p$^{Q300L}$) were incapable of causing repression of FET3 (FIG. 13E).

Our data clearly demonstrates that mPRα, mPRβ and mPRγ, when heterologously expressed in yeast, mediate progesterone-dependent repression of the FET3 gene. Control experiments showed that progesterone did not affect FET3 in yeast carrying empty expression vector or the human adiponectin receptors, indicating that this effect was not (a) mediated by an endogenous yeast protein, (b) a non-specific effect of progesterone, (c) the result of expressing a foreign membrane protein or (d) a general effect mediated by PAQR receptors. These results unambiguously demonstrate that mPRα, mPRβ and mPRγ are capable of sensing and responding to progesterone. Moreover, the $EC_{50}$ for progesterone activation of mPRα, mPRβ and mPRγ in yeast is between 1-3 nM, values that are consistent with the $K_d$'s for progesterone binding to mPRs (~5 nM) determined by Thomas et al. (2008). These $EC_{50}$ values are also close to the physiological concentration of progesterone in human serum, which has been estimated to be between 1-10 nM in men and non-pregnant women in the follicular phase of the menstrual cycle (Nadjafi et al., 2003; Tang et al., 2007). Thus, our data suggests that human mPRα, mPRβ and mPRγ are most responsive to progesterone at physiologically relevant hormone concentrations and would likely function as legitimate progesterone receptors.

Analysis of the steroid specificity of mPRα and mPRγ activation indicates that they have distinct agonist profiles from nuclear progesterone receptor and provides evidence that their profiles are similar to those of the receptors that mediate non-genomic responses of progesterone (Blackmore et al., 1990; Blackmore et al., 1996; Verikouki et al., 2008). To begin with, our data indicate that the steroid activation profile of the mPRs correlates well with a study that showed 17α-hydroxyprogesterone (17α-HP), 21-hydroxyprogesterone (21-HP) and 17α,21-dihydroxyprogesterone (17α,21-DHP) were effective agonists of the non-genomic progesterone signaling pathway but 11β,17α,21-trihydroxyprogesterone (cortisol) and testosterone were not (Blackmore et al., 1990; Blackmore et al., 1996). Another distinction between the mPRs and nPR is the fact that mifepristone (RU-486), a potent nPR antagonist, functions as a weak agonist for both mPRγ and mPRα at high concentrations RU-486 ($EC_{50}$>5 μM) and, enigmatically, as only a very weak antagonist of mPRγ at lower concentrations (100 nM), shifting the $EC_{50}$ for progesterone from ~1 nM to ~15 nM.

The ability of 17α-HP and mifepristone to activate mPRs is particularly intriguing because the former steroid has very low agonist activity towards nPR (Blackmore et al., 1990) and the latter is actually an antagonist of nPR (Sarkar et al., 2002). Both, however, seem to be able to activate non-genomic signaling (Blackmore et al., 1996; Verikouki et al., 2008). In fact, the differential reactivity of these steroids towards the genomic and non-genomic pathways has been used as evidence for the existence of distinct membrane progesterone receptors (Blackmore et al., 1996). Hence, the specificity profiles of the mPRs in yeast indicate that these receptors closely resemble the hypothetical non-genomic progesterone receptors.

The unique agonist profiles for the mPRs are also intriguing from a physiological standpoint. While the physiological levels of 17α-HP, 21-HP and 17α,21-DHP are low in human serum (~1 nM) they can be as high as 10-20 nM in pregnant women (Sippell et al., 1981). Considering that the $EC_{50}$ values for the activation of mPRα by 17α-HP, 21-HP and 17α,21-DHP are similar (~10 nM), it is possible that these steroids may indeed be physiologically relevant ligands for this receptor. On the other hand, while testosterone seems to function as an antagonist of mPRγ, the levels of testosterone required for this effect (10 μM) seem to be far too high to be physiologically important (Kaufman et al., 2005). The pharmacokinetics of RU-486 (Sarkar et al., 2002) indicate that low doses of RU-486 result in sustained circulating levels in the 100 nM range where it antagonizes mPRγ, while high doses result in sustained levels in the 5 μM range, where it agonizes mPRγ. Thus, RU-486 may have opposing effects on the mPRs depending on the dose given.

The second contentious issue that we attempted to address is the nature of the second messenger produced by the mPRs. When first discovered, structural analysis suggested that the mPRs had seven TMs (Zhu et al., 2003; Zhu et al., 2003a). This naturally led people to postulate that the mPRs were similar to GPCRs despite the fact that the mPRs bear no more similarity to GPCRs than they do to other groups of heptahelical integral membrane proteins (See FIG. 9B). Nevertheless, some preliminary evidence supports this conclusion (Thomas et al., 2006; Thomas et al., 2007; Zhu et al., 2003; Zhu et al., 2003a) and now this model seems to be either universally accepted or at least not seriously questioned. A major problem with the GPCR hypothesis is that there is no evidence for the involvement of G-proteins in signaling by any other class of PAQR receptor, suggesting that either there are significant differences between PAQR classes or the GPCR model needs revision.

The phylogenetic analysis in FIG. 9A suggests that the mPRs are distinct from other PAQR receptors and form a group of PAQRs that we have called Class II. The human genome encodes two other Class II PAQR proteins called PAQR6 and PAQR9. FIG. 10 shows that proteins in this class of PAQRs are unified by the presence of an eighth TM. We hypothesized that the presence of this eighth TM at the C-terminus of a PAQR is a feature of progesterone receptors, even though this additional TM does not seem to be required for progesterone sensing. Not surprisingly, both PAQR6 and PAQR9 sense and respond to progesterone in yeast and have similar steroid specificities to mPRα, mPRβ and mPRγ. PAQR9 is unique in that the $EC_{50}$ for progesterone activation of this receptor is approximately 10-fold higher than the other four Class II receptors. Because of their ability to sense and respond to progesterone, we propose the renaming of these receptors to mPRδ (PAQR6) and mPRε (PAQR9).

The fact that all five Class II human PAQRs function as progesterone receptors is intriguing from an evolutionary perspective. mPRγ belongs to a different subgroup of Class II receptors than mPRα and mPRβ, yet all three proteins are progesterone receptors. This suggests that either their functions have converged during evolution or that their last common ancestor was also a progesterone receptor. The phylogenetic tree in FIG. 9A includes a variety of proteins with the diagnostic eighth TM necessary for their inclusion in Class II. Intriguingly, the mPRγ clade of PAQRs, which includes mPRδ and mPRε, actually includes proteins found in tunicates, lancelets, echinoderms, molluscs, annelids, flatworms, cnidarians and even *Trichoplax adhaerens*, an organism at the very base of the metazoan lineage. On the other hand, the mPRα/β clade includes proteins from tunicates, lancelets, echinoderms, molluscs and annelids. It also should be noted that Class II proteins seemed to have been lost in ecdysozoans (nematodes, arthropods). This phylogenetic analysis suggests that mPRγ-like proteins evolved before mPRα/mPRβ-like proteins and that both families predate the evolution of vertebrates. In fact, the presence of mPRγ-like proteins in placozoans indicates that this subgroup of mPRs originated early in the evolution animals. In contrast, the nuclear progesterone receptor seems to have evolved in vertebrates (Thornton et al., 2001). Thus, the mPRs may represent the original progesterone receptors. Future experiments to test this hypothesis will involve cloning pre-vertebrate Class II PAQRs and testing their ability to respond to progesterone using our assay system.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

TABLE 1

| Strain | Genotype | Source |
|---|---|---|
| MCY5326 wild type | MATa his3Δ leu2Δ ura3Δ | Vyas et al. (2005) |
| MCY5338 (msn2Δmsn4Δ) | MATa his3Δ leu2Δ ura3Δ msn2Δ::kanMX6 msn4Δ::natMX4 | Vyas et al. (2005) |
| MCY5378 (nrg1Δnrg2Δ) | MATa his3Δ leu2Δ ura3Δ nrg1Δ::hphMX4 nrg2Δ::his3MX6 | Vyas et al. (2005) |
| MCY5385 (msn2Δmsn4Δnrg1Δnrg2Δ) | MATa his3Δ leu2Δ ura3Δ msn2Δ::kanMX6 msn4Δ::natMX4 nrg1Δ::hphMX4 nrg2Δ::his3MX6 | Vyas et al. (2005) |
| Σ1278bflo11::lacZ | MATa ura3-52 trp1::hisG leu2::hisG his3::hisG flo11::lacZ-HIS3 | van Dyk et al., (2004) |
| BY4742 wild type | MATa his3 leu2 ura3 lys2 | Euroscarf |
| ras2Δ | MATa his3 leu2 ura3 lys2 ras2::kanMX4 | Euroscarf |
| tpk1Δ | MATa his3 leu2 ura3 lys2 tpk1::kanMX4 | Euroscarf |
| tpk2Δ | MATa his3 leu2 ura3 lys2 tpk2::kanMX4 | Euroscarf |
| tpk3Δ | MATa his3 leu2 ura3 lys2 tpk3::kanMX4 | Euroscarf |
| snf1Δ | MATa his3 leu2 ura3 lys2 snf1::kanMX4 | Euroscarf |
| snf4Δ | MATa his3 leu2 ura3 lys2 snf4::kanMX4 | Euroscarf |
| sip3Δ | MATa his3 leu2 ura3 lys2 sip3::kanMX4 | Euroscarf |
| sip1Δ | MATa his3 leu2 ura3 lys2 sip1::kanMX4 | Euroscarf |
| gal83Δ | MATa his3 leu2 ura3 lys2 gal83::kanMX4 | Euroscarf |
| sak1Δ | MATa his3 leu2 ura3 lys2 sak1::kanMX4 | Euroscarf |
| msn2Δ | MATa his3 leu2 ura3 lys2 msn2::kanMX4 | Euroscarf |
| msn4Δ | MATa his3 leu2 ura3 lys2 msn4::kanMX4 | Euroscarf |
| nrg1Δ | MATa his3 leu2 ura3 lys2 nrg1::kanMX4 | Euroscarf |
| nrg2Δ | MATa his3 leu2 ura3 lys2 nrg2::kanMX4 | Euroscarf |

TABLE 2

Primers for Cloning IZH2 into 3xHA expression vector

| Primer | Sequence |
|---|---|
| To replace ZRCI with IZH2 | |
| Forward Uppercase is complementary to the pFL38 vector Lowercase is complementary to the IZH2 promoter | 5'-TTT CCC AGT CAC GAC GTT GTA AAA CGA CGG CCA GTG AAT Tat tgc tat cag cga tac taa-3' (SEQ ID NO: 173) |
| Reverse Uppercase is complementary to the 3xHA epitope Lowercase is complementary to the IZH2 open reading frame | 5'-GTC ATA GGG ATA GCC CGC ATA GTC AGG AAC ATC GTA TGG GTa gga gac aat ccc gtt ctc-3' (SEQ ID NO: 174) |
| To replace IZH2 promoter with GAL1 | |
| Forward Uppercase is complementary to the pFL38 vector Lowercase is complementary to the GAL1 promoter | TTT CCC AGT CAC GAC GTT GTA AAA CGA CGG CCA GTG AAT Tga att cga cag gtt atc agc-3' (SEQ ID NO: 175) |
| Reverse Uppercase is complementary to the IZH2 open reading frame Lowercase is complementary to the GAL1 promoter | 5'-GCT CTT GCA CAC TCT TAG TCC TTT CTA ATA AAG TTG ACA Tgt cga cct cga gcg gga-3' (SEQ ID NO: 176) |
| To clone AdipoR1 into pYES260 | |
| Forward Uppercase is complementary to the pYES260 vector Lowercase is complementary to the AdipoR1 open reading frame | 5'-GGT GGT GGC GAC CAT CAC GAG AAT CTT TAT TTT CAG GGC GAC atg tct tcc cac aaa gga tc-3' (SEQ ID NO: 177) |
| Reverse Uppercase is complementary to the pYES260 vector Lowercase is complementary to the AdipoR1 open reading frame | 5'-ATA TCT GCA GAA TTC CAG CAC ACT GGC GGC CGT TAC TAG TGG ATC Ctc aga gaa ggg tgt cat cag tac-3' (SEQ ID NO: 178) |

TABLE 2-continued

Primers for Cloning IZH2 into 3xHA expression vector

| Primer | Sequence |
|---|---|
| *To clone AdipoR1 into pYES260* | |
| Forward<br>Uppercase is complementary to the pYES260 vector<br>Lowercase is complementary to the AdipoR1 open reading frame | 5'-GGT GGT GGC GAC CAT CAC GAG AAT CTT TAT TTT CAG GGC GCC atg ggc atg tcc cct ctc tt-3'<br>(SEQ ID NO: 179) |
| Reverse<br>Uppercase is complementary to the pYES260 vector<br>Lowercase is complementary to the AdipoR1 open reading frame | 5'-ATA TCT GCA GAA TTC CAG CAC ACT GGC GGC CGT TAC TAG TGG ATC Ttc aca gtg cat cct ctt cac tgc-3'<br>(SEQ ID NO: 180) |

TABLE 3

$EC_{50}$ values for various PAQR ligands.
log $EC_{50}$ pM ($EC_{50}$)

| | Adiponectin | Progesterone |
|---|---|---|
| AdipoR1 | −0.13 ± 0.08<br>(0.7 pM) | N.D. |
| AdipoR2 | 0.38 ± 0.17<br>(2.4 pM) | N.D. |
| mPRγ | N.D. | 3.11 ± 0.44<br>(1.3 nM) |
| PAQR6 | N.D. | 3.42 ± 0.88<br>(2.6 nM) |
| mPRα | N.D. | 3.36 ± 0.08<br>(2.3 nM) |
| mPRβ | N.D. | 3.21 ± 0.61<br>(1.6 nM) |
| PAQR9 | N.D. | 4.14 ± 0.86<br>(13.8 nM) |

N.D. Not determined

TABLE 4

$EC_{50}$ values for various PAQR ligands.
log $EC_{50}$ nM ($EC_{50}$)

| | mPRγ | mPRα |
|---|---|---|
| Progesterone | 0.04 ± 0.25<br>(1.1 nM) | 0.34 ± 0.08<br>(2.2 nM) |
| 17α-hydroxyprogesterone | 0.97 ± 0.63<br>(9.3 nM) | 1.01 ± 0.44<br>(10.2 nM) |
| RU-486 | 3.83 ± 0.23<br>(6.8 μM) | 4.04 ± 0.26<br>(11.0 μM) |
| Progesterone + 10 μM Testosterone | 1.03 ± 0.53<br>(10.7 nM) | N.D. |
| Progesterone + 100 nM RU-486 | 1.19 ± 0.12<br>(15.5 nM) | N.D. |

N.D. Not determined

REFERENCES

Baida, G. E. and Kuzmin, N. P. "Mechanism of action of hemolysin III from *Bacillus cereus*" *Biochim Biophys Acta;* 1996; 1284(2):122-4.

Banerjee, D., Pillai, B., Karnani, N., Mukhopadhyay, G. and Prasad, R. "Genome-wide expression profile of steroid response in *Saccharomyces cerevisiae.*" *Biochem Biophys Res Commun;* 2004; 317(2):406-13.

Berkey, C. D., V. K. Vyas and M. Carlson, Nrg1 and nrg2 transcriptional repressors are differently regulated in response to carbon source, Eukaryot. Cell 3 (2004) 311-7.

Blackmore, P. F., Beebe, S. J., Danforth, D. R. and Alexander, N. "Progesterone and 17 alpha-hydroxyprogesterone" Novel stimulators of calcium influx in human sperm" *J Biol Chem;* 1990; 265(3):1376-80.

Blackmore, P. F., Fisher, J. F., Spilman, C. H. and Bleasdale, J. E. "Unusual steroid specificity of the cell surface progesterone receptor on human sperm" *Mol Pharmacol;* 1996; 49(4):727-39.

Cameroni, E., N. Hulo, J. Roosen, J. Winderickx and C. De Virgilio, The novel yeast PAS kinase Rim 15 orchestrates G0-associated antioxidant defense mechanisms, Cell Cycle 3 (2004) 462-8.

Cho, R. J., M. J. Campbell, E. A. Winzeler, L. Steinmetz, A. Conway, L. Wodicka, T. G. Wolfsberg, A. E. Gabrielian, D. Landsman, D. J. Lockhart and R. W. Davis, A genome-wide transcriptional analysis of the mitotic cell cycle, Mol. Cell 2 (1998) 65-73.

Claros, M. G. and von Heijne, G. "TopPred II: an improved software for membrane protein structure predictions" *Comput Appl Biosci;* 1994; 10(6):685-6.

Corton, J. M., J. G. Gillespie, S. A. Hawley and D. G. Hardie, 5-aminoimidazole-4-carboxamide ribonucleoside. A specific method for activating AMP-activated protein kinase in intact cells? Eur. J. Biochem. 229 (1995) 558-65.

Courel, M., S. Lallet, J. M. Camadro and P. L. Blaiseau, Direct activation of genes involved in intracellular iron use by the yeast iron-responsive transcription factor Aft2 without its paralog Aft1, Mol. Cell. Biol. 25 (2005) 6760-71.

Daley, D. O., Rapp, M., Granseth, E., Melen, K., Drew, D. and von Heijne, G. "Global topology analysis of the *Escherichia coli* inner membrane proteome" *Science;* 2005; 308 (5726):1321-3.

De Silva, D. M., C. C. Askwith, D. Eide and J. Kaplan, The FET3 gene product required for high affinity iron transport in yeast is a cell surface ferroxidase, J. Biol. Chem. 270 (1995) 1098-101.

Deckert, C. M., Heiker, J. T. and Beck-Sickinger, A. G. "Localization of novel adiponectin receptor constructs" *J Recept Signal Transduct Res;* 2006; 26(5-6):647-57.

Eck, R., S. Hundt, A. Hartl, E. Roemer and W. Kunkel, A multicopper oxidase gene from *Candida albicans*: cloning, characterization and disruption, Microbiology 145 (Pt 9) (1999) 2415-22.

Eide, D. and L. Guarente, Increased dosage of a transcriptional activator gene enhances iron-limited growth of *Saccharomyces cerevisiae*, J. Gen. Microbiol. 138 (1992) 347-54.

Feng, Y. and Davis, N. G. "Feedback phosphorylation of the yeast a-factor receptor requires activation of the downstream signaling pathway from G protein through mitogen-activated protein kinase" *Mol Cell Biol;* 2000; 20(2):563-74.

Harashima, T. and Heitman, J. "The Galpha protein Gpa2 controls yeast differentiation by interacting with kelch repeat proteins that mimic Gbeta subunits" *Mol Cell;* 2002; 10(1):163-73.

Haurie, V., H. Boucherie and F. Sagliocco, The Snf1 protein kinase controls the induction of genes of the iron uptake pathway at the diauxic shift in *Saccharomyces cerevisiae*, J. Biol. Chem. 278 (2003) 45391-6.

Hedbacker, K., S. P. Hong and M. Carlson, Pak1 protein kinase regulates activation and nuclear localization of Snf1-Gal83 protein kinase, Mol. Cell. Biol. 24 (2004) 8255-63.

Hurley, I., Hale, M. E. and Prince, V. E. "Duplication events and the evolution of segmental identity" *Evol Dev;* 2005; 7(6):556-67.

Jansen, G., Wu, C., Schade, B., Thomas, D. Y. and Whiteway, M. "Drag&Drop cloning in yeast" *Gene;* 2005; 344(43-51).

Jiang, Y., C. Davis and J. R. Broach, Efficient transition to growth on fermentable carbon sources in *Saccharomyces cerevisiae* requires signaling through the Ras pathway, EMBO J. 17 (1998) 6942-51.

Kadowaki, T., T. Yamauchi, N. Kubota, K. Hara, K. Ueki and K. Tobe, Adiponectin and adiponectin receptors in insulin resistance, diabetes, and the metabolic syndrome, J. Clin. Invest. 116 (2006) 1784-92.

Kaufman, J. M. and Vermeulen, A. "The decline of androgen levels in elderly men and its clinical and therapeutic implications" *Endocr Rev;* 2005; 26(6):833-76.

Kim, H., Yan, Q., Von Heijne, G., Caputo, G. A. and Lennarz, W. J. "Determination of the membrane topology of Ost4p and its subunit interactions in the oligosaccharyltransferase complex in *Saccharomyces cerevisiae*" *Proc Natl Acad Sci USA;* 2003; 100(13):7460-4.

Kim, H., Melen, K. and von Heijne, G. "Topology models for 37 *Saccharomyces cerevisiae* membrane proteins based on C-terminal reporter fusions and predictions." *J Biol Chem;* 2003a; 278(12):10208-13.

Kuchin, S., V. K. Vyas and M. Carlson, Snf1 protein kinase and the repressors Nrg1 and Nrg2 regulate FLO11, haploid invasive growth, and diploid pseudohyphal differentiation, Mol. Cell Biol 22 (2002) 3994-4000.

Kupchak, B. R., Garitaonandia, I., Villa, N. Y., Mullen, M. B., Weaver, M. G., Regalia, L. M. et al. "Probing the mechanism of FET3 repression by Izh2p overexpression." *Biochim Biophys Acta Mol Cell Res;* 2007; 1773(7):1124-32.

Lesage, P., X. Yang and M. Carlson, Analysis of the SIP3 protein identified in a two-hybrid screen for interaction with the SNF1 protein kinase, Nucleic Acids Res. 22 (1994) 597-603.

Linthorst, J. J. M., Pathogenesis-related proteins of plants, Crit. Rev. Plant Sci. 10 (1993) 123-150.

Liu, H., Krizek, J. and Bretscher, A. "Construction of a GAL1-regulated yeast cDNA expression library and its application to the identification of genes whose overexpression causes lethality in yeast." *Genetics;* 1992; 132(3): 665-73.

Lyons, T. J., A. P. Gasch, L. A. Gaither, D. Botstein, P. O. Brown and D. J. Eide, Genome-wide characterization of the Zap1p zinc-responsive regulon in yeast, Proc. Natl. Acad. Sci. U.S.A 97 (2000) 7957-62.

Lyons, T. J., N. Y. Villa, L. M. Regalia, B. R. Kupchak, A. Vagstad and D. J. Eide, Metalloregulation of yeast membrane steroid receptor homologs, Proc. Natl. Acad. Sci. U.S.A. 101 (2004) 5506-11.

MacDiarmid, C. W., M. A. Milanick and D. J. Eide, Biochemical properties of vacuolar zinc transport systems of *Saccharomyces cerevisiae*, J. Biol. Chem. 277 (2002) 39187-94.

Mao, C., Xu, R., Szulc, Z. M., Bielawski, J., Becker, K. P., Bielawska, A. et al. "Cloning and characterization of a mouse endoplasmic reticulum alkaline ceramidase: an enzyme that preferentially regulates metabolism of very long chain ceramides" *J Biol Chem;* 2003; 278(33):31184-91.

Mao, X., C. K. Kikani, R. A. Riojas, P. Langlais, L. Wang, F. J. Ramos, Q. Fang, C. Y. Christ-Roberts, J. Y. Hong, R. Y. Kim, F. Liu and L. Q. Dong, APPL1 binds to adiponectin receptors and mediates adiponectin signaling and function, Nat. Cell Biol. 8 (2006) 516-23.

McEwan, I. J. "Bakers yeast rises to the challenge: reconstitution of mammalian steroid receptor signaling in *S. cerevisiae.*" *Trends Genet;* 2001; 17(5):239-43.

Melcher, K., A modular set of prokaryotic and eukaryotic expression vectors, Anal. Biochem. 277 (2000) 109-20.

Murad, A. M., C. d'Enfert, C. Gaillardin, H. Tournu, F. Tekaia, D. Talibi, D. Marechal, V. Marchais, J. Cottin and A. J. Brown, Transcript profiling in *Candida albicans* reveals new cellular functions for the transcriptional repressors CaTup1, CaMig1 and CaNrg1, Mol. Microbiol. 42 (2001) 981-93.

Nadjafi-Triebsch, C., Huell, M., Burki, D. and Rohr, U. D. "Progesterone increase under DHEA-substitution in males" *Maturitas;* 2003; 45(3):231-5.

Narasimhan, M. L., B. Damsz, M. A. Coca, J. I. Ibeas, D. J. Yun, J. M. Pardo, P. M. Hasegawa and R. A. Bressan, A plant defense response effector induces microbial apoptosis, Mol. Cell 8 (2001) 921-30.

Narasimhan, M. L., M. A. Coca, J. Jin, T. Yamauchi, Y. Ito, T. Kadowaki, K. K. Kim, J. M. Pardo, B. Damsz, P. M. Hasegawa, D. J. Yun and R. A. Bressan, Osmotin is a homolog of mammalian adiponectin and controls apoptosis in yeast through a homolog of mammalian adiponectin receptor, Mol. Cell 17 (2005) 171-80.

Page, R. D. "TreeView: an application to display phylogenetic trees on personal computers" *Comput Appl Biosci;* 1996; 12(4):357-8.

Park, S. H., S. S. Koh, J. H. Chun, H. J. Hwang and H. S. Kang, Nrg1 is a transcriptional repressor for glucose repression of STA1 gene expression in *Saccharomyces cerevisiae*, Mol. Cell. Biol. 19 (1999) 2044-50.

Ramanan, N. and Y. Wang, A high-affinity iron permease essential for *Candida albicans* virulence, Science 288 (2000) 1062-4.

Robertson, L. S., H. C. Causton, R. A. Young and G. R. Fink, The yeast A kinases differentially regulate iron uptake and respiratory function, Proc. Natl. Acad. Sci. U.S.A 97 (2000) 5984-8.

Rutherford, J. C., L. Ojeda, J. Balk, U. Muhlenhoff, R. Lill and D. R. Winge, Activation of the iron regulon by the yeast Aft1/Aft2 transcription factors depends on mitochondrial but not cytosolic iron-sulfur protein biogenesis, J. Biol. Chem. 280 (2005) 10135-40.

Rutherford, J. C. and A. J. Bird, Metal-responsive transcription factors that regulate iron, zinc, and copper homeostasis in eukaryotic cells, Eukaryot. Cell 3 (2004) 1-13.

Santos, R., A. Dancis, D. Eide, J. M. Camadro and E. Lesuisse, Zinc suppresses the iron-accumulation phenotype of *Saccharomyces cerevisiae* lacking the yeast frataxin homologue (Yfh1), Biochem. J. 375 (2003) 247-54.

Sarkar, N. N. "The potential of mifepristone (RU486) as a female contraceptive drug" *Int J Clin Pract;* 2002; 56(2): 140-4.

Sengstag, C. "Using SUC2-HIS4C reporter domain to study topology of membrane proteins in *Saccharomyces cerevisiae.*" *Methods Enzymol;* 2000; 327(175-90).

Singh, A., S. Severance, N. Kaur, W. Wiltsie and D. J. Kosman, Assembly, activation, and trafficking of the Fet3p.Ftr1p high affinity iron permease complex in *Saccharomyces cerevisiae*, J. Biol. Chem. 281 (2006) 13355-64.

Sippell, W. G., Muller-Holve, W., Don, H. G., Bidlingmaier, F. and Knorr, D. "Concentrations of aldosterone, corticosterone, 11-deoxycorticosterone, progesterone, 17-hydroxyprogesterone, 11-deoxycortisol, cortisol, and cortisone determined simultaneously in human amniotic fluid throughout gestation" *J Clin Endocrinol Metab;* 1981; 52(3):385-92.

Slessareva, J. E., Routt, S. M., Temple, B., Bankaitis, V. A. and Dohlman, H. G. "Activation of the phosphatidylinositol 3-kinase Vps34 by a G protein alpha subunit at the endosome" *Cell;* 2006; 126(1):191-203.

Smith, A., M. P. Ward and S. Garrett, Yeast PKA represses Msn2p/Msn4p-dependent gene expression to regulate growth, stress response and glycogen accumulation, EMBO J. 17 (1998) 3556-64.

Surratt, C. K. and Adams, W. R. "G protein-coupled receptor structural motifs: relevance to the opioid receptors" *Curr Top Med Chem;* 2005; 5(3):315-24.

Tang, Y. T., T. Hu, M. Arterburn, B. Boyle, J. M. Bright, P. C. Emtage and W. D. Funk, PAQR proteins: a novel membrane receptor family defined by an ancient 7-transmembrane pass motif, J. Mol. Evol. 61 (2005) 372-80.

Tang, Y., Gong, F., Lin, G. and Lu, G. "Early follicular progesterone concentrations and in vitro fertilization pregnancy outcomes" *Fertil Steril;* 2007; 87(4):991-4.

Tatusova, T. A. and Madden, T. L. "BLAST 2 Sequences, a new tool for comparing protein and nucleotide sequences" *FEMS Microbiol Lett;* 1999; 174(2):247-50.

Thomas, P., G. Dressing, Y. Pang, H. Berg, C. Tubbs, A. Benninghoff and K. Doughty, Progestin, estrogen and androgen G-protein coupled receptors in fish gonads, Steroids 71 (2006) 310-6.

Thomas, P., Y. Pang, J. Dong, P. Groenen, J. Kelder, J. de Vlieg, Y. Zhu and C. Tubbs, Steroid and G protein binding characteristics of the seatrout and human progestin membrane receptor alpha subtypes and their evolutionary origins, Endocrinology 148 (2007) 705-18.

Thomas, P. "Characteristics of membrane progestin receptor alpha (mPRalpha) and progesterone membrane receptor component 1 (PGMRC1) and their roles in mediating rapid progestin actions" *Front Neuroendocrinol;* 2008.

Thompson, J. D., Gibson, T. J., Plewniak, F., Jeanmougin, F. and Higgins, D. G. "The CLUSTAL_X windows interface: flexible strategies for multiple sequence alignment aided by quality analysis tools." *Nucleic Acids Res;* 1997; 25(24):4876-82.

Thornton, J. W. "Evolution of vertebrate steroid receptors from an ancestral estrogen receptor by ligand exploitation and serial genome expansions" *Proc Natl Acad Sci USA;* 2001; 98(10):5671-6.

Treger, J. M., T. R. Magee and K. McEntee, Functional analysis of the stress response element and its role in the multistress response of *Saccharomyces cerevisiae*, Biochem. Biophys. Res. Commun. 243 (1998) 13-9.

van Dyk, D., I. S. Pretorius and F. F. Bauer, Mss11p is a central element of the regulatory network that controls FLO11 expression and invasive growth in *Saccharomyces cerevisiae*, Genetics 169 (2005) 91-106.

Verikouki, C. H., Hatzoglou, C. H., Gourgoulianis, K. I., Molyvdas, P. A., Kallitsaris, A. and Messinis, I. E. "Rapid effect of progesterone on transepithelial resistance of human fetal membranes: evidence for non-genomic action" *Clin Exp Pharmacol Physiol;* 2008; 35(2):174-9.

Vincent, O., R. Townley, S. Kuchin and M. Carlson, Subcellular localization of the Snf1 kinase is regulated by specific beta subunits and a novel glucose signaling mechanism, Genes Dev. 15 (2001) 1104-14.

Vyas, V. K., S. Kuchin and M. Carlson, Interaction of the repressors Nrg1 and Nrg2 with the Snf1 protein kinase in *Saccharomyces cerevisiae*, Genetics 158 (2001) 563-72.

Vyas, V. K., C. D. Berkey, T. Miyao and M. Carlson, Repressors Nrg1 and Nrg2 regulate a set of stress-responsive genes in *Saccharomyces cerevisiae*, Eukaryot. Cell 4 (2005) 1882-91.

Waters, B. M. and D. J. Eide, Combinatorial control of yeast FET4 gene expression by iron, zinc, and oxygen, J. Biol. Chem. 277 (2002) 33749-57.

Wu, Y. L., Hooks, S. B., Harden, T. K. and Dohlman, H. G. "Dominant-negative inhibition of pheromone receptor signaling by a single point mutation in the G protein alpha subunit." *J Biol Chem;* 2004; 279(34):35287-97.

Yamaguchi-Iwai, Y., R. Stearman, A. Dancis and R. D. Klausner, Iron-regulated DNA binding by the AFT1 protein controls the iron regulon in yeast, EMBO J. 15 (1996) 3377-84.

Yamauchi, T., J. Kamon, Y. Ito, A. Tsuchida, T. Yokomizo, S. Kita, T. Sugiyama, M. Miyagishi, K. Hara, M. Tsunoda, K. Murakami, T. Ohteki, S. Uchida, S. Takekawa, H. Waki, N. H. Tsuno, Y. Shibata, Y. Terauchi, P. Froguel, K. Tobe, S. Koyasu, K. Taira, T. Kitamura, T. Shimizu, R. Nagai and T. Kadowaki, Cloning of adiponectin receptors that mediate antidiabetic metabolic effects, Nature 423 (2003) 762-9.

Zeller, C. E., Parnell, S. C. and Dohlman, H. G. "The RACK1 ortholog Asc1 functions as a G-protein beta subunit coupled to glucose responsiveness in yeast" *J Biol Chem;* 2007; 282(34):25168-76.

Zhu, Y., Bond, J. and Thomas, P. "Identification, classification, and partial characterization of genes in humans and other vertebrates homologous to a fish membrane progestin receptor." *Proc Natl Acad Sci USA;* 2003; 100(5):2237-42.

Zhu, Y., Rice, C. D., Pang, Y., Pace, M. and Thomas, P. "Cloning, expression, and characterization of a membrane progestin receptor and evidence it is an intermediary in meiotic maturation of fish oocytes" *Proc Natl Acad Sci USA;* 2003a; 100(5):2231-6.

We claim:

1. A method of identifying candidate ligands of "Progestin and AdipoQ Receptor" (PAQR) receptors, comprising:
   a) providing a yeast cell expressing one or more PAQR receptor and a reporter molecule, said reporter molecule driven by a promoter containing a CCCTC binding motif providing a signal in response to activation of said one or more PAQR receptor;
   b) contacting said yeast cell with a candidate ligand; and
   c) detecting the activation of said one or more PAQR receptor by the development of a signal within the cell or in medium in which the cell is cultured, the detection of a signal indicating the activation of said one or more PAQR receptor.

2. The method according to claim 1, wherein said one or more PAQR receptor is a human PAQR receptor selected from PAQR1, PAQR2, PAQR3, PAQR4, PAQR5, PAQR6, PAQR7, PAQR8, PAQR9, PAQR10 PAQR11 or various combinations thereof.

3. The method according to claim 2, wherein said one or more human PAQR receptor or said one or more PAQR receptor is overexpressed in said yeast cell.

4. The method according to claim 1, wherein said cell is cultured in medium that contains 5%, 4.5%, 4%, 3.5%, 3%, 2.5%, 2%, 1.5%, 1%, 0.5%, 0.25%, 0.10%, 0.05% or 0.025% galactose (w/v).

5. The method according to claim 4, wherein said cell is cultured in medium that contains galactose at a concentration less than or equal to 0.10% galactose (w/v).

6. The method according to claim 4, wherein said cell is cultured in medium that contains galactose at a concentration less than or equal to 0.05% galactose (w/v).

7. The method according to claim 1, wherein said promoter is a truncated FET3 promoter that comprises nucleotides 102 to 603 of SEQ ID NO: 181.

8. The method according to claim 1, wherein expression of said one or more PAQR receptor is driven by a galactose inducible promoter.

9. The method according to claim 8, wherein said galactose inducible promoter is GAL1.

10. The method according to claim 1, wherein said yeast cell is permeabilized prior to detecting the activation of PAQR receptors and β-galactosidase activity is measured.

11. The method according to claim 1, wherein the activation of said PAQR receptor is detected by contacting intact yeast cells with a ferroxidase substrate and measuring ferroxidase activity.

12. The method according to claim 1, wherein said reporter molecule is:
   a) an enzyme;
   b) a fluorescent protein; or
   c) a protein providing antibiotic resistance.

13. The method according to claim 12, wherein said enzyme is an alpha-D-glucosidase, a beta-D-glucosidase, an esterase, a lipase, an acid or alkaline phosphatase, a beta-D-galactosidase, an alpha-L-arabinofuranosidase, a leucine aminopeptidase, a chymotrypsin, an alpha-D-galactosidase, a beta-D-glucuronidase, an aminopeptidase, or a phosphohydralase.

14. The method according to 1, wherein said promoter is FET3, ZRT1, OLE1, ZRC1 and ZPS1 or truncations thereof containing the CCCTC motif and capable of driving the expression of a gene operably linked thereto.

15. The method according to claim 1, wherein said candidate ligand is an agonist of said receptor.

16. The method according to claim 1, wherein the PAQR receptor is PAQR6 and/or PAQR9 and the candidate ligand is a progesterone receptor antagonist or agonist.

17. The method according to claim 2, wherein said one or more PAQR receptor is human PAQR1, human PAQR2 or a combination thereof.

18. The method according to claim 17, wherein said one or more PAQR receptor is human PAQR1.

19. The method according to claim 17, wherein said one or more PAQR receptor is human PAQR2.

20. The method according to claim 2, wherein said one or more PAQR receptor is a combination of human PAQR1 and human PAQR2.

* * * * *

UNITED STATES PATENT AND TRADEMARK OFFICE
CERTIFICATE OF CORRECTION

PATENT NO. : 8,809,001 B2  Page 1 of 1
APPLICATION NO. : 12/679753
DATED : August 19, 2014
INVENTOR(S) : Thomas John Lyons et al.

It is certified that error appears in the above-identified patent and that said Letters Patent is hereby corrected as shown below:

IN THE SPECIFICATION:

Column 11,
Line 48, "mstllertks vgelkkraag" should read --mstllertks vqelkkraag--.

Column 19,
Lines 2-3, "(MeEwan, 2001)" should read --(McEwan, 2001)--.

Column 31,
Line 33, "Regalia, L.M." should read --Regalla, L.M.--.
Line 51, "L.M. Regalia" should read --L.M. Regalla--.

Column 32,
Line 1, "signaling and" should read --signalling and--.
Line 64, "Don, H.G." should read --Dorr, H.G.--.

Signed and Sealed this
Third Day of February, 2015

Michelle K. Lee
*Deputy Director of the United States Patent and Trademark Office*

SEQUENCE LISTING

```
<160> NUMBER OF SEQ ID NOS: 181

<210> SEQ ID NO 1
<211> LENGTH: 1128
<212> TYPE: DNA
<213> ORGANISM: Homo sapiens
<220> FEATURE:
<221> NAME/KEY: misc_feature
<223> OTHER INFORMATION: adiponectin receptor 1
<220> FEATURE:
<221> NAME/KEY: CDS
<222> LOCATION: (1)..(1128)
```

```
<400> SEQUENCE: 1 atg tct tcc cac aaa gga tct gtg gtg gca cag ggg aat ggg gct cct       48
Met Ser Ser His Lys Gly Ser Val Val Ala Gln Gly Asn Gly Ala Pro
1               5                   10                  15 gcc agt aac agg gaa gct gac acg gtg gaa ctg gct gaa ctg gga ccc       96
Ala Ser Asn Arg Glu Ala Asp Thr Val Glu Leu Ala Glu Leu Gly Pro
            20                  25                  30 ctg cta gaa gag aag ggc aaa cgg gta atc gcc aac cca ccc aaa gct      144
Leu Leu Glu Glu Lys Gly Lys Arg Val Ile Ala Asn Pro Pro Lys Ala
        35                  40                  45 gaa gaa gag caa aca tgc cca gtg ccc cag gaa gaa gag gag gtg          192
Glu Glu Glu Gln Thr Cys Pro Val Pro Gln Glu Glu Glu Glu Val
50                  55                  60 cgg gta ctg aca ctt ccc ctg caa gcc cac cac gcc atg gag aag atg      240
Arg Val Leu Thr Leu Pro Leu Gln Ala His His Ala Met Glu Lys Met
65                  70                  75                  80 gaa gag ttt gtg tac aag gtc tgg gag gga cgt tgg agg gtc atc cca      288
Glu Glu Phe Val Tyr Lys Val Trp Glu Gly Arg Trp Arg Val Ile Pro
                85                  90                  95 tat gat gtg ctc cct gac tgg cta aag gac aac gac tat ctg cta cat      336
Tyr Asp Val Leu Pro Asp Trp Leu Lys Asp Asn Asp Tyr Leu Leu His
            100                 105                 110 ggt cat aga cct ccc atg ccc tcc ttt cgg gct tgc ttc aag agc atc      384
Gly His Arg Pro Pro Met Pro Ser Phe Arg Ala Cys Phe Lys Ser Ile
        115                 120                 125 ttc cgc att cat aca gaa act ggc aac atc tgg acc cat ctg ctt ggt      432
Phe Arg Ile His Thr Glu Thr Gly Asn Ile Trp Thr His Leu Leu Gly
130                 135                 140 ttc gtg ctg ttt ctc ttt ttg gga atc ttg acc atg ctc aga cca aat      480
Phe Val Leu Phe Leu Phe Leu Gly Ile Leu Thr Met Leu Arg Pro Asn
145                 150                 155                 160 atg tac ttc atg gcc cct cta cag gag aag gtg gtt ttt ggg atg ttc      528
Met Tyr Phe Met Ala Pro Leu Gln Glu Lys Val Val Phe Gly Met Phe
                165                 170                 175 ttt ttg ggt gca gtg ctc tgc ctc agc ttc tcc tgg ctc ttt cac acc      576
Phe Leu Gly Ala Val Leu Cys Leu Ser Phe Ser Trp Leu Phe His Thr
            180                 185                 190 gtc tat tgt cat tca gag aaa gtc tct cgg act ttt tcc aaa ctg gac      624
Val Tyr Cys His Ser Glu Lys Val Ser Arg Thr Phe Ser Lys Leu Asp
        195                 200                 205 tat tca ggg att gct ctt cta att atg ggg agc ttt gtc ccc tgg ctc      672
Tyr Ser Gly Ile Ala Leu Leu Ile Met Gly Ser Phe Val Pro Trp Leu
210                 215                 220 tat tat tcc ttc tac tgc tcc cca cag cca cgg ctc atc tac ctc tcc      720
Tyr Tyr Ser Phe Tyr Cys Ser Pro Gln Pro Arg Leu Ile Tyr Leu Ser
225                 230                 235                 240 atc gtc tgt gtc ctg ggc att tct gcc atc att gtg gcg cag tgg gac      768
Ile Val Cys Val Leu Gly Ile Ser Ala Ile Ile Val Ala Gln Trp Asp
                245                 250                 255 cgg ttt gcc act cct aag cac cgg cag aca aga gca ggc gtg ttc ctg      816
Arg Phe Ala Thr Pro Lys His Arg Gln Thr Arg Ala Gly Val Phe Leu
            260                 265                 270 gga ctt ggc ttg agt ggc gtc gtg ccc acc atg cac ttt act atc gct      864
Gly Leu Gly Leu Ser Gly Val Val Pro Thr Met His Phe Thr Ile Ala
        275                 280                 285 gag ggc ttt gtc aag gcc acc aca gtg ggc cag atg ggc tgg ttc ttc      912
Glu Gly Phe Val Lys Ala Thr Thr Val Gly Gln Met Gly Trp Phe Phe
290                 295                 300 ctc atg gct gtg atg tac atc act gga gct ggc ctt tat gct gct cga      960
Leu Met Ala Val Met Tyr Ile Thr Gly Ala Gly Leu Tyr Ala Ala Arg
```

```
Leu Met Ala Val Met Tyr Ile Thr Gly Ala Gly Leu Tyr Ala Ala Arg
305                 310                 315                 320 att cct gag cgc ttc ttt cct gga aaa ttt gac ata tgg ttc cag tct      1008
Ile Pro Glu Arg Phe Phe Pro Gly Lys Phe Asp Ile Trp Phe Gln Ser
            325                 330                 335 cat cag att ttc cat gtc ctg gtg gtg gca gca gcc ttt gtc cac ttc      1056
His Gln Ile Phe His Val Leu Val Val Ala Ala Ala Phe Val His Phe
        340                 345                 350 tat gga gtc tcc aac ctt cag gaa ttc cgt tac ggc cta gaa ggc ggc      1104
Tyr Gly Val Ser Asn Leu Gln Glu Phe Arg Tyr Gly Leu Glu Gly Gly
                355                 360                 365 tgt act gat gac acc ctt ctc tga                                      1128
Cys Thr Asp Asp Thr Leu Leu
370                 375

<210> SEQ ID NO 2
<211> LENGTH: 375
<212> TYPE: PRT
<213> ORGANISM: Homo sapiens

<400> SEQUENCE: 2

Met Ser Ser His Lys Gly Ser Val Val Ala Gln Gly Asn Gly Ala Pro
1               5                   10                  15

Ala Ser Asn Arg Glu Ala Asp Thr Val Glu Leu Ala Glu Leu Gly Pro
                20                  25                  30

Leu Leu Glu Glu Lys Gly Lys Arg Val Ile Ala Asn Pro Pro Lys Ala
            35                  40                  45

Glu Glu Glu Gln Thr Cys Pro Val Pro Gln Glu Glu Glu Glu Glu Val
50                  55                  60

Arg Val Leu Thr Leu Pro Leu Gln Ala His His Ala Met Glu Lys Met
65                  70                  75                  80

Glu Glu Phe Val Tyr Lys Val Trp Glu Gly Arg Trp Arg Val Ile Pro
                85                  90                  95

Tyr Asp Val Leu Pro Asp Trp Leu Lys Asp Asn Asp Tyr Leu Leu His
            100                 105                 110

Gly His Arg Pro Pro Met Pro Ser Phe Arg Ala Cys Phe Lys Ser Ile
        115                 120                 125

Phe Arg Ile His Thr Glu Thr Gly Asn Ile Trp Thr His Leu Leu Gly
130                 135                 140

Phe Val Leu Phe Leu Phe Leu Gly Ile Leu Thr Met Leu Arg Pro Asn
145                 150                 155                 160

Met Tyr Phe Met Ala Pro Leu Gln Glu Lys Val Val Phe Gly Met Phe
                165                 170                 175

Phe Leu Gly Ala Val Leu Cys Leu Ser Phe Ser Trp Leu Phe His Thr
            180                 185                 190

Val Tyr Cys His Ser Glu Lys Val Ser Arg Thr Phe Ser Lys Leu Asp
        195                 200                 205

Tyr Ser Gly Ile Ala Leu Leu Ile Met Gly Ser Phe Val Pro Trp Leu
210                 215                 220

Tyr Tyr Ser Phe Tyr Cys Ser Pro Gln Pro Arg Leu Ile Tyr Leu Ser
225                 230                 235                 240

Ile Val Cys Val Leu Gly Ile Ser Ala Ile Val Ala Gln Trp Asp
                245                 250                 255

Arg Phe Ala Thr Pro Lys His Arg Gln Thr Arg Ala Gly Val Phe Leu
            260                 265                 270

Gly Leu Gly Leu Ser Gly Val Val Pro Thr Met His Phe Thr Ile Ala
```

-continued

```
                    275                 280                 285
Glu Gly Phe Val Lys Ala Thr Thr Val Gly Gln Met Gly Trp Phe Phe
            290                 295                 300
Leu Met Ala Val Met Tyr Ile Thr Gly Ala Gly Leu Tyr Ala Ala Arg
305                 310                 315                 320
Ile Pro Glu Arg Phe Phe Pro Gly Lys Phe Asp Ile Trp Phe Gln Ser
                325                 330                 335
His Gln Ile Phe His Val Leu Val Ala Ala Ala Phe Val His Phe
            340                 345                 350
Tyr Gly Val Ser Asn Leu Gln Glu Phe Arg Tyr Gly Leu Glu Gly Gly
                355                 360                 365
Cys Thr Asp Asp Thr Leu Leu
            370                 375

<210> SEQ ID NO 3
<211> LENGTH: 1161
<212> TYPE: DNA
<213> ORGANISM: Homo sapiens
<220> FEATURE:
<221> NAME/KEY: misc_feature
<223> OTHER INFORMATION: adiponectin receptor 2 (ADIPOR2), mRNA
<220> FEATURE:
<221> NAME/KEY: CDS
<222> LOCATION: (1)..(1161)

<400> SEQUENCE: 3 atg aac gag cca aca gaa aac cga ttg ggg tgc agc agg act cca gag      48
Met Asn Glu Pro Thr Glu Asn Arg Leu Gly Cys Ser Arg Thr Pro Glu
1               5                   10                  15 cca gat ata agg ctc aga aaa ggg cac caa ctg gat ggt aca cga aga      96
Pro Asp Ile Arg Leu Arg Lys Gly His Gln Leu Asp Gly Thr Arg Arg
                20                  25                  30 ggt gat aat gac agc cac caa gga gat ttg gag ccc att tta gag gca     144
Gly Asp Asn Asp Ser His Gln Gly Asp Leu Glu Pro Ile Leu Glu Ala
            35                  40                  45 tct gtt cta tct tcc cat cat aaa aaa agc tct gag gaa cat gaa tac     192
Ser Val Leu Ser Ser His His Lys Lys Ser Ser Glu Glu His Glu Tyr
        50                  55                  60 agt gat gaa gct cct cag gaa gat gag ggc ttt atg ggc atg tcc cct     240
Ser Asp Glu Ala Pro Gln Glu Asp Glu Gly Phe Met Gly Met Ser Pro
65                  70                  75                  80 ctc tta caa gcc cat cat gct atg gaa aaa atg gaa gaa ttt gtt tgt     288
Leu Leu Gln Ala His His Ala Met Glu Lys Met Glu Glu Phe Val Cys
                85                  90                  95 aag gta tgg gaa ggt cgg tgg cga gtg atc cct cat gat gta cta cca     336
Lys Val Trp Glu Gly Arg Trp Arg Val Ile Pro His Asp Val Leu Pro
                100                 105                 110 gac tgg ctc aag gat aat gac ttc ctc ttg cat gga cac cgg cct cct     384
Asp Trp Leu Lys Asp Asn Asp Phe Leu Leu His Gly His Arg Pro Pro
            115                 120                 125 atg cct tct ttc cgg gcc tgt ttt aag agc att ttc aga ata cac aca     432
Met Pro Ser Phe Arg Ala Cys Phe Lys Ser Ile Phe Arg Ile His Thr
        130                 135                 140 gaa aca ggc aac att tgg aca cat ctc tta ggt tgt gta ttc ttc ctg     480
Glu Thr Gly Asn Ile Trp Thr His Leu Leu Gly Cys Val Phe Phe Leu
145                 150                 155                 160 tgc ctg ggg atc ttt tat atg ttt cgc cca aat atc tcc ttt gtg gcc     528
Cys Leu Gly Ile Phe Tyr Met Phe Arg Pro Asn Ile Ser Phe Val Ala
                165                 170                 175 cct ctg caa gag aag gtg gtc ttt gga tta ttt ttc tta gga gcc att     576
```

```
Pro Leu Gln Glu Lys Val Val Phe Gly Leu Phe Phe Leu Gly Ala Ile
            180                 185                 190 ctc tgc ctt tct ttt tca tgg ctc ttc cac aca gtc tac tgc cac tca        624
Leu Cys Leu Ser Phe Ser Trp Leu Phe His Thr Val Tyr Cys His Ser
            195                 200                 205 gag ggg gtc tct cgg ctc ttc tct aaa ctg gat tac tct ggt att gct        672
Glu Gly Val Ser Arg Leu Phe Ser Lys Leu Asp Tyr Ser Gly Ile Ala
    210                 215                 220 ctt ctg att atg gga agt ttt gtt cct tgg ctt tat tat tct ttc tac        720
Leu Leu Ile Met Gly Ser Phe Val Pro Trp Leu Tyr Tyr Ser Phe Tyr
225                 230                 235                 240 tgt aat cca caa cct tgc ttc atc tac ttg att gtc atc tgt gtg ctg        768
Cys Asn Pro Gln Pro Cys Phe Ile Tyr Leu Ile Val Ile Cys Val Leu
                245                 250                 255 ggc att gca gcc att ata gtc tcc cag tgg gac atg ttt gcc acc cct        816
Gly Ile Ala Ala Ile Ile Val Ser Gln Trp Asp Met Phe Ala Thr Pro
            260                 265                 270 cag tat cgg gga gta aga gca gga gtg ttt ttg ggc cta ggc ctg agt        864
Gln Tyr Arg Gly Val Arg Ala Gly Val Phe Leu Gly Leu Gly Leu Ser
            275                 280                 285 gga atc att cct acc ttg cac tat gtc atc tcg gag ggg ttc ctt aag        912
Gly Ile Ile Pro Thr Leu His Tyr Val Ile Ser Glu Gly Phe Leu Lys
    290                 295                 300 gcc gcc acc ata ggg cag ata ggc tgg ttg atg ctg atg gcc agc ctc        960
Ala Ala Thr Ile Gly Gln Ile Gly Trp Leu Met Leu Met Ala Ser Leu
305                 310                 315                 320 tac atc aca gga gct gcc ctg tat gct gcc cgg atc ccc gaa cgc ttt       1008
Tyr Ile Thr Gly Ala Ala Leu Tyr Ala Ala Arg Ile Pro Glu Arg Phe
                325                 330                 335 ttc cct ggc aaa tgt gac atc tgg ttt cac tct cat cag ctg ttt cat       1056
Phe Pro Gly Lys Cys Asp Ile Trp Phe His Ser His Gln Leu Phe His
            340                 345                 350 atc ttt gtg gtt gct gga gct ttt gtt cac ttc cat ggt gtc tca aac       1104
Ile Phe Val Val Ala Gly Ala Phe Val His Phe His Gly Val Ser Asn
            355                 360                 365 ctc cag gag ttt cgt ttc atg atc ggc ggg ggc tgc agt gaa gag gat       1152
Leu Gln Glu Phe Arg Phe Met Ile Gly Gly Gly Cys Ser Glu Glu Asp
    370                 375                 380 gca ctg tga                                                            1161
Ala Leu
385

<210> SEQ ID NO 4
<211> LENGTH: 386
<212> TYPE: PRT
<213> ORGANISM: Homo sapiens

<400> SEQUENCE: 4

Met Asn Glu Pro Thr Glu Asn Arg Leu Gly Cys Ser Arg Thr Pro Glu
1               5                   10                  15

Pro Asp Ile Arg Leu Arg Lys Gly His Gln Leu Asp Gly Thr Arg Arg
            20                  25                  30

Gly Asp Asn Asp Ser His Gln Gly Asp Leu Glu Pro Ile Leu Glu Ala
        35                  40                  45

Ser Val Leu Ser Ser His Lys Lys Ser Ser Glu Glu His Glu Tyr
    50                  55                  60

Ser Asp Glu Ala Pro Gln Glu Asp Glu Gly Phe Met Gly Met Ser Pro
65                  70                  75                  80

Leu Leu Gln Ala His His Ala Met Glu Lys Met Glu Glu Phe Val Cys
```

```
                    85                  90                  95
Lys Val Trp Glu Gly Arg Trp Arg Val Ile Pro His Asp Val Leu Pro
                100                 105                 110

Asp Trp Leu Lys Asp Asn Asp Phe Leu Leu His Gly His Arg Pro Pro
            115                 120                 125

Met Pro Ser Phe Arg Ala Cys Phe Lys Ser Ile Phe Arg Ile His Thr
    130                 135                 140

Glu Thr Gly Asn Ile Trp Thr His Leu Leu Gly Cys Val Phe Leu
145                 150                 155                 160

Cys Leu Gly Ile Phe Tyr Met Phe Arg Pro Asn Ile Ser Phe Val Ala
                165                 170                 175

Pro Leu Gln Glu Lys Val Val Phe Gly Leu Phe Phe Leu Gly Ala Ile
            180                 185                 190

Leu Cys Leu Ser Phe Ser Trp Leu Phe His Thr Val Tyr Cys His Ser
    195                 200                 205

Glu Gly Val Ser Arg Leu Phe Ser Lys Leu Asp Tyr Ser Gly Ile Ala
    210                 215                 220

Leu Leu Ile Met Gly Ser Phe Val Pro Trp Leu Tyr Tyr Ser Phe Tyr
225                 230                 235                 240

Cys Asn Pro Gln Pro Cys Phe Ile Tyr Leu Ile Val Ile Cys Val Leu
                245                 250                 255

Gly Ile Ala Ala Ile Ile Val Ser Gln Trp Asp Met Phe Ala Thr Pro
            260                 265                 270

Gln Tyr Arg Gly Val Arg Ala Gly Val Phe Leu Gly Leu Gly Leu Ser
    275                 280                 285

Gly Ile Ile Pro Thr Leu His Tyr Val Ile Ser Glu Gly Phe Leu Lys
    290                 295                 300

Ala Ala Thr Ile Gly Gln Ile Gly Trp Leu Met Leu Met Ala Ser Leu
305                 310                 315                 320

Tyr Ile Thr Gly Ala Ala Leu Tyr Ala Ala Arg Ile Pro Glu Arg Phe
                325                 330                 335

Phe Pro Gly Lys Cys Asp Ile Trp Phe His Ser His Gln Leu Phe His
            340                 345                 350

Ile Phe Val Val Ala Gly Ala Phe Val His Phe His Gly Val Ser Asn
    355                 360                 365

Leu Gln Glu Phe Arg Phe Met Ile Gly Gly Cys Ser Glu Glu Asp
    370                 375                 380

Ala Leu
385

<210> SEQ ID NO 5
<211> LENGTH: 810
<212> TYPE: DNA
<213> ORGANISM: Homo sapiens
<220> FEATURE:
<221> NAME/KEY: misc_feature
<223> OTHER INFORMATION: progestin and adipoQ receptor family member
      III, mRNA (cDNA clone MGC:48508 IMAGE:5297045)
<220> FEATURE:
<221> NAME/KEY: CDS
<222> LOCATION: (1)..(810)

<400> SEQUENCE: 5 atg cat cag aag ctg ctg aag agc gcg cat tac atc gag ctg ggc agc      48
Met His Gln Lys Leu Leu Lys Ser Ala His Tyr Ile Glu Leu Gly Ser
1               5                   10                  15 tac cag tac tgg ccg gtc ctg gtg ccc cgt ggc atc cgc ctg tac acc      96
```

```
                Tyr Gln Tyr Trp Pro Val Leu Val Pro Arg Gly Ile Arg Leu Tyr Thr
                            20                  25                  30 tac gag cag atc ccc ggg tcc ctc aag gac aac ccg tac atc acc gac        144
Tyr Glu Gln Ile Pro Gly Ser Leu Lys Asp Asn Pro Tyr Ile Thr Asp
            35                  40                  45 ggc tac cgg gcc tac ctg ccg tcc agg ctg tgt atc aaa agt ttg ttt        192
Gly Tyr Arg Ala Tyr Leu Pro Ser Arg Leu Cys Ile Lys Ser Leu Phe
 50                  55                  60 att tta tct aat gag aca gta aac atc tgg agt cat ttg ctg ggt ttc        240
Ile Leu Ser Asn Glu Thr Val Asn Ile Trp Ser His Leu Leu Gly Phe
 65                  70                  75                  80 ttt ctc ttc ttc acc ctg gga ata tat gac atg aca tct gtg tta cct        288
Phe Leu Phe Phe Thr Leu Gly Ile Tyr Asp Met Thr Ser Val Leu Pro
                    85                  90                  95 tca gca agt gcg tcc aga gaa gat ttt gta att tgt tct att tgt ctt        336
Ser Ala Ser Ala Ser Arg Glu Asp Phe Val Ile Cys Ser Ile Cys Leu
                100                 105                 110 ttc tgc ttc cag gtc tgt atg ctt tgc tct gtg ggc tat cat ctt ttt        384
Phe Cys Phe Gln Val Cys Met Leu Cys Ser Val Gly Tyr His Leu Phe
            115                 120                 125 tcc tgc cat cgg tca gaa aaa aca tgt cga aga tgg atg gca tta gat        432
Ser Cys His Arg Ser Glu Lys Thr Cys Arg Arg Trp Met Ala Leu Asp
        130                 135                 140 tat gca gga att tct att gga ata ctg ggc tgc tat gtc tca gga gta        480
Tyr Ala Gly Ile Ser Ile Gly Ile Leu Gly Cys Tyr Val Ser Gly Val
145                 150                 155                 160 ttt tac gca ttt tat tgt aat aac tac tgg cgt cag gtg tac ttg atc        528
Phe Tyr Ala Phe Tyr Cys Asn Asn Tyr Trp Arg Gln Val Tyr Leu Ile
                    165                 170                 175 aca gtg ctt gct atg atc ctg gca gtg ttc ttt gcg cag att cat ccc        576
Thr Val Leu Ala Met Ile Leu Ala Val Phe Phe Ala Gln Ile His Pro
                180                 185                 190 aat tac ctc acg cag caa tgg caa agg ctc cgt tct atc atc ttt tgt        624
Asn Tyr Leu Thr Gln Gln Trp Gln Arg Leu Arg Ser Ile Ile Phe Cys
            195                 200                 205 tct gtt tcg gga tat gga gtg att cct act ctt cac tgg gtt tgg ctc        672
Ser Val Ser Gly Tyr Gly Val Ile Pro Thr Leu His Trp Val Trp Leu
        210                 215                 220 aat gga gga att ggt gct cct att gta cag gac ttt gca ccc cgt gta        720
Asn Gly Gly Ile Gly Ala Pro Ile Val Gln Asp Phe Ala Pro Arg Val
225                 230                 235                 240 att gtg atg tat atg att gct ctt ctt gct ttc cta ttc tac att tcc        768
Ile Val Met Tyr Met Ile Ala Leu Leu Ala Phe Leu Phe Tyr Ile Ser
                    245                 250                 255 aaa gtc cca gag cgg tac ttt cca gaa tca ctt cca cgg tga                810
Lys Val Pro Glu Arg Tyr Phe Pro Glu Ser Leu Pro Arg
                260                 265

<210> SEQ ID NO 6
<211> LENGTH: 269
<212> TYPE: PRT
<213> ORGANISM: Homo sapiens

<400> SEQUENCE: 6

Met His Gln Lys Leu Leu Lys Ser Ala His Tyr Ile Glu Leu Gly Ser
 1               5                  10                  15

Tyr Gln Tyr Trp Pro Val Leu Val Pro Arg Gly Ile Arg Leu Tyr Thr
            20                  25                  30

Tyr Glu Gln Ile Pro Gly Ser Leu Lys Asp Asn Pro Tyr Ile Thr Asp
        35                  40                  45
```

```
Gly Tyr Arg Ala Tyr Leu Pro Ser Arg Leu Cys Ile Lys Ser Leu Phe
        50                  55                  60

Ile Leu Ser Asn Glu Thr Val Asn Ile Trp Ser His Leu Leu Gly Phe
 65                  70                  75                  80

Phe Leu Phe Phe Thr Leu Gly Ile Tyr Asp Met Thr Ser Val Leu Pro
                85                  90                  95

Ser Ala Ser Ala Ser Arg Glu Asp Phe Val Ile Cys Ser Ile Cys Leu
               100                 105                 110

Phe Cys Phe Gln Val Cys Met Leu Cys Ser Val Gly Tyr His Leu Phe
               115                 120                 125

Ser Cys His Arg Ser Glu Lys Thr Cys Arg Arg Trp Met Ala Leu Asp
       130                 135                 140

Tyr Ala Gly Ile Ser Ile Gly Ile Leu Gly Cys Tyr Val Ser Gly Val
145                 150                 155                 160

Phe Tyr Ala Phe Tyr Cys Asn Asn Tyr Trp Arg Gln Val Tyr Leu Ile
               165                 170                 175

Thr Val Leu Ala Met Ile Leu Ala Val Phe Phe Ala Gln Ile His Pro
               180                 185                 190

Asn Tyr Leu Thr Gln Gln Trp Gln Arg Leu Arg Ser Ile Ile Phe Cys
       195                 200                 205

Ser Val Ser Gly Tyr Gly Val Ile Pro Thr Leu His Trp Val Trp Leu
210                 215                 220

Asn Gly Gly Ile Gly Ala Pro Ile Val Gln Asp Phe Ala Pro Arg Val
225                 230                 235                 240

Ile Val Met Tyr Met Ile Ala Leu Leu Ala Phe Leu Pro Tyr Ile Ser
               245                 250                 255

Lys Val Pro Glu Arg Tyr Phe Pro Glu Ser Leu Pro Arg
       260                 265

<210> SEQ ID NO 7
<211> LENGTH: 2459
<212> TYPE: DNA
<213> ORGANISM: Homo sapiens
<220> FEATURE:
<221> NAME/KEY: misc_feature
<223> OTHER INFORMATION: progestin and adipoQ receptor family member IV
<220> FEATURE:
<221> NAME/KEY: CDS
<222> LOCATION: (89)..(910)

<400> SEQUENCE: 7
ccacgcgtcc ggccttcccg cgctgcggcc ccactgagga ggaggctcgg ggacagcagg         60
agcacgggct gcccgcgcgg tgcggacc atg gcg ttc ctg gcc ggg ccg cgc          112
                                Met Ala Phe Leu Ala Gly Pro Arg
                                 1               5 ctg ctg gac tgg gcc agc tcg ccg ccg cac ctg cag ttc aat aag ttc         160
Leu Leu Asp Trp Ala Ser Ser Pro Pro His Leu Gln Phe Asn Lys Phe
 10                  15                  20 gtg ctg acc ggg tac cgg ccc gcc agc agc ggc tcg ggc tgc ctg cgc         208
Val Leu Thr Gly Tyr Arg Pro Ala Ser Ser Gly Ser Gly Cys Leu Arg
 25                  30                  35                  40 agc ctc ttc tac ctg cac aac gaa ctg ggc aac atc tac acg cac ggg         256
Ser Leu Phe Tyr Leu His Asn Glu Leu Gly Asn Ile Tyr Thr His Gly
                45                  50                  55 ctg gcc ctg ctg ggc ttc ctg gtg ctg gtg cca atg acc atg ccc tgg         304
Leu Ala Leu Leu Gly Phe Leu Val Leu Val Pro Met Thr Met Pro Trp
        60                  65                  70
```

```
                                                            -continued ggt cag ctg ggc aag gat ggc tgg ctg gga ggc aca cat tgc gtg gcc        352
Gly Gln Leu Gly Lys Asp Gly Trp Leu Gly Gly Thr His Cys Val Ala
            75                  80                  85 tgc ctt gca ccc cct gca ggc tcc gtg ctc tat cac ctc ttt atg tgc        400
Cys Leu Ala Pro Pro Ala Gly Ser Val Leu Tyr His Leu Phe Met Cys
    90                  95                 100 cac caa ggg ggc agc gct gtg tac gcc cgg ctc ctc gcc ctg gac atg        448
His Gln Gly Gly Ser Ala Val Tyr Ala Arg Leu Leu Ala Leu Asp Met
105                 110                 115                 120 tgt ggg gtc tgc ctt gtc aac acc ctt ggg gcc ctg ccc atc atc cac        496
Cys Gly Val Cys Leu Val Asn Thr Leu Gly Ala Leu Pro Ile Ile His
            125                 130                 135 tgc acc ctg gcc tgc agg ccc tgg ctg cgc ccg gct gcc ctg gtg ggc        544
Cys Thr Leu Ala Cys Arg Pro Trp Leu Arg Pro Ala Ala Leu Val Gly
    140                 145                 150 tac act gtg ttg tcg ggt gtg gcc ggc tgg cgt gct ctc acc gcc ccc        592
Tyr Thr Val Leu Ser Gly Val Ala Gly Trp Arg Ala Leu Thr Ala Pro
                155                 160                 165 tcc acc agt gct cgg ctc cgg gca ttt gga tgg cag gct gct gcc cgc        640
Ser Thr Ser Ala Arg Leu Arg Ala Phe Gly Trp Gln Ala Ala Ala Arg
170                 175                 180 cta ctg gta ttt ggg gcc cgg gga gtg ggt ctg ggt tca ggg gct cca        688
Leu Leu Val Phe Gly Ala Arg Gly Val Gly Leu Gly Ser Gly Ala Pro
185                 190                 195                 200 ggc tcc ctg ccc tgc tac ctg cgc atg gac gca ctg gcg ctg ctt ggg        736
Gly Ser Leu Pro Cys Tyr Leu Arg Met Asp Ala Leu Ala Leu Leu Gly
                205                 210                 215 gga ctg gta aat gta gcc cgt ctg ccc gag cgc tgg gga cct ggc cgc        784
Gly Leu Val Asn Val Ala Arg Leu Pro Glu Arg Trp Gly Pro Gly Arg
            220                 225                 230 ttt gac tac tgg ggc aac tcc cac cag atc atg cac ctg ctg agc gtg        832
Phe Asp Tyr Trp Gly Asn Ser His Gln Ile Met His Leu Leu Ser Val
                235                 240                 245 ggc tcc atc ctg cag ctg cac gcc ggc gtc gtg ccc gac ctg ctc tgg        880
Gly Ser Ile Leu Gln Leu His Ala Gly Val Val Pro Asp Leu Leu Trp
    250                 255                 260 gct gcc cac cac gcc tgt ccc cgg gac tga gctgccatgc agcctgccc           930
Ala Ala His His Ala Cys Pro Arg Asp
265                 270 acagcagcct cctagagtta gcaacaccag gtgttcctcc caactcgtct gcaagggct        990 ggctccttgg atgcttccag ctcatgagat gtctcagcag gagccctgtt cacccgttct       1050
tccctgtgga ctgacctctt ccacccacgc cgtggcgctc caacttcctt ccctgccttt       1110
tccctccaag ctcctatttt actgtgtcag ctggaaggaa acctttccct cttgggacct       1170 ctttacccte tgtgacctgt ggggttagac cagagaggga ctctgggggtc atgtcttgct      1230 ctgagagttc aagtcctgcc aggccgccag cccagagcct cctcacccta tcctgttcct       1290
cccaccaggc ctgtggccag tcttcctgat ctccatcttt ctgccctgca taccagccct       1350
cccagcagcc acaagcttgc ccgccctggc tccctctgcc cagagactat ggagtaaggc       1410
attcaggaca aaaggaccaa gggggcgtgg accgtcttg taccagctgg ccacaggcac        1470
aagggctgca gctgcttctt ccaggaaact gacacaggga gctcagcggc tcagatcct        1530 gggacccctg ggccgtgcct gccctccacc ttgagtgcca tactcccaac agctccaggt       1590
acccaccggg ggatgtgcct gctcaggaaa cctctttgct ccacacagca tggggcttca      1650
gctgctggcc caaggccagg agcgctgggt tctgcagcag gctcagcct cagggcgtt        1710 aagaccctgg atgacatcaa taagggaca ggaagggcca tgttgccaca tgagcaagct       1770
```

```
tgggtgctcc caaggttcaa atacttttta ttagacacgg ccaggcagag aagaccatgg    1830
gagttcccga ggggccccag ctttcaaggg cgacgggaga gacacaggat aaaaggttaa    1890
aagtgcagag gcagagtctg gggctcaggt tgggtctagg gtgtcctcaa acaggctgag    1950
gaggttccga ggctcaaagg aggggaagga gccccgagga ggctctgagt tgatgtcact    2010
taggtccagg gcatccctgg gaggagagag tagtgacact caggatccaa aagctagccc    2070
tgcccacccc agcccctgga cctgcttacc tgggtgtgca cctgctccgg ggggtggagg    2130
tgctccccac agtccgggcc aggacagcct caggggagag tgaaggcctg caggagggca    2190
ggcgagacaa ggagggtgtc cagggctagg gagtgccgga tgaaaccagc tctgtccctg    2250
tgcaggctcc aggctcccgc ctgacaaaca ggcagggagc cacagtcagg gacaataaaa    2310
acttggtgca ctctgaaagc agcacttgga cagccttcaa agtccttcca tctggctgca    2370
ctccaaggcc ccctctgtcc ttttcagaac acatggactt ggaggcagat ttgaaataaa    2430
cttttagtaa atgtaaaaaa aaaaaaaaa                                     2459
```

<210> SEQ ID NO 8
<211> LENGTH: 273
<212> TYPE: PRT
<213> ORGANISM: Homo sapiens

<400> SEQUENCE: 8

```
Met Ala Phe Leu Ala Gly Pro Arg Leu Leu Asp Trp Ala Ser Ser Pro
1               5                   10                  15

Pro His Leu Gln Phe Asn Lys Phe Val Leu Thr Gly Tyr Arg Pro Ala
            20                  25                  30

Ser Ser Gly Ser Gly Cys Leu Arg Ser Leu Phe Tyr Leu His Asn Glu
        35                  40                  45

Leu Gly Asn Ile Tyr Thr His Gly Leu Ala Leu Leu Gly Phe Leu Val
    50                  55                  60

Leu Val Pro Met Thr Met Pro Trp Gly Gln Leu Gly Lys Asp Gly Trp
65                  70                  75                  80

Leu Gly Gly Thr His Cys Val Ala Cys Leu Ala Pro Pro Ala Gly Ser
                85                  90                  95

Val Leu Tyr His Leu Phe Met Cys His Gln Gly Gly Ser Ala Val Tyr
            100                 105                 110

Ala Arg Leu Leu Ala Leu Asp Met Cys Gly Val Cys Leu Val Asn Thr
        115                 120                 125

Leu Gly Ala Leu Pro Ile Ile His Cys Thr Leu Ala Cys Arg Pro Trp
    130                 135                 140

Leu Arg Pro Ala Ala Leu Val Gly Tyr Thr Val Leu Ser Gly Val Ala
145                 150                 155                 160

Gly Trp Arg Ala Leu Thr Ala Pro Ser Thr Ser Ala Arg Leu Arg Ala
                165                 170                 175

Phe Gly Trp Gln Ala Ala Ala Arg Leu Leu Val Phe Gly Ala Arg Gly
            180                 185                 190

Val Gly Leu Gly Ser Gly Ala Pro Gly Ser Leu Pro Cys Tyr Leu Arg
        195                 200                 205

Met Asp Ala Leu Ala Leu Gly Gly Leu Val Asn Val Ala Arg Leu
    210                 215                 220

Pro Glu Arg Trp Gly Pro Gly Arg Phe Asp Tyr Trp Gly Asn Ser His
225                 230                 235                 240

Gln Ile Met His Leu Leu Ser Val Gly Ser Ile Leu Gln Leu His Ala
```

```
                        245                 250                 255
        Gly Val Val Pro Asp Leu Leu Trp Ala Ala His His Ala Cys Pro Arg
                    260                 265                 270

Asp

<210> SEQ ID NO 9
<211> LENGTH: 993
<212> TYPE: DNA
<213> ORGANISM: Homo sapiens
<220> FEATURE:
<221> NAME/KEY: misc_feature
<223> OTHER INFORMATION: progestin and adipoQ receptor family member V
      (PAQR5), transcript variant 2, mRNA
<220> FEATURE:
<221> NAME/KEY: CDS
<222> LOCATION: (1)..(993)

<400> SEQUENCE: 9 atg ctg agc ctg aag ctc ccc agg ctg ttt agc ata gac cag ata ccc       48
Met Leu Ser Leu Lys Leu Pro Arg Leu Phe Ser Ile Asp Gln Ile Pro
1               5                   10                  15 cag gtg ttc cat gag caa ggc atc ctg ttc ggc tac cgc cat cca cag       96
Gln Val Phe His Glu Gln Gly Ile Leu Phe Gly Tyr Arg His Pro Gln
            20                  25                  30 agt tct gcc act gcc tgc atc ctc agc ctt ttc caa atg acc aat gag      144
Ser Ser Ala Thr Ala Cys Ile Leu Ser Leu Phe Gln Met Thr Asn Glu
        35                  40                  45 act ctc aac att tgg act cac ttg ctg ccc ttc tgg ttc ttt gca tgg      192
Thr Leu Asn Ile Trp Thr His Leu Leu Pro Phe Trp Phe Phe Ala Trp
    50                  55                  60 agg ttt gtg act gca ctg tat atg aca gac atc aag aat gac agc tac      240
Arg Phe Val Thr Ala Leu Tyr Met Thr Asp Ile Lys Asn Asp Ser Tyr
65                  70                  75                  80 tcc tgg ccc atg ctt gtg tac atg tgc acc agc tgc gtg tac cca ctt      288
Ser Trp Pro Met Leu Val Tyr Met Cys Thr Ser Cys Val Tyr Pro Leu
                85                  90                  95 gtg tcc agc tgt gcg cac acc ttc agc tct atg tcc aag aat gcc cgg      336
Val Ser Ser Cys Ala His Thr Phe Ser Ser Met Ser Lys Asn Ala Arg
            100                 105                 110 cac att tgc tac ttc ctg gac tat ggt gcc gtc aac ctc ttc agc ctg      384
His Ile Cys Tyr Phe Leu Asp Tyr Gly Ala Val Asn Leu Phe Ser Leu
        115                 120                 125 ggc tca gcc att gcc tac tct gca tac acg ttc ccg gat gcg ctc atg      432
Gly Ser Ala Ile Ala Tyr Ser Ala Tyr Thr Phe Pro Asp Ala Leu Met
    130                 135                 140 tgc acc act ttc cat gac tac tac gtg gcc ctg gct gta ctg aac acc      480
Cys Thr Thr Phe His Asp Tyr Tyr Val Ala Leu Ala Val Leu Asn Thr
145                 150                 155                 160 atc ctc agc aca ggc ctc tcc tgc tac tcc agg ttt ctt gaa atc cag      528
Ile Leu Ser Thr Gly Leu Ser Cys Tyr Ser Arg Phe Leu Glu Ile Gln
                165                 170                 175 aag ccc aga ctc tgt aag gtg att cgt gtc ctc gcc ttt gct tat ccg      576
Lys Pro Arg Leu Cys Lys Val Ile Arg Val Leu Ala Phe Ala Tyr Pro
            180                 185                 190 tac acc tgg gac tcc ctc ccc atc ttc tac agg cta ttc ctg ttc cca      624
Tyr Thr Trp Asp Ser Leu Pro Ile Phe Tyr Arg Leu Phe Leu Phe Pro
        195                 200                 205 ggg gag agt gca caa aat gaa gcc acc tcg tac cac cag aag cac atg      672
Gly Glu Ser Ala Gln Asn Glu Ala Thr Ser Tyr His Gln Lys His Met
    210                 215                 220 atc atg acc ctc ctg gcc tct ttc ttg tac tct gca cat ctg cca gaa      720
```

```
Ile Met Thr Leu Leu Ala Ser Phe Leu Tyr Ser Ala His Leu Pro Glu
225                 230                 235                 240 cgc cta gcc cct gga cgc ttt gac tac atc ggt cac agt cac cag ctg     768
Arg Leu Ala Pro Gly Arg Phe Asp Tyr Ile Gly His Ser His Gln Leu
                    245                 250                 255 ttt cac gtg tgt gtg atc ctg gcc acg cac atg cag atg gaa gcc ata     816
Phe His Val Cys Val Ile Leu Ala Thr His Met Gln Met Glu Ala Ile
                260                 265                 270 ctt ctg gac aag act ctg agg aag gaa tgg ctc ctg gcc acc tcc aag     864
Leu Leu Asp Lys Thr Leu Arg Lys Glu Trp Leu Leu Ala Thr Ser Lys
            275                 280                 285 ccc ttc tct ttc tct cag ata gct gga gcc ata ctt ctg tgc atc atc     912
Pro Phe Ser Phe Ser Gln Ile Ala Gly Ala Ile Leu Leu Cys Ile Ile
        290                 295                 300 ttc agc ctc agc aac ata att tat ttc tca gct gct ctg tat cgg att     960
Phe Ser Leu Ser Asn Ile Ile Tyr Phe Ser Ala Ala Leu Tyr Arg Ile
305                 310                 315                 320 ccc aag cca gaa tta cat aaa aaa gaa aca tga                         993
Pro Lys Pro Glu Leu His Lys Lys Glu Thr
                325                 330

<210> SEQ ID NO 10
<211> LENGTH: 330
<212> TYPE: PRT
<213> ORGANISM: Homo sapiens

<400> SEQUENCE: 10

Met Leu Ser Leu Lys Leu Pro Arg Leu Phe Ser Ile Asp Gln Ile Pro
1               5                   10                  15

Gln Val Phe His Glu Gln Gly Ile Leu Phe Gly Tyr Arg His Pro Gln
                20                  25                  30

Ser Ser Ala Thr Ala Cys Ile Leu Ser Leu Phe Gln Met Thr Asn Glu
            35                  40                  45

Thr Leu Asn Ile Trp Thr His Leu Leu Pro Phe Trp Phe Phe Ala Trp
        50                  55                  60

Arg Phe Val Thr Ala Leu Tyr Met Thr Asp Ile Lys Asn Asp Ser Tyr
65                  70                  75                  80

Ser Trp Pro Met Leu Val Tyr Met Cys Thr Ser Cys Val Tyr Pro Leu
                85                  90                  95

Val Ser Ser Cys Ala His Thr Phe Ser Ser Met Ser Lys Asn Ala Arg
            100                 105                 110

His Ile Cys Tyr Phe Leu Asp Tyr Gly Ala Val Asn Leu Phe Ser Leu
        115                 120                 125

Gly Ser Ala Ile Ala Tyr Ser Ala Tyr Thr Phe Pro Asp Ala Leu Met
    130                 135                 140

Cys Thr Thr Phe His Asp Tyr Tyr Val Ala Leu Ala Val Leu Asn Thr
145                 150                 155                 160

Ile Leu Ser Thr Gly Leu Ser Cys Tyr Ser Arg Phe Leu Glu Ile Gln
                165                 170                 175

Lys Pro Arg Leu Cys Lys Val Ile Arg Val Leu Ala Phe Ala Tyr Pro
            180                 185                 190

Tyr Thr Trp Asp Ser Leu Pro Ile Phe Tyr Arg Leu Phe Leu Phe Pro
        195                 200                 205

Gly Glu Ser Ala Gln Asn Glu Ala Thr Ser Tyr His Gln Lys His Met
    210                 215                 220

Ile Met Thr Leu Leu Ala Ser Phe Leu Tyr Ser Ala His Leu Pro Glu
225                 230                 235                 240
```

```
Arg Leu Ala Pro Gly Arg Phe Asp Tyr Ile Gly His Ser His Gln Leu
            245                 250                 255

Phe His Val Cys Val Ile Leu Ala Thr His Met Gln Met Glu Ala Ile
        260                 265                 270

Leu Leu Asp Lys Thr Leu Arg Lys Glu Trp Leu Leu Ala Thr Ser Lys
        275                 280                 285

Pro Phe Ser Phe Ser Gln Ile Ala Gly Ala Ile Leu Leu Cys Ile Ile
        290                 295                 300

Phe Ser Leu Ser Asn Ile Ile Tyr Phe Ser Ala Ala Leu Tyr Arg Ile
305                 310                 315                 320

Pro Lys Pro Glu Leu His Lys Lys Glu Thr
                325                 330

<210> SEQ ID NO 11
<211> LENGTH: 1056
<212> TYPE: DNA
<213> ORGANISM: Homo sapiens
<220> FEATURE:
<221> NAME/KEY: misc_feature
<223> OTHER INFORMATION: progestin and adipoQ receptor family member VI
      (PAQR6), transcript variant 1, mRNA
<220> FEATURE:
<221> NAME/KEY: CDS
<222> LOCATION: (1)..(1056)

<400> SEQUENCE: 11 atg tcg ccc cgc atg cgc cac atc tgc tac ttc ctc gac tac ggc gcg      48
Met Ser Pro Arg Met Arg His Ile Cys Tyr Phe Leu Asp Tyr Gly Ala
1               5                   10                  15 ctc agc ctc tac agt ctg ggc tgc gcc ttc ccc tat gcc gcc tac tcc      96
Leu Ser Leu Tyr Ser Leu Gly Cys Ala Phe Pro Tyr Ala Ala Tyr Ser
            20                  25                  30 atg ccg gcc tcc tgg ctg cac ggc cac ctg cac cag ttc ttt gtg cct     144
Met Pro Ala Ser Trp Leu His Gly His Leu His Gln Phe Phe Val Pro
        35                  40                  45 gcc gcc gca ctc aac tcc ttc ctg tgc acc ggc ctc tcc tgc tac tcc     192
Ala Ala Ala Leu Asn Ser Phe Leu Cys Thr Gly Leu Ser Cys Tyr Ser
    50                  55                  60 cgt ttc ctg gag ctg gaa agc cct ggg ctc agt aag gtc ctc cgc aca     240
Arg Phe Leu Glu Leu Glu Ser Pro Gly Leu Ser Lys Val Leu Arg Thr
65                  70                  75                  80 gga gcc ttc gcc tat cca ttc ctg ttc gac aac ctc cca ctc ttt tat     288
Gly Ala Phe Ala Tyr Pro Phe Leu Phe Asp Asn Leu Pro Leu Phe Tyr
                85                  90                  95 cgg ctc ggg ctg tgc tgg ggc agg ggc cac ggc tgt ggg cag gag gcc     336
Arg Leu Gly Leu Cys Trp Gly Arg Gly His Gly Cys Gly Gln Glu Ala
            100                 105                 110 ctg agc acc agc cat ggc tac cat ctc ttc tgc gcg ctg ctc act ggc     384
Leu Ser Thr Ser His Gly Tyr His Leu Phe Cys Ala Leu Leu Thr Gly
        115                 120                 125 ttc ctc ttc gcc tcc cac ctg cct gaa agg ctg gca cca gga cgc ttt     432
Phe Leu Phe Ala Ser His Leu Pro Glu Arg Leu Ala Pro Gly Arg Phe
    130                 135                 140 gat tac atc ggt gag ggc acg cct ggc ccg gcc cgg gaa gag gca ggg     480
Asp Tyr Ile Gly Glu Gly Thr Pro Gly Pro Ala Arg Glu Glu Ala Gly
145                 150                 155                 160 gca gat gcc ttc cca gag cac aga atg aac tgg gcc aca gcc acc agt     528
Ala Asp Ala Phe Pro Glu His Arg Met Asn Trp Ala Thr Ala Thr Ser
                165                 170                 175 tat tcc aca tct gtg cag tgc tgg gca ccc act tcc agc tgg agg cag     576
```

```
Tyr Ser Thr Ser Val Gln Cys Trp Ala Pro Thr Ser Ser Trp Arg Gln
                180                 185                 190 tgc tgg ctg ata tgg gat cac gca gag cct ggc tgg cca cac agg aac    624
Cys Trp Leu Ile Trp Asp His Ala Glu Pro Gly Trp Pro His Arg Asn
            195                 200                 205 ctg ccc tgg gcc tgg cag gca cag tgg cca cac tgg tct tgg ctg cag    672
Leu Pro Trp Ala Trp Gln Ala Gln Trp Pro His Trp Ser Trp Leu Gln
    210                 215                 220 ctg gga acc tac tca tta ttg ctg ctt tca cag cca ccc tgc ttc ggg    720
Leu Gly Thr Tyr Ser Leu Leu Leu Leu Ser Gln Pro Pro Cys Phe Gly
225                 230                 235                 240 ccc cca gta cat gcc ctc tgc tgc agg gtg gcc cac tgg agg ggg gta    768
Pro Pro Val His Ala Leu Cys Cys Arg Val Ala His Trp Arg Gly Val
                245                 250                 255 ccc agg cca aac aac agt gag gcc cca tcc ctg acc ctg tcc tgg agg    816
Pro Arg Pro Asn Asn Ser Glu Ala Pro Ser Leu Thr Leu Ser Trp Arg
            260                 265                 270 ggg cag agg cca ggc ccc agt gct gac gag gag ccc aga ttt ggg cct    864
Gly Gln Arg Pro Gly Pro Ser Ala Asp Glu Glu Pro Arg Phe Gly Pro
    275                 280                 285 aat cag gtg ggg acg cat ctc agc ctg gaa cca aca ggg gct gag gag    912
Asn Gln Val Gly Thr His Leu Ser Leu Glu Pro Thr Gly Ala Glu Glu
290                 295                 300 aga ggg cac agg aga gag ggc aga gaa gag gag ggg tgt cta ggg gga    960
Arg Gly His Arg Arg Glu Gly Arg Glu Glu Glu Gly Cys Leu Gly Gly
305                 310                 315                 320 ctg gca gag tgt gag agg gac cgt gag ggg gct ctt gat ggg agt gga   1008
Leu Ala Glu Cys Glu Arg Asp Arg Glu Gly Ala Leu Asp Gly Ser Gly
                325                 330                 335 aga agt gct gag ggt ctg aga ggg gag atg cat gcg tgt cca ggc tga   1056
Arg Ser Ala Glu Gly Leu Arg Gly Glu Met His Ala Cys Pro Gly
            340                 345                 350

<210> SEQ ID NO 12
<211> LENGTH: 351
<212> TYPE: PRT
<213> ORGANISM: Homo sapiens

<400> SEQUENCE: 12

Met Ser Pro Arg Met Arg His Ile Cys Tyr Phe Leu Asp Tyr Gly Ala
1               5                   10                  15

Leu Ser Leu Tyr Ser Leu Gly Cys Ala Phe Pro Tyr Ala Ala Tyr Ser
                20                  25                  30

Met Pro Ala Ser Trp Leu His Gly His Leu His Gln Phe Phe Val Pro
            35                  40                  45

Ala Ala Ala Leu Asn Ser Phe Leu Cys Thr Gly Leu Ser Cys Tyr Ser
        50                  55                  60

Arg Phe Leu Glu Leu Glu Ser Pro Gly Leu Ser Lys Val Leu Arg Thr
65                  70                  75                  80

Gly Ala Phe Ala Tyr Pro Phe Leu Phe Asp Asn Leu Pro Leu Phe Tyr
                85                  90                  95

Arg Leu Gly Leu Cys Trp Gly Arg Gly His Gly Cys Gly Gln Glu Ala
            100                 105                 110

Leu Ser Thr Ser His Gly Tyr His Leu Phe Cys Ala Leu Leu Thr Gly
        115                 120                 125

Phe Leu Phe Ala Ser His Leu Pro Glu Arg Leu Ala Pro Gly Arg Phe
    130                 135                 140

Asp Tyr Ile Gly Glu Gly Thr Pro Gly Pro Ala Arg Glu Glu Ala Gly
```

```
                145                 150                 155                 160
Ala Asp Ala Phe Pro Glu His Arg Met Asn Trp Ala Thr Ala Thr Ser
                        165                 170                 175

Tyr Ser Thr Ser Val Gln Cys Trp Ala Pro Thr Ser Ser Trp Arg Gln
                180                 185                 190

Cys Trp Leu Ile Trp Asp His Ala Glu Pro Gly Trp Pro His Arg Asn
                    195                 200                 205

Leu Pro Trp Ala Trp Gln Ala Gln Trp Pro His Trp Ser Trp Leu Gln
    210                 215                 220

Leu Gly Thr Tyr Ser Leu Leu Leu Ser Gln Pro Pro Cys Phe Gly
225                 230                 235                 240

Pro Pro Val His Ala Leu Cys Cys Arg Val Ala His Trp Arg Gly Val
                    245                 250                 255

Pro Arg Pro Asn Asn Ser Glu Ala Pro Ser Leu Thr Leu Ser Trp Arg
                260                 265                 270

Gly Gln Arg Pro Gly Pro Ser Ala Asp Glu Glu Pro Arg Phe Gly Pro
                275                 280                 285

Asn Gln Val Gly Thr His Leu Ser Leu Glu Pro Thr Gly Ala Glu Glu
    290                 295                 300

Arg Gly His Arg Arg Glu Gly Arg Glu Glu Gly Cys Leu Gly Gly
305                 310                 315                 320

Leu Ala Glu Cys Glu Arg Asp Arg Glu Gly Ala Leu Asp Gly Ser Gly
                    325                 330                 335

Arg Ser Ala Glu Gly Leu Arg Gly Glu Met His Ala Cys Pro Gly
                340                 345                 350

<210> SEQ ID NO 13
<211> LENGTH: 1041
<212> TYPE: DNA
<213> ORGANISM: Homo sapiens
<220> FEATURE:
<221> NAME/KEY: misc_feature
<223> OTHER INFORMATION: progestin and adipoQ receptor family member
      VII, mRNA (cDNA clone MGC:22013 IMAGE:4400504)
<220> FEATURE:
<221> NAME/KEY: CDS
<222> LOCATION: (1)..(1041)

<400> SEQUENCE: 13 atg gcc atg gcc cag aaa ctc agc cac ctc ctg ccg agt ctg cgg cag      48
Met Ala Met Ala Gln Lys Leu Ser His Leu Leu Pro Ser Leu Arg Gln
1               5                   10                  15 gtc atc cag gag cct cag cta tct ctg cag cca gag cct gtc ttc acg      96
Val Ile Gln Glu Pro Gln Leu Ser Leu Gln Pro Glu Pro Val Phe Thr
                20                  25                  30 gtg gat cga gct gag gtg ccg ccg ctc ttc tgg aag ccg tac atc tat     144
Val Asp Arg Ala Glu Val Pro Pro Leu Phe Trp Lys Pro Tyr Ile Tyr
            35                  40                  45 gcg ggc tac cgg ccg ctg cat cag acc tgg cgc ttc tat ttc cgc acg     192
Ala Gly Tyr Arg Pro Leu His Gln Thr Trp Arg Phe Tyr Phe Arg Thr
        50                  55                  60 ctg ttc cag cag cac aac gag gcc gtg aat gtc tgg acc cac ctg ctg     240
Leu Phe Gln Gln His Asn Glu Ala Val Asn Val Trp Thr His Leu Leu
65                  70                  75                  80 gcg gcc ctg gta ctg ctg ctg cgg ctg gcc ctc ttt gtg gag acc gtg     288
Ala Ala Leu Val Leu Leu Leu Arg Leu Ala Leu Phe Val Glu Thr Val
                    85                  90                  95 gac ttc tgg gga gac cca cac gcc ctg ccc ctc ttc atc att gtc ctt     336
Asp Phe Trp Gly Asp Pro His Ala Leu Pro Leu Phe Ile Ile Val Leu
```

|  |  |  |  |  |  |  |  |  |  |  |  |  |  |  |  |
|---|---|---|---|---|---|---|---|---|---|---|---|---|---|---|---|
|  |  |  | 100 |  |  |  | 105 |  |  |  | 110 |  |  |  |  |
| gcc | tct | ttc | acc | tac | ctc | tcc | ttc | agt | gcc | ttg | gct | cac | ctc | ctg | cag | 384 |
| Ala | Ser | Phe | Thr | Tyr | Leu | Ser | Phe | Ser | Ala | Leu | Ala | His | Leu | Leu | Gln |  |
|  |  | 115 |  |  |  |  | 120 |  |  |  |  | 125 |  |  |  |  |
| gcc | aag | tct | gag | ttc | tgg | cat | tac | agc | ttc | ttc | ctg | gac | tat | gtg | | 432 |
| Ala | Lys | Ser | Glu | Phe | Trp | His | Tyr | Ser | Phe | Phe | Leu | Asp | Tyr | Val | |
| 130 |  |  |  |  | 135 |  |  |  |  | 140 |  |  |  |  |  |
| ggg | gtg | gcc | gtg | tac | cag | ttt | ggc | agt | gcc | ttg | gca | cac | ttc | tac | tat | 480 |
| Gly | Val | Ala | Val | Tyr | Gln | Phe | Gly | Ser | Ala | Leu | Ala | His | Phe | Tyr | Tyr |  |
| 145 |  |  |  |  | 150 |  |  |  |  | 155 |  |  |  |  | 160 |  |
| gct | atc | gag | ccc | gcc | tgg | cat | gcc | cag | gtg | cag | gct | gtt | ttt | ctg | ccc | 528 |
| Ala | Ile | Glu | Pro | Ala | Trp | His | Ala | Gln | Val | Gln | Ala | Val | Phe | Leu | Pro |  |
|  |  |  |  | 165 |  |  |  |  | 170 |  |  |  |  | 175 |  |  |
| atg | gct | gcc | ttt | ctc | gcc | tgg | ctt | tcc | tgc | att | ggc | tcc | tgc | tat | aac | 576 |
| Met | Ala | Ala | Phe | Leu | Ala | Trp | Leu | Ser | Cys | Ile | Gly | Ser | Cys | Tyr | Asn |  |
|  |  |  | 180 |  |  |  |  | 185 |  |  |  |  | 190 |  |  |  |
| aag | tac | atc | cag | aaa | cca | ggc | ctg | ctg | ggc | cgc | aca | tgc | cag | gag | gtg | 624 |
| Lys | Tyr | Ile | Gln | Lys | Pro | Gly | Leu | Leu | Gly | Arg | Thr | Cys | Gln | Glu | Val |  |
|  |  | 195 |  |  |  |  | 200 |  |  |  |  | 205 |  |  |  |  |
| ccc | tcc | gtc | ctg | gcc | tac | gca | ctg | gac | att | agt | cct | gtg | gtg | cat | cgt | 672 |
| Pro | Ser | Val | Leu | Ala | Tyr | Ala | Leu | Asp | Ile | Ser | Pro | Val | Val | His | Arg |  |
| 210 |  |  |  |  | 215 |  |  |  |  | 220 |  |  |  |  |  |  |
| atc | ttc | atg | tcc | tcc | gac | ccc | acc | acg | gat | gat | cca | gct | ctt | ctc | tac | 720 |
| Ile | Phe | Met | Ser | Ser | Asp | Pro | Thr | Thr | Asp | Asp | Pro | Ala | Leu | Leu | Tyr |  |
| 225 |  |  |  |  | 230 |  |  |  |  | 235 |  |  |  |  | 240 |  |
| cac | aag | tgc | cag | gtg | gtc | ttc | ttt | ctg | ctg | gct | gct | gcc | ttc | ttc | tct | 768 |
| His | Lys | Cys | Gln | Val | Val | Phe | Phe | Leu | Leu | Ala | Ala | Ala | Phe | Phe | Ser |  |
|  |  |  |  | 245 |  |  |  |  | 250 |  |  |  |  | 255 |  |  |
| acc | ttc | atg | ccc | gag | cgc | tgg | ttc | cct | ggc | agc | tgc | cat | gtc | ttc | ggg | 816 |
| Thr | Phe | Met | Pro | Glu | Arg | Trp | Phe | Pro | Gly | Ser | Cys | His | Val | Phe | Gly |  |
|  |  |  | 260 |  |  |  |  | 265 |  |  |  |  | 270 |  |  |  |
| cag | ggc | cac | caa | ctt | ttc | cac | atc | ttc | ttg | gtg | ctg | tgc | acg | ctg | gct | 864 |
| Gln | Gly | His | Gln | Leu | Phe | His | Ile | Phe | Leu | Val | Leu | Cys | Thr | Leu | Ala |  |
|  |  | 275 |  |  |  |  | 280 |  |  |  |  | 285 |  |  |  |  |
| cag | ctg | gag | gct | gtg | gca | ctg | gac | tat | gag | gcc | cga | cgg | ccc | atc | tat | 912 |
| Gln | Leu | Glu | Ala | Val | Ala | Leu | Asp | Tyr | Glu | Ala | Arg | Arg | Pro | Ile | Tyr |  |
| 290 |  |  |  |  | 295 |  |  |  |  | 300 |  |  |  |  |  |  |
| gag | cct | ctg | cac | acg | cac | tgg | cct | cac | aac | ttt | tct | ggc | ctc | ttc | ctg | 960 |
| Glu | Pro | Leu | His | Thr | His | Trp | Pro | His | Asn | Phe | Ser | Gly | Leu | Phe | Leu |  |
| 305 |  |  |  |  | 310 |  |  |  |  | 315 |  |  |  |  | 320 |  |
| ctc | acg | gtg | ggc | agc | agc | atc | ctc | act | gca | ttc | ctc | ctg | agc | cag | ctg | 1008 |
| Leu | Thr | Val | Gly | Ser | Ser | Ile | Leu | Thr | Ala | Phe | Leu | Leu | Ser | Gln | Leu |  |
|  |  |  |  | 325 |  |  |  |  | 330 |  |  |  |  | 335 |  |  |
| gta | cag | cgc | aaa | ctt | gat | cag | aag | acc | aag | tga |  |  |  |  |  | 1041 |
| Val | Gln | Arg | Lys | Leu | Asp | Gln | Lys | Thr | Lys |  |  |  |  |  |  |  |
|  |  |  | 340 |  |  |  |  | 345 |  |  |  |  |  |  |  |  |

<210> SEQ ID NO 14
<211> LENGTH: 346
<212> TYPE: PRT
<213> ORGANISM: Homo sapiens

<400> SEQUENCE: 14

Met Ala Met Ala Gln Lys Leu Ser His Leu Leu Pro Ser Leu Arg Gln
1               5                   10                  15

Val Ile Gln Glu Pro Gln Leu Ser Leu Gln Pro Glu Pro Val Phe Thr
            20                  25                  30

Val Asp Arg Ala Glu Val Pro Pro Leu Phe Trp Lys Pro Tyr Ile Tyr
        35                  40                  45

```
Ala Gly Tyr Arg Pro Leu His Gln Thr Trp Arg Phe Tyr Phe Arg Thr
    50                  55                  60

Leu Phe Gln Gln His Asn Glu Ala Val Asn Val Trp Thr His Leu Leu
 65                  70                  75                  80

Ala Ala Leu Val Leu Leu Leu Arg Leu Ala Leu Phe Val Glu Thr Val
                 85                  90                  95

Asp Phe Trp Gly Asp Pro His Ala Leu Pro Leu Phe Ile Ile Val Leu
            100                 105                 110

Ala Ser Phe Thr Tyr Leu Ser Phe Ser Ala Leu Ala His Leu Leu Gln
        115                 120                 125

Ala Lys Ser Glu Phe Trp His Tyr Ser Phe Phe Leu Asp Tyr Val
    130                 135                 140

Gly Val Ala Val Tyr Gln Phe Gly Ser Ala Leu Ala His Phe Tyr Tyr
145                 150                 155                 160

Ala Ile Glu Pro Ala Trp His Ala Gln Val Gln Ala Val Phe Leu Pro
                165                 170                 175

Met Ala Ala Phe Leu Ala Trp Leu Ser Cys Ile Gly Ser Cys Tyr Asn
            180                 185                 190

Lys Tyr Ile Gln Lys Pro Gly Leu Leu Gly Arg Thr Cys Gln Glu Val
        195                 200                 205

Pro Ser Val Leu Ala Tyr Ala Leu Asp Ile Ser Pro Val Val His Arg
210                 215                 220

Ile Phe Met Ser Ser Asp Pro Thr Thr Asp Pro Ala Leu Leu Tyr
225                 230                 235                 240

His Lys Cys Gln Val Val Phe Phe Leu Leu Ala Ala Ala Phe Ser
                245                 250                 255

Thr Phe Met Pro Glu Arg Trp Phe Pro Gly Ser Cys His Val Phe Gly
            260                 265                 270

Gln Gly His Gln Leu Phe His Ile Phe Leu Val Leu Cys Thr Leu Ala
        275                 280                 285

Gln Leu Glu Ala Val Ala Leu Asp Tyr Glu Ala Arg Arg Pro Ile Tyr
    290                 295                 300

Glu Pro Leu His Thr His Trp Pro His Asn Phe Ser Gly Leu Phe Leu
305                 310                 315                 320

Leu Thr Val Gly Ser Ser Ile Leu Thr Ala Phe Leu Leu Ser Gln Leu
                325                 330                 335

Val Gln Arg Lys Leu Asp Gln Lys Thr Lys
            340                 345

<210> SEQ ID NO 15
<211> LENGTH: 1065
<212> TYPE: DNA
<213> ORGANISM: Homo sapiens
<220> FEATURE:
<221> NAME/KEY: misc_feature
<223> OTHER INFORMATION: progestin and adipoQ receptor family member
      VIII (PAQR8), mRNA
<220> FEATURE:
<221> NAME/KEY: CDS
<222> LOCATION: (1)..(1065)

<400> SEQUENCE: 15 atg acg acc gcc atc ttg gag cgc ctg agc acc ctg tcg gtc agc ggg    48
Met Thr Thr Ala Ile Leu Glu Arg Leu Ser Thr Leu Ser Val Ser Gly
 1               5                  10                  15 cag cag ctg cgc cgc ctg ccc aag atc ctg gag gat ggg ctt ccc aag    96
Gln Gln Leu Arg Arg Leu Pro Lys Ile Leu Glu Asp Gly Leu Pro Lys
            20                  25                  30
```

-continued

```
atg cct tgc act gtc cca gaa acg gat gtg ccc cag ctc ttc cgg gag        144
Met Pro Cys Thr Val Pro Glu Thr Asp Val Pro Gln Leu Phe Arg Glu
    35                  40                  45 cct tac atc cgc acc ggc tac cgc ccc acg ggg cac gag tgg cgc tac        192
Pro Tyr Ile Arg Thr Gly Tyr Arg Pro Thr Gly His Glu Trp Arg Tyr
 50                  55                  60 tac ttc ttc agc ctc ttt cag aaa cac aac gag gtg gtc aac gtc tgg        240
Tyr Phe Phe Ser Leu Phe Gln Lys His Asn Glu Val Val Asn Val Trp
65                  70                  75                  80 acc cat tta ctg gca gcc ctg gcc gtc ctc ttg cga ttc tgg gcc ttt        288
Thr His Leu Leu Ala Ala Leu Ala Val Leu Leu Arg Phe Trp Ala Phe
                85                  90                  95 gcc gag gct gag gcc ttg cca tgg gcg tct acc cac tcc ctg cct ctg        336
Ala Glu Ala Glu Ala Leu Pro Trp Ala Ser Thr His Ser Leu Pro Leu
            100                 105                 110 ctc ctc ttc atc ctg tcg tca atc act tac ctc acc tgc agc ctt ctg        384
Leu Leu Phe Ile Leu Ser Ser Ile Thr Tyr Leu Thr Cys Ser Leu Leu
        115                 120                 125 gcc cac ctg ctg cag tcc aag tca gag ctc tcc cac tac acc ttc tac        432
Ala His Leu Leu Gln Ser Lys Ser Glu Leu Ser His Tyr Thr Phe Tyr
    130                 135                 140 ttt gtg gac tat gtt ggc gtg agc gtt tac caa tat ggc agt gct ttg        480
Phe Val Asp Tyr Val Gly Val Ser Val Tyr Gln Tyr Gly Ser Ala Leu
145                 150                 155                 160 gct cat ttc ttc tac agc tct gac cag gcc tgg tat gac cgg ttc tgg        528
Ala His Phe Phe Tyr Ser Ser Asp Gln Ala Trp Tyr Asp Arg Phe Trp
                165                 170                 175 ctt ttc ttc ttg cca gca gct gcc ttc tgt ggc tgg tta tct tgt gct        576
Leu Phe Phe Leu Pro Ala Ala Ala Phe Cys Gly Trp Leu Ser Cys Ala
            180                 185                 190 ggc tgt tgc tat gcc aaa tat cgt tac cgg agg cct tat cca gtc atg        624
Gly Cys Cys Tyr Ala Lys Tyr Arg Tyr Arg Arg Pro Tyr Pro Val Met
        195                 200                 205 agg aag atc tgt caa gtg gtg cca gca ggt ctg gct ttt atc cta gac        672
Arg Lys Ile Cys Gln Val Val Pro Ala Gly Leu Ala Phe Ile Leu Asp
    210                 215                 220 atc agc cct gtg gca cac cgt gtg gcg ctc tgt cac ctg gct ggc tgc        720
Ile Ser Pro Val Ala His Arg Val Ala Leu Cys His Leu Ala Gly Cys
225                 230                 235                 240 cag gag caa gca gcc tgg tac cac acc ctc cag atc ctc ttc ttc ctg        768
Gln Glu Gln Ala Ala Trp Tyr His Thr Leu Gln Ile Leu Phe Phe Leu
                245                 250                 255 gtt agc gct tat ttc ttc tcc tgc ccc gtg cct gag aag tac ttc ccg        816
Val Ser Ala Tyr Phe Phe Ser Cys Pro Val Pro Glu Lys Tyr Phe Pro
            260                 265                 270 ggt tcc tgt gac atc gtg ggc cat ggg cat cag atc ttc cat gca ttt        864
Gly Ser Cys Asp Ile Val Gly His Gly His Gln Ile Phe His Ala Phe
        275                 280                 285 ctg tcc atc tgt acg ctc tcc cag ctg gag gcc atc ctc ctg gac tac        912
Leu Ser Ile Cys Thr Leu Ser Gln Leu Glu Ala Ile Leu Leu Asp Tyr
    290                 295                 300 cag ggg cgg cag gag atc ttc ctg cag cgc cat gga ccc cta tct gtc        960
Gln Gly Arg Gln Glu Ile Phe Leu Gln Arg His Gly Pro Leu Ser Val
305                 310                 315                 320 cac atg gcc tgc ctc tcc ttc ttc ctg gct gcc tgc agt gct gcc              1008
His Met Ala Cys Leu Ser Phe Phe Leu Ala Ala Cys Ser Ala Ala
                325                 330                 335 acc gca gcc ctt ctg agg cac aaa gtc aag gcc aga ctg acc aag aaa        1056
Thr Ala Ala Leu Leu Arg His Lys Val Lys Ala Arg Leu Thr Lys Lys
```

```
                    340             345             350
gat tcc tga                                                           1065
Asp Ser <210> SEQ ID NO 16
<211> LENGTH: 354
<212> TYPE: PRT
<213> ORGANISM: Homo sapiens

<400> SEQUENCE: 16

Met Thr Thr Ala Ile Leu Glu Arg Leu Ser Thr Leu Ser Val Ser Gly
1               5                   10                  15

Gln Gln Leu Arg Arg Leu Pro Lys Ile Leu Glu Asp Gly Leu Pro Lys
            20                  25                  30

Met Pro Cys Thr Val Pro Glu Thr Asp Val Pro Gln Leu Phe Arg Glu
        35                  40                  45

Pro Tyr Ile Arg Thr Gly Tyr Arg Pro Thr Gly His Glu Trp Arg Tyr
    50                  55                  60

Tyr Phe Phe Ser Leu Phe Gln Lys His Asn Glu Val Val Asn Val Trp
65                  70                  75                  80

Thr His Leu Leu Ala Ala Leu Ala Val Leu Leu Arg Phe Trp Ala Phe
                85                  90                  95

Ala Glu Ala Glu Ala Leu Pro Trp Ala Ser Thr His Ser Leu Pro Leu
            100                 105                 110

Leu Leu Phe Ile Leu Ser Ser Ile Thr Tyr Leu Thr Cys Ser Leu Leu
        115                 120                 125

Ala His Leu Leu Gln Ser Lys Ser Glu Leu Ser His Tyr Thr Phe Tyr
    130                 135                 140

Phe Val Asp Tyr Val Gly Val Ser Val Tyr Gln Tyr Gly Ser Ala Leu
145                 150                 155                 160

Ala His Phe Phe Tyr Ser Ser Asp Gln Ala Trp Tyr Asp Arg Phe Trp
                165                 170                 175

Leu Phe Phe Leu Pro Ala Ala Ala Phe Cys Gly Trp Leu Ser Cys Ala
            180                 185                 190

Gly Cys Cys Tyr Ala Lys Tyr Arg Tyr Arg Arg Pro Tyr Pro Val Met
        195                 200                 205

Arg Lys Ile Cys Gln Val Val Pro Ala Gly Leu Ala Phe Ile Leu Asp
    210                 215                 220

Ile Ser Pro Val Ala His Arg Val Ala Leu Cys His Leu Ala Gly Cys
225                 230                 235                 240

Gln Glu Gln Ala Ala Trp Tyr His Thr Leu Gln Ile Leu Phe Phe Leu
                245                 250                 255

Val Ser Ala Tyr Phe Phe Ser Cys Pro Val Pro Glu Lys Tyr Phe Pro
            260                 265                 270

Gly Ser Cys Asp Ile Val Gly His Gly His Gln Ile Phe His Ala Phe
        275                 280                 285

Leu Ser Ile Cys Thr Leu Ser Gln Leu Glu Ala Ile Leu Leu Asp Tyr
    290                 295                 300

Gln Gly Arg Gln Glu Ile Phe Leu Gln Arg His Gly Pro Leu Ser Val
305                 310                 315                 320

His Met Ala Cys Leu Ser Phe Phe Leu Ala Ala Cys Ser Ala Ala
                325                 330                 335

Thr Ala Ala Leu Leu Arg His Lys Val Lys Ala Arg Leu Thr Lys Lys
            340                 345                 350
```

Asp Ser

<210> SEQ ID NO 17
<211> LENGTH: 1134
<212> TYPE: DNA
<213> ORGANISM: Homo sapiens
<220> FEATURE:
<221> NAME/KEY: misc_feature
<223> OTHER INFORMATION: progestin and adipoQ receptor family member IX
      (PAQR9), mRNA
<220> FEATURE:
<221> NAME/KEY: CDS
<222> LOCATION: (1)..(1134)

<400> SEQUENCE: 17

```
atg ccg cgg cgc ctg cag ccc cgg ggc gcg ggc aca aaa ggc cct ccg      48
Met Pro Arg Arg Leu Gln Pro Arg Gly Ala Gly Thr Lys Gly Pro Pro
1               5                   10                  15 gcc ccg gcc ccg gca gct tcg ggg gcc gcc cgg aac tcc cac tct gcc      96
Ala Pro Ala Pro Ala Ala Ser Gly Ala Ala Arg Asn Ser His Ser Ala
            20                  25                  30 gcc tcc cgg gac ccc cca gcg tct gcc aag ccg ctg ctg cgc tgg gac     144
Ala Ser Arg Asp Pro Pro Ala Ser Ala Lys Pro Leu Leu Arg Trp Asp
        35                  40                  45 gag gtg ccc gac gac ttc gtg gag tgc ttc atc ctg tcg ggc tac cgg     192
Glu Val Pro Asp Asp Phe Val Glu Cys Phe Ile Leu Ser Gly Tyr Arg
    50                  55                  60 cgt ctg ccg tgc acg gcc cag gag tgc cta gcc tcg gtg ctg aag cct     240
Arg Leu Pro Cys Thr Ala Gln Glu Cys Leu Ala Ser Val Leu Lys Pro
65                  70                  75                  80 acc aac gag acg ctc aac ttc tgg acg cac ttc atc ccg ctg ctg ctg     288
Thr Asn Glu Thr Leu Asn Phe Trp Thr His Phe Ile Pro Leu Leu Leu
                85                  90                  95 ttc ctg agc aag ttc tgc cgt ctg ttc ttc ctg agc ggc ggc gac gtg     336
Phe Leu Ser Lys Phe Cys Arg Leu Phe Phe Leu Ser Gly Gly Asp Val
            100                 105                 110 ccc ttc cac cac ccg tgg ctg cta ccg ttg tgg tgc tac gcg tcg gga     384
Pro Phe His His Pro Trp Leu Leu Pro Leu Trp Cys Tyr Ala Ser Gly
        115                 120                 125 gtg ctg ctg acc ttc gcc atg agc tgc acg gcg cac gtg ttc agc tgc     432
Val Leu Leu Thr Phe Ala Met Ser Cys Thr Ala His Val Phe Ser Cys
    130                 135                 140 ctg tcg ctg cgt ctg cgc gcc gcc ttc ttc tac ctg gac tac gcg tcc     480
Leu Ser Leu Arg Leu Arg Ala Ala Phe Phe Tyr Leu Asp Tyr Ala Ser
145                 150                 155                 160 atc agc tac tac ggc ttc ggc agc acg gtg gcc tac tac tac tac ctg     528
Ile Ser Tyr Tyr Gly Phe Gly Ser Thr Val Ala Tyr Tyr Tyr Tyr Leu
                165                 170                 175 ttg cca ggc ctc agc ttg ctg gat gcc aga gtc atg act cca tac ttg     576
Leu Pro Gly Leu Ser Leu Leu Asp Ala Arg Val Met Thr Pro Tyr Leu
            180                 185                 190 cag cag cgc ctg ggc tgg cac gtg gac tgc acg cgc ctt atc gcc gcc     624
Gln Gln Arg Leu Gly Trp His Val Asp Cys Thr Arg Leu Ile Ala Ala
        195                 200                 205 tac cgc gcc ctg gtg ctg cct gtg gcc ttc gtg ctg gcg gtg gct tgc     672
Tyr Arg Ala Leu Val Leu Pro Val Ala Phe Val Leu Ala Val Ala Cys
    210                 215                 220 act gtg gcc tgc tgc aag agc cgt acc gac tgg tgt acc tac ccg ttc     720
Thr Val Ala Cys Cys Lys Ser Arg Thr Asp Trp Cys Thr Tyr Pro Phe
225                 230                 235                 240 gcg ctg cgc acc ttc gtc ttc gtc atg ccg ctc agc atg gcc tgc ccc     768
Ala Leu Arg Thr Phe Val Phe Val Met Pro Leu Ser Met Ala Cys Pro
```

```
att atg ctc gag agc tgg ctc ttc gac ctg cgt ggg gag aac ccc aca      816
Ile Met Leu Glu Ser Trp Leu Phe Asp Leu Arg Gly Glu Asn Pro Thr
        260                 265                 270 ctc ttc gtg cac ttc tac cgc tac ttc tgg ctg gtg gtg gcc gcc          864
Leu Phe Val His Phe Tyr Arg Tyr Phe Trp Leu Val Val Ala Ala
    275                 280                 285 ttc ttc aac gtg agc aag atc ccc gag cgc atc cag ccg ggt ctt ttc      912
Phe Phe Asn Val Ser Lys Ile Pro Glu Arg Ile Gln Pro Gly Leu Phe
290                 295                 300 gac att atc ggc cac agc cac cag ctc ttc cac atc ttc acc ttc ctc      960
Asp Ile Ile Gly His Ser His Gln Leu Phe His Ile Phe Thr Phe Leu
305                 310                 315                 320 agc atc tac gac cag gtg tac tac gta gaa gag ggc ctg cgc cag ttc     1008
Ser Ile Tyr Asp Gln Val Tyr Tyr Val Glu Glu Gly Leu Arg Gln Phe
            325                 330                 335 ctc cag gcg ccg cct gcc gca ccc act ttc tcg ggt act gtg ggc tac     1056
Leu Gln Ala Pro Pro Ala Ala Pro Thr Phe Ser Gly Thr Val Gly Tyr
            340                 345                 350 atg ctg ctg ctg gtg gtc tgc ctg ggg ctg gta atc agg aag ttc cta     1104
Met Leu Leu Leu Val Val Cys Leu Gly Leu Val Ile Arg Lys Phe Leu
        355                 360                 365 aac agc tcc gaa ttc tgc agt aaa aag tga                             1134
Asn Ser Ser Glu Phe Cys Ser Lys Lys
    370                 375
```

<210> SEQ ID NO 18
<211> LENGTH: 377
<212> TYPE: PRT
<213> ORGANISM: Homo sapiens

<400> SEQUENCE: 18

```
Met Pro Arg Arg Leu Gln Pro Arg Gly Ala Gly Thr Lys Gly Pro Pro
1               5                   10                  15

Ala Pro Ala Pro Ala Ala Ser Gly Ala Ala Arg Asn Ser His Ser Ala
            20                  25                  30

Ala Ser Arg Asp Pro Pro Ala Ser Ala Lys Pro Leu Leu Arg Trp Asp
        35                  40                  45

Glu Val Pro Asp Asp Phe Val Glu Cys Phe Ile Leu Ser Gly Tyr Arg
    50                  55                  60

Arg Leu Pro Cys Thr Ala Gln Glu Cys Leu Ala Ser Val Leu Lys Pro
65                  70                  75                  80

Thr Asn Glu Thr Leu Asn Phe Trp Thr His Phe Ile Pro Leu Leu Leu
                85                  90                  95

Phe Leu Ser Lys Phe Cys Arg Leu Phe Phe Leu Ser Gly Gly Asp Val
            100                 105                 110

Pro Phe His His Pro Trp Leu Leu Pro Leu Trp Cys Tyr Ala Ser Gly
        115                 120                 125

Val Leu Leu Thr Phe Ala Met Ser Cys Thr Ala His Val Phe Ser Cys
    130                 135                 140

Leu Ser Leu Arg Leu Arg Ala Ala Phe Phe Tyr Leu Asp Tyr Ala Ser
145                 150                 155                 160

Ile Ser Tyr Tyr Gly Phe Gly Ser Thr Val Ala Tyr Tyr Tyr Leu
                165                 170                 175

Leu Pro Gly Leu Ser Leu Leu Asp Ala Arg Val Met Thr Pro Tyr Leu
            180                 185                 190

Gln Gln Arg Leu Gly Trp His Val Asp Cys Thr Arg Leu Ile Ala Ala
```

```
                195                 200                 205
Tyr Arg Ala Leu Val Leu Pro Val Ala Phe Val Leu Ala Val Ala Cys
        210                 215                 220

Thr Val Ala Cys Cys Lys Ser Arg Thr Asp Trp Cys Thr Tyr Pro Phe
225                 230                 235                 240

Ala Leu Arg Thr Phe Val Phe Val Met Pro Leu Ser Met Ala Cys Pro
                245                 250                 255

Ile Met Leu Glu Ser Trp Leu Phe Asp Leu Arg Gly Glu Asn Pro Thr
            260                 265                 270

Leu Phe Val His Phe Tyr Arg Arg Tyr Phe Trp Leu Val Ala Ala
        275                 280                 285

Phe Phe Asn Val Ser Lys Ile Pro Glu Arg Ile Gln Pro Gly Leu Phe
290                 295                 300

Asp Ile Ile Gly His Ser His Gln Leu Phe His Ile Phe Thr Phe Leu
305                 310                 315                 320

Ser Ile Tyr Asp Gln Val Tyr Tyr Val Glu Glu Gly Leu Arg Gln Phe
                325                 330                 335

Leu Gln Ala Pro Pro Ala Ala Pro Thr Phe Ser Gly Thr Val Gly Tyr
            340                 345                 350

Met Leu Leu Leu Val Val Cys Leu Gly Leu Val Ile Arg Lys Phe Leu
        355                 360                 365

Asn Ser Ser Glu Phe Cys Ser Lys Lys
        370                 375

<210> SEQ ID NO 19
<211> LENGTH: 741
<212> TYPE: DNA
<213> ORGANISM: Homo sapiens
<220> FEATURE:
<221> NAME/KEY: misc_feature
<223> OTHER INFORMATION: monocyte to macrophage
      differentiation-associated 2 (MMD2), transcript variant 2, mRNA
<220> FEATURE:
<221> NAME/KEY: CDS
<222> LOCATION: (1)..(741)

<400> SEQUENCE: 19 atg ttc gcc ccc cgg ctg ctg gat ttc cag aag acg aaa tac gcg agg       48
Met Phe Ala Pro Arg Leu Leu Asp Phe Gln Lys Thr Lys Tyr Ala Arg
1               5                   10                  15 ttc atg aac cac cga gtc cct gcc cac aag agg tac cag ccc aca gag       96
Phe Met Asn His Arg Val Pro Ala His Lys Arg Tyr Gln Pro Thr Glu
                20                  25                  30 tat gaa cat gcg gcc aac tgt gcc acc cat gct ttc tgg atc atc ccc      144
Tyr Glu His Ala Ala Asn Cys Ala Thr His Ala Phe Trp Ile Ile Pro
            35                  40                  45 agc atc ctg ggc agc tcc aac ctc tac ttc ctg tcg gac gat gac tgg      192
Ser Ile Leu Gly Ser Ser Asn Leu Tyr Phe Leu Ser Asp Asp Asp Trp
        50                  55                  60 gag acc atc tct gcc tgg atc tac ggc ctc ggc ctc tgc ggc ctc ttc      240
Glu Thr Ile Ser Ala Trp Ile Tyr Gly Leu Gly Leu Cys Gly Leu Phe
65                  70                  75                  80 gtg gtg tcc act gtg ttt cac acc atc tcc tgg aag aag agc cac ctc      288
Val Val Ser Thr Val Phe His Thr Ile Ser Trp Lys Lys Ser His Leu
                85                  90                  95 agg atg gtg gaa cac tgt cta cac atg ttc gac cgg atg gtc atc tat      336
Arg Met Val Glu His Cys Leu His Met Phe Asp Arg Met Val Ile Tyr
                100                 105                 110 ttc ttc ata gcg gct tcc tac gca ccc tgg ctg aac ctt cgg gag ctg      384
Phe Phe Ile Ala Ala Ser Tyr Ala Pro Trp Leu Asn Leu Arg Glu Leu
```

```
Phe Phe Ile Ala Ala Ser Tyr Ala Pro Trp Leu Asn Leu Arg Glu Leu
            115                 120                 125 ggc ccc tgg gcc tcc cac atg cgc tgg ctg gtc tgg att atg gct tcc       432
Gly Pro Trp Ala Ser His Met Arg Trp Leu Val Trp Ile Met Ala Ser
130                 135                 140 gtg ggc acc atc tat gtc ttc ttc cat gag cgg tac aag ctt gtg           480
Val Gly Thr Ile Tyr Val Phe Phe His Glu Arg Tyr Lys Leu Val
145                 150                 155                 160 gag ctt ctc tgc tac gtc gta atg ggc ttc ttc ccc gcc ctg gtc atc       528
Glu Leu Leu Cys Tyr Val Val Met Gly Phe Phe Pro Ala Leu Val Ile
                165                 170                 175 ctc tcc atg ccc aac acc gag ggc atc tgg gag ctg gtg acc gga ggg       576
Leu Ser Met Pro Asn Thr Glu Gly Ile Trp Glu Leu Val Thr Gly Gly
            180                 185                 190 gtc ttc tac tgc ctg ggc atg gtc ttc ttc aag agt gac ggg agg atc       624
Val Phe Tyr Cys Leu Gly Met Val Phe Phe Lys Ser Asp Gly Arg Ile
        195                 200                 205 ccc ttt gcc cac gcc atc tgg cat ctc ttt gta gca ttt ggt gct ggt       672
Pro Phe Ala His Ala Ile Trp His Leu Phe Val Ala Phe Gly Ala Gly
    210                 215                 220 acc cac tac tat gcc atc tgg agg tac ctc tat ctg ccc agc acc ctg       720
Thr His Tyr Tyr Ala Ile Trp Arg Tyr Leu Tyr Leu Pro Ser Thr Leu
225                 230                 235                 240 cag acc aag gtg tcc aaa tga                                           741
Gln Thr Lys Val Ser Lys
                245

<210> SEQ ID NO 20
<211> LENGTH: 246
<212> TYPE: PRT
<213> ORGANISM: Homo sapiens

<400> SEQUENCE: 20

Met Phe Ala Pro Arg Leu Leu Asp Phe Gln Lys Thr Lys Tyr Ala Arg
1               5                   10                  15

Phe Met Asn His Arg Val Pro Ala His Lys Arg Tyr Gln Pro Thr Glu
                20                  25                  30

Tyr Glu His Ala Ala Asn Cys Ala Thr His Ala Phe Trp Ile Ile Pro
            35                  40                  45

Ser Ile Leu Gly Ser Ser Asn Leu Tyr Phe Leu Ser Asp Asp Asp Trp
50                  55                  60

Glu Thr Ile Ser Ala Trp Ile Tyr Gly Leu Gly Leu Cys Gly Leu Phe
65                  70                  75                  80

Val Val Ser Thr Val Phe His Thr Ile Ser Trp Lys Lys Ser His Leu
                85                  90                  95

Arg Met Val Glu His Cys Leu His Met Phe Asp Arg Met Val Ile Tyr
                100                 105                 110

Phe Phe Ile Ala Ala Ser Tyr Ala Pro Trp Leu Asn Leu Arg Glu Leu
            115                 120                 125

Gly Pro Trp Ala Ser His Met Arg Trp Leu Val Trp Ile Met Ala Ser
        130                 135                 140

Val Gly Thr Ile Tyr Val Phe Phe His Glu Arg Tyr Lys Leu Val
145                 150                 155                 160

Glu Leu Leu Cys Tyr Val Val Met Gly Phe Phe Pro Ala Leu Val Ile
                165                 170                 175

Leu Ser Met Pro Asn Thr Glu Gly Ile Trp Glu Leu Val Thr Gly Gly
            180                 185                 190
```

```
Val Phe Tyr Cys Leu Gly Met Val Phe Phe Lys Ser Asp Gly Arg Ile
            195                 200                 205

Pro Phe Ala His Ala Ile Trp His Leu Phe Val Ala Phe Gly Ala Gly
    210                 215                 220

Thr His Tyr Tyr Ala Ile Trp Arg Tyr Leu Tyr Leu Pro Ser Thr Leu
225                 230                 235                 240

Gln Thr Lys Val Ser Lys
                245

<210> SEQ ID NO 21
<211> LENGTH: 717
<212> TYPE: DNA
<213> ORGANISM: Homo sapiens
<220> FEATURE:
<221> NAME/KEY: misc_feature
<223> OTHER INFORMATION: monocyte to macrophage
      differentiation-associated (MMD), mRNA
<220> FEATURE:
<221> NAME/KEY: CDS
<222> LOCATION: (1)..(717)

<400> SEQUENCE: 21 atg cgg ttc aag aat cga ttc cag cgg ttc atg aac cat cga gct cca      48
Met Arg Phe Lys Asn Arg Phe Gln Arg Phe Met Asn His Arg Ala Pro
1               5                   10                  15 gcc aat ggc cgc tac aag cca act tgc tat gaa cat gct gct aac tgt      96
Ala Asn Gly Arg Tyr Lys Pro Thr Cys Tyr Glu His Ala Ala Asn Cys
            20                  25                  30 tac aca cac gca ttc ctc att gtt ccg gcc atc gtg ggc agt gcc ctc     144
Tyr Thr His Ala Phe Leu Ile Val Pro Ala Ile Val Gly Ser Ala Leu
        35                  40                  45 ctc cat cgg ctg tct gat gac tgc tgg gaa aag ata aca gca tgg att     192
Leu His Arg Leu Ser Asp Asp Cys Trp Glu Lys Ile Thr Ala Trp Ile
    50                  55                  60 tat gga atg gga ctc tgt gcc ctc ttc atc gtt tct aca gta ttt cac     240
Tyr Gly Met Gly Leu Cys Ala Leu Phe Ile Val Ser Thr Val Phe His
65                  70                  75                  80 att gta tca tgg aaa aag agc cac tta agg aca gtg gag cat tgt ttt     288
Ile Val Ser Trp Lys Lys Ser His Leu Arg Thr Val Glu His Cys Phe
                85                  90                  95 cac atg tgt gat aga atg gtt atc tat ttc ttc att gct gct tct tat     336
His Met Cys Asp Arg Met Val Ile Tyr Phe Phe Ile Ala Ala Ser Tyr
            100                 105                 110 gct cca tgg tta aat ctt cgt gaa ctt gga ccc ctg gca tct cat atg     384
Ala Pro Trp Leu Asn Leu Arg Glu Leu Gly Pro Leu Ala Ser His Met
        115                 120                 125 cgt tgg ttt atc tgg ctc atg gca gct gga gga acc att tat gta ttt     432
Arg Trp Phe Ile Trp Leu Met Ala Ala Gly Gly Thr Ile Tyr Val Phe
    130                 135                 140 ctc tac cat gaa aaa tat aag gtg gtt gaa ctc ttt tat ctc aca         480
Leu Tyr His Glu Lys Tyr Lys Val Val Glu Leu Phe Tyr Leu Thr
145                 150                 155                 160 atg gga ttc tct cca gcc ttg gtg gtg aca tca atg aac aac acc gat     528
Met Gly Phe Ser Pro Ala Leu Val Val Thr Ser Met Asn Asn Thr Asp
                165                 170                 175 gga ctt cag gaa ctt gcc tgt ggg ggc tta att tat tgc ttg gga gtt     576
Gly Leu Gln Glu Leu Ala Cys Gly Gly Leu Ile Tyr Cys Leu Gly Val
            180                 185                 190 gtg ttc ttc aag agt gat ggc atc att cca ttt gcc cac gcc atc tgg     624
Val Phe Phe Lys Ser Asp Gly Ile Ile Pro Phe Ala His Ala Ile Trp
        195                 200                 205
```

| cac ctg ttt gtg gcc acg gca gct gca gtg cat tac tac gcc att tgg | 672 |
|---|---|
| His Leu Phe Val Ala Thr Ala Ala Ala Val His Tyr Tyr Ala Ile Trp | |
| 210 215 220 | |

| aaa tac ctt tac cga agt cct acg gac ttt atg cgg cat tta tga | 717 |
|---|---|
| Lys Tyr Leu Tyr Arg Ser Pro Thr Asp Phe Met Arg His Leu | |
| 225 230 235 | |

<210> SEQ ID NO 22
<211> LENGTH: 238
<212> TYPE: PRT
<213> ORGANISM: Homo sapiens

<400> SEQUENCE: 22

Met Arg Phe Lys Asn Arg Phe Gln Arg Phe Met Asn His Arg Ala Pro
1               5                   10                  15

Ala Asn Gly Arg Tyr Lys Pro Thr Cys Tyr Glu His Ala Ala Asn Cys
            20                  25                  30

Tyr Thr His Ala Phe Leu Ile Val Pro Ala Ile Val Gly Ser Ala Leu
        35                  40                  45

Leu His Arg Leu Ser Asp Asp Cys Trp Glu Lys Ile Thr Ala Trp Ile
    50                  55                  60

Tyr Gly Met Gly Leu Cys Ala Leu Phe Ile Val Ser Thr Val Phe His
65                  70                  75                  80

Ile Val Ser Trp Lys Lys Ser His Leu Arg Thr Val Glu His Cys Phe
                85                  90                  95

His Met Cys Asp Arg Met Val Ile Tyr Phe Phe Ile Ala Ala Ser Tyr
            100                 105                 110

Ala Pro Trp Leu Asn Leu Arg Glu Leu Gly Pro Leu Ala Ser His Met
        115                 120                 125

Arg Trp Phe Ile Trp Leu Met Ala Ala Gly Gly Thr Ile Tyr Val Phe
    130                 135                 140

Leu Tyr His Glu Lys Tyr Lys Val Val Glu Leu Phe Phe Tyr Leu Thr
145                 150                 155                 160

Met Gly Phe Ser Pro Ala Leu Val Val Thr Ser Met Asn Asn Thr Asp
                165                 170                 175

Gly Leu Gln Glu Leu Ala Cys Gly Gly Leu Ile Tyr Cys Leu Gly Val
            180                 185                 190

Val Phe Phe Lys Ser Asp Gly Ile Ile Pro Phe Ala His Ala Ile Trp
        195                 200                 205

His Leu Phe Val Ala Thr Ala Ala Ala Val His Tyr Tyr Ala Ile Trp
    210                 215                 220

Lys Tyr Leu Tyr Arg Ser Pro Thr Asp Phe Met Arg His Leu
225                 230                 235

<210> SEQ ID NO 23
<211> LENGTH: 954
<212> TYPE: DNA
<213> ORGANISM: Saccharomyces cerevisiae
<220> FEATURE:
<221> NAME/KEY: misc_feature
<223> OTHER INFORMATION: chromosome XV, complete chromosome sequence.
<220> FEATURE:
<221> NAME/KEY: CDS
<222> LOCATION: (1)..(954)

<400> SEQUENCE: 23

| cta gga gac aat ccc gtt ctc cat ctt tat atg gac taa ctc ata act | 48 |
|---|---|
| Leu Gly Asp Asn Pro Val Leu His Leu Tyr Met Asp     Leu Ile Thr | |
| 1               5                   10                  15 | |

-continued

| | | |
|---|---|---|
| att taa taa acc tct caa gtg gca caa tgc cgc aat aac aac tag aaa<br>Ile         Thr Ser Gln Val Ala Gln Cys Arg Asn Asn Asn      Lys<br>                20                              25 | 96 |
| atg gaa aag ttg gtg aga atg acc cca aat atc aaa ttt acc ggg gca<br>Met Glu Lys Leu Val Arg Met Thr Pro Asn Ile Lys Phe Thr Gly Ala<br>    30                  35                  40 | 144 |
| aat ctt ttc agg aaa ccg cat tcc ata aag aac agc gcc aat tat ata<br>Asn Leu Phe Arg Lys Pro His Ser Ile Lys Asn Ser Ala Asn Tyr Ile<br>45                  50                  55                  60 | 192 |
| tag gac acc ccc aag taa tac cca aaa gag ctg aat ttg ggt cca aat<br>Asp Thr Pro Lys     Tyr Pro Lys Glu Leu Asn Leu Gly Pro Asn<br>                      65                          70 | 240 |
| ttc tga aaa act ata gca gta aag gcc gct gaa tat tgg aat aat tga<br>Phe     Lys Thr Ile Ala Val Lys Ala Ala Glu Tyr Trp Asn Asn<br>75                  80                  85 | 288 |
| gga taa acc aaa aca aac aaa tag ccc agc tct gta agg tct cca ctc<br>Gly     Thr Lys Thr Asn Lys     Pro Ser Ser Val Arg Ser Pro Leu<br>          90                        95                  100 | 336 |
| tct ttt ccg aaa ctt atc ttt tag tga cac aat act aca cgc gat ccc<br>Ser Phe Pro Lys Leu Ile Phe         His Asn Thr Thr Arg Asp Pro<br>         105                        110                  115 | 384 |
| aaa gct aac ggt aat aag cgc aaa tag gca aaa tag gga aaa ttt ctc<br>Lys Ala Asn Gly Asn Lys Arg Lys     Ala Lys     Gly Lys Phe Leu<br>                120                        125                  130 | 432 |
| aaa ata gcc gta gta caa aat act gac cat tga cgt aac aat caa tat<br>Lys Ile Ala Val Val Gln Asn Thr Asp His     Arg Asn Asn Gln Tyr<br>                      135                        140                  145 | 480 |
| aca aat acc aag gta gtc caa ctt att tcc taa ggt agc aat tct taa<br>Thr Asn Thr Lys Val Val Gln Leu Ile Ser     Gly Ser Asn Ser<br>                150                        155 | 528 |
| gga gtg act ctt tag aca atg aaa gga gct act caa tat taa aca tgc<br>Gly Val Thr Leu     Thr Met Lys Gly Ala Thr Gln Tyr     Thr Cys<br>160                      165                        170 | 576 |
| aaa cgc ccc cga ata aaa gag gtc gat tac cat atg atc tag cca tgt<br>Lys Arg Pro Arg Ile Lys Glu Val Asp Tyr His Met Ile     Pro Cys<br>         175                        180                  185 | 624 |
| agt tgt tgc aaa cac ttt gat agt aga ttt atc tag caa cag tac agt<br>Ser Cys Cys Lys His Phe Asp Ser Arg Phe Ile     Gln Gln Tyr Ser<br>         190                        195                  200 | 672 |
| gaa gaa ccc gag agc agg aat taa atg tga ata aat att gac act ttc<br>Glu Glu Pro Glu Ser Arg Asn     Met     Ile Asn Ile Asp Thr Phe<br>         205                        210                  215 | 720 |
| att atg caa ata aaa caa act ttt aaa agt ttc aat gaa gct act agt<br>Ile Met Gln Ile Lys Gln Thr Phe Lys Ser Phe Asn Glu Ala Thr Ser<br>         220                        225                  230 | 768 |
| ttc ttt cac gta tcc atg taa aat aaa atc att gtc tct ttg cca ttc<br>Phe Phe His Val Ser Met     Asn Lys Ile Ile Val Ser Leu Pro Phe<br>235                        240                        245 | 816 |
| cgg aat ttc atc cca act ata tag cct tct tag tac ttt ttt agc ttt<br>Arg Asn Phe Ile Pro Thr Ile     Pro Ser     Tyr Phe Phe Ser Phe<br>         250                        255                  260 | 864 |
| agc gac ctc tgc ggg att tgc gga tgt ttt ccc tgc agc tct ctt ctt<br>Ser Asp Leu Cys Gly Ile Cys Gly Cys Phe Pro Cys Ser Ser Leu Leu<br>         265                        270                  275 | 912 |
| cag ctc ttg cac act ctt agt cct ttc taa taa agt tga cat<br>Gln Leu Leu His Thr Leu Ser Pro Phe         Ser     His<br>         280                        285 | 954 |

<210> SEQ ID NO 24
<211> LENGTH: 12

```
<212> TYPE: PRT
<213> ORGANISM: Saccharomyces cerevisiae

<400> SEQUENCE: 24

Leu Gly Asp Asn Pro Val Leu His Leu Tyr Met Asp
1               5                   10

<210> SEQ ID NO 25
<211> LENGTH: 4
<212> TYPE: PRT
<213> ORGANISM: Saccharomyces cerevisiae

<400> SEQUENCE: 25

Leu Ile Thr Ile
1

<210> SEQ ID NO 26
<211> LENGTH: 11
<212> TYPE: PRT
<213> ORGANISM: Saccharomyces cerevisiae

<400> SEQUENCE: 26

Thr Ser Gln Val Ala Gln Cys Arg Asn Asn Asn
1               5                   10

<210> SEQ ID NO 27
<211> LENGTH: 33
<212> TYPE: PRT
<213> ORGANISM: Saccharomyces cerevisiae

<400> SEQUENCE: 27

Lys Met Glu Lys Leu Val Arg Met Thr Pro Asn Ile Lys Phe Thr Gly
1               5                   10                  15

Ala Asn Leu Phe Arg Lys Pro His Ser Ile Lys Asn Ser Ala Asn Tyr
            20                  25                  30

Ile

<210> SEQ ID NO 28
<211> LENGTH: 4
<212> TYPE: PRT
<213> ORGANISM: Saccharomyces cerevisiae

<400> SEQUENCE: 28

Asp Thr Pro Lys
1

<210> SEQ ID NO 29
<211> LENGTH: 11
<212> TYPE: PRT
<213> ORGANISM: Saccharomyces cerevisiae

<400> SEQUENCE: 29

Tyr Pro Lys Glu Leu Asn Leu Gly Pro Asn Phe
1               5                   10

<210> SEQ ID NO 30
<211> LENGTH: 13
<212> TYPE: PRT
<213> ORGANISM: Saccharomyces cerevisiae

<400> SEQUENCE: 30

Lys Thr Ile Ala Val Lys Ala Ala Glu Tyr Trp Asn Asn
1               5                   10
```

```
<210> SEQ ID NO 31
<211> LENGTH: 5
<212> TYPE: PRT
<213> ORGANISM: Saccharomyces cerevisiae

<400> SEQUENCE: 31

Thr Lys Thr Asn Lys
1               5

<210> SEQ ID NO 32
<211> LENGTH: 15
<212> TYPE: PRT
<213> ORGANISM: Saccharomyces cerevisiae

<400> SEQUENCE: 32

Pro Ser Ser Val Arg Ser Pro Leu Ser Phe Pro Lys Leu Ile Phe
1               5                   10                  15

<210> SEQ ID NO 33
<211> LENGTH: 15
<212> TYPE: PRT
<213> ORGANISM: Saccharomyces cerevisiae

<400> SEQUENCE: 33

His Asn Thr Thr Arg Asp Pro Lys Ala Asn Gly Asn Lys Arg Lys
1               5                   10                  15

<210> SEQ ID NO 34
<211> LENGTH: 14
<212> TYPE: PRT
<213> ORGANISM: Saccharomyces cerevisiae

<400> SEQUENCE: 34

Gly Lys Phe Leu Lys Ile Ala Val Val Gln Asn Thr Asp His
1               5                   10

<210> SEQ ID NO 35
<211> LENGTH: 15
<212> TYPE: PRT
<213> ORGANISM: Saccharomyces cerevisiae

<400> SEQUENCE: 35

Arg Asn Asn Gln Tyr Thr Asn Thr Lys Val Val Gln Leu Ile Ser
1               5                   10                  15

<210> SEQ ID NO 36
<211> LENGTH: 4
<212> TYPE: PRT
<213> ORGANISM: Saccharomyces cerevisiae

<400> SEQUENCE: 36

Gly Ser Asn Ser
1

<210> SEQ ID NO 37
<211> LENGTH: 4
<212> TYPE: PRT
<213> ORGANISM: Saccharomyces cerevisiae

<400> SEQUENCE: 37

Gly Val Thr Leu
1

<210> SEQ ID NO 38
```

```
<211> LENGTH: 8
<212> TYPE: PRT
<213> ORGANISM: Saccharomyces cerevisiae

<400> SEQUENCE: 38

Thr Met Lys Gly Ala Thr Gln Tyr
1               5

<210> SEQ ID NO 39
<211> LENGTH: 15
<212> TYPE: PRT
<213> ORGANISM: Saccharomyces cerevisiae

<400> SEQUENCE: 39

Thr Cys Lys Arg Pro Arg Ile Lys Glu Val Asp Tyr His Met Ile
1               5                   10                  15

<210> SEQ ID NO 40
<211> LENGTH: 13
<212> TYPE: PRT
<213> ORGANISM: Saccharomyces cerevisiae

<400> SEQUENCE: 40

Pro Cys Ser Cys Cys Lys His Phe Asp Ser Arg Phe Ile
1               5                   10

<210> SEQ ID NO 41
<211> LENGTH: 11
<212> TYPE: PRT
<213> ORGANISM: Saccharomyces cerevisiae

<400> SEQUENCE: 41

Gln Gln Tyr Ser Glu Glu Pro Glu Ser Arg Asn
1               5                   10

<210> SEQ ID NO 42
<211> LENGTH: 28
<212> TYPE: PRT
<213> ORGANISM: Saccharomyces cerevisiae

<400> SEQUENCE: 42

Ile Asn Ile Asp Thr Phe Ile Met Gln Ile Lys Gln Thr Phe Lys Ser
1               5                   10                  15

Phe Asn Glu Ala Thr Ser Phe Phe His Val Ser Met
            20                  25

<210> SEQ ID NO 43
<211> LENGTH: 16
<212> TYPE: PRT
<213> ORGANISM: Saccharomyces cerevisiae

<400> SEQUENCE: 43

Asn Lys Ile Ile Val Ser Leu Pro Phe Arg Asn Phe Ile Pro Thr Ile
1               5                   10                  15

<210> SEQ ID NO 44
<211> LENGTH: 30
<212> TYPE: PRT
<213> ORGANISM: Saccharomyces cerevisiae

<400> SEQUENCE: 44

Tyr Phe Phe Ser Phe Ser Asp Leu Cys Gly Ile Cys Gly Cys Phe Pro
1               5                   10                  15

Cys Ser Ser Leu Leu Gln Leu Leu His Thr Leu Ser Pro Phe
```

<210> SEQ ID NO 45
<211> LENGTH: 375
<212> TYPE: PRT
<213> ORGANISM: Monodelphis domestica

<400> SEQUENCE: 45

```
Met Ser Ser Ser Lys Gly Ser Ala Val Gly Pro Gly Asn Gly Ala Pro
1               5                   10                  15
Ala Ser Asn Arg Glu Thr Asp Thr Val Glu Leu Ala Glu Leu Gly Pro
            20                  25                  30
Leu Leu Ile Glu Lys Gly Lys Arg Met Thr Pro Ser Ser Thr Lys Val
        35                  40                  45
Glu Glu Glu Gln Thr Cys Pro Val Pro Gln Glu Glu Glu Glu Glu Val
50                  55                  60
Arg Val Leu Thr Leu Pro Leu Gln Ala His His Ala Met Glu Lys Met
65                  70                  75                  80
Glu Glu Phe Val Tyr Lys Val Trp Glu Gly Arg Trp Arg Val Ile Pro
                85                  90                  95
Tyr Asp Val Leu Pro Asp Trp Leu Lys Asp Asn Asp Tyr Leu Leu His
            100                 105                 110
Gly His Arg Pro Pro Met Pro Ser Phe Arg Ala Cys Phe Lys Ser Ile
        115                 120                 125
Phe Arg Ile His Thr Glu Thr Gly Asn Ile Trp Thr His Leu Leu Gly
130                 135                 140
Phe Val Leu Phe Leu Phe Leu Gly Ile Leu Thr Met Leu Arg Pro Asn
145                 150                 155                 160
Met Tyr Phe Met Ala Pro Leu Gln Glu Lys Val Val Phe Gly Met Phe
                165                 170                 175
Phe Leu Gly Ala Val Leu Cys Leu Ser Phe Ser Trp Leu Phe His Thr
            180                 185                 190
Val Tyr Cys His Ser Glu Lys Val Ser Arg Thr Phe Ser Lys Leu Asp
        195                 200                 205
Tyr Ser Gly Ile Ala Leu Leu Ile Met Gly Ser Phe Val Pro Trp Leu
210                 215                 220
Tyr Tyr Ser Phe Tyr Cys Ser Pro Gln Pro Arg Leu Ile Tyr Leu Ser
225                 230                 235                 240
Ile Val Cys Val Leu Gly Ile Ser Ala Ile Ile Val Ala Gln Trp Asp
                245                 250                 255
Arg Phe Ala Thr Pro Lys His Arg Gln Thr Arg Ala Gly Val Phe Leu
            260                 265                 270
Gly Leu Gly Leu Ser Gly Val Val Pro Thr Met His Phe Thr Ile Ala
        275                 280                 285
Glu Gly Phe Val Lys Ala Thr Thr Val Gly Gln Met Gly Trp Phe Phe
290                 295                 300
Leu Met Ala Val Met Tyr Ile Thr Gly Ala Gly Leu Tyr Ala Ala Arg
305                 310                 315                 320
Ile Pro Glu Arg Phe Phe Pro Gly Lys Phe Asp Ile Trp Phe Gln Ser
                325                 330                 335
His Gln Ile Phe His Val Leu Val Ala Ala Ala Phe Val His Phe
            340                 345                 350
Tyr Gly Val Ser Asn Leu Gln Glu Phe Arg Tyr Gly Leu Glu Gly Gly
        355                 360                 365
```

-continued

```
Cys Thr Asp Asp Ser Leu Leu
    370                 375

<210> SEQ ID NO 46
<211> LENGTH: 375
<212> TYPE: PRT
<213> ORGANISM: Gallus gallus

<400> SEQUENCE: 46

Met Ala Ser Arg Lys Ala Ala Ala Ala Gln Gly Asn Gly Leu Ala
1               5                   10                  15

Ala Ala Gly Arg Asp Arg Ala His Leu Glu Leu Ala Glu Leu Gly Pro
            20                  25                  30

Leu Leu Glu Glu Lys Gly Glu Gln Gly Ala Ala Gly Thr Ala Ser Ala
                35                  40                  45

Glu Asp Pro Pro Cys Pro Val Ala Arg Glu Glu Glu Glu Val Val
    50                  55                  60

Arg Val Leu Thr Leu Pro Leu Gln Ala His His Ala Met Glu Lys Met
65                  70                  75                  80

Glu Glu Phe Val Tyr Lys Val Trp Glu Gly Arg Trp Arg Val Ile Pro
                85                  90                  95

Tyr Asp Val Leu Pro Asp Trp Leu Lys Asp Asn Asp Tyr Leu Leu His
            100                 105                 110

Gly His Arg Pro Pro Met Pro Ser Phe Arg Ala Cys Phe Lys Ser Ile
            115                 120                 125

Phe Arg Ile His Thr Glu Thr Gly Asn Ile Trp Thr His Leu Leu Gly
    130                 135                 140

Phe Val Leu Phe Leu Cys Leu Gly Ile Leu Thr Met Leu Arg Pro Asn
145                 150                 155                 160

Met Tyr Phe Met Ala Pro Leu Gln Glu Lys Val Val Phe Gly Met Phe
                165                 170                 175

Phe Leu Gly Ala Val Leu Cys Leu Ser Phe Ser Trp Leu Phe His Thr
            180                 185                 190

Val Tyr Cys His Ser Glu Lys Val Ser Arg Thr Phe Ser Lys Leu Asp
            195                 200                 205

Tyr Ser Gly Ile Ala Leu Leu Ile Met Gly Ser Phe Val Pro Trp Leu
    210                 215                 220

Tyr Tyr Ser Phe Tyr Cys Ser Pro Gln Pro Arg Leu Ile Tyr Leu Ser
225                 230                 235                 240

Ile Val Cys Val Leu Gly Ile Ser Ala Ile Val Ala Gln Trp Asp
                245                 250                 255

Arg Phe Ala Thr Pro Lys His Arg Gln Thr Arg Ala Gly Val Phe Leu
            260                 265                 270

Gly Leu Gly Leu Ser Gly Val Val Pro Thr Met His Phe Thr Ile Ala
    275                 280                 285

Glu Gly Phe Val Lys Ala Thr Thr Val Gly Gln Met Gly Trp Phe Phe
290                 295                 300

Leu Met Ala Val Met Tyr Ile Thr Gly Ala Gly Leu Tyr Ala Ala Arg
305                 310                 315                 320

Ile Pro Glu Arg Phe Phe Pro Gly Lys Phe Asp Ile Trp Phe Gln Ser
                325                 330                 335

His Gln Ile Phe His Val Leu Val Ala Ala Ala Phe Val His Phe
            340                 345                 350

Tyr Gly Val Ser Asn Leu Gln Glu Phe Arg Tyr Gly Leu Glu Gly Gly
    355                 360                 365
```

```
Cys Thr Asp Ser Leu Leu
    370             375

<210> SEQ ID NO 47
<211> LENGTH: 378
<212> TYPE: PRT
<213> ORGANISM: Xenopus tropicalis

<400> SEQUENCE: 47

Met Ala Thr Cys Lys Pro Leu Ser Ser Gly Gln Glu Ser Ala Leu Ser
1               5                   10                  15

Ser Ser Ser Ser Arg Gly Glu Thr Asp Asp Leu Glu Leu Ala Glu Leu
            20                  25                  30

Gly Pro Leu Leu Glu Ala Arg Arg Glu Arg Ile Gly Gln Thr Ser Ser
        35                  40                  45

Gly Asp Glu Asn Gln Ala Ser Lys Val Ser Pro Glu Glu Glu Glu
    50                  55                  60

Glu Glu Val Arg Val Leu Thr Leu Pro Leu Gln Ala His His Ala Met
65                  70                  75                  80

Glu Lys Met Glu Glu Phe Val Tyr Lys Val Trp Glu Gly Arg Trp Arg
                85                  90                  95

Val Ile Pro Tyr Asp Val Leu Pro Asp Trp Leu Lys Asp Asn Asp Tyr
            100                 105                 110

Leu Leu His Gly His Arg Pro Pro Met Pro Ser Phe Arg Ala Cys Phe
        115                 120                 125

Arg Ser Ile Phe Arg Ile His Thr Glu Thr Gly Asn Ile Trp Thr His
    130                 135                 140

Leu Leu Gly Phe Val Leu Phe Leu Ser Leu Gly Val Leu Thr Met Leu
145                 150                 155                 160

Arg Pro Asn Met Tyr Phe Met Ala Pro Leu Gln Glu Lys Val Val Phe
                165                 170                 175

Gly Met Phe Phe Leu Gly Ala Val Leu Cys Leu Ser Phe Ser Trp Leu
            180                 185                 190

Phe His Thr Val Tyr Cys His Ser Glu Lys Val Ser Arg Thr Phe Ser
        195                 200                 205

Lys Leu Asp Tyr Ser Gly Ile Ala Leu Leu Ile Met Gly Ser Phe Val
    210                 215                 220

Pro Trp Leu Tyr Tyr Ser Phe Tyr Cys Ser Pro Gln Pro Arg Leu Ile
225                 230                 235                 240

Tyr Leu Ser Ile Val Cys Val Leu Gly Ile Thr Ala Ile Val Val Ala
                245                 250                 255

Gln Trp Asp Arg Phe Ala Thr Pro Lys His Arg Pro Thr Arg Ala Gly
            260                 265                 270

Val Phe Leu Gly Leu Gly Leu Ser Gly Ile Val Pro Thr Leu His Phe
        275                 280                 285

Thr Ile Ala Glu Gly Phe Val Lys Ala Thr Thr Val Gly Gln Met Gly
    290                 295                 300

Trp Phe Phe Leu Met Ala Val Met Tyr Ile Thr Gly Ala Gly Leu Tyr
305                 310                 315                 320

Ala Ala Arg Ile Pro Glu Arg Phe Phe Pro Gly Lys Phe Asp Ile Trp
                325                 330                 335

Phe Gln Ser His Gln Ile Phe His Val Leu Val Val Ala Ala Ala Phe
            340                 345                 350

Ile His Phe Tyr Gly Ile Ser Asn Leu Gln Glu Phe Arg Tyr Ala Leu
```

```
                355                 360                 365
Glu Gly Gly Cys Thr Asp Asp Ser Leu Leu
            370                 375

<210> SEQ ID NO 48
<211> LENGTH: 377
<212> TYPE: PRT
<213> ORGANISM: Danio rerio

<400> SEQUENCE: 48

Met Thr Thr Cys His His Gly Asp Cys Gly Ser Asn Ser Asp Ala Glu
1               5                   10                  15

Arg Arg Ala Thr Asp Asp Glu Ala Asn Met Glu Asp Ala Glu Leu Ser
            20                  25                  30

Glu Leu Gly Pro Leu Leu Thr Ser Pro Ala Asn Ser Glu Glu Ser Arg
        35                  40                  45

Gly Ala Ser Ala Ser Pro Asp Glu Asn Glu Asp Glu Lys Glu Glu Gly
    50                  55                  60

Gly Leu Arg Val Val Thr Leu Pro Met Gln Ala His His Ala Met Glu
65                  70                  75                  80

Lys Met Glu Glu Phe Val His Lys Ile Trp Glu Gly His Trp Arg Val
                85                  90                  95

Ile Pro Tyr His Leu Leu Pro Asp Trp Leu Lys Asp Asn Asp Tyr Leu
            100                 105                 110

Leu His Gly His Arg Pro Pro Met Pro Ser Phe Arg Ala Cys Phe Gly
        115                 120                 125

Ser Ile Phe Arg Ile His Thr Glu Thr Gly Asn Ile Trp Thr His Leu
    130                 135                 140

Leu Gly Leu Ile Leu Phe Leu Cys Leu Gly Thr Leu Thr Met Leu Arg
145                 150                 155                 160

Pro Asn Val Ser Phe Met Ala Pro Val Gln Glu Lys Val Val Phe Gly
                165                 170                 175

Val Phe Phe Leu Gly Ala Val Leu Cys Leu Cys Phe Ser Trp Leu Phe
            180                 185                 190

His Thr Val Tyr Cys His Ser Glu Lys Val Ser Arg Thr Phe Ser Lys
        195                 200                 205

Leu Asp Tyr Ser Gly Ile Ala Leu Leu Ile Met Gly Ser Phe Val Pro
    210                 215                 220

Trp Leu Tyr Tyr Ser Phe Tyr Cys Ser Pro Gln Pro Arg Leu Ile Tyr
225                 230                 235                 240

Leu Ser Val Val Cys Val Leu Gly Val Ala Ala Ile Ile Val Ala Gln
                245                 250                 255

Trp Asp Arg Phe Ala Thr Pro Arg His Arg Ser Thr Arg Ala Gly Val
            260                 265                 270

Phe Leu Gly Leu Gly Leu Ser Gly Leu Val Pro Thr Met His Phe Thr
        275                 280                 285

Ile Ala Glu Gly Phe Val Lys Ala Thr Thr Val Gly Gln Met Gly Trp
    290                 295                 300

Phe Tyr Leu Met Gly Ala Met Tyr Ile Ser Gly Ala Ala Leu Tyr Ala
305                 310                 315                 320

Ala Arg Ile Pro Glu Arg Tyr Phe Pro Gly Arg Cys Asp Ile Trp Phe
                325                 330                 335

Gln Ser His Gln Ile Phe His Val Leu Val Gly Ala Ala Phe Val
            340                 345                 350
```

His Phe Tyr Gly Ile Ser Asn Leu Gln Glu Phe Arg Tyr Gly Leu Glu
            355                 360                 365

Gly Gly Cys Thr Asp Asp Thr Leu Leu
            370                 375

<210> SEQ ID NO 49
<211> LENGTH: 375
<212> TYPE: PRT
<213> ORGANISM: Danio rerio

<400> SEQUENCE: 49

Met Ser Gly Gln Ile Arg Ser Ala Ser His Ala Asp Cys Arg Val Thr
1               5                   10                  15

Glu Glu Cys His Val Pro Ala Asp Val Glu Leu Met Glu Leu Gly Pro
            20                  25                  30

Leu Leu Glu Glu Asn Gly Pro Met Gly Ala Lys Gly Leu Gln Ser Glu
        35                  40                  45

Gly Ala Gly Ala Leu Ala Asp Asp Glu Glu Asp Glu Glu Val Gly
    50                  55                  60

Glu Val Leu Thr Leu Pro Leu Gln Ala His His Ala Met Glu Lys Met
65                  70                  75                  80

Glu Glu Phe Val His Lys Val Trp Glu Gly Arg Trp Arg Val Ile Pro
                85                  90                  95

Phe His Val Leu Pro Glu Trp Leu Lys Asp Asn Asp Tyr Leu Leu His
            100                 105                 110

Gly His Arg Pro Pro Met Pro Ser Phe Arg Ala Cys Phe Gly Ser Ile
        115                 120                 125

Phe Arg Ile His Thr Glu Thr Gly Asn Ile Trp Thr His Leu Leu Gly
    130                 135                 140

Leu Ile Leu Phe Leu Cys Leu Gly Thr Leu Thr Met Leu Arg Pro Asn
145                 150                 155                 160

Met Tyr Phe Met Ala Pro Leu Gln Glu Lys Val Val Phe Gly Met Phe
                165                 170                 175

Phe Leu Gly Ala Val Leu Cys Leu Ser Phe Ser Trp Leu Phe His Thr
            180                 185                 190

Val Tyr Cys His Ser Glu Lys Val Ser Arg Thr Phe Ser Lys Leu Asp
        195                 200                 205

Tyr Ser Gly Ile Ala Leu Leu Ile Met Gly Ser Phe Val Pro Trp Leu
    210                 215                 220

Tyr Tyr Ser Phe Tyr Cys Ser Pro Gln Pro Arg Leu Ile Tyr Leu Thr
225                 230                 235                 240

Ile Val Cys Val Leu Gly Ile Ala Ala Ile Val Ala Gln Trp Asp
                245                 250                 255

Arg Phe Ser Thr Pro Arg His Arg Pro Thr Arg Ala Gly Val Phe Met
            260                 265                 270

Ser Leu Gly Leu Ser Gly Ile Val Pro Thr Met His Phe Thr Ile Glu
        275                 280                 285

Glu Gly Phe Val Lys Ala Thr Thr Val Gly Gln Met Gly Trp Phe Tyr
    290                 295                 300

Leu Met Gly Ala Met Tyr Ile Thr Gly Ala Gly Leu Tyr Ala Ala Arg
305                 310                 315                 320

Ile Pro Glu Arg Tyr Phe Pro Gly Lys Cys Asp Ile Trp Phe His Ser
                325                 330                 335

His Gln Ile Phe His Val Leu Val Val Ala Ala Ala Phe Ile His Phe
            340                 345                 350

```
Tyr Gly Val Ser Asn Leu Gln Glu Phe Arg Tyr Gly Leu Glu Gly Gly
        355                 360                 365

Cys Thr Asp Asp Thr Leu Leu
        370                 375

<210> SEQ ID NO 50
<211> LENGTH: 386
<212> TYPE: PRT
<213> ORGANISM: Homo sapiens

<400> SEQUENCE: 50

Met Asn Glu Pro Thr Glu Asn Arg Leu Gly Cys Ser Arg Thr Pro Glu
1               5                   10                  15

Pro Asp Ile Arg Leu Arg Lys Gly His Gln Leu Asp Gly Thr Arg Arg
            20                  25                  30

Gly Asp Asn Asp Ser His Gln Gly Asp Leu Glu Pro Ile Leu Glu Ala
        35                  40                  45

Ser Val Leu Ser Ser His His Lys Lys Ser Ser Glu Glu His Glu Tyr
    50                  55                  60

Ser Asp Glu Ala Pro Gln Glu Asp Glu Gly Phe Met Gly Met Ser Pro
65                  70                  75                  80

Leu Leu Gln Ala His His Ala Met Glu Lys Met Glu Glu Phe Val Cys
                85                  90                  95

Lys Val Trp Glu Gly Arg Trp Arg Val Ile Pro His Asp Val Leu Pro
            100                 105                 110

Asp Trp Leu Lys Asp Asn Asp Phe Leu Leu His Gly His Arg Pro Pro
        115                 120                 125

Met Pro Ser Phe Arg Ala Cys Phe Lys Ser Ile Phe Arg Ile His Thr
    130                 135                 140

Glu Thr Gly Asn Ile Trp Thr His Leu Leu Gly Cys Val Ser Phe Leu
145                 150                 155                 160

Cys Leu Gly Ile Phe Tyr Met Phe Arg Pro Asn Ile Ser Phe Val Ala
                165                 170                 175

Pro Leu Gln Glu Lys Val Val Phe Gly Leu Phe Phe Leu Gly Ala Ile
            180                 185                 190

Leu Cys Leu Ser Phe Ser Trp Leu Phe His Thr Val Tyr Cys His Ser
        195                 200                 205

Glu Gly Val Ser Arg Leu Phe Ser Lys Leu Asp Tyr Ser Gly Ile Ala
    210                 215                 220

Leu Leu Ile Met Gly Ser Phe Val Pro Trp Leu Tyr Tyr Ser Phe Tyr
225                 230                 235                 240

Cys Asn Pro Gln Pro Cys Phe Ile Tyr Leu Ile Val Ile Cys Val Leu
                245                 250                 255

Gly Ile Ala Ala Ile Ile Val Ser Gln Trp Asp Met Phe Ala Thr Pro
            260                 265                 270

Gln Tyr Arg Gly Val Arg Ala Gly Val Phe Leu Gly Leu Gly Leu Ser
        275                 280                 285

Gly Ile Ile Pro Thr Leu His Tyr Val Ile Ser Glu Gly Phe Leu Lys
    290                 295                 300

Ala Ala Thr Ile Gly Gln Ile Gly Trp Leu Met Leu Met Ala Ser Leu
305                 310                 315                 320

Tyr Ile Thr Gly Ala Ala Leu Tyr Ala Ala Arg Ile Pro Glu Arg Phe
                325                 330                 335

Phe Pro Gly Lys Cys Asp Ile Trp Phe His Ser His Gln Leu Phe His
```

```
                   340                 345                 350
Ile Phe Val Val Ala Gly Ala Phe Val His Phe His Gly Val Ser Asn
                355                 360                 365

Leu Gln Glu Phe Arg Phe Met Ile Gly Gly Gly Cys Ser Glu Glu Asp
        370                 375                 380

Ala Leu
385

<210> SEQ ID NO 51
<211> LENGTH: 387
<212> TYPE: PRT
<213> ORGANISM: Monodelphis domestica

<400> SEQUENCE: 51

Met Asn Glu Thr Ala Asp Leu Val Ser Gly Cys Asn Ser Thr Pro Glu
1               5                   10                  15

Pro Val Ile Arg Leu Arg Lys Gly Tyr Gln Ser Asp Val Ser Ala Lys
            20                  25                  30

Gly His Asn Asp Asn His Gln Gly Glu Asp Leu Gly Pro Asp Leu Ala
        35                  40                  45

Ala Ser Ile Pro Cys Ser Tyr Phe Lys Asn Lys Ser Glu Glu His Asp
    50                  55                  60

Cys Asn His Gly Gln Ser Gln Glu Asp Glu Gly Phe Met Ala Met Ser
65                  70                  75                  80

Pro Leu Leu Gln Ala His His Ala Met Glu Arg Met Glu Glu Phe Val
                85                  90                  95

Cys Lys Val Trp Glu Gly Arg Trp Arg Val Ile Pro His Asp Val Leu
            100                 105                 110

Pro Asp Trp Leu Lys Asp Asn Asp Phe Leu Leu His Gly His Arg Pro
        115                 120                 125

Pro Met Pro Ser Phe Arg Ala Cys Phe Lys Ser Ile Phe Arg Ile His
    130                 135                 140

Thr Glu Thr Gly Asn Ile Trp Thr His Leu Leu Gly Cys Val Phe Phe
145                 150                 155                 160

Leu Cys Leu Gly Ile Phe Tyr Met Phe Arg Pro Asn Ile Ser Phe Val
                165                 170                 175

Ala Pro Leu Gln Glu Lys Val Val Phe Gly Leu Phe Phe Leu Gly Ala
            180                 185                 190

Ile Leu Cys Leu Ser Phe Ser Trp Leu Phe His Thr Val Tyr Cys His
        195                 200                 205

Ser Glu Ala Val Ser Arg Ile Phe Ser Lys Leu Asp Tyr Ser Gly Ile
    210                 215                 220

Ala Leu Leu Ile Met Gly Ser Phe Val Pro Trp Leu Tyr Tyr Ser Phe
225                 230                 235                 240

Tyr Cys Asn Pro Gln Pro Cys Phe Ile Tyr Leu Ile Val Ile Cys Val
                245                 250                 255

Leu Gly Ile Ala Ala Ile Ile Val Ser Gln Trp Asp Met Phe Ala Thr
            260                 265                 270

Pro Gln Tyr Arg Gly Val Arg Ala Gly Val Phe Leu Gly Leu Gly Leu
        275                 280                 285

Ser Gly Ile Ile Pro Thr Leu His Tyr Val Phe Ser Glu Gly Phe Leu
    290                 295                 300

Lys Ala Ala Thr Ile Gly Gln Ile Gly Trp Leu Leu Leu Met Ala Cys
305                 310                 315                 320
```

Leu Tyr Ile Thr Gly Ala Ala Leu Tyr Ala Ala Arg Ile Pro Glu Arg
                325                 330                 335

Phe Phe Pro Gly Lys Cys Asp Ile Trp Phe His Ser His Gln Leu Phe
                340                 345                 350

His Ile Phe Val Val Ala Gly Ala Phe Val His Phe His Gly Val Ser
                355                 360                 365

Asn Leu Gln Glu Phe Arg Phe Met Ile Gly Gly Cys Ser Glu Glu
            370                 375                 380

Asp Ala Leu
385

<210> SEQ ID NO 52
<211> LENGTH: 386
<212> TYPE: PRT
<213> ORGANISM: Gallus gallus

<400> SEQUENCE: 52

Met Asn Glu Leu Thr Glu Leu Asp Asn Ala Gly Ser Pro Glu Pro Gly
1               5                   10                  15

Leu Arg Leu Arg Lys Gly His Met Ser Asp Ser Ala Thr Thr Gln Thr
                20                  25                  30

Ala Phe Glu Glu Asp Ser Ser Glu Gln Arg Leu Leu Leu Val Glu Pro
            35                  40                  45

Pro Leu Ser Ser Asn Gln Glu Asn Ser Ser Glu Asp Ser Asn His Asn
        50                  55                  60

Asp Glu Ser Pro Gln Glu Asp Glu Gly Phe Met Gly Met Ser Pro Leu
65                  70                  75                  80

Leu Gln Ala His His Ala Met Glu Arg Met Glu Glu Phe Val Cys Lys
                85                  90                  95

Val Trp Glu Gly Arg Trp Arg Val Ile Pro His Asp Val Leu Pro Asp
                100                 105                 110

Trp Leu Lys Asp Asn Asp Tyr Leu Leu His Gly His Arg Pro Pro Met
            115                 120                 125

Pro Ser Phe Arg Ala Cys Phe Lys Ser Ile Phe Arg Ile His Thr Glu
        130                 135                 140

Thr Gly Asn Ile Trp Thr His Leu Leu Gly Cys Val Phe Phe Leu Cys
145                 150                 155                 160

Leu Gly Ile Phe Tyr Met Phe Arg Pro Asn Met Ser Phe Val Ala Pro
                165                 170                 175

Val Gln Glu Lys Val Val Val Gly Leu Phe Phe Leu Gly Ala Ile Leu
                180                 185                 190

Cys Leu Ser Phe Ser Trp Leu Phe His Thr Val Tyr Cys His Ser Glu
            195                 200                 205

Gly Val Ser Arg Leu Phe Ser Lys Leu Asp Tyr Ser Gly Ile Ala Leu
        210                 215                 220

Leu Ile Met Gly Ser Phe Val Pro Trp Leu Tyr Tyr Ser Phe Tyr Cys
225                 230                 235                 240

Asn Pro Gln Pro Cys Phe Ile Tyr Leu Ile Val Ile Cys Val Leu Gly
                245                 250                 255

Ile Ala Ala Ile Ile Val Ser Gln Trp Asp Met Phe Ala Thr Pro Gln
                260                 265                 270

Tyr Arg Gly Val Arg Ala Gly Val Phe Leu Gly Leu Gly Leu Ser Gly
            275                 280                 285

Val Ile Pro Thr Leu His Phe Val Ile Ser Glu Gly Leu Leu Lys Ala
        290                 295                 300

```
Ala Thr Met Gly Gln Ile Gly Trp Leu Ala Leu Met Ala Cys Leu Tyr
305                 310                 315                 320

Ile Thr Gly Ala Ala Leu Tyr Ala Ala Arg Ile Pro Glu Arg Phe Phe
                325                 330                 335

Pro Gly Lys Cys Asp Ile Trp Phe His Ser His Gln Leu Phe His Val
            340                 345                 350

Phe Val Val Ala Gly Ala Phe Val His Phe His Gly Val Ser Asn Leu
                355                 360                 365

Gln Glu Phe Arg Phe Thr Val Gly Gly Gly Cys Thr Glu Glu Glu Gly
        370                 375                 380

Met Gln
385

<210> SEQ ID NO 53
<211> LENGTH: 387
<212> TYPE: PRT
<213> ORGANISM: Xenopus tropicalis

<400> SEQUENCE: 53

Met Asn Thr Gln Glu Asn Glu Gln Gly Cys Ser Thr Gly Pro Glu
1               5                   10                  15

Ser Val Leu Arg Leu Arg Lys Gly His Met Pro Val Thr Ser Glu Glu
                20                  25                  30

Thr Asp Ser Gln His Glu Gln Phe Asp His Leu Cys Pro Leu Leu Ala
                35                  40                  45

Asp Pro Pro Pro Cys Pro Ala Gln Asp Asn Asn Val Glu Glu Asn Glu
        50                  55                  60

Ser Thr Glu Glu Pro Ala Gln Glu Asp Glu Gly Phe Met Gly Met Ala
65                  70                  75                  80

Pro Leu Leu Gln Ala His His Ala Met Glu Arg Val Glu Glu Phe Val
                85                  90                  95

Cys Lys Val Trp Glu Gly Arg Trp Arg Val Ile Pro His Asp Val Leu
                100                 105                 110

Pro Asp Trp Leu Lys Asp Asn Asp Tyr Leu Leu His Gly His Arg Pro
            115                 120                 125

Pro Met Pro Ser Phe Arg Ala Cys Phe Lys Ser Ile Phe Arg Ile His
        130                 135                 140

Thr Glu Thr Gly Asn Ile Trp Thr His Leu Leu Gly Cys Val Phe Phe
145                 150                 155                 160

Leu Cys Leu Gly Ile Phe Tyr Met Phe Arg Pro Asn Met Ala Phe Ile
                165                 170                 175

Ala Pro Val Gln Glu Lys Val Val Phe Gly Met Phe Phe Leu Gly Ala
            180                 185                 190

Ile Leu Cys Leu Ser Phe Ser Trp Leu Phe His Thr Val Tyr Cys His
        195                 200                 205

Ser Glu Gly Val Ser Arg Val Phe Ser Lys Leu Asp Tyr Ser Gly Ile
    210                 215                 220

Ala Leu Leu Ile Met Gly Ser Phe Val Pro Trp Leu Tyr Tyr Ser Phe
225                 230                 235                 240

Tyr Cys Asn Pro Gln Pro Cys Phe Ile Tyr Leu Ile Ile Ile Cys Val
                245                 250                 255

Leu Gly Ile Ala Ala Ile Ile Val Ser Gln Trp Asp Leu Phe Ala Thr
                260                 265                 270

Pro Gln Tyr Arg Gly Val Arg Ala Gly Val Phe Val Gly Leu Gly Leu
```

```
                    275                 280                 285

Ser Gly Ile Ile Pro Thr Leu His Phe Val Ile Ala Glu Gly Phe Leu
    290                 295                 300

Lys Ala Ala Thr Met Gly Gln Ile Gly Trp Leu Val Leu Met Ala Ser
305                 310                 315                 320

Leu Tyr Ile Thr Gly Ala Ala Leu Tyr Ala Ala Arg Ile Pro Glu Arg
                    325                 330                 335

Phe Phe Pro Gly Lys Cys Asp Ile Trp Phe His Ser His Gln Leu Phe
                340                 345                 350

His Ile Phe Val Val Ala Gly Ala Phe Val His Phe His Gly Val Ser
                355                 360                 365

Asn Leu Gln Glu Val Arg Phe Thr Val Gly Gly Cys Ala Ala Gln
370                 375                 380

Glu Val Leu
385

<210> SEQ ID NO 54
<211> LENGTH: 358
<212> TYPE: PRT
<213> ORGANISM: Danio rerio

<400> SEQUENCE: 54

Met Arg Ser Cys Thr Asp His Arg Ser Asp Ser Pro Gly Gln Asn Cys
1               5                   10                  15

Leu His Ala Arg Arg Val Met His Glu Lys Glu Glu Thr Thr Val Arg
                20                  25                  30

Glu Glu Glu Asp Glu Glu Glu Glu Glu Glu Glu Glu Asp Lys Ser
            35                  40                  45

Ser Asp Glu Gly Leu Leu Leu Gln Ala His His Ala Met Glu Arg Met
    50                  55                  60

Glu Glu Phe Val His Lys Val Trp Glu Gly Arg Trp Arg Val Ile Pro
65                  70                  75                  80

His Asp Val Leu Pro Asp Trp Leu Lys Asp Asn Asp Phe Leu Leu His
                85                  90                  95

Gly His Arg Pro Pro Met Pro Ser Phe Arg Ala Cys Phe Lys Ser Ile
                100                 105                 110

Phe Arg Ile His Thr Glu Thr Gly Asn Ile Trp Thr His Leu Leu Gly
            115                 120                 125

Cys Leu Phe Phe Leu Cys Leu Gly Ile Val Tyr Met Phe Arg Pro Asn
    130                 135                 140

Met Ser Phe Val Ala Pro Phe Gln Glu Lys Ile Val Ile Gly Met Phe
145                 150                 155                 160

Phe Leu Gly Ala Ile Leu Cys Leu Ser Phe Ser Trp Leu Phe His Thr
                165                 170                 175

Val Tyr Cys His Ser Glu Gly Val Ser Arg Val Phe Ser Lys Leu Asp
                180                 185                 190

Tyr Ser Gly Ile Ala Phe Leu Ile Met Gly Ser Phe Val Pro Trp Leu
            195                 200                 205

Tyr Tyr Ser Phe Tyr Cys Ser Pro Gln Pro Cys Phe Ile Tyr Leu Ile
    210                 215                 220

Val Val Cys Ile Leu Gly Ile Ala Ala Ile Thr Val Ser Gln Cys Asp
225                 230                 235                 240

Phe Phe Ala Thr Pro Gln Tyr Arg Gly Val Arg Ala Gly Val Phe Val
                245                 250                 255
```

```
Gly Leu Gly Leu Ser Gly Val Val Pro Thr Leu His Phe Met Ile Ala
            260                 265                 270

Glu Gly Phe Leu Lys Ala Thr Thr Met Gly Gln Met Gly Trp Leu Phe
            275                 280                 285

Leu Met Ala Val Leu Tyr Ile Thr Gly Ala Cys Leu Tyr Ala Ala Arg
        290                 295                 300

Ile Pro Glu Arg Phe Phe Pro Gly Lys Cys Asp Ile Trp Phe His Ser
305                 310                 315                 320

His Gln Leu Phe His Ile Leu Val Val Ala Gly Ala Phe Val His Phe
                    325                 330                 335

His Gly Val Ser Asn Leu Gln Glu Phe Arg Tyr Glu Ala Gly Gly Gly
                340                 345                 350

Cys Ala Glu Asn Ala Val
            355

<210> SEQ ID NO 55
<211> LENGTH: 316
<212> TYPE: PRT
<213> ORGANISM: Saccharomyces cerevisiae

<400> SEQUENCE: 55

Met Ser Ile Thr Thr Arg Arg Arg Asn Gln Asp Ser Val Cys Cys
1               5                   10                  15

Lys Ala Thr Arg Ala Ser Ile Lys Val Glu Ala Val Ser Gly Gln Thr
                20                  25                  30

Val Phe Glu Lys Gln Lys Leu Leu His Asn Phe Asp Glu Leu Pro Glu
            35                  40                  45

Trp Gln Lys Asp Asn Asp Lys Ile Leu Thr Gly Tyr Val Arg Glu Thr
    50                  55                  60

Leu Ser Trp Lys Lys Cys Leu Tyr Ser Leu Phe Tyr Trp Asn Asn Glu
65                  70                  75                  80

Thr Val Asn Ile Tyr Thr His Leu Val Pro Ala Ile Val Tyr Phe Val
                85                  90                  95

Phe Ala Ile Thr Leu Thr Asn Tyr Phe Leu Ile Pro Val Phe Pro Ser
            100                 105                 110

Thr Ser Trp Ser Asp Tyr Thr Val Ile Asn Ile Phe Leu Met Gly Ala
        115                 120                 125

Phe Ser Cys Leu Met Cys Ser Cys Phe His Cys Met Lys Gln His
    130                 135                 140

Ser Glu Lys Gln Ser Asn Phe Trp Ser Lys Leu Asp Tyr Leu Gly Ile
145                 150                 155                 160

Ile Ser Leu Ile Ser Cys Ser Met Ile Pro Ile Tyr Phe Gly Tyr
                165                 170                 175

Phe Asp His Ile Ser Tyr Phe Ser Leu Phe Thr Ile Val Thr Leu Val
            180                 185                 190

Leu Ala Thr Phe Cys Thr Val Cys Val Leu His Asp Lys Phe Asn Thr
        195                 200                 205

Ser Thr Phe Arg Pro Phe Arg Ala Met Phe Ile Leu Phe Gly Phe
    210                 215                 220

Ser Gly Leu Leu Pro Leu Thr Thr Gly Phe Phe Lys Phe Gly Ile Gln
225                 230                 235                 240

Gly Val Leu Asn Arg Ile Lys Val Ser Phe Val Phe Trp Glu Ala Leu
                245                 250                 255

Phe Tyr Ile Ser Gly Ala Val Ile Tyr Gly Phe Arg Ile Pro Glu Thr
            260                 265                 270
```

Leu Ala Pro Gly Lys Phe Asp Phe Gly Ser Ser His Gln Ile Phe
            275                 280                 285

His Ile Met Val Val Leu Gly Ser Val Cys His Leu Lys Ala Ile Ile
    290                 295                 300

Asp Ser Tyr Lys Leu Met His Ser His Ile His Pro
305                 310                 315

<210> SEQ ID NO 56
<211> LENGTH: 317
<212> TYPE: PRT
<213> ORGANISM: Saccharomyces cerevisiae

<400> SEQUENCE: 56

Met Ser Thr Leu Leu Glu Arg Thr Lys Ser Val Gln Glu Leu Lys Lys
1               5                   10                  15

Arg Ala Ala Gly Lys Thr Ser Ala Asn Pro Ala Glu Val Ala Lys Ala
                20                  25                  30

Lys Lys Val Leu Arg Arg Leu Tyr Ser Trp Asp Glu Ile Pro Glu Trp
            35                  40                  45

Gln Arg Asp Asn Asp Phe Ile Leu His Gly Tyr Val Lys Glu Thr Ser
    50                  55                  60

Ser Phe Ile Glu Thr Phe Lys Ser Leu Phe Tyr Leu His Asn Glu Ser
65                  70                  75                  80

Val Asn Ile Tyr Ser His Leu Ile Pro Ala Leu Gly Phe Phe Thr Val
                85                  90                  95

Leu Leu Leu Asp Lys Ser Thr Ile Lys Val Phe Ala Thr Thr Thr Trp
            100                 105                 110

Leu Asp His Met Val Ile Asp Leu Phe Tyr Ser Gly Ala Phe Ala Cys
    115                 120                 125

Leu Ile Leu Ser Ser Ser Phe His Cys Leu Lys Ser His Ser Leu Arg
130                 135                 140

Ile Ala Thr Leu Gly Asn Lys Leu Asp Tyr Leu Gly Ile Cys Ile Leu
145                 150                 155                 160

Ile Val Thr Ser Met Val Ser Ile Leu Tyr Tyr Gly Tyr Phe Glu Lys
                165                 170                 175

Phe Ser Leu Phe Cys Leu Phe Ala Leu Ile Thr Val Ser Phe Gly Ile
            180                 185                 190

Ala Cys Ser Ile Val Ser Leu Lys Asp Lys Phe Arg Lys Arg Glu Trp
    195                 200                 205

Arg Pro Tyr Arg Ala Gly Leu Phe Val Cys Phe Gly Leu Ser Ser Ile
210                 215                 220

Ile Pro Ile Phe Ser Gly Leu Tyr Cys Tyr Ser Phe Ser Glu Ile Trp
225                 230                 235                 240

Thr Gln Ile Gln Leu Phe Trp Val Leu Leu Gly Val Leu Tyr Ile
                245                 250                 255

Ile Gly Ala Val Leu Tyr Gly Met Arg Phe Pro Glu Lys Ile Cys Pro
            260                 265                 270

Gly Lys Phe Asp Ile Trp Gly His Ser His Gln Leu Phe His Phe Leu
    275                 280                 285

Val Val Ile Ala Ala Leu Cys His Leu Arg Gly Leu Leu Asn Ser Tyr
    290                 295                 300

Glu Leu Val His Ile Lys Met Glu Asn Gly Ile Val Ser
305                 310                 315

```
<210> SEQ ID NO 57
<211> LENGTH: 330
<212> TYPE: PRT
<213> ORGANISM: Homo sapiens

<400> SEQUENCE: 57

Met Leu Ser Leu Lys Leu Pro Arg Leu Phe Ser Ile Asp Gln Ile Pro
1               5                   10                  15

Gln Val Phe His Glu Gln Gly Ile Leu Phe Gly Tyr Arg His Pro Gln
            20                  25                  30

Ser Ser Ala Thr Ala Cys Ile Leu Ser Leu Phe Gln Met Thr Asn Glu
        35                  40                  45

Thr Leu Asn Ile Trp Thr His Leu Leu Pro Phe Trp Phe Phe Ala Trp
    50                  55                  60

Arg Phe Val Thr Ala Leu Tyr Met Thr Asp Ile Lys Asn Asp Ser Tyr
65                  70                  75                  80

Ser Trp Pro Met Leu Val Tyr Met Cys Thr Ser Cys Val Tyr Pro Leu
                85                  90                  95

Val Ser Ser Cys Ala His Thr Phe Ser Ser Met Ser Lys Asn Ala Arg
            100                 105                 110

His Ile Cys Tyr Phe Leu Asp Tyr Gly Ala Val Asn Leu Phe Ser Leu
        115                 120                 125

Gly Ser Ala Ile Ala Tyr Ser Ala Tyr Thr Phe Pro Asp Ala Leu Met
    130                 135                 140

Cys Thr Thr Phe His Asp Tyr Val Ala Leu Ala Val Leu Asn Thr
145                 150                 155                 160

Ile Leu Ser Thr Gly Leu Ser Cys Tyr Ser Arg Phe Leu Glu Val Gln
                165                 170                 175

Lys Pro Arg Leu Cys Lys Val Ile Arg Val Leu Ala Phe Ala Tyr Pro
            180                 185                 190

Tyr Thr Trp Asp Ser Leu Pro Ile Phe Tyr Arg Leu Phe Leu Phe Pro
        195                 200                 205

Gly Glu Ser Ala Gln Asn Glu Ala Thr Ser Tyr His Gln Lys His Met
    210                 215                 220

Ile Met Thr Leu Leu Ala Ser Phe Leu Tyr Ser Ala His Leu Pro Glu
225                 230                 235                 240

Arg Leu Ala Pro Gly Arg Phe Asp Tyr Ile Gly His Ser His Gln Leu
                245                 250                 255

Phe His Val Cys Val Ile Leu Ala Thr His Met Gln Met Glu Ala Ile
            260                 265                 270

Leu Leu Asp Lys Thr Leu Arg Lys Glu Trp Leu Leu Ala Thr Ser Lys
        275                 280                 285

Pro Phe Ser Phe Ser Gln Ile Ala Gly Ala Ile Leu Leu Cys Ile Ile
    290                 295                 300

Phe Ser Leu Ser Asn Ile Ile Tyr Phe Ser Ala Ala Leu Tyr Arg Ile
305                 310                 315                 320

Pro Lys Pro Glu Leu His Lys Lys Glu Thr
                325                 330

<210> SEQ ID NO 58
<211> LENGTH: 330
<212> TYPE: PRT
<213> ORGANISM: Monodelphis domestica

<400> SEQUENCE: 58

Met Leu Ser Leu Lys Leu Pro Lys Leu Phe Asn Ile Asp Gln Val Pro
```

```
              1               5                  10                 15
        Gln Val Phe His Glu Arg Gly Ile Ile Cys Gly Tyr Arg His Pro Gln
                         20                  25                 30

Ser Ser Ala Ile Ala Cys Val Leu Ser Leu Phe Gln Met Thr Asn Glu
                         35                  40                 45

Thr Leu Asn Ile Trp Thr His Leu Leu Pro Ser Trp Tyr Phe Met Trp
                         50                  55                 60

Arg Phe Met Ala Thr Leu Tyr Met Val Asp Phe Trp Asn Asp Ser Tyr
        65                   70                  75                 80

Ser Trp Pro Leu Leu Ile Tyr Leu Ser Thr Ser Phe Ile Tyr Pro Phe
                             85                  90                 95

Ala Ser Ser Cys Ala His Thr Phe Ser Ser Met Ser Lys Asn Ala Arg
                         100                 105                110

His Ile Cys Tyr Phe Leu Asp Tyr Gly Ala Val Asn Leu Phe Ser Leu
                         115                 120                125

Gly Ser Ala Ile Ala Tyr Ser Ala Tyr Thr Phe Pro Asp Met Leu Val
                         130                 135                140

Arg Thr Thr Phe His His Tyr Phe Val Ser Leu Ala Val Leu Asn Thr
        145                  150                 155                160

Ile Leu Ser Ile Gly Leu Ser Cys Tyr Ser Arg Phe Leu Glu Leu Gln
                             165                 170                175

Lys Pro Lys Leu Cys Lys Thr Leu Arg Ile Leu Ala Phe Ala Tyr Pro
                         180                 185                190

Tyr Ala Trp Asp Thr Val Pro Ile Ile Tyr Arg Leu Phe Leu Ser Ser
                         195                 200                205

Glu Glu Ser Ser Gly Glu Ala Ala Asn Pro Tyr His Gln Lys His Thr
        210                  215                 220

Val Ile Ala Ile Leu Ala Cys Phe Leu Tyr Ala Ala His Leu Pro Glu
        225                  230                 235                240

Arg Leu Ala Pro Gly Arg Phe Asp Tyr Ile Gly His Ser His Gln Leu
                         245                 250                255

Phe His Val Cys Val Ile Leu Ala Thr His Leu Gln Met Glu Ala Ile
                         260                 265                270

Phe Leu Asp Met Thr Leu Arg Lys Glu Trp Leu Leu Ala Thr Ser Ile
                         275                 280                285

Pro Pro Ser Phe Ser Gln Thr Ala Gly Ala Val Cys Leu Cys Ile Ile
                         290                 295                300

Phe Ser Ile Ile Asn Ile Ile Tyr Phe Ser Ile Ser Leu Tyr Gln Thr
        305                  310                 315                320

Pro Glu Pro Glu Ser Gln Lys Lys Glu Thr
                         325                 330

<210> SEQ ID NO 59
<211> LENGTH: 327
<212> TYPE: PRT
<213> ORGANISM: Gallus gallus

<400> SEQUENCE: 59

Met Leu Ser Leu Lys Leu Pro Arg Leu Leu Ser Ile His Gln Val Pro
        1                    5                  10                 15

Lys Val Tyr Gln Glu Gln Gly Ile Leu Cys Gly Tyr Arg Pro Pro Arg
                             20                  25                 30

Ile Ser Ala Ala Asp Cys Val Leu Ser Ala Phe Gln Met Thr Asn Glu
                         35                  40                 45
```

```
Thr Leu Asn Ile Trp Thr His Phe Leu Pro Ala Trp Tyr Phe Val Trp
 50                  55                  60

Met Leu Val Gly Arg Leu Trp Gly Pro Gly Arg Asp Pro Ala
 65                  70                  75                  80

Trp Pro Leu Leu Ala Tyr Leu Leu Ser Cys Cys Ile Tyr Pro Leu Ala
                     85                  90                  95

Ser Ser Cys Ala His Thr Phe Ser Pro Met Ser Ala Arg Ala Arg His
                100                 105                 110

Val Cys Tyr Phe Phe Asp Tyr Ala Ala Leu Ser Met Tyr Ser Leu Gly
                115                 120                 125

Ser Ala Leu Ala Tyr Ser Ala Tyr Val Phe Pro Glu Glu Trp Val Gly
        130                 135                 140

Ser Ile Phe His Cys Cys Tyr Val Pro Val Ala Val Leu Asn Thr Val
145                 150                 155                 160

Leu Ser Thr Ser Leu Ala Cys Tyr Ser Arg Phe Leu Glu Leu Glu Arg
                165                 170                 175

Pro Trp Leu Ser Lys Ala Ser Arg Thr Leu Ala Phe Val Tyr Pro Tyr
            180                 185                 190

Leu Phe Asp Ser Ile Pro Leu Phe Tyr Arg Val Tyr Val Cys Ala Ala
        195                 200                 205

Arg Ser Cys Ala Asp Pro Thr Val Ala Ala His Tyr Arg His Thr Ala
210                 215                 220

Phe Ala Phe Leu Thr Cys Phe Ile Phe Ala Thr His Leu Pro Glu Arg
225                 230                 235                 240

Leu Ala Pro Gly His Phe Asp Tyr Ile Gly His Ser His Gln Val Phe
                245                 250                 255

His Val Cys Gly Ile Leu Gly Thr His Phe Gln Leu Glu Ala Ile Leu
            260                 265                 270

Met Asp Met Ser Glu Arg Gln Ala Arg Leu Pro Ala Thr Ser Leu Leu
        275                 280                 285

Gln Ala Leu Ala Pro Met Gly Thr Cys Met Ala Val Gly Leu Ala Val
    290                 295                 300

Ile Ala His Cys Ser Ala Gln Leu Cys Arg Ala Pro Glu Pro Ser His
305                 310                 315                 320

Arg Glu Lys Leu His Gly Gln
                325
```

```
<210> SEQ ID NO 60
<211> LENGTH: 330
<212> TYPE: PRT
<213> ORGANISM: Xenopus tropicalis

<400> SEQUENCE: 60
```

```
Met Leu Ser Trp Lys Leu Pro Arg Leu Leu Thr Ile Gln Gln Val Pro
 1               5                   10                  15

Lys Val Phe His Glu Asp Ser Ile Ile Cys Gly Tyr Arg Ser Pro Cys
                20                  25                  30

Ser Ser Ala Thr Ala Cys Val Leu Ser Leu Phe Gln Met Thr Asn Glu
            35                  40                  45

Thr Val Asn Ile Trp Thr His Phe Ile Pro Thr Trp Tyr Phe Leu Trp
        50                  55                  60

Lys Met Leu Ser Phe Leu Tyr Ser Gly Phe Trp Asp Asp Pro Phe Leu
65                  70                  75                  80

Trp Pro Leu Leu Val Tyr Gln Leu Ser Cys Cys Ile Tyr Pro Leu Met
                85                  90                  95
```

```
Ser Thr Cys Ala His Thr Phe Ser Val Met Ser Thr Lys Ala Arg His
            100                 105                 110

Ile Cys Phe Phe Leu Asp Tyr Gly Ala Val Ser Leu Tyr Ser Leu Gly
            115                 120                 125

Ala Ala Ile Ala Tyr Ser Ala Tyr Val Phe Pro Asp Arg Trp Val Gly
130                 135                 140

Gly Thr Phe His Arg Trp Tyr Val Phe Cys Ala Val Met Asn Thr Gly
145                 150                 155                 160

Ile Cys Thr Ala Leu Ala Cys Tyr Ser Arg Ile Pro Glu Val Ala Arg
            165                 170                 175

Pro Arg Leu Ser Lys Val Leu Arg Thr Thr Ala Phe Ala Tyr Pro Tyr
            180                 185                 190

Leu Phe Asp Ser Ile Pro Leu Phe Tyr Arg Leu Phe Leu Cys Ser Gly
            195                 200                 205

Ser Gly Cys Ala Gln Asn Ala Ala Leu Pro Met His Ile Trp His Ser
            210                 215                 220

Ile Leu Ala Phe Leu Thr Ala Phe Leu Phe Ala Thr His Leu Pro Glu
225                 230                 235                 240

Arg Leu Ala Pro Gly Cys Phe Asp Tyr Val Gly His Ser His Gln Leu
            245                 250                 255

Phe His Val Cys Gly Ile Leu Gly Thr Tyr Ile Gln Met Glu Val Leu
            260                 265                 270

Ile Lys Asp Met Asn Leu Arg Lys Lys Trp Leu Met Asp Lys Asp Asn
            275                 280                 285

Ile Pro Ser Phe Ser Asn Thr Leu Gly Ala Trp Gly Leu Gly Met Ile
            290                 295                 300

Met Ser Phe Ile Val Ile Ala Cys Phe Ser Leu Ala Leu Tyr Trp Lys
305                 310                 315                 320

Pro Gln Thr Gln Lys Asn Lys Arg Lys Met
            325                 330

<210> SEQ ID NO 61
<211> LENGTH: 332
<212> TYPE: PRT
<213> ORGANISM: Danio rerio

<400> SEQUENCE: 61

Met Leu Ser Leu Ile Lys Leu Gln Arg Val Phe Asn Val His Gln Val
1               5                   10                  15

Pro Lys Ala Phe His Glu Asp Gly Ile Ile Ser Gly Tyr Arg His Pro
            20                  25                  30

Arg Ser Ser Ala Thr Glu Cys Val Trp Ser Leu Phe Gln Leu Thr Asn
        35                  40                  45

Glu Thr Leu Asn Val Trp Thr His Phe Leu Pro Thr Trp Tyr Phe Leu
    50                  55                  60

Trp Lys Leu Met Thr Val Leu Leu Met Glu Asp Val Trp Asn Glu Ala
65                  70                  75                  80

Tyr Thr Trp Pro Leu Leu Val Phe Leu Phe Ser Cys Cys Val Tyr Pro
                85                  90                  95

Leu Ala Ser Ser Cys Ala His Thr Phe Ser Ser Met Ser Thr Arg Ala
            100                 105                 110

Arg His Ile Cys Tyr Phe Phe Asp Tyr Gly Ala Leu Ser Phe Tyr Ser
            115                 120                 125

Leu Gly Ser Ala Ile Ser Tyr Ser Ala Tyr Val Phe Pro Asp Ala Trp
```

-continued

```
            130                 135                 140
Leu Ser Ser Ser Phe His Ala Tyr Tyr Ile Ser Val Ala Val Phe Asn
145                 150                 155                 160

Thr Val Leu Ser Thr Ser Leu Ala Cys Tyr Ser Arg Phe Ser Glu Arg
                165                 170                 175

Gln Cys Pro Arg Met Ser Lys Val Leu Arg Ile Leu Ala Phe Ala Tyr
            180                 185                 190

Pro Tyr Leu Phe Asp Asn Ile Pro Leu Phe Tyr Arg Leu Phe Val Cys
            195                 200                 205

Val Gly Glu Gly Cys Thr Asp Asn Glu Ala Asn Ser Val His Val Gln
            210                 215                 220

His Thr Leu Leu Ala Phe Leu Thr Ser Phe Leu Phe Ala Thr His Leu
225                 230                 235                 240

Pro Glu Arg Leu Ala Pro Gly Arg Phe Asp Tyr Ile Gly His Ser His
                245                 250                 255

Gln Leu Phe His Val Cys Ala Ile Ile Gly Thr His Phe Gln Met Lys
            260                 265                 270

Ala Ile Glu Met Asp Met Gly Leu Arg Arg Ser Gln Leu Leu Ala Ser
            275                 280                 285

Ala Pro Ala Ile Ser Phe Asn Asn Thr Ile Gly Ala Ala Leu Leu Cys
            290                 295                 300

Val Ser Val Ser Leu Gly Ile Ile Cys Val Tyr Ser Leu Pro Leu Leu
305                 310                 315                 320

Tyr Ser Ser Asn Pro Lys Asn Thr Ala Asn Lys Glu
                325                 330
```

<210> SEQ ID NO 62
<211> LENGTH: 332
<212> TYPE: PRT
<213> ORGANISM: Danio rerio

<400> SEQUENCE: 62

```
Met Leu Ser Leu Ile Lys Leu Gln Arg Val Phe Asn Val His Gln Val
1               5                   10                  15

Pro Lys Ala Phe His Glu Asp Gly Ile Ile Ser Gly Tyr Arg His Pro
                20                  25                  30

Arg Ser Ser Ala Thr Glu Cys Val Trp Ser Leu Phe Gln Leu Thr Asn
            35                  40                  45

Glu Thr Leu Asn Val Trp Thr His Phe Leu Pro Thr Trp Tyr Phe Leu
50                  55                  60

Trp Lys Leu Met Thr Val Leu Met Glu Asp Val Trp Asn Glu Ala
65                  70                  75                  80

Tyr Thr Trp Pro Leu Leu Val Phe Leu Phe Ser Cys Cys Val Tyr Pro
                85                  90                  95

Leu Ala Ser Ser Cys Ala His Thr Phe Ser Ser Met Ser Thr Arg Ala
            100                 105                 110

Arg His Ile Cys Tyr Phe Phe Asp Tyr Gly Ala Leu Ser Phe Tyr Ser
            115                 120                 125

Leu Gly Ser Ala Ile Ser Tyr Ser Ala Tyr Val Phe Pro Asp Ala Trp
130                 135                 140

Leu Ser Ser Ser Phe His Ala Tyr Tyr Ile Ser Val Ala Val Phe Asn
145                 150                 155                 160

Thr Val Leu Ser Thr Ser Leu Ala Cys Tyr Ser Arg Phe Ser Glu Arg
                165                 170                 175
```

```
Gln Cys Pro Arg Met Ser Lys Val Leu Arg Ile Leu Ala Phe Ala Tyr
                180                 185                 190

Pro Tyr Leu Phe Asp Asn Ile Pro Leu Phe Tyr Arg Leu Phe Val Cys
            195                 200                 205

Val Gly Glu Gly Cys Thr Asp Asn Glu Ala Asn Ser Val His Val Gln
210                 215                 220

His Thr Leu Leu Ala Phe Leu Thr Ser Phe Leu Phe Ala Thr His Leu
225                 230                 235                 240

Pro Glu Arg Leu Ala Pro Gly Arg Phe Asp Tyr Ile Gly His Ser His
                245                 250                 255

Gln Leu Phe His Val Cys Ala Ile Ile Gly Thr His Phe Gln Met Lys
            260                 265                 270

Ala Ile Glu Met Asp Met Gly Leu Arg Arg Ser Gln Leu Leu Ala Ser
        275                 280                 285

Ala Pro Ala Ile Ser Phe Asn Asn Thr Ile Gly Ala Ala Leu Leu Cys
    290                 295                 300

Val Ser Val Ser Leu Gly Ile Ile Cys Val Tyr Ser Leu Pro Leu Leu
305                 310                 315                 320

Tyr Ser Ser Asn Pro Lys Asn Thr Ala Asn Lys Glu
                325                 330

<210> SEQ ID NO 63
<211> LENGTH: 326
<212> TYPE: PRT
<213> ORGANISM: Danio rerio

<400> SEQUENCE: 63

Met Leu Asn Leu Ile Lys Leu Pro Gln Val Phe Thr Ile Asn Gln Val
1               5                   10                  15

Pro Lys Val Phe His Glu Asp Gly Ile Ile Ser Gly Tyr Arg His Pro
            20                  25                  30

Cys Ser Ser Ala Lys Asp Cys Val Leu Ser Leu Phe Gln Leu Thr Asn
        35                  40                  45

Glu Thr Leu Asn Ile Trp Thr His Phe Leu Pro Thr Trp Phe Phe Leu
50                  55                  60

Trp Lys Leu Leu Thr Val Val Leu Val Leu Glu Asp Trp Arg Asp Pro
65                  70                  75                  80

Phe Ile Trp Pro Phe Leu Val Phe Leu Leu Ser Cys Cys Val Tyr Pro
                85                  90                  95

Leu Ala Ser Ser Cys Ala His Thr Phe Ser Thr Met Ser Glu Arg Ala
            100                 105                 110

Arg His Ile Cys Phe Phe Phe Asp Tyr Gly Ala Leu Ser Phe Tyr Ser
        115                 120                 125

Leu Gly Ser Ala Ile Ile Tyr Ser Ser Tyr Ser Phe Pro Asp Lys Trp
    130                 135                 140

Val Asn Gly Thr Phe His Leu Asn Tyr Val Ser Ile Ala Val Val Asn
145                 150                 155                 160

Ser Ile Ile Ser Thr Ala Leu Ala Cys Tyr Ser Arg Leu Gly Gln Lys
                165                 170                 175

Leu Cys Lys Cys Leu Arg Ile Ile Ala Phe Val Tyr Pro Tyr Leu Phe
            180                 185                 190

Asp Asn Ile Pro Leu Phe Tyr Arg Ile Phe Val Cys Ala Gly Glu Gly
        195                 200                 205

Cys Thr Val Asn Glu Ala Asn Thr Val His Tyr Gln His Thr Ser Leu
    210                 215                 220
```

```
Ala Phe Phe Thr Gly Phe Leu Phe Ala Thr His Leu Pro Glu Arg Leu
225                 230                 235                 240

Ala Pro Gly Ser Phe Asp Tyr Ile Gly His Ser His Gln Leu Phe His
            245                 250                 255

Val Phe Ala Ile Ile Gly Thr Tyr Phe Gln Met Thr Ala Ile Glu Leu
        260                 265                 270

Asp Met Ala Ala Arg Lys Gln Trp Leu His Ala His Leu Pro Pro Val
            275                 280                 285

Thr Phe Leu Asn Thr Val Gly Ala Ala Phe Phe Ser Val Val Ser Gly
        290                 295                 300

Leu Cys Ile Val Tyr Val Phe Ser Leu Ser Leu Phe Ser Thr Arg Gly
305                 310                 315                 320

Val Lys Asn Lys Ser Phe
                325

<210> SEQ ID NO 64
<211> LENGTH: 344
<212> TYPE: PRT
<213> ORGANISM: Homo sapiens

<400> SEQUENCE: 64

Met Leu Ser Leu Lys Leu Pro Gln Leu Leu Gln Val His Gln Val Pro
1               5                   10                  15

Arg Val Phe Trp Glu Asp Gly Ile Met Ser Gly Tyr Arg Arg Pro Thr
            20                  25                  30

Ser Ser Ala Leu Asp Cys Val Leu Ser Ser Phe Gln Met Thr Asn Glu
        35                  40                  45

Thr Val Asn Ile Trp Thr His Phe Leu Pro Thr Trp Tyr Phe Leu Trp
    50                  55                  60

Arg Leu Leu Ala Leu Ala Gly Gly Pro Gly Phe Arg Ala Glu Pro Tyr
65              70                  75                  80

His Trp Pro Leu Leu Val Phe Leu Leu Pro Ala Cys Leu Tyr Pro Phe
                85                  90                  95

Ala Ser Cys Cys Ala His Thr Phe Ser Ser Met Ser Pro Arg Met Arg
            100                 105                 110

His Ile Cys Tyr Phe Leu Asp Tyr Gly Ala Leu Ser Leu Tyr Ser Leu
        115                 120                 125

Gly Cys Ala Phe Pro Tyr Ala Ala Tyr Ser Met Pro Ala Ser Trp Leu
    130                 135                 140

His Gly His Leu His Gln Phe Phe Val Pro Ala Ala Ala Leu Asn Ser
145                 150                 155                 160

Phe Leu Cys Thr Gly Leu Ser Cys Tyr Ser Arg Phe Leu Glu Leu Glu
                165                 170                 175

Ser Pro Gly Leu Ser Lys Val Leu Arg Thr Gly Ala Phe Ala Tyr Pro
            180                 185                 190

Phe Leu Phe Asp Asn Leu Pro Leu Phe Tyr Arg Leu Gly Leu Cys Trp
        195                 200                 205

Gly Arg Gly His Gly Cys Gly Gln Glu Ala Leu Ser Thr Ser His Gly
    210                 215                 220

Tyr His Leu Phe Cys Ala Leu Leu Thr Gly Phe Leu Phe Ala Ser His
225                 230                 235                 240

Leu Pro Glu Arg Leu Ala Pro Gly Arg Phe Asp Tyr Ile Gly His Ser
                245                 250                 255

His Gln Leu Phe His Ile Cys Ala Val Leu Gly Thr His Phe Gln Leu
```

```
                  260                 265                 270
Glu Ala Val Leu Ala Asp Met Gly Ser Arg Arg Ala Trp Leu Ala Thr
                275                 280                 285
Gln Glu Pro Ala Leu Gly Leu Ala Gly Thr Val Ala Thr Leu Val Leu
            290                 295                 300
Ala Ala Ala Gly Asn Leu Leu Ile Ile Ala Ala Phe Thr Ala Thr Leu
305                 310                 315                 320
Leu Arg Ala Pro Ser Thr Cys Pro Leu Leu Gln Gly Gly Pro Leu Glu
                325                 330                 335
Gly Gly Thr Gln Ala Lys Gln Gln
                340

<210> SEQ ID NO 65
<211> LENGTH: 343
<212> TYPE: PRT
<213> ORGANISM: Monodelphis domestica

<400> SEQUENCE: 65

Met Leu Ser Ile Lys Leu Pro Gln Leu Leu Arg Val His Gln Val Pro
1               5                   10                  15
Arg Val Phe Trp Glu Asp Gly Ile Ile Ser Gly Tyr Arg His Pro Thr
                20                  25                  30
Ser Ser Ala Leu Asp Cys Val Leu Ser Ser Phe Gln Met Thr Asn Glu
            35                  40                  45
Thr Val Asn Ile Trp Thr His Phe Leu Pro Thr Trp Tyr Phe Leu Trp
        50                  55                  60
Arg Phe Leu Ala Leu Ala Glu Gly Pro Gly Phe Trp Asp Pro Tyr His
65                  70                  75                  80
Trp Pro Leu Leu Val Phe Leu Leu Ile Cys Leu Tyr Pro Phe Thr
                85                  90                  95
Ser Cys Cys Ala His Thr Phe Ser Ser Met Ser Pro Arg Ala Arg His
                100                 105                 110
Ile Cys Tyr Phe Leu Asp Tyr Gly Ala Leu Ser Leu Tyr Ser Leu Gly
            115                 120                 125
Cys Ala Leu Thr Tyr Gly Ala Tyr Ala Met Pro Ser Ser Trp Leu Asn
        130                 135                 140
Ser Asn Leu His Gln Leu Phe Val Pro Ala Ala Ala Val Asn Ser Leu
145                 150                 155                 160
Leu Cys Thr Phe Leu Ser Cys Tyr Ser Arg Phe Leu Glu Leu Glu Asn
                165                 170                 175
Pro Arg Leu Ser Lys Val Leu Arg Thr Val Ala Phe Ala Tyr Pro Phe
            180                 185                 190
Phe Phe Asp Asn Leu Pro Leu Phe Tyr Arg Leu Leu Leu Cys Ser Arg
        195                 200                 205
Gly Ser Phe Ser Cys Gly Gln Glu Ala Leu Ser Val Asn His Ser Tyr
210                 215                 220
His Leu Leu Cys Ala Leu Leu Thr Gly Phe Leu Phe Ala Ser His Phe
225                 230                 235                 240
Pro Glu Cys Leu Ala Pro Gly Arg Phe Asp Tyr Ile Gly His Ser His
                245                 250                 255
Gln Leu Phe His Ile Cys Ala Val Leu Gly Thr His Phe Gln Leu Glu
            260                 265                 270
Ala Val Leu Ala Asp Met Gly Ser Arg Arg Ala Trp Leu Ala Thr Gln
        275                 280                 285
```

```
Glu Pro Ala Leu Gly Leu Ala Gly Thr Val Ala Thr Leu Val Leu Ala
    290                 295                 300

Ala Ala Gly Asn Leu Leu Ile Ile Ala Ala Phe Thr Ala Thr Leu Leu
305                 310                 315                 320

Arg Ala Pro Ser Thr Cys Pro Leu Leu Gln Gly Gly Pro Leu Glu Gly
                325                 330                 335

Gly Thr Gln Ala Lys Gln Gln
            340
```

<210> SEQ ID NO 66
<211> LENGTH: 340
<212> TYPE: PRT
<213> ORGANISM: Xenopus tropicalis

<400> SEQUENCE: 66

```
Met Leu Thr Ile Lys Leu Pro Gln Leu Phe Arg Val His Gln Met Pro
1               5                   10                  15

Arg Val Phe Trp Glu Asp Gly Ile Ile Ser Gly Tyr Arg His Pro Lys
            20                  25                  30

Ser Ser Ala Leu Asp Cys Leu Leu Ser Ser Phe Gln Met Thr Asn Glu
        35                  40                  45

Thr Val Asn Ile Trp Thr His Phe Leu Pro Thr Trp Tyr Phe Leu Trp
    50                  55                  60

Arg Phe Leu Leu Ser His Thr Leu Asp Phe Trp Gly His Ser Tyr
65                  70                  75                  80

Asn Trp Pro Leu Leu Val Tyr Met Met Leu Ile Cys Leu Tyr Pro Phe
                85                  90                  95

Thr Ser Ser Phe Ala His Thr Phe Ser Ser Met Ser Ala His Ala Arg
            100                 105                 110

His Ile Cys Tyr Phe Leu Asp Tyr Gly Ala Leu Ser Leu Tyr Ser Leu
        115                 120                 125

Gly Ser Ala Phe Ile Tyr Ser Ala Tyr Ile Met Pro Asp Arg Trp Ile
    130                 135                 140

Asn Ser Ala Leu His Arg Tyr Phe Val Pro Ile Ala Ala Phe Asn Thr
145                 150                 155                 160

Phe Ile Cys Thr Gly Leu Ser Cys Tyr Ser Arg Phe Leu Glu Val Asp
                165                 170                 175

Gln Pro Gln Leu Ser Lys Val Leu Arg Thr Val Ala Phe Val His Pro
            180                 185                 190

Phe Met Phe Asp Asn Ile Pro Leu Phe Phe Arg Leu Ile Phe Cys Phe
        195                 200                 205

Gly Glu Asp Cys Asn Trp Asn Glu Ala Val Arg Leu His Phe Thr His
    210                 215                 220

Leu Ser Phe Ala Phe Leu Thr Gly Phe Leu Phe Ala Ser His Leu Pro
225                 230                 235                 240

Glu Arg Leu Ala Pro Gly Arg Phe Asp Tyr Phe Gly His Ser His Gln
                245                 250                 255

Leu Phe His Ile Cys Ala Val Leu Gly Thr His Phe Gln Leu Glu Ala
            260                 265                 270

Val Leu Cys Asp Arg Ala Ala Arg Glu Ala Trp Leu Ala Ala His Ser
        275                 280                 285

Asp Gly Asp Ser Leu Ala Val Thr Leu Gly Val Val Ala Thr Ala Leu
    290                 295                 300

Ile Gly Asn Leu Ile Leu Ile Cys Phe Phe Thr Ala Thr Leu Leu Trp
305                 310                 315                 320
```

Ser Pro Arg Ala Asn Ser Ile Leu Gln Asn His Ser Pro Gly Asp Ala
            325                 330                 335

Arg Phe Lys Glu
            340

<210> SEQ ID NO 67
<211> LENGTH: 332
<212> TYPE: PRT
<213> ORGANISM: Danio rerio

<400> SEQUENCE: 67

Met Leu Ser Leu Arg Leu Pro Gln Leu Phe Asp Ile His Gln Val Pro
1               5                   10                  15

Lys Val Phe Arg Glu Asp Gly Ile Met Ser Gly Tyr Arg His Pro Arg
            20                  25                  30

Ser Ser Ala Leu Asp Cys Ile Leu Ser Ser Phe Gln Met Thr Asn Glu
        35                  40                  45

Thr Val Asn Ile Trp Thr His Phe Leu Pro Thr Trp Tyr Phe Leu Trp
    50                  55                  60

Arg Phe Ser Val Leu Cys Ser Ser Leu Asp Phe Val Thr Asp Ser Tyr
65                  70                  75                  80

Thr Trp Pro Leu Leu Val Tyr Met Leu Leu Ile Cys Leu Tyr Pro Phe
                85                  90                  95

Thr Ser Ser Cys Ala His Thr Phe Ser Thr Met Ser Ala Glu Ala Arg
            100                 105                 110

His Ile Cys Tyr Phe Phe Asp Tyr Gly Ala Leu Ser Leu Tyr Ser Leu
        115                 120                 125

Gly Cys Ala Ile Ser Tyr Gly Ser Tyr Ala Met Pro Asp Ser Trp Val
    130                 135                 140

Asn Ser Trp Leu His Gln His Phe Val Thr Ile Gly Ile Cys Asn Ser
145                 150                 155                 160

Leu Phe Cys Thr Ser Met Ser Cys Tyr Thr Arg Phe Ile Glu Leu Gln
                165                 170                 175

Phe Pro His Lys Ser Lys Ile Leu Arg Thr Ser Ala Phe Val Val Pro
            180                 185                 190

Phe Leu Phe Asp Ser Phe Pro Leu Phe Tyr Arg Leu Leu Ser Cys Cys
        195                 200                 205

Trp Gly Ser Cys Ser Pro Ser Glu Ala Leu Ala Ser His Ser Tyr His
    210                 215                 220

Leu Leu Phe Ala Phe Leu Thr Cys Phe Leu Phe Ala Ser His Leu Pro
225                 230                 235                 240

Glu Arg Leu Ala Pro Gly Arg Phe Asp Tyr Ile Gly His Ser His Gln
                245                 250                 255

Leu Phe His Ile Cys Ala Val Val Gly Thr His Phe Gln Met Glu Ala
            260                 265                 270

Ala Leu Ser Asp Met Ala Ser Arg Lys Asp Trp Leu Ile Ser Tyr Ser
        275                 280                 285

Gly Leu Pro Thr Phe Gln Gly Thr Met Gly Ala Leu Ala Leu Gly Val
    290                 295                 300

Leu Leu Asn Leu Ala Ile Ile Gly Val Phe Ser Ala Ser Leu Ile Gln
305                 310                 315                 320

Thr Pro Arg Gln Ser Thr Ser His Pro His Gln Glu
                325                 330

```
<210> SEQ ID NO 68
<211> LENGTH: 346
<212> TYPE: PRT
<213> ORGANISM: Homo sapiens

<400> SEQUENCE: 68

Met Ala Met Ala Gln Lys Leu Ser His Leu Leu Pro Ser Leu Arg Gln
1               5                   10                  15

Val Ile Gln Glu Pro Gln Leu Ser Leu Gln Pro Glu Pro Val Phe Thr
            20                  25                  30

Val Asp Arg Ala Glu Val Pro Pro Leu Phe Trp Lys Pro Tyr Ile Tyr
        35                  40                  45

Ala Gly Tyr Arg Pro Leu His Gln Thr Trp Arg Phe Tyr Phe Arg Thr
    50                  55                  60

Leu Phe Gln Gln His Asn Glu Ala Val Asn Val Trp Thr His Leu Leu
65                  70                  75                  80

Ala Ala Leu Val Leu Leu Arg Leu Ala Leu Phe Val Glu Thr Val
                85                  90                  95

Asp Phe Trp Gly Asp Pro His Ala Leu Pro Leu Phe Ile Ile Val Leu
            100                 105                 110

Ala Ser Phe Thr Tyr Leu Ser Phe Ser Ala Leu Ala His Leu Leu Gln
        115                 120                 125

Ala Lys Ser Glu Phe Trp His Tyr Ser Phe Phe Phe Leu Asp Tyr Val
    130                 135                 140

Gly Val Ala Val Tyr Gln Phe Gly Ser Ala Leu Ala His Phe Tyr Tyr
145                 150                 155                 160

Ala Ile Glu Pro Ala Trp His Ala Gln Val Gln Ala Val Phe Leu Pro
                165                 170                 175

Met Ala Ala Phe Leu Ala Trp Leu Ser Cys Ile Gly Ser Cys Tyr Asn
            180                 185                 190

Lys Tyr Ile Gln Lys Pro Gly Leu Leu Gly Arg Thr Cys Gln Glu Val
        195                 200                 205

Pro Ser Val Leu Ala Tyr Ala Leu Asp Ile Ser Pro Val Val His Arg
    210                 215                 220

Ile Phe Val Ser Ser Asp Pro Thr Thr Asp Pro Ala Leu Leu Tyr
225                 230                 235                 240

His Lys Cys Gln Val Val Phe Phe Leu Leu Ala Ala Ala Phe Phe Ser
                245                 250                 255

Thr Phe Met Pro Glu Arg Trp Phe Pro Gly Ser Cys His Val Phe Gly
            260                 265                 270

Gln Gly His Gln Leu Phe His Ile Phe Leu Val Leu Cys Thr Leu Ala
        275                 280                 285

Gln Leu Glu Ala Val Ala Leu Asp Tyr Glu Ala Arg Arg Pro Ile Tyr
    290                 295                 300

Glu Pro Leu His Thr His Trp Pro His Asn Phe Ser Gly Leu Phe Leu
305                 310                 315                 320

Leu Thr Val Gly Ser Ser Ile Leu Thr Ala Phe Leu Leu Ser Gln Leu
                325                 330                 335

Val Gln Arg Lys Leu Asp Gln Lys Thr Lys
            340                 345

<210> SEQ ID NO 69
<211> LENGTH: 351
<212> TYPE: PRT
<213> ORGANISM: Monodelphis domestica
```

<400> SEQUENCE: 69

Met Ala Thr Ala Ile Ala Gln Lys Leu Ser Arg Phe Pro Ser Val
1               5                   10                  15

Arg Gln Leu Gly Gln Met Pro Arg Ile Leu Gly Glu Leu Ala Ala Pro
            20                  25                  30

Leu Pro Asp Ser Thr Val Gly Arg Ala Glu Val Pro Arg Leu Phe Trp
            35                  40                  45

Lys Pro Tyr Ile Tyr Ser Gly Tyr Arg Pro Leu His Arg Thr Trp Arg
    50                  55                  60

Phe Tyr Phe Leu Ser Leu Phe Gln Lys His Asn Glu Ala Val Asn Val
65                  70                  75                  80

Trp Thr His Leu Val Ala Ala Met Val Leu Leu Arg Leu Ala Tyr
                85                  90                  95

Phe Ala Gly Ser Val Asp Phe Val Gly Asp Pro His Ala Arg Pro Leu
                100                 105                 110

Phe Leu Ile Val Leu Ala Ser Ile Thr Tyr Leu Phe Phe Ser Ala Val
            115                 120                 125

Ala His Leu Leu Gln Ala Lys Ser Glu Phe Trp His Tyr Ser Phe Phe
    130                 135                 140

Phe Leu Asp Tyr Val Gly Val Ala Val Tyr Gln Phe Gly Ser Ala Leu
145                 150                 155                 160

Ala His Phe Tyr Tyr Ala Ile Glu Pro Ala Trp His Ala Arg Met Ala
                165                 170                 175

Ala Phe Phe Leu Pro Ala Ala Ala Phe Leu Ala Trp Leu Ser Cys Ala
            180                 185                 190

Gly Ser Cys Tyr Thr Lys Tyr Arg Gln Leu Pro Gly Met Leu Gly Arg
    195                 200                 205

Ile Cys Gln Glu Met Pro Ser Gly Leu Ala Tyr Ala Leu Asp Ile Ser
210                 215                 220

Pro Val Val His Arg Ile Tyr Val Ala Gln Val Leu Gly Gln Glu Asp
225                 230                 235                 240

Pro Ala Val Leu Tyr His Lys Cys Gln Val Ala Phe Phe Leu Leu Ala
                245                 250                 255

Ala Ala Phe Phe Ser Ala Cys Ser Pro Glu Arg Trp Phe Pro Gly Lys
            260                 265                 270

Cys His Thr Phe Gly Gln Gly His Gln Leu Phe His Val Phe Leu Val
    275                 280                 285

Leu Cys Thr Leu Ala Gln Leu Glu Ala Val Ala Leu Asp Tyr Glu Ala
290                 295                 300

Arg Arg Ser Ile Tyr Glu Gly Leu His Arg His Ala Leu His Asn Phe
305                 310                 315                 320

Ser Ala Leu Phe Leu Leu Thr Val Val Cys Ser Val Leu Thr Ala Leu
                325                 330                 335

Phe Leu Ser His Arg Val Arg Gln Glu Leu Arg Cys Lys Glu Asp
            340                 345                 350

<210> SEQ ID NO 70
<211> LENGTH: 341
<212> TYPE: PRT
<213> ORGANISM: Gallus gallus

<400> SEQUENCE: 70

Met Ala Ala Val Val Ala Glu Lys Leu Ser Arg Leu Phe Ile Ser Val
1               5                   10                  15

Arg Gln Val Pro Gln Leu Leu Ala Pro Pro Val Pro Thr Thr Val Ser
            20                  25                  30

Ser Ser Glu Val Pro Arg Val Phe Trp Lys Pro Tyr Ile His Thr Gly
        35                  40                  45

Tyr Arg Pro Val His Gln Thr Trp Arg Tyr Tyr Phe Ser Thr Leu Phe
    50                  55                  60

Gln Gln His Asn Glu Ala Ile Asn Val Trp Thr His Leu Val Ala Thr
65                  70                  75                  80

Leu Ile Leu Leu Arg Phe Gln Gln Leu Ser Gln Arg Val Asp Phe
                85                  90                  95

Gly Gln Asp Pro His Ala Gln Pro Leu Leu Ile Ile Thr Ala Ser
                100                 105                 110

Ile Thr Tyr Leu Thr Phe Ser Thr Leu Ala His Leu Leu Gln Ala Lys
                115                 120                 125

Ser Glu Phe Trp His Tyr Ser Phe Phe Met Asp Tyr Val Gly Val
                130                 135                 140

Ala Ile Tyr Gln Tyr Gly Ser Ala Leu Val His Tyr Tyr Ala Ile
145                 150                 155                 160

Glu Pro Ser Trp His Glu Lys Ile Gln Gly Phe Phe Met Pro Thr Ala
                165                 170                 175

Ala Leu Leu Ala Trp Leu Ser Cys Ala Gly Ser Cys Tyr Ala Lys Phe
                180                 185                 190

Arg Tyr His Gln Ser Ala Gly Leu Leu Gly Arg Leu Cys Gln Glu Met
                195                 200                 205

Pro Ser Gly Leu Ala Tyr Leu Leu Asp Ile Ser Pro Val Val His Arg
210                 215                 220

Ile Cys Thr Ala Ser Pro Ala Glu Arg Thr Asp Pro Ala Leu Leu Tyr
225                 230                 235                 240

His Lys Cys Gln Val Leu Phe Phe Leu Ile Gly Ala Phe Phe Phe Ser
                245                 250                 255

His Pro Tyr Pro Glu Lys Leu Leu Pro Gly Lys Cys Tyr Phe Phe Gly
                260                 265                 270

Gln Ser His Gln Ile Phe His Val Phe Leu Val Leu Cys Thr Leu Ala
                275                 280                 285

Gln Ile Glu Ala Val Val Leu Asp Tyr Glu Ser Arg Arg His Ile Tyr
290                 295                 300

Ser Ser Leu Gln Gly Asp Leu Ala His His Phe Ser Ala Leu Cys Val
305                 310                 315                 320

Phe Thr Val Thr Cys Ser Val Leu Thr Ala Ala Tyr Met Ala Arg Lys
                325                 330                 335

Val Arg Asp Lys Leu
                340

<210> SEQ ID NO 71
<211> LENGTH: 354
<212> TYPE: PRT
<213> ORGANISM: Danio rerio

<400> SEQUENCE: 71

Met Ala Thr Val Val Met Glu Gln Ile Gly Arg Leu Phe Ile Asn Ala
1               5                   10                  15

Gln Gln Leu Arg Gln Ile Pro Arg Phe Leu Glu Ser Ala Phe Pro Lys
            20                  25                  30

Leu Pro Cys Thr Val Met Val Ser Asp Val Pro Trp Val Phe Arg Glu
        35                  40                  45

Ser His Ile Ile Thr Gly Tyr Arg Pro Pro Asp Gln Asn Trp Arg Tyr
    50                  55                  60

Tyr Phe Leu Thr Leu Phe Gln Arg His Asn Glu Ser Val Asn Val Trp
65                  70                  75                  80

Thr His Leu Leu Ala Ser Leu Ile Ile Leu Val Lys Phe Gln Glu Leu
                85                  90                  95

Ser Glu Thr Val Asp Phe Leu Arg Asp Pro His Ala Gln Pro Met Phe
                100                 105                 110

Ile Leu Leu Leu Ala Ala Phe Thr Tyr Leu Gly Cys Ser Ala Leu Ala
                115                 120                 125

His Leu Leu Ser Ala Lys Ser Glu Ile Ser His Tyr Thr Phe Tyr Phe
    130                 135                 140

Leu Asp Tyr Val Gly Val Ala Val Tyr Gln Tyr Gly Ser Ala Leu Ala
145                 150                 155                 160

His Phe Tyr Tyr Val Val Glu Glu Trp His Ala Gln Val Arg Thr
                165                 170                 175

Phe Phe Leu Pro Ala Ser Ala Phe Leu Ala Trp Leu Ser Cys Thr Gly
                180                 185                 190

Cys Cys Tyr Gly Lys Tyr Ala Ser Pro Lys Leu Pro Lys Phe Val His
            195                 200                 205

Lys Leu Phe Gln Val Val Pro Ser Gly Leu Ala Tyr Cys Leu Asp Ile
    210                 215                 220

Ser Pro Val Leu His Arg Ile Tyr Arg Cys Tyr Ser Ser Glu His Trp
225                 230                 235                 240

Cys Ala Asp Gln Ala Val Val Tyr His Cys Tyr Gln Val Leu Phe Phe
                245                 250                 255

Leu Ile Ser Ala Tyr Phe Phe Ser Tyr Pro His Pro Glu Arg Trp Phe
                260                 265                 270

Pro Gly Arg Cys Asp Phe Ile Gly Gln Gly His Gln Ile Phe His Val
            275                 280                 285

Phe Leu Val Leu Cys Thr Leu Val Gln Ile Glu Ala Val Arg Leu Asp
    290                 295                 300

Tyr Thr Glu Arg Arg Leu Tyr Glu His Leu His Gly Asp Leu Ala
305                 310                 315                 320

His Asp Ala Val Ala Leu Phe Ile Phe Thr Ala Cys Cys Ser Ala Leu
                325                 330                 335

Thr Ala Phe Tyr Val Arg Lys Arg Val Lys Thr Tyr Leu Glu Glu Lys
                340                 345                 350

Gln Glu

<210> SEQ ID NO 72
<211> LENGTH: 357
<212> TYPE: PRT
<213> ORGANISM: Danio rerio

<400> SEQUENCE: 72

Met Lys Lys Ile Gly Arg Leu Phe Phe Asn Leu Gln Lys Met Met Gln
1               5                   10                  15

Ile Pro Gln Met Leu Ser Glu Thr Ile Ser Ser Met Pro Lys Thr Leu
                20                  25                  30

Ser Asp Lys Glu Ala Pro Cys Phe Phe Arg Lys His Tyr Ile His Ser
            35                  40                  45

Gly Tyr Arg Ala Val His Gln Lys Trp Arg Tyr Tyr Phe Leu Ser Leu
    50                  55                  60

```
Phe Gln Trp His Asn Glu Ser Ile Asn Val Trp Thr His Leu Leu Gly
 65                  70                  75                  80

Ala Leu Val Val Leu Arg Ala Val Gln Leu Ala Glu Thr Val Asp
                 85                  90                  95

Phe Ile Asn Asp Ala His Ser Trp Pro Leu Ile Leu Leu Leu Thr
            100                 105                 110

Ser Met Ala Tyr Met Gly Phe Ser Thr Val Ala His Leu Leu Ala Ala
            115                 120                 125

Lys Ser Val Phe His His Tyr Ala Phe Phe Leu Asp Tyr Val Gly
            130                 135                 140

Val Ala Leu Tyr Gln Tyr Gly Ser Ala Val Val His Tyr Tyr Ala
145                 150                 155                 160

Ile Glu Glu Ser Trp His Glu Ser Val Arg Gly Cys Phe Met Pro Ile
                165                 170                 175

Ala Ser Phe Leu Cys Cys Leu Ser Cys Phe Gly Cys Cys Tyr Gly Thr
            180                 185                 190

Tyr Cys Asn Tyr Thr His His Pro Trp Val Arg Lys Val Gly Gln Ile
            195                 200                 205

Val Pro Ser Ala Leu Ala Tyr Glu Trp Asp Thr Ser Pro Val Phe His
210                 215                 220

Arg Leu Val Ile Trp Tyr Pro Phe Trp Val Thr Gly Asp Phe Arg Ser
225                 230                 235                 240

Ser Pro Ala Leu Leu Phe His Phe Gly Gln Val Ala Phe Phe Leu Ser
                245                 250                 255

Ser Ala Phe Phe Phe Thr His Pro Ile Pro Gln Ser Trp Phe Pro Gly
            260                 265                 270

His Cys Asp Phe Leu Gly Gln Gly His Gln Val Phe His Val Leu Ile
            275                 280                 285

Phe Leu Cys Thr Val Cys Gln Ile Gln Ala Ser Tyr Leu Asp Tyr Leu
290                 295                 300

Asn Arg Arg Asp Val Tyr Val Thr Leu His Thr Asn Gly Glu Ala Ser
305                 310                 315                 320

Phe Phe Val Leu Leu Phe Ile Leu Thr Leu Val Met Ser Thr Leu Ile
                325                 330                 335

Ala Phe Tyr Ile Leu Ala Lys Val Lys Arg Ala Val Ser Asn Thr Glu
            340                 345                 350

Lys Gln Arg Lys Glu
        355

<210> SEQ ID NO 73
<211> LENGTH: 354
<212> TYPE: PRT
<213> ORGANISM: Homo sapiens

<400> SEQUENCE: 73

Met Thr Thr Ala Ile Leu Glu Arg Leu Ser Thr Leu Ser Val Ser Gly
  1               5                  10                  15

Gln Gln Leu Arg Arg Leu Pro Lys Ile Leu Glu Asp Gly Leu Pro Lys
                 20                  25                  30

Met Pro Cys Thr Val Pro Glu Thr Asp Val Pro Gln Leu Phe Arg Glu
             35                  40                  45

Pro Tyr Ile Arg Thr Gly Tyr Arg Pro Thr Gly His Glu Trp Arg Tyr
        50                  55                  60

Tyr Phe Phe Ser Leu Phe Gln Lys His Asn Glu Val Val Asn Val Trp
```

```
                65                  70                  75                  80
Thr His Leu Leu Ala Ala Leu Ala Val Leu Leu Arg Phe Trp Ala Phe
                    85                  90                  95

Ala Glu Ala Glu Ala Leu Pro Trp Ala Ser Thr His Ser Leu Pro Leu
                100                 105                 110

Leu Leu Phe Ile Leu Ser Ser Ile Thr Tyr Leu Thr Cys Ser Leu Leu
                115                 120                 125

Ala His Leu Leu Gln Ser Lys Ser Glu Leu Ser His Tyr Thr Phe Tyr
            130                 135                 140

Phe Val Asp Tyr Val Gly Val Ser Val Tyr Gln Tyr Gly Ser Ala Leu
145                 150                 155                 160

Ala His Phe Phe Tyr Ser Ser Asp Gln Ala Trp Tyr Asp Arg Phe Trp
                165                 170                 175

Leu Phe Phe Leu Pro Ala Ala Phe Cys Gly Trp Leu Ser Cys Ala
                180                 185                 190

Gly Cys Cys Tyr Ala Lys Tyr Arg Tyr Arg Arg Pro Tyr Pro Val Met
                195                 200                 205

Arg Lys Ile Cys Gln Val Val Pro Ala Gly Leu Ala Phe Ile Leu Asp
            210                 215                 220

Ile Ser Pro Val Ala His Arg Val Ala Leu Cys His Leu Ala Gly Cys
225                 230                 235                 240

Gln Glu Gln Ala Ala Trp Tyr His Thr Leu Gln Ile Leu Phe Phe Leu
                245                 250                 255

Val Ser Ala Tyr Phe Phe Ser Cys Pro Val Pro Glu Lys Tyr Phe Pro
                260                 265                 270

Gly Ser Cys Asp Ile Val Gly His Gly His Gln Ile Phe His Ala Phe
                275                 280                 285

Leu Ser Ile Cys Thr Leu Ser Gln Leu Glu Ala Ile Leu Leu Asp Tyr
            290                 295                 300

Gln Gly Arg Gln Glu Ile Phe Leu Gln Arg His Gly Pro Leu Ser Val
305                 310                 315                 320

His Met Ala Cys Leu Ser Phe Phe Leu Ala Ala Cys Ser Ala Ala
                325                 330                 335

Thr Ala Ala Leu Leu Arg His Lys Val Lys Ala Arg Leu Thr Lys Lys
                340                 345                 350

Asp Ser

<210> SEQ ID NO 74
<211> LENGTH: 354
<212> TYPE: PRT
<213> ORGANISM: Monodelphis domestica

<400> SEQUENCE: 74

Met Thr Thr Ala Ile Leu Glu Arg Leu Ser Thr Leu Ser Val Ser Gly
1               5                   10                  15

Gln Gln Leu Arg Arg Leu Pro Lys Leu Leu Glu Asp Gly Phe Pro Lys
                20                  25                  30

Met Pro Cys Thr Val Pro Glu Ser Asp Val Pro Gln Leu Phe Arg Glu
            35                  40                  45

Pro Tyr Ile His Thr Gly Tyr Arg Pro Thr Gly His Glu Trp Arg Tyr
        50                  55                  60

Tyr Phe Phe Ser Leu Phe Gln Lys His Asn Glu Val Val Asn Val Trp
65                  70                  75                  80

Thr His Leu Leu Ala Ala Leu Ala Val Leu Leu Arg Phe Arg Ala Phe
```

```
                85                  90                  95
Ala Glu Thr Glu Ala Leu Pro Trp Thr Ser Ala His Ser Leu Pro Leu
            100                 105                 110

Leu Leu Phe Ile Leu Ser Ser Ile Thr Tyr Leu Thr Cys Ser Leu Leu
            115                 120                 125

Ala His Leu Leu Gln Ser Lys Ser Glu Leu Ser His Tyr Thr Phe Tyr
        130                 135                 140

Phe Val Asp Tyr Val Gly Val Ser Val Tyr Gln Tyr Gly Ser Ala Leu
145                 150                 155                 160

Ala His Phe Phe Tyr Ser Ser Asp Pro Ala Trp Tyr Glu Arg Phe Trp
                165                 170                 175

Leu Phe Phe Leu Pro Ala Ala Ala Phe Cys Gly Trp Leu Ser Cys Ala
            180                 185                 190

Gly Cys Cys Tyr Ala Lys Tyr Arg Tyr Arg Arg Pro Tyr Pro Val Met
            195                 200                 205

Arg Lys Val Cys Gln Val Val Pro Ala Gly Leu Ala Phe Val Leu Asp
        210                 215                 220

Ile Ser Pro Val Ala His Arg Val Ala Leu Cys His Leu Ser Gly Cys
225                 230                 235                 240

Gln Glu Gln Ala Ala Trp Tyr His Thr Leu Gln Ile Phe Phe Phe Leu
                245                 250                 255

Val Ser Ala Tyr Phe Phe Ser Cys Pro Val Pro Glu Lys Tyr Phe Pro
            260                 265                 270

Gly Ser Cys Asp Ile Val Gly His Gly His Gln Ile Phe His Ala Phe
            275                 280                 285

Leu Ser Val Cys Thr Leu Ser Gln Leu Glu Ala Ile Leu Leu Asp Tyr
        290                 295                 300

Gln Gly Arg Gln Glu Ile Phe Leu Gln Arg His Ser Pro Leu Ser Val
305                 310                 315                 320

Tyr Leu Ala Cys Leu Ser Phe Phe Leu Leu Ala Ala Cys Ser Gly Thr
                325                 330                 335

Thr Ala Ala Phe Leu Arg Arg Lys Ile Lys Ala Gly Leu Thr Lys Lys
            340                 345                 350

Asp Ser

<210> SEQ ID NO 75
<211> LENGTH: 352
<212> TYPE: PRT
<213> ORGANISM: Gallus gallus

<400> SEQUENCE: 75

Met Thr Ala Ile Leu Glu Arg Leu Ser Thr Leu Ser Leu Ser Gly Pro
1               5                  10                  15

Gln Leu Ser Arg Leu Pro Arg Leu Leu Glu Asp Gly Phe Pro Lys Met
                20                  25                  30

Pro Cys Thr Val Gln Glu Gly Glu Val Pro Gln Leu Phe Arg Glu Pro
            35                  40                  45

Tyr Ile His Thr Gly Tyr Arg Pro Thr Gly Gln Asp Trp Arg Tyr Tyr
        50                  55                  60

Phe Leu Ser Leu Phe Gln Lys His Asn Glu Val Asn Val Trp Thr
65                  70                  75                  80

His Leu Leu Ala Ala Leu Ala Val Leu Leu Arg Phe Lys Ala Phe Val
                85                  90                  95

Glu Gly Glu Gln Leu Pro Leu Asp Ala Trp Ser Leu Pro Leu Leu Ile
```

```
              100                 105                 110
Phe Val Leu Ser Ser Val Thr Tyr Leu Thr Cys Ser Leu Leu Ala His
            115                 120                 125
Leu Leu Gln Ser Lys Ser Glu Leu Tyr His Tyr Thr Phe Tyr Phe Val
        130                 135                 140
Asp Tyr Val Gly Val Ser Thr Tyr Gln Tyr Gly Ser Ala Leu Ala His
145                 150                 155                 160
Phe Tyr Tyr Ser Ser Asp Gln Ala Trp Tyr Asp Lys Phe Trp Leu Phe
                165                 170                 175
Phe Leu Pro Ala Ala Ala Phe Cys Gly Trp Leu Ser Cys Ala Gly Cys
            180                 185                 190
Cys Tyr Ala Lys Tyr Arg Tyr Arg Arg Pro Tyr Pro Ile Met Arg Lys
        195                 200                 205
Met Cys Gln Val Ile Pro Ala Gly Leu Ala Phe Ile Leu Asp Ile Ser
210                 215                 220
Pro Val Ala His Arg Val Ile Val Cys His Leu Gly Gly Cys Glu Glu
225                 230                 235                 240
Asp Ala Ala Trp Tyr His Thr Tyr Gln Ile Leu Phe Phe Leu Ile Ser
                245                 250                 255
Ala Tyr Phe Phe Ser Cys Pro Val Pro Glu Lys Tyr Phe Pro Gly Ser
            260                 265                 270
Cys Asp Ile Val Gly His Ala His Gln Ile Phe His Thr Phe Leu Ala
        275                 280                 285
Ile Cys Thr Leu Ser Gln Leu Glu Ala Ile Cys Leu Asp Tyr Lys Asn
        290                 295                 300
Arg Gln Glu Ile Phe Leu Lys Arg His Arg Pro Phe Ser Ile Tyr Leu
305                 310                 315                 320
Ser Cys Ile Ser Phe Phe Gly Leu Val Ala Cys Ser Ala Ile Thr Ala
                325                 330                 335
Tyr Ile Leu Arg Cys Arg Ile Lys Ala Ile Leu Ala Lys Lys Asp Ser
            340                 345                 350

<210> SEQ ID NO 76
<211> LENGTH: 353
<212> TYPE: PRT
<213> ORGANISM: Xenopus tropicalis

<400> SEQUENCE: 76

Met Thr Thr Ala Ile Leu Glu Cys Ile Ser Thr Leu Ser Ile Ser Val
1               5                   10                  15
Gln Gln Leu Arg Arg Leu Pro Arg Phe Leu Glu Gly Gly Thr Thr Lys
            20                  25                  30
Met Pro Leu Thr Val Lys Asp Ser Asp Val Pro Arg Leu Phe Arg Glu
        35                  40                  45
Pro Tyr Ile Gln Thr Gly Tyr Arg Pro Thr Asp Gln Asp Trp Lys Tyr
    50                  55                  60
Tyr Phe Leu Ser Leu Phe Gln Lys His Asn Glu Ser Ile Asn Val Trp
65                  70                  75                  80
Thr His Leu Leu Val Ala Leu Ala Val Val Leu Arg Phe Val Ala Leu
                85                  90                  95
Val Glu Ala Gly Ser Leu Ser Leu Asp Ile Ile Ser Leu Pro Phe Tyr
            100                 105                 110
Leu Tyr Val Leu Ser Ser Leu Thr Tyr Leu Thr Cys Ser Ile Leu Ala
        115                 120                 125
```

His Leu Leu Gln Ser Lys Ser Glu Leu Ala His Tyr Thr Phe Tyr Phe
    130                 135                 140

Met Asp Tyr Val Gly Val Ser Thr Tyr Gln Tyr Gly Ser Ala Leu Ala
145                 150                 155                 160

His Tyr Tyr Tyr Ser Ser Asn Gln Ala Trp Tyr Asp Lys Ala Trp Tyr
                165                 170                 175

Phe Phe Leu Pro Gly Ala Ala Phe Leu Gly Trp Met Ser Cys Ala Gly
            180                 185                 190

Cys Cys Tyr Ala Lys Tyr Cys Tyr Lys Arg Pro Tyr Pro Val Met Arg
        195                 200                 205

Lys Ile Phe Gln Val Val Pro Ala Gly Leu Ala Tyr Met Leu Asp Ile
    210                 215                 220

Ser Pro Val Ile His Arg Ile Val Thr Cys His Met Glu Gly Cys Thr
225                 230                 235                 240

Asp Lys Ala Ile Trp Val His Ala Leu Gln Ile Ile Phe Phe Leu Ile
                245                 250                 255

Ser Ser Tyr Phe Phe Ser Cys Pro Val Pro Glu Lys Tyr Phe Pro Gly
            260                 265                 270

Ser Cys Asp Phe Val Gly His Gly His Gln Ile Phe His Val Phe Leu
        275                 280                 285

Gly Leu Cys Thr Leu Ser Gln Leu Glu Ala Leu Phe Ile Asp Tyr Gln
    290                 295                 300

Thr Arg His Glu Leu Phe Ser Leu Arg Tyr Ser Ser Asn Gly Thr Leu
305                 310                 315                 320

Val Asn Cys Leu Ser Phe Phe Met Leu Ile Leu Cys Ser Thr Gly Thr
                325                 330                 335

Ala Met Tyr Ala Arg Arg Arg Ile Lys Asn Lys Leu Ala Arg Lys Glu
            340                 345                 350

Leu

<210> SEQ ID NO 77
<211> LENGTH: 352
<212> TYPE: PRT
<213> ORGANISM: Danio rerio

<400> SEQUENCE: 77

Met Ser Ser Gly Val Leu Gly Arg Leu Ser Thr Leu Thr Leu Ser Leu
1               5                   10                  15

Gln Gln Leu Gly Gln Leu Pro His Leu Ser Asn Trp Leu Pro Arg Leu
            20                  25                  30

Pro Arg Arg Gln Ala Thr Val His Ala Ser Glu Val Pro Ser Leu Phe
        35                  40                  45

Arg Glu Pro Tyr Ile Leu Ser Gly Tyr Arg Pro Val His Gln Glu Trp
    50                  55                  60

Arg Ser Tyr Phe Cys Ser Leu Phe Gln Cys His Asn Glu Leu Leu Asn
65                  70                  75                  80

Val Trp Thr His Leu Leu Ala Ile Pro Ala Val Leu Leu Gln Phe Ser
                85                  90                  95

Phe Phe Ala Gly Ala Trp Gly Leu Thr Leu Asn Leu Ala Ser Leu Pro
            100                 105                 110

Leu Phe Leu Tyr Val Leu Ser Ser Leu Thr Tyr Leu Ser Phe Ser Val
        115                 120                 125

Ala Ala His Leu Leu Gln Ser His Ser Glu Leu Ala His Tyr Ser Leu
    130                 135                 140

```
Phe Phe Val Asp Tyr Val Gly Val Ala Val Tyr Gln Tyr Gly Cys Ser
145                 150                 155                 160

Met Gly His Tyr Phe Tyr Cys Ser Glu Pro Glu Trp Arg His Ser Leu
            165                 170                 175

Val Gly Val Leu Phe Leu Pro Gly Ala Ala Met Leu Ala Trp Leu Ser
            180                 185                 190

Cys Ala Ser Cys Cys Tyr Ser Lys Phe Arg Tyr Arg Pro Tyr Pro
            195                 200                 205

Phe His Arg Lys Ile Cys Gln Ile Ile Pro Thr Ser Leu Ala Tyr Leu
            210                 215                 220

Leu Asp Ile Ser Pro Val Ala His Arg Leu Leu Thr Lys Ser Trp Asp
225                 230                 235                 240

Glu Pro Val Leu Val Phe His Ala Met Gln Val Ala Phe Phe Leu Leu
                245                 250                 255

Ala Ala Leu Phe Phe Ser Cys Pro Val Pro Glu Arg Phe Phe Pro Gly
                260                 265                 270

Arg Cys Asp Ile Val Gly His Gly His Gln Ile Phe His Ile Phe Leu
            275                 280                 285

Val Leu Cys Thr Met Cys Gln Leu Glu Ala Met Phe Arg Asp Phe Leu
            290                 295                 300

Val His Gln Gln Ser Val Val Asp Ala His Gly Glu His Phe Ile Leu
305                 310                 315                 320

Leu Ala Gly Gly Ser Phe Phe Leu Leu Val Leu Cys Ser Ile Leu Thr
                325                 330                 335

Ala Val Leu Met Arg Gly Ala Val Gln Arg Gln Leu Arg Lys Lys Asp
                340                 345                 350

<210> SEQ ID NO 78
<211> LENGTH: 377
<212> TYPE: PRT
<213> ORGANISM: Homo sapiens

<400> SEQUENCE: 78

Met Pro Arg Arg Leu Gln Pro Arg Gly Ala Gly Thr Lys Gly Pro Pro
1               5                   10                  15

Ala Pro Ala Pro Ala Ala Ser Gly Ala Ala Arg Asn Ser His Ser Ala
                20                  25                  30

Ala Ser Arg Asp Pro Pro Ala Ser Ala Lys Pro Leu Leu Arg Trp Asp
            35                  40                  45

Glu Val Pro Asp Asp Phe Val Glu Cys Phe Ile Leu Ser Gly Tyr Arg
50                  55                  60

Arg Leu Pro Cys Thr Ala Gln Glu Cys Leu Ala Ser Val Leu Lys Pro
65                  70                  75                  80

Thr Asn Glu Thr Leu Asn Phe Trp Thr His Phe Ile Pro Leu Leu Leu
                85                  90                  95

Phe Leu Ser Lys Phe Cys Arg Leu Phe Leu Ser Gly Gly Asp Val
                100                 105                 110

Pro Phe His His Pro Trp Leu Leu Pro Leu Trp Cys Tyr Ala Ser Gly
            115                 120                 125

Val Leu Leu Thr Phe Ala Met Ser Cys Thr Ala His Val Phe Ser Cys
            130                 135                 140

Leu Ser Leu Arg Leu Arg Ala Ala Phe Phe Tyr Leu Asp Tyr Ala Ser
145                 150                 155                 160

Ile Ser Tyr Tyr Gly Phe Gly Ser Thr Val Ala Tyr Tyr Tyr Tyr Leu
                165                 170                 175
```

```
Leu Pro Gly Leu Ser Leu Leu Asp Ala Arg Val Met Thr Pro Tyr Leu
            180                 185                 190

Gln Gln Arg Leu Gly Trp His Val Asp Cys Thr Arg Leu Ile Ala Ala
        195                 200                 205

Tyr Arg Ala Leu Val Leu Pro Val Ala Phe Val Leu Ala Val Ala Cys
    210                 215                 220

Thr Val Ala Cys Cys Lys Ser Arg Thr Asp Trp Cys Thr Tyr Pro Phe
225                 230                 235                 240

Ala Leu Arg Thr Phe Val Phe Val Met Pro Leu Ser Met Ala Cys Pro
                245                 250                 255

Ile Met Leu Glu Ser Trp Leu Phe Asp Leu Arg Gly Glu Asn Pro Thr
                260                 265                 270

Leu Phe Val His Phe Tyr Arg Arg Tyr Phe Trp Leu Val Val Ala Ala
                275                 280                 285

Phe Phe Asn Val Ser Lys Ile Pro Glu Arg Ile Gln Pro Gly Leu Phe
            290                 295                 300

Asp Ile Ile Gly His Ser His Gln Leu Phe His Ile Phe Thr Phe Leu
305                 310                 315                 320

Ser Ile Tyr Asp Gln Val Tyr Tyr Val Glu Glu Gly Leu Arg Gln Phe
                325                 330                 335

Leu Gln Ala Pro Pro Ala Ala Pro Thr Phe Ser Gly Thr Val Gly Tyr
                340                 345                 350

Met Leu Leu Leu Val Val Cys Leu Gly Leu Val Ile Arg Lys Phe Leu
                355                 360                 365

Asn Ser Ser Glu Phe Cys Ser Lys Lys
            370                 375

<210> SEQ ID NO 79
<211> LENGTH: 376
<212> TYPE: PRT
<213> ORGANISM: Monodelphis domestica

<400> SEQUENCE: 79

Met Pro Leu Arg Leu Gln Pro Arg Gly Ala Gly Thr Lys Asn Pro Ser
1               5                   10                  15

Ala Ala Ser Ser Ser Ser Ala Pro Ala Leu Thr Ala Ala Ser Pro
            20                  25                  30

Ser Pro Thr Leu Pro Gly Pro Lys Pro Leu Leu Arg Trp Asp Glu Val
            35                  40                  45

Pro Asp Asp Phe Val Glu Cys Phe Ile Leu Ser Gly Tyr Arg Arg Leu
        50                  55                  60

Pro Cys Thr Ala Gln Glu Cys Val Ala Ser Val Leu Lys Pro Thr Asn
65                  70                  75                  80

Glu Thr Leu Asn Phe Trp Thr His Phe Ile Pro Leu Leu Phe Leu
                85                  90                  95

Ser Lys Phe Cys Arg Leu Phe Phe Leu Ser Gly Arg Asp Asp Leu Pro
            100                 105                 110

Phe His His Pro Trp Leu Leu Pro Leu Trp Cys Tyr Ala Ser Gly Val
        115                 120                 125

Leu Leu Thr Phe Ala Met Ser Cys Thr Ala His Val Phe Ser Cys Leu
            130                 135                 140

Ser Leu Arg Leu Arg Ala Thr Phe Phe Tyr Leu Asp Tyr Ala Ser Ile
145                 150                 155                 160

Ser Tyr Tyr Gly Phe Gly Ser Thr Val Ala Tyr Tyr Tyr Tyr Leu Leu
```

```
                  165                 170                 175
Pro Gly Leu Ser Leu Leu Asp Ala Ser Val Met Thr Pro Tyr Val Gln
            180                 185                 190

Gln Arg Leu Gly Trp His Val Asp Cys Thr Arg Leu Ile Ala Ala Tyr
        195                 200                 205

Arg Ala Leu Val Leu Pro Val Ala Phe Val Leu Ala Val Ala Cys Thr
210                 215                 220

Val Ala Cys Cys Lys Ser Arg Ser Asp Trp Cys Thr Tyr Pro Phe Ala
225                 230                 235                 240

Leu Arg Thr Phe Val Phe Val Met Pro Leu Ser Met Ala Cys Pro Ile
            245                 250                 255

Met Leu Glu Ser Trp Leu Phe Asp Leu Arg Gly Glu Asn Pro Thr Leu
        260                 265                 270

Phe Val His Phe Tyr Arg Arg Tyr Phe Trp Leu Val Val Ala Ala Phe
    275                 280                 285

Phe Asn Val Ser Lys Ile Pro Glu Arg Ile Gln Pro Gly Leu Phe Asp
290                 295                 300

Ile Ile Gly His Ser His Gln Leu Phe His Ile Phe Thr Phe Leu Ser
305                 310                 315                 320

Ile Tyr Asp Gln Met His Tyr Val Glu Glu Gly Leu Arg Gln Phe Leu
            325                 330                 335

Glu Ala Pro Pro Ala Ser Pro Thr Phe Ser Gly Thr Val Gly Tyr Met
        340                 345                 350

Ile Leu Leu Val Leu Cys Leu Gly Leu Val Ile Arg Lys Phe Leu Asn
    355                 360                 365

Val Ala Asp Leu Cys Lys Glu Asp
370                 375

<210> SEQ ID NO 80
<211> LENGTH: 377
<212> TYPE: PRT
<213> ORGANISM: Gallus gallus

<400> SEQUENCE: 80

Met Ala Arg Arg Leu Gln Pro Arg Gly Ala Gly Thr Lys Gly Pro Pro
1               5                   10                  15

Ala Ala Thr Ala Ala Ala Ser Glu Ala Gly Pro Arg Pro His Pro Ser
            20                  25                  30

Ala Ala Ala Glu Pro Leu Ala Ser Ala Lys Pro Leu Leu Arg Trp Asp
        35                  40                  45

Glu Val Pro Asp Asp Phe Val Glu Cys Phe Ile Leu Ser Gly Tyr Arg
    50                  55                  60

Arg Leu Pro Cys Thr Ala Gln Glu Cys Leu Ala Ser Val Leu Lys Pro
65                  70                  75                  80

Thr Asn Glu Thr Leu Asn Phe Trp Thr His Phe Ile Pro Leu Leu Leu
                85                  90                  95

Phe Leu Ser Lys Phe Cys Arg Leu Phe Leu Ser Gly Arg Asp Val
            100                 105                 110

Pro Phe His His Pro Trp Leu Leu Pro Leu Trp Cys Tyr Ala Ser Gly
        115                 120                 125

Val Leu Leu Thr Phe Ala Met Ser Cys Thr Ala His Val Phe Ser Cys
    130                 135                 140

Leu Ser Leu Arg Leu Arg Ala Ala Phe Tyr Leu Asp Tyr Ala Ser
145                 150                 155                 160
```

```
Ile Ser Tyr Tyr Gly Phe Ala Ser Thr Val Ala Tyr Ser Tyr Tyr Leu
            165                 170                 175

Leu Pro Gly Leu Ser Leu Leu Asp Ala Gly Val Leu Ser Arg Tyr Val
        180                 185                 190

Gln Gln Gln Leu Gly Trp Gln Leu Asp Cys Ser Leu Pro Ile Ala Ala
            195                 200                 205

Tyr Arg Ala Leu Val Leu Pro Val Ala Leu Ala Leu Ala Val Gly Cys
        210                 215                 220

Thr Ala Ala Cys Cys Arg Ser Arg Ala Ala Cys Cys Ala Tyr Pro Phe
225                 230                 235                 240

Ala Val Arg Thr Phe Val Phe Ala Met Pro Leu Ser Met Ala Cys Pro
            245                 250                 255

Ile Met Leu Glu Ser Leu Ile Phe Asp Leu Arg Thr Arg Asn Pro Thr
            260                 265                 270

Leu Phe Val Tyr Phe Arg Arg Tyr Phe Trp Leu Leu Val Ala Ala
        275                 280                 285

Phe Phe Asn Val Ser Lys Ile Pro Glu Arg Ile Gln Pro Gly Leu Phe
        290                 295                 300

Asp Ile Val Gly His Ser His Gln Leu Phe His Ile Phe Thr Phe Leu
305                 310                 315                 320

Ser Ile Tyr Asp Gln Val His Tyr Val Glu Asp Gly Leu Ala Glu Phe
            325                 330                 335

Leu Lys Ala Ala Pro Ala Pro Thr Tyr Leu Gly Thr Val Gly Tyr
        340                 345                 350

Met Leu Leu Leu Thr Val Cys Leu Ala Val Val Arg Arg Phe Leu
        355                 360                 365

Asn Val Ala Asp Leu Cys Lys Gln Asp
    370                 375

<210> SEQ ID NO 81
<211> LENGTH: 347
<212> TYPE: PRT
<213> ORGANISM: Xenopus tropicalis

<400> SEQUENCE: 81

Met Pro Leu Gln Ser Tyr Thr Arg Asp Lys Asp Lys Thr Pro Leu Leu
1               5                   10                  15

Arg Trp Asp Glu Val Pro Asp Asp Phe Val Glu Cys Phe Ile Leu Ser
            20                  25                  30

Gly Tyr Arg Arg Leu His Leu Thr Ala Gln Glu Cys Leu Ala Ser Ile
        35                  40                  45

Phe Gln Pro Thr Asn Glu Thr Leu Asn Phe Trp Thr His Phe Ile Pro
    50                  55                  60

Leu Val Leu Phe Val Ser Lys Phe Tyr His Val Phe Leu Ala Thr
65                  70                  75                  80

Glu Leu Pro Phe His His Pro Ala Leu Leu Pro Leu Trp Cys Tyr Ala
            85                  90                  95

Ser Gly Val Leu Leu Thr Phe Ala Met Ser Cys Thr Ala His Val Phe
            100                 105                 110

Ser Cys Arg Ser Leu Arg Leu Arg Ala Ala Phe Phe Phe Leu Asp Tyr
        115                 120                 125

Ala Ser Ile Ser Tyr Tyr Gly Phe Ala Ser Thr Val Ala Tyr Ser Tyr
    130                 135                 140

Tyr Leu Leu Pro Arg Leu Ser Leu Leu Asp Pro Ala Val Met Thr Pro
145                 150                 155                 160
```

```
Tyr Leu Gln Ser Leu Gly Trp His Gln Val Asp Tyr Ser Met Leu Met
                165                 170                 175

Gly Leu Tyr Gly Lys Leu Val Leu Pro Val Ala Phe Ile Leu Ala Val
            180                 185                 190

Thr Cys Thr Val Ala Cys Cys Lys Ser Arg Ala Glu Asp Cys Ser Tyr
        195                 200                 205

Pro Phe Ala Ile Arg Thr Phe Val Phe Ala Met Pro Leu Ser Met Ala
    210                 215                 220

Cys Pro Val Met Ile Glu Ser Leu Leu Phe Asp Leu Arg Lys Arg Asn
225                 230                 235                 240

Pro Thr Leu Phe Val His Phe Tyr Arg Arg Tyr Phe Trp Leu Leu Val
                245                 250                 255

Ala Ala Phe Phe Asn Val Ser Lys Ile Pro Glu Arg Ile His Pro Gly
            260                 265                 270

Leu Phe Asp Ile Ile Gly His Ser His Gln Leu Phe His Ile Phe Thr
        275                 280                 285

Phe Leu Ser Ile Tyr Asp Gln Met His Tyr Val Glu Gln Gly Leu Glu
    290                 295                 300

Leu Phe Leu Lys Ser Pro Ser Ser Pro Pro Thr Leu Gln Gly Thr Ile
305                 310                 315                 320

Gly Tyr Met Leu Leu Leu Thr Leu Cys Leu Val Phe Val Val Arg Thr
                325                 330                 335

Tyr Leu Lys Gly Leu Ser Asn Thr Lys Gln Asp
            340                 345

<210> SEQ ID NO 82
<211> LENGTH: 374
<212> TYPE: PRT
<213> ORGANISM: Danio rerio

<400> SEQUENCE: 82

Met Trp Ser Leu Pro Leu Val Arg His Thr Asp Val Pro Val Arg Val
1               5                   10                  15

Thr Glu Ser Phe Ile Leu Ser Gly Tyr Arg Phe Pro Asn Tyr Ser Leu
            20                  25                  30

Arg Gln Cys Leu Ala Ser Ala Phe Arg Pro Thr Asn Glu Thr Gly Asn
        35                  40                  45

Phe Trp Thr His Phe Leu Pro Ile Phe Val Phe Ala Phe His Phe Met
    50                  55                  60

Glu Val Phe Thr Trp Glu Lys Val Pro Glu Pro Ser Asp Pro Phe Phe
65                  70                  75                  80

Tyr Pro Phe Trp Asn Tyr Phe Leu Gly Val Leu Tyr Leu Leu Leu Ala
                85                  90                  95

Ser Ser Leu Ala His Leu Leu Asn Ser Met Ser Leu Ile Ile Arg Glu
            100                 105                 110

Ile Cys Phe Phe Val Asp Tyr Gly Thr Ile Ser Ala Tyr Thr Val Gly
        115                 120                 125

Ser Ser Leu Ala Tyr Phe Tyr Tyr Ile His Pro Gln Ala Gly Ile Pro
    130                 135                 140

Glu Asn Gly Pro Cys Gly His Asn Ser Ser Glu Arg Lys Ser Leu Asn
145                 150                 155                 160

Ser Asp Glu Gln Thr Trp Pro Ser Glu Ser Pro Thr Gln Val Gln
                165                 170                 175

Leu Phe Phe Glu Ser Leu Tyr Ile Pro Ser Thr Cys Leu Val Ala Ile
```

```
                180               185               190
        Ile Cys Val Leu Thr Cys Cys Asn Thr Arg Gln Arg Trp Arg Lys Tyr
                    195               200               205
        Arg Tyr Ala Val Arg Thr Leu Val Phe Leu Leu Pro Phe Phe Val Ser
                210               215               220
        Ser Thr Pro Val Phe Tyr Arg Leu Leu Ser Leu Ser Ser Asn Ser Thr
        225               230               235               240
        Ser Ser Phe Ser Pro His Leu Ser Ser Thr Met Ala Ala Phe Phe Tyr
                        245               250               255
        Arg His Cys Phe Trp Leu Val Val Ser Ala Val Phe Asn Ile Ser Lys
                    260               265               270
        Ile Pro Glu Arg Val Ser Pro Gly Asn Phe Asp Ile Trp Gly His Ser
                275               280               285
        His Gln Trp Phe His Cys Cys Thr Phe Leu Ser Ile Leu Asp Glu Leu
                290               295               300
        His Met Ile Lys Val Glu Ile Arg Ala Leu Leu Leu Asn Pro Met Leu
        305               310               315               320
        Leu Leu Pro Pro Ser Thr Pro Pro Arg Leu Pro Gly Pro Thr Phe Trp
                        325               330               335
        Ser Thr Tyr Gly Ile Met Val Leu Leu Gln Gly Cys Ile Ala Ser Ile
                    340               345               350
        Ile Ala Trp Phe Gly Trp Gln Ala Tyr Gln Ile Tyr Ala Pro Glu Gln
                355               360               365
        Lys Lys Leu Lys Cys Cys
                370

<210> SEQ ID NO 83
<211> LENGTH: 1194
<212> TYPE: PRT
<213> ORGANISM: Homo sapiens
<220> FEATURE:
<221> NAME/KEY: MISC_FEATURE
<223> OTHER INFORMATION: Metabotropic glutamate receptor 1

<400> SEQUENCE: 83

Met Val Gly Leu Leu Phe Phe Phe Pro Ala Ile Phe Leu Glu Val
        1               5               10                  15
        Ser Leu Leu Pro Arg Ser Pro Gly Arg Lys Val Leu Leu Ala Gly Ala
                    20                  25                  30
        Ser Ser Gln Arg Ser Val Ala Arg Met Asp Gly Asp Val Ile Ile Gly
                        35                  40                  45
        Ala Leu Phe Ser Val His His Gln Pro Pro Ala Glu Lys Val Pro Glu
                50                  55                  60
        Arg Lys Cys Gly Glu Ile Arg Glu Gln Tyr Gly Ile Gln Arg Val Glu
        65                  70                  75                  80
        Ala Met Phe His Thr Leu Asp Lys Ile Asn Ala Asp Pro Val Leu Leu
                            85                  90                  95
        Pro Asn Ile Thr Leu Gly Ser Glu Ile Arg Asp Ser Cys Trp His Ser
                        100                 105                 110
        Ser Val Ala Leu Glu Gln Ser Ile Glu Phe Ile Arg Asp Ser Leu Ile
                    115                 120                 125
        Ser Ile Arg Asp Glu Lys Asp Gly Ile Asn Arg Cys Leu Pro Asp Gly
                130                 135                 140
        Gln Ser Leu Pro Pro Gly Arg Thr Lys Lys Pro Ile Ala Gly Val Ile
        145                 150                 155                 160
```

-continued

Gly Pro Gly Ser Ser Val Ala Ile Gln Val Gln Asn Leu Leu Gln
            165                 170                 175

Leu Phe Asp Ile Pro Gln Ile Ala Tyr Ser Ala Thr Ser Ile Asp Leu
        180                 185                 190

Ser Asp Lys Thr Leu Tyr Lys Tyr Phe Leu Arg Val Val Pro Ser Asp
    195                 200                 205

Thr Leu Gln Ala Arg Ala Met Leu Asp Ile Val Lys Arg Tyr Asn Trp
210                 215                 220

Thr Tyr Val Ser Ala Val His Thr Glu Gly Asn Tyr Gly Glu Ser Gly
225                 230                 235                 240

Met Asp Ala Phe Lys Glu Leu Ala Ala Gln Glu Gly Leu Cys Ile Ala
                245                 250                 255

His Ser Asp Lys Ile Tyr Ser Asn Ala Gly Glu Lys Ser Phe Asp Arg
            260                 265                 270

Leu Leu Arg Lys Leu Arg Glu Arg Leu Pro Lys Ala Arg Val Val Val
        275                 280                 285

Cys Phe Cys Glu Gly Met Thr Val Arg Gly Leu Leu Ser Ala Met Arg
    290                 295                 300

Arg Leu Gly Val Val Gly Glu Phe Ser Leu Ile Gly Ser Asp Gly Trp
305                 310                 315                 320

Ala Asp Arg Asp Glu Val Ile Glu Gly Tyr Glu Val Glu Ala Asn Gly
                325                 330                 335

Gly Ile Thr Ile Lys Leu Gln Ser Pro Glu Val Arg Ser Phe Asp Asp
            340                 345                 350

Tyr Phe Leu Lys Leu Arg Leu Asp Thr Asn Thr Arg Asn Pro Trp Phe
        355                 360                 365

Pro Glu Phe Trp Gln His Arg Phe Gln Cys Arg Leu Pro Gly His Leu
    370                 375                 380

Leu Glu Asn Pro Asn Phe Lys Arg Ile Cys Thr Gly Asn Glu Ser Leu
385                 390                 395                 400

Glu Glu Asn Tyr Val Gln Asp Ser Lys Met Gly Phe Val Ile Asn Ala
                405                 410                 415

Ile Tyr Ala Met Ala His Gly Leu Gln Asn Met His His Ala Leu Cys
            420                 425                 430

Pro Gly His Val Gly Leu Cys Asp Ala Met Lys Pro Ile Asp Gly Ser
        435                 440                 445

Lys Leu Leu Asp Phe Leu Ile Lys Ser Ser Phe Ile Gly Val Ser Gly
    450                 455                 460

Glu Glu Val Trp Phe Asp Glu Lys Gly Asp Ala Pro Gly Arg Tyr Asp
465                 470                 475                 480

Ile Met Asn Leu Gln Tyr Thr Glu Ala Asn Arg Tyr Asp Tyr Val His
                485                 490                 495

Val Gly Thr Trp His Glu Gly Val Leu Asn Ile Asp Asp Tyr Lys Ile
            500                 505                 510

Gln Met Asn Lys Ser Gly Val Val Arg Ser Val Cys Ser Glu Pro Cys
        515                 520                 525

Leu Lys Gly Gln Ile Lys Val Ile Arg Lys Gly Glu Val Ser Cys Cys
    530                 535                 540

Trp Ile Cys Thr Ala Cys Lys Glu Asn Glu Tyr Val Gln Asp Glu Phe
545                 550                 555                 560

Thr Cys Lys Ala Cys Asp Leu Gly Trp Trp Pro Asn Ala Asp Leu Thr
                565                 570                 575

Gly Cys Glu Pro Ile Pro Val Arg Tyr Leu Glu Trp Ser Asn Ile Glu

```
                580             585             590
Ser Ile Ile Ala Ile Ala Phe Ser Cys Leu Gly Ile Leu Val Thr Leu
            595                 600                 605
Phe Val Thr Leu Ile Phe Val Leu Tyr Arg Asp Thr Pro Val Val Lys
        610                 615                 620
Ser Ser Ser Arg Glu Leu Cys Tyr Ile Ile Leu Ala Gly Ile Phe Leu
625                 630                 635                 640
Gly Tyr Val Cys Pro Phe Thr Leu Ile Ala Lys Pro Thr Thr Thr Ser
                645                 650                 655
Cys Tyr Leu Gln Arg Leu Leu Val Gly Leu Ser Ser Ala Met Cys Tyr
            660                 665                 670
Ser Ala Leu Val Thr Lys Thr Asn Arg Ile Ala Arg Ile Leu Ala Gly
        675                 680                 685
Ser Lys Lys Lys Ile Cys Thr Arg Lys Pro Arg Phe Met Ser Ala Trp
    690                 695                 700
Ala Gln Val Ile Ile Ala Ser Ile Leu Ile Ser Val Gln Leu Thr Leu
705                 710                 715                 720
Val Val Thr Leu Ile Ile Met Glu Pro Pro Met Pro Ile Leu Ser Tyr
                725                 730                 735
Pro Ser Ile Lys Glu Val Tyr Leu Ile Cys Asn Thr Ser Asn Leu Gly
            740                 745                 750
Val Val Ala Pro Leu Gly Tyr Asn Gly Leu Leu Ile Met Ser Cys Thr
        755                 760                 765
Tyr Tyr Ala Phe Lys Thr Arg Asn Val Pro Ala Asn Phe Asn Glu Ala
    770                 775                 780
Lys Tyr Ile Ala Phe Thr Met Tyr Thr Thr Cys Ile Ile Trp Leu Ala
785                 790                 795                 800
Phe Val Pro Ile Tyr Phe Gly Ser Asn Tyr Lys Ile Ile Thr Thr Cys
                805                 810                 815
Phe Ala Val Ser Leu Ser Val Thr Val Ala Leu Gly Cys Met Phe Thr
            820                 825                 830
Pro Lys Met Tyr Ile Ile Ile Ala Lys Pro Glu Arg Asn Val Arg Ser
        835                 840                 845
Ala Phe Thr Thr Ser Asp Val Val Arg Met His Val Gly Asp Gly Lys
    850                 855                 860
Leu Pro Cys Arg Ser Asn Thr Phe Leu Asn Ile Phe Arg Arg Lys Lys
865                 870                 875                 880
Ala Gly Ala Gly Asn Ala Asn Ser Asn Gly Lys Ser Val Ser Trp Ser
                885                 890                 895
Glu Pro Gly Gly Gly Gln Val Pro Lys Gly Gln His Met Trp His Arg
            900                 905                 910
Leu Ser Val His Val Lys Thr Asn Glu Thr Ala Cys Asn Gln Thr Ala
        915                 920                 925
Val Ile Lys Pro Leu Thr Lys Ser Tyr Gln Gly Ser Gly Lys Ser Leu
    930                 935                 940
Thr Phe Ser Asp Thr Ser Thr Lys Thr Leu Tyr Asn Val Glu Glu Glu
945                 950                 955                 960
Glu Asp Ala Gln Pro Ile Arg Phe Ser Pro Pro Gly Pro Ser Met
                965                 970                 975
Val Val His Arg Arg Val Pro Ser Ala Ala Thr Thr Pro Pro Leu Pro
            980                 985                 990
Pro His Leu Thr Ala Glu Glu Thr  Pro Leu Phe Leu Ala  Glu Pro Ala
        995                 1000                 1005
```

```
Leu Pro Lys Gly Leu Pro Pro Leu Gln Gln Gln Gln Pro
    1010            1015            1020

Pro Pro Gln Gln Lys Ser Leu Met Asp Gln Leu Gln Gly Val Val
    1025            1030            1035

Ser Asn Phe Ser Thr Ala Ile Pro Asp Phe His Ala Val Leu Ala
    1040            1045            1050

Gly Pro Gly Gly Pro Gly Asn Gly Leu Arg Ser Leu Tyr Pro Pro
    1055            1060            1065

Pro Pro Pro Pro Gln His Leu Gln Met Leu Pro Leu Gln Leu Ser
    1070            1075            1080

Thr Phe Gly Glu Glu Leu Val Ser Pro Pro Ala Asp Asp Asp Asp
    1085            1090            1095

Asp Ser Glu Arg Phe Lys Leu Leu Gln Glu Tyr Val Tyr Glu His
    1100            1105            1110

Glu Arg Glu Gly Asn Thr Glu Glu Asp Glu Leu Glu Glu Glu Glu
    1115            1120            1125

Glu Asp Leu Gln Ala Ala Ser Lys Leu Thr Pro Asp Asp Ser Pro
    1130            1135            1140

Ala Leu Thr Pro Pro Ser Pro Phe Arg Asp Ser Val Ala Ser Gly
    1145            1150            1155

Ser Ser Val Pro Ser Ser Pro Val Ser Glu Ser Val Leu Cys Thr
    1160            1165            1170

Pro Pro Asn Val Ser Tyr Ala Ser Val Ile Leu Arg Asp Tyr Lys
    1175            1180            1185

Gln Ser Ser Ser Thr Leu
    1190

<210> SEQ ID NO 84
<211> LENGTH: 1078
<212> TYPE: PRT
<213> ORGANISM: Homo sapiens
<220> FEATURE:
<221> NAME/KEY: MISC_FEATURE
<223> OTHER INFORMATION: extracellular calcium receptor

<400> SEQUENCE: 84

Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
                20                  25                  30

Ile Leu Gly Gly Leu Phe Pro Ile His Phe Gly Val Ala Ala Lys Asp
            35                  40                  45

Gln Asp Leu Lys Ser Arg Pro Glu Ser Val Glu Cys Ile Arg Tyr Asn
        50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
```

-continued

```
            145                 150                 155                 160
Tyr Ile Pro Gln Val Ser Tyr Ala Ser Ser Ser Arg Leu Leu Ser Asn
                    165                 170                 175
Lys Asn Gln Phe Lys Ser Phe Leu Arg Thr Ile Pro Asn Asp Glu His
                    180                 185                 190
Gln Ala Thr Ala Met Ala Asp Ile Ile Glu Tyr Phe Arg Trp Asn Trp
                    195                 200                 205
Val Gly Thr Ile Ala Ala Asp Asp Tyr Gly Arg Pro Gly Ile Glu
            210                 215                 220
Lys Phe Arg Glu Glu Ala Glu Arg Asp Ile Cys Ile Asp Phe Ser
225                 230                 235                 240
Glu Leu Ile Ser Gln Tyr Ser Asp Glu Glu Ile Gln His Val Val
                    245                 250                 255
Glu Val Ile Gln Asn Ser Thr Ala Lys Val Ile Val Phe Ser Ser
                    260                 265                 270
Gly Pro Asp Leu Glu Pro Leu Ile Lys Glu Ile Val Arg Arg Asn Ile
            275                 280                 285
Thr Gly Lys Ile Trp Leu Ala Ser Glu Ala Trp Ala Ser Ser Ser Leu
            290                 295                 300
Ile Ala Met Pro Gln Tyr Phe His Val Val Gly Thr Ile Gly Phe
305                 310                 315                 320
Ala Leu Lys Ala Gly Gln Ile Pro Gly Phe Arg Glu Phe Leu Lys Lys
                    325                 330                 335
Val His Pro Arg Lys Ser Val His Asn Gly Phe Ala Lys Glu Phe Trp
                    340                 345                 350
Glu Glu Thr Phe Asn Cys His Leu Gln Glu Gly Ala Lys Gly Pro Leu
            355                 360                 365
Pro Val Asp Thr Phe Leu Arg Gly His Glu Glu Ser Gly Asp Arg Phe
            370                 375                 380
Ser Asn Ser Ser Thr Ala Phe Arg Pro Leu Cys Thr Gly Asp Glu Asn
385                 390                 395                 400
Ile Ser Ser Val Glu Thr Pro Tyr Ile Asp Tyr Thr His Leu Arg Ile
                    405                 410                 415
Ser Tyr Asn Val Tyr Leu Ala Val Tyr Ser Ile Ala His Ala Leu Gln
                    420                 425                 430
Asp Ile Tyr Thr Cys Leu Pro Gly Arg Gly Leu Phe Thr Asn Gly Ser
                    435                 440                 445
Cys Ala Asp Ile Lys Lys Val Glu Ala Trp Gln Val Leu Lys His Leu
450                 455                 460
Arg His Leu Asn Phe Thr Asn Asn Met Gly Glu Gln Val Thr Phe Asp
465                 470                 475                 480
Glu Cys Gly Asp Leu Val Gly Asn Tyr Ser Ile Ile Asn Trp His Leu
                    485                 490                 495
Ser Pro Glu Asp Gly Ser Ile Val Phe Lys Glu Val Gly Tyr Tyr Asn
                    500                 505                 510
Val Tyr Ala Lys Lys Gly Glu Arg Leu Phe Ile Asn Glu Glu Lys Ile
                    515                 520                 525
Leu Trp Ser Gly Phe Ser Arg Glu Val Pro Ser Asn Cys Ser Arg
                    530                 535                 540
Asp Cys Leu Ala Gly Thr Arg Lys Gly Ile Ile Glu Gly Glu Pro Thr
545                 550                 555                 560
Cys Cys Phe Glu Cys Val Glu Cys Pro Asp Gly Glu Tyr Ser Asp Glu
                    565                 570                 575
```

```
                    -continued

Thr Asp Ala Ser Ala Cys Asn Lys Cys Pro Asp Asp Phe Trp Ser Asn
                580                 585                 590

Glu Asn His Thr Ser Cys Ile Ala Lys Glu Ile Glu Phe Leu Ser Trp
            595                 600                 605

Thr Glu Pro Phe Gly Ile Ala Leu Thr Leu Phe Ala Val Leu Gly Ile
        610                 615                 620

Phe Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
                645                 650                 655

Ser Leu Leu Cys Cys Phe Ser Ser Ser Leu Phe Phe Ile Gly Glu Pro
            660                 665                 670

Gln Asp Trp Thr Cys Arg Leu Arg Gln Pro Ala Phe Gly Ile Ser Phe
        675                 680                 685

Val Leu Cys Ile Ser Cys Ile Leu Val Lys Thr Asn Arg Val Leu Leu
    690                 695                 700

Val Phe Glu Ala Lys Ile Pro Thr Ser Phe His Arg Lys Trp Trp Gly
705                 710                 715                 720

Leu Asn Leu Gln Phe Leu Leu Val Phe Leu Cys Thr Phe Met Gln Ile
                725                 730                 735

Val Ile Cys Val Ile Trp Leu Tyr Thr Ala Pro Pro Ser Ser Tyr Arg
            740                 745                 750

Asn Gln Glu Leu Glu Asp Glu Ile Ile Phe Ile Thr Cys His Glu Gly
        755                 760                 765

Ser Leu Met Ala Leu Gly Phe Leu Ile Gly Tyr Thr Cys Leu Leu Ala
    770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
            820                 825                 830

Val Ser Ala Val Glu Val Ile Ala Ile Leu Ala Ala Ser Phe Gly Leu
        835                 840                 845

Leu Ala Cys Ile Phe Phe Asn Lys Ile Tyr Ile Ile Leu Phe Lys Pro
    850                 855                 860

Ser Arg Asn Thr Ile Glu Glu Val Arg Cys Ser Thr Ala Ala His Ala
865                 870                 875                 880

Phe Lys Val Ala Ala Arg Ala Thr Leu Arg Arg Ser Asn Val Ser Arg
                885                 890                 895

Lys Arg Ser Ser Ser Leu Gly Gly Ser Thr Gly Ser Thr Pro Ser Ser
            900                 905                 910

Ser Ile Ser Ser Lys Ser Asn Ser Glu Asp Pro Phe Pro Gln Pro Glu
        915                 920                 925

Arg Gln Lys Gln Gln Gln Pro Leu Ala Leu Thr Gln Gln Glu Gln Gln
    930                 935                 940

Gln Gln Pro Leu Thr Leu Pro Gln Gln Arg Ser Gln Gln Gln Pro
945                 950                 955                 960

Arg Cys Lys Gln Lys Val Ile Phe Gly Ser Gly Thr Val Thr Phe Ser
                965                 970                 975

Leu Ser Phe Asp Glu Pro Gln Lys Asn Ala Met Ala His Arg Asn Ser
            980                 985                 990
```

-continued

```
Thr His Gln Asn Ser Leu Glu Ala  Gln Lys Ser Ser Asp  Thr Leu Thr
        995                 1000                1005

Arg His Gln Pro Leu Leu Pro  Leu Gln Cys Gly Glu  Thr Asp Leu
    1010                1015                1020

Asp Leu Thr Val Gln Glu Thr  Gly Leu Gln Gly Pro  Val Gly Gly
    1025                1030                1035

Asp Gln Arg Pro Glu Val Glu  Asp Pro Glu Glu Leu  Ser Pro Ala
    1040                1045                1050

Leu Val Val Ser Ser Ser Gln  Ser Phe Val Ile Ser  Gly Gly Gly
    1055                1060                1065

Ser Thr Val Thr Glu Asn Val  Val Asn Ser
    1070                1075

<210> SEQ ID NO 85
<211> LENGTH: 930
<212> TYPE: PRT
<213> ORGANISM: Homo sapiens
<220> FEATURE:
<221> NAME/KEY: MISC_FEATURE
<223> OTHER INFORMATION: GABA B receptor 1

<400> SEQUENCE: 85

Met Leu Leu Leu Leu Leu Ala  Pro Leu Phe Leu Arg  Pro Pro Gly
1               5                   10                  15

Ala Gly Gly Ala Gln Thr Pro  Asn Ala Thr Ser Glu  Gly Cys Gln Ile
            20                  25                  30

Ile His Pro Pro Trp Glu Gly  Gly Ile Arg Tyr Arg  Gly Leu Thr Arg
        35                  40                  45

Asp Gln Val Lys Ala Ile Asn  Phe Leu Pro Val Asp  Tyr Glu Ile Glu
    50                  55                  60

Tyr Val Cys Arg Gly Glu Arg  Glu Val Val Gly Pro  Lys Val Arg Lys
65                  70                  75                  80

Cys Leu Ala Asn Gly Ser Trp  Thr Asp Met Asp Thr  Pro Ser Arg Cys
                85                  90                  95

Val Arg Ile Cys Ser Lys Ser  Tyr Leu Thr Leu Glu  Asn Gly Lys Val
            100                 105                 110

Phe Leu Thr Gly Gly Asp Leu  Pro Ala Leu Asp Gly  Ala Arg Val Asp
        115                 120                 125

Phe Arg Cys Asp Pro Asp Phe  His Leu Val Gly Ser  Ser Arg Ser Ile
    130                 135                 140

Cys Ser Gln Gly Gln Trp Ser  Thr Pro Lys Pro His  Cys Gln Val Asn
145                 150                 155                 160

Arg Thr Pro His Ser Glu Arg  Arg Ala Val Tyr Ile  Gly Ala Leu Phe
                165                 170                 175

Pro Met Ser Gly Gly Trp Pro  Gly Gly Gln Ala Cys  Gln Pro Ala Val
            180                 185                 190

Glu Met Ala Leu Glu Asp Val  Asn Ser Arg Arg Asp  Ile Leu Pro Asp
        195                 200                 205

Tyr Glu Leu Lys Leu Ile His  His Asp Ser Lys Cys  Asp Pro Gly Gln
    210                 215                 220

Ala Thr Lys Tyr Leu Tyr Glu  Leu Leu Tyr Asn Asp  Pro Ile Lys Ile
225                 230                 235                 240

Ile Leu Met Pro Gly Cys Ser  Ser Val Ser Thr Leu  Val Ala Glu Ala
                245                 250                 255

Ala Arg Met Trp Asn Leu Ile  Val Leu Ser Tyr Gly  Ser Ser Ser Pro
            260                 265                 270
```

-continued

```
Ala Leu Ser Asn Arg Gln Arg Phe Pro Thr Phe Arg Thr His Pro
            275                 280                 285

Ser Ala Thr Leu His Asn Pro Thr Arg Val Lys Leu Phe Glu Lys Trp
    290                 295                 300

Gly Trp Lys Lys Ile Ala Thr Ile Gln Gln Thr Thr Glu Val Phe Thr
305                 310                 315                 320

Ser Leu Asp Asp Leu Glu Glu Arg Val Lys Glu Ala Gly Ile Glu Ile
                325                 330                 335

Thr Phe Arg Gln Ser Phe Phe Ser Asp Pro Ala Val Pro Val Lys Asn
            340                 345                 350

Leu Lys Arg Gln Asp Ala Arg Ile Ile Val Gly Leu Phe Tyr Glu Thr
        355                 360                 365

Glu Ala Arg Lys Val Phe Cys Glu Val Tyr Lys Glu Arg Leu Phe Gly
    370                 375                 380

Lys Lys Tyr Val Trp Phe Leu Ile Gly Trp Tyr Ala Asp Asn Trp Phe
385                 390                 395                 400

Lys Ile Tyr Asp Pro Ser Ile Asn Cys Thr Val Asp Glu Met Thr Glu
                405                 410                 415

Ala Val Glu Gly His Ile Thr Thr Glu Ile Val Met Leu Asn Pro Ala
            420                 425                 430

Asn Thr Arg Ser Ile Ser Asn Met Thr Ser Gln Glu Phe Val Glu Lys
        435                 440                 445

Leu Thr Lys Arg Leu Lys Arg His Pro Glu Glu Thr Gly Gly Phe Gln
    450                 455                 460

Glu Ala Pro Leu Ala Tyr Asp Ala Ile Trp Ala Leu Ala Leu Ala Leu
465                 470                 475                 480

Asn Lys Thr Ser Gly Gly Gly Arg Ser Gly Val Arg Leu Glu Asp
                485                 490                 495

Phe Asn Tyr Asn Asn Gln Thr Ile Thr Asp Gln Ile Tyr Arg Ala Met
                500                 505                 510

Asn Ser Ser Ser Phe Glu Gly Val Ser Gly His Val Val Phe Asp Ala
        515                 520                 525

Ser Gly Ser Arg Met Ala Trp Thr Leu Ile Glu Gln Leu Gln Gly Gly
    530                 535                 540

Ser Tyr Lys Lys Ile Gly Tyr Tyr Asp Ser Thr Lys Asp Asp Leu Ser
545                 550                 555                 560

Trp Ser Lys Thr Asp Lys Trp Ile Gly Gly Ser Pro Pro Ala Asp Gln
                565                 570                 575

Thr Leu Val Ile Lys Thr Phe Arg Phe Leu Ser Gln Lys Leu Phe Ile
            580                 585                 590

Ser Val Ser Val Leu Ser Ser Leu Gly Ile Val Leu Ala Val Val Cys
        595                 600                 605

Leu Ser Phe Asn Ile Tyr Asn Ser His Val Arg Tyr Ile Gln Asn Ser
    610                 615                 620

Gln Pro Asn Leu Asn Asn Leu Thr Ala Val Gly Cys Ser Leu Ala Leu
625                 630                 635                 640

Ala Ala Val Phe Pro Leu Gly Leu Asp Gly Tyr His Ile Gly Arg Asn
                645                 650                 655

Gln Phe Pro Phe Val Cys Gln Ala Arg Leu Trp Leu Gly Leu Gly
            660                 665                 670

Phe Ser Leu Gly Tyr Gly Ser Met Phe Thr Lys Ile Trp Trp Val His
    675                 680                 685
```

```
Thr Val Phe Thr Lys Lys Glu Glu Lys Lys Glu Trp Arg Lys Thr Leu
    690                 695                 700
Glu Pro Trp Lys Leu Tyr Ala Thr Val Gly Leu Leu Val Gly Met Asp
705                 710                 715                 720
Val Leu Thr Leu Ala Ile Trp Gln Ile Val Asp Pro Leu His Arg Thr
                    725                 730                 735
Ile Glu Thr Phe Ala Lys Glu Pro Lys Glu Asp Ile Asp Val Ser
                740                 745                 750
Ile Leu Pro Gln Leu Glu His Cys Ser Ser Arg Lys Met Asn Thr Trp
                755                 760                 765
Leu Gly Ile Phe Tyr Gly Tyr Lys Gly Leu Leu Leu Leu Gly Ile
770                 775                 780
Phe Leu Ala Tyr Glu Thr Lys Ser Val Ser Thr Glu Lys Ile Asn Asp
785                 790                 795                 800
His Arg Ala Val Gly Met Ala Ile Tyr Asn Val Ala Val Leu Cys Leu
                    805                 810                 815
Ile Thr Ala Pro Val Thr Met Ile Leu Ser Ser Gln Gln Asp Ala Ala
                820                 825                 830
Phe Ala Phe Ala Ser Leu Ala Ile Val Phe Ser Ser Tyr Ile Thr Leu
835                 840                 845
Val Val Leu Phe Val Pro Lys Met Arg Arg Leu Ile Thr Arg Gly Glu
850                 855                 860
Trp Gln Ser Glu Ala Gln Asp Thr Met Lys Thr Gly Ser Ser Thr Asn
865                 870                 875                 880
Asn Asn Glu Glu Glu Lys Ser Arg Leu Leu Lys Glu Asn Arg Glu
                885                 890                 895
Leu Glu Lys Ile Ile Ala Glu Ser Gly Gly Leu Pro Arg Gly Pro Pro
                900                 905                 910
Glu Pro Pro Asp Arg Leu Ser Cys Asp Gly Ser Arg Val His Leu Leu
                915                 920                 925
Tyr Lys
    930

<210> SEQ ID NO 86
<211> LENGTH: 330
<212> TYPE: PRT
<213> ORGANISM: Homo sapiens
<220> FEATURE:
<221> NAME/KEY: MISC_FEATURE
<223> OTHER INFORMATION: bile acid receptor

<400> SEQUENCE: 86

Met Thr Pro Asn Ser Thr Gly Glu Val Pro Ser Pro Ile Pro Lys Gly
1                   5                   10                  15
Ala Leu Gly Leu Ser Leu Ala Leu Ala Ser Leu Ile Ile Thr Ala Asn
                20                  25                  30
Leu Leu Leu Ala Leu Gly Ile Ala Trp Asp Arg Arg Leu Arg Ser Pro
            35                  40                  45
Pro Ala Gly Cys Phe Phe Leu Ser Leu Leu Ala Gly Leu Leu Thr
50                  55                  60
Gly Leu Ala Leu Pro Thr Leu Pro Gly Leu Trp Asn Gln Ser Arg Arg
65                  70                  75                  80
Gly Tyr Trp Ser Cys Leu Leu Val Tyr Leu Ala Pro Asn Phe Ser Phe
                85                  90                  95
Leu Ser Leu Leu Ala Asn Leu Leu Leu Val His Gly Glu Arg Tyr Met
                100                 105                 110
```

```
Ala Val Leu Arg Pro Leu Gln Pro Gly Ser Ile Arg Leu Ala Leu
            115                 120                 125

Leu Leu Thr Trp Ala Gly Pro Leu Leu Phe Ala Ser Leu Pro Ala Leu
130             135                 140

Gly Trp Asn His Trp Thr Pro Gly Ala Asn Cys Ser Ser Gln Ala Ile
145             150                 155                 160

Phe Pro Ala Pro Tyr Leu Tyr Leu Glu Val Tyr Gly Leu Leu Leu Pro
                165                 170                 175

Ala Val Gly Ala Ala Ala Phe Leu Ser Val Arg Val Leu Ala Thr Ala
            180                 185                 190

His Arg Gln Leu Gln Asp Ile Cys Arg Leu Glu Arg Ala Val Cys Arg
            195                 200                 205

Asp Glu Pro Ser Ala Leu Ala Arg Ala Leu Thr Trp Arg Gln Ala Arg
210             215                 220

Ala Gln Ala Gly Ala Met Leu Leu Phe Gly Leu Cys Trp Gly Pro Tyr
225             230                 235                 240

Val Ala Thr Leu Leu Leu Ser Val Leu Ala Tyr Glu Gln Arg Pro Pro
                245                 250                 255

Leu Gly Pro Gly Thr Leu Leu Ser Leu Leu Ser Leu Gly Ser Ala Ser
            260                 265                 270

Ala Ala Ala Val Pro Val Ala Met Gly Leu Gly Asp Gln Arg Tyr Thr
275             280                 285

Ala Pro Trp Arg Ala Ala Gln Arg Cys Leu Gln Gly Leu Trp Gly
            290                 295                 300

Arg Ala Ser Arg Asp Ser Pro Gly Pro Ser Ile Ala Tyr His Pro Ser
305             310                 315                 320

Ser Gln Ser Ser Val Asp Leu Asp Leu Asn
                325                 330

<210> SEQ ID NO 87
<211> LENGTH: 431
<212> TYPE: PRT
<213> ORGANISM: Saccharomyces cerevisiae
<220> FEATURE:
<221> NAME/KEY: MISC_FEATURE
<223> OTHER INFORMATION: a-factor receptor

<400> SEQUENCE: 87

Met Ser Asp Ala Ala Pro Ser Leu Ser Asn Leu Phe Tyr Asp Pro Thr
1               5                   10                  15

Tyr Asn Pro Gly Gln Ser Thr Ile Asn Tyr Thr Ser Ile Tyr Gly Asn
            20                  25                  30

Gly Ser Thr Ile Thr Phe Asp Glu Leu Gln Gly Leu Val Asn Ser Thr
        35                  40                  45

Val Thr Gln Ala Ile Met Phe Gly Val Arg Cys Gly Ala Ala Ala Leu
50                  55                  60

Thr Leu Ile Val Met Trp Met Thr Ser Arg Ser Arg Lys Thr Pro Ile
65                  70                  75                  80

Phe Ile Ile Asn Gln Val Ser Leu Phe Leu Ile Ile Leu His Ser Ala
                85                  90                  95

Leu Tyr Phe Lys Tyr Leu Leu Ser Asn Tyr Ser Ser Val Thr Tyr Ala
            100                 105                 110

Leu Thr Gly Phe Pro Gln Phe Ile Ser Arg Gly Asp Val His Val Tyr
        115                 120                 125

Gly Ala Thr Asn Ile Ile Gln Val Leu Leu Val Ala Ser Ile Glu Thr
```

```
            130                 135                 140
Ser Leu Val Phe Gln Ile Lys Val Ile Phe Thr Gly Asp Asn Phe Lys
145                 150                 155                 160

Arg Ile Gly Leu Met Leu Thr Ser Ile Ser Phe Thr Leu Gly Ile Ala
                165                 170                 175

Thr Val Thr Met Tyr Phe Val Ser Ala Val Lys Gly Met Ile Val Thr
                180                 185                 190

Tyr Asn Asp Val Ser Ala Thr Gln Asp Lys Tyr Phe Asn Ala Ser Thr
                195                 200                 205

Ile Leu Leu Ala Ser Ser Ile Asn Phe Met Ser Phe Val Leu Val Val
                210                 215                 220

Lys Leu Ile Leu Ala Ile Arg Ser Arg Arg Phe Leu Gly Leu Lys Gln
225                 230                 235                 240

Phe Asp Ser Phe His Ile Leu Leu Ile Met Ser Cys Gln Ser Leu Leu
                245                 250                 255

Val Pro Ser Ile Ile Phe Ile Leu Ala Tyr Ser Leu Lys Pro Asn Gln
                260                 265                 270

Gly Thr Asp Val Leu Thr Thr Val Ala Thr Leu Leu Ala Val Leu Ser
                275                 280                 285

Leu Pro Leu Ser Ser Met Trp Ala Thr Ala Ala Asn Asn Ala Ser Lys
                290                 295                 300

Thr Asn Thr Ile Thr Ser Asp Phe Thr Thr Ser Thr Asp Arg Phe Tyr
305                 310                 315                 320

Pro Gly Thr Leu Ser Ser Phe Gln Thr Asp Ser Ile Asn Asn Asp Ala
                325                 330                 335

Lys Ser Ser Leu Arg Ser Arg Leu Tyr Asp Leu Tyr Pro Arg Arg Lys
                340                 345                 350

Glu Thr Thr Ser Asp Lys His Ser Glu Arg Thr Phe Val Ser Glu Thr
                355                 360                 365

Ala Asp Asp Ile Glu Lys Asn Gln Phe Tyr Gln Leu Pro Thr Pro Thr
                370                 375                 380

Ser Ser Lys Asn Thr Arg Ile Gly Pro Phe Ala Asp Ala Ser Tyr Lys
385                 390                 395                 400

Glu Gly Glu Val Glu Pro Val Asp Met Tyr Thr Pro Asp Thr Ala Ala
                405                 410                 415

Asp Glu Glu Ala Arg Lys Phe Trp Thr Glu Asp Asn Asn Asn Leu
                420                 425                 430

<210> SEQ ID NO 88
<211> LENGTH: 382
<212> TYPE: PRT
<213> ORGANISM: Homo sapiens
<220> FEATURE:
<221> NAME/KEY: MISC_FEATURE
<223> OTHER INFORMATION: sphingosine-1-phosphate receptor

<400> SEQUENCE: 88

Met Gly Pro Thr Ser Val Pro Leu Val Lys Ala His Arg Ser Ser Val
1               5                   10                  15

Ser Asp Tyr Val Asn Tyr Asp Ile Ile Val Arg His Tyr Asn Tyr Thr
                20                  25                  30

Gly Lys Leu Asn Ile Ser Ala Asp Lys Glu Asn Ser Ile Lys Leu Thr
                35                  40                  45

Ser Val Val Phe Ile Leu Ile Cys Cys Phe Ile Ile Leu Glu Asn Ile
                50                  55                  60
```

```
Phe Val Leu Leu Thr Ile Trp Lys Thr Lys Lys Phe His Arg Pro Met
 65                  70                  75                  80

Tyr Tyr Phe Ile Gly Asn Leu Ala Leu Ser Asp Leu Leu Ala Gly Val
             85                   90                  95

Ala Tyr Thr Ala Asn Leu Leu Leu Ser Gly Ala Thr Thr Tyr Lys Leu
            100                 105                 110

Thr Pro Ala Gln Trp Phe Leu Arg Glu Gly Ser Met Phe Val Ala Leu
        115                 120                 125

Ser Ala Ser Val Phe Ser Leu Leu Ala Ile Ala Ile Glu Arg Tyr Ile
    130                 135                 140

Thr Met Leu Lys Met Lys Leu His Asn Gly Ser Asn Asn Phe Arg Leu
145                 150                 155                 160

Phe Leu Leu Ile Ser Ala Cys Trp Val Ile Ser Leu Ile Leu Gly Gly
                165                 170                 175

Leu Pro Ile Met Gly Trp Asn Cys Ile Ser Ala Leu Ser Ser Cys Ser
            180                 185                 190

Thr Val Leu Pro Leu Tyr His Lys His Tyr Ile Leu Phe Cys Thr Thr
        195                 200                 205

Val Phe Thr Leu Leu Leu Leu Ser Ile Val Ile Leu Tyr Cys Arg Ile
    210                 215                 220

Tyr Ser Leu Val Arg Thr Arg Ser Arg Arg Leu Thr Phe Arg Lys Asn
225                 230                 235                 240

Ile Ser Lys Ala Ser Arg Ser Ser Glu Lys Ser Leu Ala Leu Leu Lys
                245                 250                 255

Thr Val Ile Ile Val Leu Ser Val Phe Ile Ala Cys Trp Ala Pro Leu
            260                 265                 270

Phe Ile Leu Leu Leu Leu Asp Val Gly Cys Lys Val Lys Thr Cys Asp
        275                 280                 285

Ile Leu Phe Arg Ala Glu Tyr Phe Leu Val Leu Ala Val Leu Asn Ser
    290                 295                 300

Gly Thr Asn Pro Ile Ile Tyr Thr Leu Thr Asn Lys Glu Met Arg Arg
305                 310                 315                 320

Ala Phe Ile Arg Ile Met Ser Cys Cys Lys Cys Pro Ser Gly Asp Ser
                325                 330                 335

Ala Gly Lys Phe Lys Arg Pro Ile Ile Ala Gly Met Glu Phe Ser Arg
            340                 345                 350

Ser Lys Ser Asp Asn Ser Ser His Pro Gln Lys Asp Glu Gly Asp Asn
        355                 360                 365

Pro Glu Thr Ile Met Ser Ser Gly Asn Val Asn Ser Ser Ser
    370                 375                 380

<210> SEQ ID NO 89
<211> LENGTH: 593
<212> TYPE: PRT
<213> ORGANISM: Homo sapiens
<220> FEATURE:
<221> NAME/KEY: MISC_FEATURE
<223> OTHER INFORMATION: parathyroid hormone receptor

<400> SEQUENCE: 89

Met Gly Thr Ala Arg Ile Ala Pro Gly Leu Ala Leu Leu Leu Cys Cys
  1               5                  10                  15

Pro Val Leu Ser Ser Ala Tyr Ala Leu Val Asp Ala Asp Asp Val Met
             20                  25                  30

Thr Lys Glu Glu Gln Ile Phe Leu Leu His Arg Ala Gln Ala Gln Cys
         35                  40                  45
```

```
Glu Lys Arg Leu Lys Glu Val Leu Gln Arg Pro Ala Ser Ile Met Glu
 50                  55                  60

Ser Asp Lys Gly Trp Thr Ser Ala Ser Thr Ser Gly Lys Pro Arg Lys
 65                  70                  75                  80

Asp Lys Ala Ser Gly Lys Leu Tyr Pro Glu Ser Glu Asp Lys Glu
                 85                  90                  95

Ala Pro Thr Gly Ser Arg Tyr Arg Gly Arg Pro Cys Leu Pro Glu Trp
                100                 105                 110

Asp His Ile Leu Cys Trp Pro Leu Gly Ala Pro Gly Glu Val Val Ala
                115                 120                 125

Val Pro Cys Pro Asp Tyr Ile Tyr Asp Phe Asn His Lys Gly His Ala
130                 135                 140

Tyr Arg Arg Cys Asp Arg Asn Gly Ser Trp Glu Leu Val Pro Gly His
145                 150                 155                 160

Asn Arg Thr Trp Ala Asn Tyr Ser Glu Cys Val Lys Phe Leu Thr Asn
                165                 170                 175

Glu Thr Arg Glu Arg Glu Val Phe Asp Arg Leu Gly Met Ile Tyr Thr
                180                 185                 190

Val Gly Tyr Ser Val Ser Leu Ala Ser Leu Thr Val Ala Val Leu Ile
                195                 200                 205

Leu Ala Tyr Phe Arg Arg Leu His Cys Thr Arg Asn Tyr Ile His Met
210                 215                 220

His Leu Phe Leu Ser Phe Met Leu Arg Ala Val Ser Ile Phe Val Lys
225                 230                 235                 240

Asp Ala Val Leu Tyr Ser Gly Ala Thr Leu Asp Glu Ala Glu Arg Leu
                245                 250                 255

Thr Glu Glu Leu Arg Ala Ile Ala Gln Ala Pro Pro Pro Ala
                260                 265                 270

Thr Ala Ala Gly Tyr Ala Gly Cys Arg Val Ala Val Thr Phe Phe
                275                 280                 285

Leu Tyr Phe Leu Ala Thr Asn Tyr Tyr Trp Ile Leu Val Glu Gly Leu
290                 295                 300

Tyr Leu His Ser Leu Ile Phe Met Ala Phe Phe Ser Glu Lys Lys Tyr
305                 310                 315                 320

Leu Trp Gly Phe Thr Val Phe Gly Trp Gly Leu Pro Ala Val Phe Val
                325                 330                 335

Ala Val Trp Val Ser Val Arg Ala Thr Leu Ala Asn Thr Gly Cys Trp
                340                 345                 350

Asp Leu Ser Ser Gly Asn Lys Lys Trp Ile Ile Gln Val Pro Ile Leu
                355                 360                 365

Ala Ser Ile Val Leu Asn Phe Ile Leu Phe Ile Asn Ile Val Arg Val
                370                 375                 380

Leu Ala Thr Lys Leu Arg Glu Thr Asn Ala Gly Arg Cys Asp Thr Arg
385                 390                 395                 400

Gln Gln Tyr Arg Lys Leu Leu Lys Ser Thr Leu Val Leu Met Pro Leu
                405                 410                 415

Phe Gly Val His Tyr Ile Val Phe Met Ala Thr Pro Tyr Thr Glu Val
                420                 425                 430

Ser Gly Thr Leu Trp Gln Val Gln Met His Tyr Glu Met Leu Phe Asn
                435                 440                 445

Ser Phe Gln Gly Phe Phe Val Ala Ile Ile Tyr Cys Phe Cys Asn Gly
                450                 455                 460
```

Glu Val Gln Ala Glu Ile Lys Lys Ser Trp Ser Arg Trp Thr Leu Ala
465                 470                 475                 480

Leu Asp Phe Lys Arg Lys Ala Arg Ser Gly Ser Ser Ser Tyr Ser Tyr
                485                 490                 495

Gly Pro Met Val Ser His Thr Ser Val Thr Asn Val Gly Pro Arg Val
            500                 505                 510

Gly Leu Gly Leu Pro Leu Ser Pro Arg Leu Leu Pro Thr Ala Thr Thr
        515                 520                 525

Asn Gly His Pro Gln Leu Pro Gly His Ala Lys Pro Gly Thr Pro Ala
    530                 535                 540

Leu Glu Thr Leu Glu Thr Thr Pro Ala Met Ala Ala Pro Lys Asp
545                 550                 555                 560

Asp Gly Phe Leu Asn Gly Ser Cys Ser Gly Leu Asp Glu Glu Ala Ser
                565                 570                 575

Gly Pro Glu Arg Pro Pro Ala Leu Leu Gln Glu Glu Trp Glu Thr Val
                580                 585                 590

Met

<210> SEQ ID NO 90
<211> LENGTH: 375
<212> TYPE: PRT
<213> ORGANISM: Homo sapiens
<220> FEATURE:
<221> NAME/KEY: MISC_FEATURE
<223> OTHER INFORMATION: estrogen receptor

<400> SEQUENCE: 90

Met Asp Val Thr Ser Gln Ala Arg Gly Val Gly Leu Glu Met Tyr Pro
1               5                   10                  15

Gly Thr Ala Gln Pro Ala Ala Pro Asn Thr Thr Ser Pro Glu Leu Asn
            20                  25                  30

Leu Ser His Pro Leu Leu Gly Thr Ala Leu Ala Asn Gly Thr Gly Glu
        35                  40                  45

Leu Ser Glu His Gln Gln Tyr Val Ile Gly Leu Phe Leu Ser Cys Leu
    50                  55                  60

Tyr Thr Ile Phe Leu Phe Pro Ile Gly Phe Val Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Val Ala Asp Leu Ile Leu Val Ala Asp Ser
            100                 105                 110

Leu Ile Glu Val Phe Asn Leu His Glu Arg Tyr Tyr Asp Ile Ala Val
        115                 120                 125

Leu Cys Thr Phe Met Ser Leu Phe Leu Gln Val Asn Met Tyr Ser Ser
    130                 135                 140

Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Gln His Thr Asp Glu Ala Cys Phe Cys Phe
        195                 200                 205

Ala Asp Val Arg Glu Val Gln Trp Leu Glu Val Thr Leu Gly Phe Ile
    210                 215                 220

```
Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
            245                 250                 255

Ala Leu Arg Met Ile Leu Ala Val Val Leu Val Phe Phe Val Cys Trp
            260                 265                 270

Leu Pro Glu Asn Val Phe Ile Ser Val His Leu Leu Gln Arg Thr Gln
            275                 280                 285

Pro Gly Ala Ala Pro Cys Lys Gln Ser Phe Arg His Ala His Pro Leu
            290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Ile Glu Gln Lys Thr Asn Leu Pro Ala Leu Asn Arg Phe Cys
                340                 345                 350

His Ala Ala Leu Lys Ala Val Ile Pro Asp Ser Thr Glu Gln Ser Asp
                355                 360                 365

Val Arg Phe Ser Ser Ala Val
                370                 375

<210> SEQ ID NO 91
<211> LENGTH: 600
<212> TYPE: PRT
<213> ORGANISM: Saccharomyces cerevisiae
<220> FEATURE:
<221> NAME/KEY: MISC_FEATURE
<223> OTHER INFORMATION: sucrose receptor

<400> SEQUENCE: 91

Met Ile Thr Glu Gly Phe Pro Pro Asn Leu Asn Ala Leu Lys Gly Ser
1               5                   10                  15

Ser Leu Leu Glu Lys Arg Val Asp Ser Leu Arg Gln Leu Asn Thr Thr
            20                  25                  30

Thr Val Asn Gln Leu Leu Gly Leu Pro Gly Met Thr Ser Thr Phe Thr
            35                  40                  45

Ala Pro Gln Leu Leu Gln Leu Arg Ile Ile Ala Ile Thr Ala Ser Ala
50                  55                  60

Val Ser Leu Ile Ala Gly Cys Leu Gly Met Phe Phe Leu Ser Lys Met
65                  70                  75                  80

Asp Lys Arg Arg Lys Val Phe Arg His Asp Leu Ile Ala Phe Leu Ile
                85                  90                  95

Ile Cys Asp Phe Leu Lys Ala Phe Ile Leu Met Ile Tyr Pro Met Ile
                100                 105                 110

Ile Leu Ile Asn Asn Ser Val Tyr Ala Thr Pro Ala Phe Phe Asn Thr
            115                 120                 125

Leu Gly Trp Phe Thr Ala Phe Ala Ile Glu Gly Ala Asp Met Ala Ile
            130                 135                 140

Met Ile Phe Ala Ile His Phe Ala Ile Leu Ile Phe Lys Pro Asn Trp
145                 150                 155                 160

Lys Trp Arg Asn Lys Arg Ser Gly Asn Met Glu Gly Gly Leu Tyr Lys
                165                 170                 175

Lys Arg Ser Tyr Ile Trp Pro Ile Thr Ala Leu Val Pro Ala Ile Leu
                180                 185                 190

Ala Ser Leu Ala Phe Ile Asn Tyr Asn Lys Leu Asn Asp Asp Ser Asp
                195                 200                 205
```

-continued

```
Thr Thr Ile Ile Leu Asp Asn Asn Tyr Asn Phe Pro Asp Ser Pro
    210                 215                 220
Arg Gln Gly Gly Tyr Lys Pro Trp Ser Ala Trp Cys Tyr Leu Pro Pro
225                 230                 235                 240
Lys Pro Tyr Trp Tyr Lys Ile Val Leu Ser Trp Gly Pro Arg Tyr Phe
                245                 250                 255
Ile Ile Ile Phe Ile Phe Ala Val Tyr Leu Ser Ile Tyr Ile Phe Ile
            260                 265                 270
Thr Ser Glu Ser Lys Arg Ile Lys Ala Gln Ile Gly Asp Phe Asn His
        275                 280                 285
Asn Val Leu Glu Glu Lys Glu Lys Lys Leu Asn Val Asp Asn
    290                 295                 300
Asn Asn Thr Asn Pro Ala Asp Asn Ile Pro Thr Leu Ser Asn Glu Ala
305                 310                 315                 320
Phe Thr Pro Ser Gln Gln Phe Ser Gln Glu Arg Val Asn Asn Asn Ala
                325                 330                 335
Asp Arg Cys Glu Asn Ser Ser Phe Thr Asn Val Gln His Phe Gln
            340                 345                 350
Ala Gln Thr Tyr Lys Gln Met Lys Lys Arg Arg Ala Gln Ile Gln Lys
        355                 360                 365
Asn Leu Arg Ala Ile Phe Ile Tyr Pro Leu Ser Tyr Ile Gly Ile Trp
    370                 375                 380
Leu Phe Pro Ile Ile Ala Asp Ala Leu Gln Tyr Asn His Glu Ile Lys
385                 390                 395                 400
His Gly Pro Thr Met Trp Val Thr Tyr Ile Asp Thr Cys Val Arg Pro
                405                 410                 415
Leu Ser Cys Leu Val Asp Val Ile Val Tyr Leu Phe Lys Glu Lys Pro
            420                 425                 430
Trp Asn Tyr Ser Trp Ala Lys Thr Glu Ser Lys Tyr Leu Ile Glu Lys
        435                 440                 445
Tyr Ile Leu Lys Gly Glu Leu Gly Glu Lys Glu Ile Leu Lys Phe Cys
    450                 455                 460
His Ser Asn Trp Gly Lys Arg Gly Trp Tyr Tyr Arg Gly Lys Trp Lys
465                 470                 475                 480
Lys Arg Lys Cys Trp Lys Tyr Ser Thr Asn Pro Leu Lys Arg Ile Leu
                485                 490                 495
Trp Phe Val Glu Arg Phe Phe Lys Gln Leu Phe Glu Leu Lys Leu His
            500                 505                 510
Phe Ser Phe Tyr Asp Asn Cys Asp Asp Phe Glu Tyr Trp Glu Asn Tyr
        515                 520                 525
Tyr Ser Ala Lys Asp Ser Asn Asp Asn Lys Arg Thr Glu Ser Asp Glu
    530                 535                 540
Thr Lys Thr Asn Ser Ser Asp Arg Ser Leu Pro Ser Asn Ser Leu Glu
545                 550                 555                 560
Leu Gln Ala Met Leu Asn Asn Ile Thr Ala Glu Val Glu Val Pro
                565                 570                 575
Leu Phe Trp Arg Ile Ile His His Ile Pro Met Leu Gly Gly Ile Asp
            580                 585                 590
Leu Asp Glu Leu Asn Arg Leu Leu
        595                 600
```

<210> SEQ ID NO 92
<211> LENGTH: 477

```
<212> TYPE: PRT
<213> ORGANISM: Homo sapiens
<220> FEATURE:
<221> NAME/KEY: MISC_FEATURE
<223> OTHER INFORMATION: glucagon receptor

<400> SEQUENCE: 92

Met Pro Pro Cys Gln Pro Gln Arg Pro Leu Leu Leu Leu Leu Leu Leu
1               5                   10                  15

Leu Ala Cys Gln Pro Gln Val Pro Ser Ala Gln Val Met Asp Phe Leu
            20                  25                  30

Phe Glu Lys Trp Lys Leu Tyr Gly Asp Gln Cys His His Asn Leu Ser
            35                  40                  45

Leu Leu Pro Pro Pro Thr Glu Leu Val Cys Asn Arg Thr Phe Asp Lys
50                  55                  60

Tyr Ser Cys Trp Pro Asp Thr Pro Ala Asn Thr Thr Ala Asn Ile Ser
65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
            100                 105                 110

Gln Pro Trp Arg Asp Ala Ser Gln Cys Gln Met Asp Gly Glu Glu Ile
            115                 120                 125

Glu Val Gln Lys Glu Val Ala Lys Met Tyr Ser Ser Phe Gln Val Met
130                 135                 140

Tyr Thr Val Gly Tyr Ser Leu Ser Leu Gly Ala Leu Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
            180                 185                 190

Val Ile Asp Gly Leu Leu Arg Thr Arg Tyr Ser Gln Lys Ile Gly Asp
            195                 200                 205

Asp Leu Ser Val Ser Thr Trp Leu Ser Asp Gly Ala Val Ala Gly Cys
210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
            260                 265                 270

Gly Ala Pro Met Leu Phe Val Val Pro Trp Ala Val Val Lys Cys Leu
            275                 280                 285

Phe Glu Asn Val Gln Cys Trp Thr Ser Asn Asp Asn Met Gly Phe Trp
290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
                325                 330                 335

Gln Met His His Thr Asp Tyr Lys Phe Arg Leu Ala Lys Ser Thr Leu
            340                 345                 350

Thr Leu Ile Pro Leu Leu Gly Val His Glu Val Val Phe Ala Phe Val
            355                 360                 365

Thr Asp Glu His Ala Gln Gly Thr Leu Arg Ser Ala Lys Leu Phe Phe
370                 375                 380
```

-continued

```
Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
            405                 410                 415

Arg Trp Arg Leu Gly Lys Val Leu Trp Glu Glu Arg Asn Thr Ser Asn
        420                 425                 430

His Arg Ala Ser Ser Ser Pro Gly His Gly Pro Pro Ser Lys Glu Leu
    435                 440                 445

Gln Phe Gly Arg Gly Gly Ser Gln Asp Ser Ser Ala Glu Thr Pro
450                 455                 460

Leu Ala Gly Gly Leu Pro Arg Leu Ala Glu Ser Pro Phe
465                 470                 475

<210> SEQ ID NO 93
<211> LENGTH: 474
<212> TYPE: PRT
<213> ORGANISM: Homo sapiens
<220> FEATURE:
<221> NAME/KEY: MISC_FEATURE
<223> OTHER INFORMATION: (AAs 145-414 GPCR domain) calcitonin receptor

<400> SEQUENCE: 93

Met Arg Phe Thr Phe Thr Ser Arg Cys Leu Ala Leu Phe Leu Leu Leu
1               5                   10                  15

Asn His Pro Thr Pro Ile Leu Pro Ala Phe Ser Asn Gln Thr Tyr Pro
            20                  25                  30

Thr Ile Glu Pro Lys Pro Phe Leu Tyr Val Val Gly Arg Lys Lys Met
        35                  40                  45

Met Asp Ala Gln Tyr Lys Cys Tyr Asp Arg Met Gln Gln Leu Pro Ala
    50                  55                  60

Tyr Gln Gly Glu Gly Pro Tyr Cys Asn Arg Thr Trp Asp Gly Trp Leu
65                  70                  75                  80

Cys Trp Asp Asp Thr Pro Ala Gly Val Leu Ser Tyr Gln Phe Cys Pro
                85                  90                  95

Asp Tyr Phe Pro Asp Phe Asp Pro Ser Glu Lys Val Thr Lys Tyr Cys
            100                 105                 110

Asp Glu Lys Gly Val Trp Phe Lys His Pro Glu Asn Asn Arg Thr Trp
        115                 120                 125

Ser Asn Tyr Thr Met Cys Asn Ala Phe Thr Pro Glu Lys Leu Lys Asn
    130                 135                 140

Ala Tyr Val Leu Tyr Tyr Leu Ala Ile Val Gly His Ser Leu Ser Ile
145                 150                 155                 160

Phe Thr Leu Val Ile Ser Leu Gly Ile Phe Val Phe Phe Arg Ser Leu
                165                 170                 175

Gly Cys Gln Arg Val Thr Leu His Lys Asn Met Phe Leu Thr Tyr Ile
            180                 185                 190

Leu Asn Ser Met Ile Ile Ile His Leu Val Glu Val Val Pro Asn
        195                 200                 205

Gly Glu Leu Val Arg Arg Asp Pro Val Ser Cys Lys Ile Leu His Phe
    210                 215                 220

Phe His Gln Tyr Met Met Ala Cys Asn Tyr Phe Trp Met Leu Cys Glu
225                 230                 235                 240

Gly Ile Tyr Leu His Thr Leu Ile Val Val Ala Val Phe Thr Glu Lys
                245                 250                 255

Gln Arg Leu Arg Trp Tyr Tyr Leu Leu Gly Trp Gly Phe Pro Leu Val
```

```
                    260                 265                 270
Pro Thr Thr Ile His Ala Ile Thr Arg Ala Val Tyr Phe Asn Asp Asn
                275                 280                 285

Cys Trp Leu Ser Val Glu Thr His Leu Leu Tyr Ile Ile His Gly Pro
            290                 295                 300

Val Met Ala Ala Leu Val Val Asn Phe Phe Phe Leu Leu Asn Ile Val
305                 310                 315                 320

Arg Val Leu Val Thr Lys Met Arg Glu Thr His Glu Ala Glu Ser His
                325                 330                 335

Met Tyr Leu Lys Ala Val Lys Ala Thr Met Ile Leu Val Pro Leu Leu
            340                 345                 350

Gly Ile Gln Phe Val Val Phe Pro Trp Arg Pro Ser Asn Lys Met Leu
                355                 360                 365

Gly Lys Ile Tyr Asp Tyr Val Met His Ser Leu Ile His Phe Gln Gly
            370                 375                 380

Phe Phe Val Ala Thr Ile Tyr Cys Phe Cys Asn Asn Glu Val Gln Thr
385                 390                 395                 400

Thr Val Lys Arg Gln Trp Ala Gln Phe Lys Ile Gln Trp Asn Gln Arg
                405                 410                 415

Trp Gly Arg Arg Pro Ser Asn Arg Ser Ala Arg Ala Ala Ala Ala Ala
            420                 425                 430

Ala Glu Ala Gly Asp Ile Pro Ile Tyr Ile Cys His Gln Gln Leu Arg
                435                 440                 445

Asn Glu Pro Ala Asn Asn Gln Gly Glu Glu Ser Ala Glu Ile Ile Pro
            450                 455                 460

Leu Asn Ile Ile Glu Gln Glu Ser Ser Ala
465                 470

<210> SEQ ID NO 94
<211> LENGTH: 62
<212> TYPE: DNA
<213> ORGANISM: Artificial sequence
<220> FEATURE:
<223> OTHER INFORMATION: Forward PAQR1 primer

<400> SEQUENCE: 94
ggtggtggcg accatcacga gaatctttat tttcagggcg acatgtcttc ccacaaagga    60
tc                                                                  62

<210> SEQ ID NO 95
<211> LENGTH: 69
<212> TYPE: DNA
<213> ORGANISM: Artificial sequence
<220> FEATURE:
<223> OTHER INFORMATION: Reverse PAQR1 primer

<400> SEQUENCE: 95
atatctgcag aattccagca cactggcggc cgttactagt ggatcctcag agaagggtgt    60
catcagtac                                                           69

<210> SEQ ID NO 96
<211> LENGTH: 62
<212> TYPE: DNA
<213> ORGANISM: Artificial sequence
<220> FEATURE:
<223> OTHER INFORMATION: Forward PAQR5 primer

<400> SEQUENCE: 96
```

```
ggtggtggcg accatcacga gaatctttat tttcagggcg ccatggtgag cctgaagctc      60
cc                                                                    62
```

<210> SEQ ID NO 97
<211> LENGTH: 69
<212> TYPE: DNA
<213> ORGANISM: Artificial sequence
<220> FEATURE:
<223> OTHER INFORMATION: Reverse PAQR5 primer

<400> SEQUENCE: 97

```
atatctgcag aattccagca cactggcggc cgttactagt ggatcctcag agaagggtgt      60
catcagtac                                                             69
```

<210> SEQ ID NO 98
<211> LENGTH: 62
<212> TYPE: DNA
<213> ORGANISM: Artificial sequence
<220> FEATURE:
<223> OTHER INFORMATION: Forward PAQR6 primer

<400> SEQUENCE: 98

```
ggtggtggcg accatcacga gaatctttat tttcagggcg acatgttcag tctcaagctg      60
cc                                                                    62
```

<210> SEQ ID NO 99
<211> LENGTH: 69
<212> TYPE: DNA
<213> ORGANISM: Artificial sequence
<220> FEATURE:
<223> OTHER INFORMATION: Reverse PAQR6 primer

<400> SEQUENCE: 99

```
atatctgcag aattccagca cactggcggc cgttactagt ggatccttac tgttgtttgg      60
cctgggtac                                                             69
```

<210> SEQ ID NO 100
<211> LENGTH: 62
<212> TYPE: DNA
<213> ORGANISM: Artificial sequence
<220> FEATURE:
<223> OTHER INFORMATION: Forward PAQR7 primer

<400> SEQUENCE: 100

```
ggtggtggcg accatcacga gaatctttat tttcagggcg acatgtccat ggcccagaaa      60
ct                                                                    62
```

<210> SEQ ID NO 101
<211> LENGTH: 69
<212> TYPE: DNA
<213> ORGANISM: Artificial sequence
<220> FEATURE:
<223> OTHER INFORMATION: Reverse PAQR7 primer

<400> SEQUENCE: 101

```
atatctgcag aattccagca cactggcggc cgttactagt ggatcctcac ttggtcttct      60
catcaagtt                                                             69
```

<210> SEQ ID NO 102
<211> LENGTH: 62
<212> TYPE: DNA
<213> ORGANISM: Artificial sequence

```
<220> FEATURE:
<223> OTHER INFORMATION: Forward PAQR8 primer

<400> SEQUENCE: 102
ggtggtggcg accatcacga gaatctttat tttcagggcg acatgtcgac cgccatcttg      60
ga                                                                    62

<210> SEQ ID NO 103
<211> LENGTH: 69
<212> TYPE: DNA
<213> ORGANISM: Artificial sequence
<220> FEATURE:
<223> OTHER INFORMATION: Reverse PAQR8 primer

<400> SEQUENCE: 103
atatctgcag aattccagca cactggcggc cgttactagt ggatcctcag gaatctttct      60
tggtcagtc                                                             69

<210> SEQ ID NO 104
<211> LENGTH: 62
<212> TYPE: DNA
<213> ORGANISM: Artificial sequence
<220> FEATURE:
<223> OTHER INFORMATION: Forward PAQR9 primer

<400> SEQUENCE: 104
ggtggtggcg accatcacga gaatctttat tttcagggcg ccatggcgcg gcgcctgcag      60
cc                                                                    62

<210> SEQ ID NO 105
<211> LENGTH: 69
<212> TYPE: DNA
<213> ORGANISM: Artificial sequence
<220> FEATURE:
<223> OTHER INFORMATION: Reverse PAQR9 primer

<400> SEQUENCE: 105
atatctgcag aattccagca cactggcggc cgttactagt ggatcctcac tttttactgc      60
agaattcgg                                                             69

<210> SEQ ID NO 106
<211> LENGTH: 55
<212> TYPE: DNA
<213> ORGANISM: Artificial sequence
<220> FEATURE:
<223> OTHER INFORMATION: Forward PAQR2 primer

<400> SEQUENCE: 106
gaattcgata tcaagcttat cgataccgtc gacaatgaac gagccaacag aaaac          55

<210> SEQ ID NO 107
<211> LENGTH: 55
<212> TYPE: DNA
<213> ORGANISM: Artificial sequence
<220> FEATURE:
<223> OTHER INFORMATION: Reverse PAQR2 primer

<400> SEQUENCE: 107
gcgtgacata actaattaca tgactcgagg tcgactcaca gtgcatcctc ttcac           55

<210> SEQ ID NO 108
<211> LENGTH: 220
<212> TYPE: PRT
```

<213> ORGANISM: Bacillus cereus

<400> SEQUENCE: 108

```
Met Arg Gly Val Ile Met Asn Ala Tyr Val Arg Glu Pro Val Asn Ala
1               5                   10                  15

Phe Thr His Leu Gly Gly Ala Ile Leu Ser Phe Ile Ala Leu Leu Ala
            20                  25                  30

Met Leu Val Lys Val Ser Ile Lys Met Pro Ser Phe Ala Ala Ile Thr
        35                  40                  45

Ala Val Ile Leu Phe Gly Ile Gly Met Met Val Leu Tyr Thr Ala Ser
    50                  55                  60

Ala Val Tyr His Ser Val Val Ala Asn Glu Arg Val Ile Tyr Phe Phe
65                  70                  75                  80

Arg Lys Leu Asp His Ser Met Ile Phe Ile Leu Ile Ala Gly Thr Tyr
                85                  90                  95

Ala Pro Phe Cys Leu Ile Thr Leu Asn Ser Ala Ser Gly Leu Leu Leu
            100                 105                 110

Phe Cys Leu Val Tyr Ala Thr Ala Ile Cys Gly Ile Val Phe Lys Met
        115                 120                 125

Phe Trp Phe Asn Cys Pro Arg Trp Leu Ser Thr Ala Ile Tyr Ile Thr
    130                 135                 140

Met Gly Trp Leu Ile Val Leu Phe Phe Ala Pro Leu Ala Glu Asn Leu
145                 150                 155                 160

Ser Thr Gly Gly Ile Val Phe Leu Val Leu Gly Gly Ile Phe Tyr Thr
                165                 170                 175

Ile Gly Gly Phe Ile Tyr Gly Thr Lys Pro Lys Trp Leu Glu Phe Lys
            180                 185                 190

Tyr Met Gly His His Glu Ile Phe His Val Phe Val Leu Leu Gly Ser
        195                 200                 205

Leu Ala His Phe Leu Ser Val Tyr Cys Tyr Val Ile
    210                 215                 220
```

<210> SEQ ID NO 109
<211> LENGTH: 236
<212> TYPE: PRT
<213> ORGANISM: Bacillus cereus

<400> SEQUENCE: 109

```
Met Val Arg Glu Lys Thr Tyr Tyr Phe Met Ile Val Glu Arg Ile Thr
1               5                   10                  15

Ile Met Thr Glu Lys Met Thr Arg Met Thr Gln Phe Val Lys Glu Glu
            20                  25                  30

Ile Ala Asn Ala Ile Thr His Gly Ile Gly Ala Ile Leu Ser Ile Pro
        35                  40                  45

Ala Leu Ile Ile Leu Ile Ile His Ala Ser Lys His Gly Thr Ala Ser
    50                  55                  60

Ala Val Val Ala Phe Thr Val Tyr Gly Val Ser Met Phe Leu Leu Tyr
65                  70                  75                  80

Leu Phe Ser Thr Leu Leu His Ser Ile His His Pro Lys Val Glu Lys
                85                  90                  95

Leu Phe Thr Ile Leu Asp His Ser Ala Ile Tyr Leu Leu Ile Ala Gly
            100                 105                 110

Thr Tyr Thr Pro Phe Leu Leu Ile Thr Leu Arg Gly Pro Leu Gly Trp
        115                 120                 125

Thr Leu Leu Ala Ile Ile Trp Thr Leu Ala Ile Gly Gly Ile Ile Phe
```

```
            130                 135                 140
Lys Ile Phe Phe Val Arg Arg Phe Ile Lys Ala Ser Thr Leu Cys Tyr
145                 150                 155                 160

Ile Ile Met Gly Trp Leu Ile Ile Val Ala Ile Lys Pro Leu Tyr Glu
                165                 170                 175

Asn Leu Thr Gly His Gly Phe Ser Leu Leu Leu Ala Gly Gly Ile Leu
                180                 185                 190

Tyr Ser Val Gly Ala Ile Phe Phe Leu Trp Glu Lys Leu Pro Phe Asn
                195                 200                 205

His Ala Ile Trp His Leu Phe Val Leu Gly Gly Ser Ala Met Met Phe
                210                 215                 220

Phe Cys Val Leu Phe Tyr Val Leu Pro Thr Ala Ser
225                 230                 235

<210> SEQ ID NO 110
<211> LENGTH: 219
<212> TYPE: PRT
<213> ORGANISM: Escherichia coli

<400> SEQUENCE: 110

Met Val Gln Lys Pro Leu Ile Lys Gln Gly Tyr Ser Leu Ala Glu Glu
1               5                   10                  15

Ile Ala Asn Ser Val Ser His Gly Ile Gly Leu Val Phe Gly Ile Val
                20                  25                  30

Gly Leu Val Leu Leu Leu Val Gln Ala Val Asp Leu Asn Ala Ser Ala
                35                  40                  45

Thr Ala Ile Thr Ser Tyr Ser Leu Tyr Gly Gly Ser Met Ile Leu Leu
            50                  55                  60

Phe Leu Ala Ser Thr Leu Tyr His Ala Ile Pro His Gln Arg Ala Lys
65                  70                  75                  80

Met Trp Leu Lys Lys Phe Asp His Cys Ala Ile Tyr Leu Leu Ile Ala
                85                  90                  95

Gly Thr Tyr Thr Pro Phe Leu Leu Val Gly Leu Asp Ser Pro Leu Ala
                100                 105                 110

Arg Gly Leu Met Ile Val Ile Trp Ser Leu Ala Leu Leu Gly Ile Leu
                115                 120                 125

Phe Lys Leu Thr Ile Ala His Arg Phe Lys Ile Leu Ser Leu Val Thr
130                 135                 140

Tyr Leu Ala Met Gly Trp Leu Ser Leu Val Val Ile Tyr Glu Met Ala
145                 150                 155                 160

Val Lys Leu Ala Ala Gly Ser Val Thr Leu Leu Ala Val Gly Gly Val
                165                 170                 175

Val Tyr Ser Leu Gly Val Ile Phe Tyr Val Cys Lys Arg Ile Pro Tyr
                180                 185                 190

Asn His Ala Ile Trp His Gly Phe Val Leu Gly Gly Ser Val Cys His
                195                 200                 205

Phe Leu Ala Ile Tyr Leu Tyr Ile Gly Gln Ala
                210                 215

<210> SEQ ID NO 111
<211> LENGTH: 214
<212> TYPE: PRT
<213> ORGANISM: Vibrio vulnificus

<400> SEQUENCE: 111

Met Ser Val Ser Gln Tyr Ser Val Arg Glu Glu Val Ala Asn Ala Val
```

```
  1               5                  10                 15
Thr His Gly Leu Gly Met Ile Phe Gly Ile Val Gly Leu Val Met Leu
                20                 25                 30

Leu Val Lys Ala Thr Glu His His Ala Asp Gly Leu Thr Ile Ala Ser
                35                 40                 45

Met Ala Ile Tyr Gly Ser Ser Ile Ile Val Leu Phe Leu Ala Ser Thr
                50                 55                 60

Leu Tyr His Ala Ile Pro Tyr Pro Lys Ala Lys Arg Trp Leu Lys Thr
65                  70                 75                 80

Phe Asp His Ser Ala Ile Tyr Leu Leu Ile Ala Gly Ser Tyr Thr Pro
                85                 90                 95

Phe Leu Leu Val Ser Leu Arg Thr Pro Leu Ala Ile Gly Leu Met Ile
                100                105                110

Val Ile Trp Ser Ile Ala Leu Leu Gly Ile Ile Met Lys Val Ala Phe
                115                120                125

Val Tyr Arg Phe Lys Arg Phe Ser Leu Val Ser Tyr Leu Leu Met Gly
                130                135                140

Trp Leu Ser Leu Ile Val Ile Tyr Gln Leu Ala Ile Ser Leu Asp Ile
145                 150                155                160

Gly Gly Leu Thr Leu Leu Ala Ala Gly Gly Leu Ile Tyr Ser Leu Gly
                165                170                175

Val Ile Phe Tyr Val Ala Lys Lys Ile Pro Tyr Asn His Ala Ile Trp
                180                185                190

His Cys Phe Val Leu Val Gly Cys Val Cys His Phe Leu Ala Ile Tyr
                195                200                205

Leu Tyr Val Asn Pro Val
                210

<210> SEQ ID NO 112
<211> LENGTH: 543
<212> TYPE: PRT
<213> ORGANISM: Saccharomyces cerevisiae

<400> SEQUENCE: 112

Met Met Asp Ser Ser Ser Lys Ser Leu Thr Gln Tyr Ile Pro Ser Pro
1               5                  10                 15

Met Gly Ser Leu Ser Arg Leu Lys Gln Lys Gly Val Asp Asn Phe Gln
                20                 25                 30

Lys Val Lys Lys Ser Gly Lys Ser Ile Tyr Asn Tyr Asn Tyr Ser Lys
                35                 40                 45

Phe Val Pro His Pro Phe Ser Thr Ile Asp Glu Ser Val Lys His Ser
                50                 55                 60

Glu Ser Gly Arg Tyr Asp Asp Leu Glu Ile Ile Arg Pro Thr Lys Glu
65                  70                 75                 80

Lys Glu Val Thr Ser Ser Val Tyr Lys Arg Asn Ser Gly Lys Ser Leu
                85                 90                 95

Asn Thr Glu Ser Gln Phe Ser Leu Gly Asp Ser Asp Ala Ala Thr Leu
                100                105                110

Val Asn Ser Val Ala Thr Phe Lys Leu Asn Asn Ala Ser Thr Ser Thr
                115                120                125

Ser Leu Val Ser Ser Ser Thr Val Cys Ser Gln Ala Lys Ser Ser
                130                135                140

Leu Arg Ser Pro Thr Ser Arg Leu Asn Asp Thr Lys Ile Lys Glu Glu
145                 150                155                160
```

```
Asn Asn Tyr Ile Ser Ser Val Lys Asp Tyr Cys Gly Pro Met Arg Lys
            165                 170                 175

Ser Met Val Lys Thr Glu Ile Leu Ile Glu Glu Pro Leu Asn Pro Thr
        180                 185                 190

Thr Asp Ile Lys Ser Phe Ile Asn Ser Tyr Asn His Gly Lys Ala Tyr
            195                 200                 205

Ser Leu Gly Glu Thr Gln His Leu His Tyr Gln Leu Pro Phe Pro
    210                 215                 220

Trp Arg Glu Asn Arg Tyr Ile Ile His Gly Tyr Arg Phe Tyr Asn Thr
225                 230                 235                 240

His Ser Lys Ser Leu Leu Ser Ile Phe Asn Trp Tyr Gly Trp His Asn
                245                 250                 255

Glu Thr Ser Asn Ile Trp Ser His Leu Leu Gly Ala Ile Tyr Ile Ile
                260                 265                 270

Tyr Leu Ala Ile Tyr Asp Phe Pro Gln Ser Glu Val Trp Arg Asn Ser
                275                 280                 285

Gln Val Pro Pro Gln Ala Arg Trp Ile Val Phe Met Phe Leu Ala Ala
    290                 295                 300

Ala Leu Lys Cys Met Leu Ser Ser Val Phe Trp His Thr Phe Asn Gly
305                 310                 315                 320

Thr Ser Phe Leu Lys Leu Arg Ser Lys Phe Ala Cys Val Asp Tyr Ser
                325                 330                 335

Gly Ile Thr Ile Leu Ile Thr Ala Ser Ile Leu Thr Thr Glu Phe Val
                340                 345                 350

Thr Met Tyr Ser Cys Tyr Trp Ala Met Tyr Thr Tyr Met Ser Ile Ser
                355                 360                 365

Leu Ala Leu Gly Val Phe Gly Val Phe Met Asn Trp Ser Pro Arg Phe
    370                 375                 380

Asp Arg Pro Glu Ala Arg Pro Leu Arg Ile Arg Phe Phe Ile Leu Leu
385                 390                 395                 400

Ala Thr Met Gly Val Leu Ser Phe Leu His Leu Ile Phe Leu Thr Asp
                405                 410                 415

Leu His Tyr Ala Ala Thr Leu Phe Ser Pro Val Thr Tyr Lys Ser Val
                420                 425                 430

Val Trp Tyr Leu Val Gly Val Phe Tyr Gly Ser Phe Ile Pro Glu
    435                 440                 445

Arg Phe Arg Ser Asp Val Gln Val Asp Lys Thr Ile Pro Thr Asn Tyr
450                 455                 460

Glu Leu Ser Thr Asp Leu Glu Ile Ile Thr Lys Gln Arg Glu Ile His
465                 470                 475                 480

Phe Arg Glu Val Pro Thr Ala His Ser Lys Cys Ser Ser Cys Pro Ser
                485                 490                 495

His Ala Lys Ser Phe Lys Ser Leu Trp Trp Val Asp Tyr Phe Gly Cys
                500                 505                 510

Ser His Thr Phe Trp His Phe Val Val Leu Gly Val Ile Gly His
    515                 520                 525

Tyr Arg Ala Ile Leu Asp Met Phe Ala Lys Arg Trp Ile Leu Ser
530                 535                 540

<210> SEQ ID NO 113
<211> LENGTH: 311
<212> TYPE: PRT
<213> ORGANISM: Homo sapiens

<400> SEQUENCE: 113
```

Met His Gln Lys Leu Leu Lys Ser Ala His Tyr Ile Glu Leu Gly Ser
1               5                   10                  15

Tyr Gln Tyr Trp Pro Val Leu Val Pro Arg Gly Ile Arg Leu Tyr Thr
            20                  25                  30

Tyr Glu Gln Ile Pro Gly Ser Leu Lys Asp Asn Pro Tyr Ile Thr Asp
        35                  40                  45

Gly Tyr Arg Ala Tyr Leu Pro Ser Arg Leu Cys Ile Lys Ser Leu Phe
    50                  55                  60

Ile Leu Ser Asn Glu Thr Val Asn Ile Trp Ser His Leu Leu Gly Phe
65                  70                  75                  80

Phe Leu Phe Phe Thr Leu Gly Ile Tyr Asp Met Thr Ser Val Leu Pro
                85                  90                  95

Ser Ala Ser Ala Ser Arg Glu Asp Phe Val Ile Cys Ser Ile Cys Leu
            100                 105                 110

Phe Cys Phe Gln Val Cys Met Leu Cys Ser Val Gly Tyr His Leu Phe
        115                 120                 125

Ser Cys His Arg Ser Glu Lys Thr Cys Arg Arg Trp Met Ala Leu Asp
    130                 135                 140

Tyr Ala Gly Ile Ser Ile Gly Ile Leu Gly Cys Tyr Val Ser Gly Val
145                 150                 155                 160

Phe Tyr Ala Phe Tyr Cys Asn Asn Tyr Trp Arg Gln Val Tyr Leu Ile
                165                 170                 175

Thr Val Leu Ala Met Ile Leu Ala Val Phe Phe Ala Gln Ile His Pro
            180                 185                 190

Asn Tyr Leu Thr Gln Gln Trp Gln Arg Leu Arg Ser Ile Ile Phe Cys
        195                 200                 205

Ser Val Ser Gly Tyr Gly Val Ile Pro Thr Leu His Trp Val Trp Leu
    210                 215                 220

Asn Gly Gly Ile Gly Ala Pro Ile Val Gln Asp Phe Ala Pro Arg Val
225                 230                 235                 240

Ile Val Met Tyr Met Ile Ala Leu Leu Ala Phe Leu Phe Tyr Ile Ser
                245                 250                 255

Lys Val Pro Glu Arg Tyr Phe Pro Gly Gln Leu Asn Tyr Leu Gly Ser
            260                 265                 270

Ser His Gln Ile Trp His Ile Leu Ala Val Val Met Leu Tyr Trp Trp
        275                 280                 285

His Gln Ser Thr Val Tyr Val Met Gln Tyr Arg His Ser Lys Pro Cys
    290                 295                 300

Pro Asp Tyr Val Ser His Leu
305                 310

<210> SEQ ID NO 114
<211> LENGTH: 307
<212> TYPE: PRT
<213> ORGANISM: Danio rerio

<400> SEQUENCE: 114

Met Pro Gln Asn Ile Leu Lys Ser Thr His Tyr Ile Glu Leu Gly Ser
1               5                   10                  15

Tyr Gln Tyr Trp Pro Val Leu Val Pro Arg Gly Ile Arg Leu Tyr Thr
            20                  25                  30

Tyr Glu Gln Ile Pro Met Phe Leu Lys Glu Asn Pro Tyr Ile Thr Asp
        35                  40                  45

Gly Tyr Arg Ala His Leu Pro Ser Lys Leu Cys Leu Lys Ser Ile Phe

```
            50                  55                  60
Ile Leu Ser Asn Glu Thr Val Asn Ile Trp Ser His Leu Leu Gly Phe
 65                  70                  75                  80

Leu Leu Phe Phe Ser Leu Gly Val Asn Asp Met Ala Thr Val Leu Pro
                 85                  90                  95

Ser Ala Gly Ala Ser Arg Glu Asp Tyr Val Ile Tyr Ser Ile Gly Leu
            100                 105                 110

Leu Cys Phe Gln Val Cys Met Leu Cys Ser Val Gly Tyr His Leu Phe
        115                 120                 125

Cys Cys His Arg Ser Glu Lys Thr Cys Arg Arg Trp Leu Ala Leu Asp
    130                 135                 140

Tyr Ala Gly Ile Ser Val Gly Ile Leu Gly Cys Tyr Val Pro Gly Val
145                 150                 155                 160

Phe Tyr Ala Phe Tyr Cys Asn Ser Phe Trp Arg Gln Val Tyr Leu Leu
                165                 170                 175

Thr Val Leu Ala Leu Ile Leu Ala Val Phe Ala Ala Gln Ile His Pro
            180                 185                 190

Leu Tyr Leu Ser Gln Gln Trp Lys Lys Leu Arg Ser Leu Met Phe Cys
        195                 200                 205

Leu Val Ala Ala Tyr Gly Ile Ile Pro Ala Cys His Trp Val Trp Ile
    210                 215                 220

Asn Gly Gly Phe Ser Ser Glu Ile Val Lys Val Phe Pro Arg Val
225                 230                 235                 240

Met Ile Met Tyr Leu Ile Ala Ala Ser Ala Phe Leu Phe Tyr Val Ser
                245                 250                 255

Lys Ile Pro Glu Arg Tyr Phe Pro Gly Gln Leu Asn Tyr Val Gly Ala
            260                 265                 270

Ser His Gln Leu Trp His Val Leu Val Val Met Phe Tyr Trp Trp
        275                 280                 285

His Gln Thr Ala Val Tyr Ile Met Asn Tyr Arg His Asn Gln Pro Cys
    290                 295                 300

Gly Ser Thr
305

<210> SEQ ID NO 115
<211> LENGTH: 273
<212> TYPE: PRT
<213> ORGANISM: Homo sapiens

<400> SEQUENCE: 115

Met Ala Phe Leu Ala Gly Pro Arg Leu Leu Asp Trp Ala Ser Ser Pro
  1               5                  10                  15

Pro His Leu Gln Phe Asn Lys Phe Val Leu Thr Gly Tyr Arg Pro Ala
                 20                  25                  30

Ser Ser Gly Ser Gly Cys Leu Arg Ser Leu Phe Tyr Leu His Asn Glu
            35                  40                  45

Leu Gly Asn Ile Tyr Thr His Gly Leu Ala Leu Gly Phe Leu Val
        50                  55                  60

Leu Val Pro Met Thr Met Pro Trp Gly Gln Leu Gly Lys Asp Gly Trp
 65                  70                  75                  80

Leu Gly Gly Thr His Cys Val Ala Cys Leu Ala Pro Ala Gly Ser
                 85                  90                  95

Val Leu Tyr His Leu Phe Met Cys His Gln Gly Gly Ser Ala Val Tyr
            100                 105                 110
```

```
Ala Arg Leu Leu Ala Leu Asp Met Cys Gly Val Cys Leu Val Asn Thr
        115                 120                 125

Leu Gly Ala Leu Pro Ile Ile His Cys Thr Leu Ala Cys Arg Pro Trp
        130                 135                 140

Leu Arg Pro Ala Ala Leu Val Gly Tyr Thr Val Leu Ser Gly Val Ala
145                 150                 155                 160

Gly Trp Arg Ala Leu Thr Ala Pro Ser Thr Ser Ala Arg Leu Arg Ala
                165                 170                 175

Phe Gly Trp Gln Ala Ala Ala Arg Leu Val Phe Gly Ala Arg Gly
                    180                 185                 190

Val Gly Leu Gly Ser Gly Ala Pro Gly Ser Leu Pro Cys Tyr Leu Arg
        195                 200                 205

Met Asp Ala Leu Ala Leu Leu Gly Gly Leu Val Asn Val Ala Arg Leu
        210                 215                 220

Pro Glu Arg Trp Gly Pro Gly Arg Phe Asp Tyr Trp Gly Asn Ser His
225                 230                 235                 240

Gln Ile Met His Leu Leu Ser Val Gly Ser Ile Leu Gln Leu His Ala
                245                 250                 255

Gly Val Val Pro Asp Leu Leu Trp Ala Ala His His Ala Cys Pro Arg
                260                 265                 270

Asp

<210> SEQ ID NO 116
<211> LENGTH: 272
<212> TYPE: PRT
<213> ORGANISM: Danio rerio

<400> SEQUENCE: 116

Met Ala Phe Leu Asn Gly Pro Arg Leu Leu Asp Trp Ala Asn Ser Pro
1               5                   10                  15

Pro His Leu Gln Phe Asn Lys Tyr Val Leu Thr Gly Tyr Arg Pro Ile
            20                  25                  30

Ser Thr Val Gln Glu Cys Ile Lys Ser Leu Phe Tyr Leu His Asn Glu
        35                  40                  45

Leu Gly Asn Ile Tyr Thr His Gly Ile Pro Leu Leu Cys Phe Leu Val
    50                  55                  60

Leu Leu Pro Leu Asn Ile Pro Trp Ser Gln Ile Ser Val Thr Trp Leu
65                  70                  75                  80

Gly Val Val His Phe Leu Ala Cys Leu Ser Pro Gln Leu Gly Ser Val
                85                  90                  95

Val Tyr His Leu Phe Met Asn His Glu Gly Gly Pro Val Tyr Lys
            100                 105                 110

Thr Leu Leu Thr Leu Asp Met Cys Gly Ile Cys Met Ile Asn Thr Leu
        115                 120                 125

Gly Ala Leu Pro Ile Val Tyr Ser Thr Leu Leu Cys Tyr Pro Phe Thr
        130                 135                 140

Arg Thr Val Ala Leu Leu Met Tyr Ile Leu Leu Ser Ser Tyr Ala Ile
145                 150                 155                 160

Tyr Cys Ala Ile Thr Ala Arg Ser Arg Val Arg Arg Leu Arg Ser Phe
                165                 170                 175

Ala Trp Gln Ala Leu Phe Arg Phe Ser Phe Leu Leu Arg Trp Val
                    180                 185                 190

Gly Val Gly Gly Gly Ser Pro Thr Ser Leu Arg His Phe Leu Thr Met
        195                 200                 205
```

```
Asp Ala Leu Ala Val Leu Gly Gly Val Ile Asn Ile Thr Arg Ile Pro
            210                 215                 220

Glu Arg Phe Arg Pro Gly Leu Phe Asp Tyr Trp Cys Asn Ser His Gln
225                 230                 235                 240

Ile Met His Val Leu Val Val Ser Ile Leu Tyr Leu His Trp Gly
            245                 250                 255

Val Leu Asp Asp Leu Leu Trp Ile Asn Thr Tyr His Cys Pro Ser Asp
            260                 265                 270
```

<210> SEQ ID NO 117
<211> LENGTH: 278
<212> TYPE: PRT
<213> ORGANISM: Danio rerio

<400> SEQUENCE: 117

```
Met Gly Tyr Phe Thr Gly Pro Lys Leu Leu Asp Phe Lys Ser Ser Pro
1               5                   10                  15

Pro His Leu Gln Phe Asn Lys Tyr Val His Thr Gly Tyr Arg Pro Ile
            20                  25                  30

Ser Thr Cys Arg Glu Cys Leu Arg Ser Leu Phe Tyr Leu His Asn Glu
        35                  40                  45

Phe Gly Asn Ile Tyr Thr His Gly Val Pro Phe Ile Cys Phe Leu Leu
    50                  55                  60

Phe Leu Pro Val Ser Ile Pro Trp Ala Glu Val Asp Glu Trp Trp Ile
65                  70                  75                  80

Gly Ile Val His Tyr Leu Ala Cys Leu Ser Pro Thr Ile Cys Ser Val
                85                  90                  95

Phe Tyr His Leu Phe Met Asn His Glu Gly Ala Pro Ile Tyr Asp
            100                 105                 110

Thr Leu Leu Cys Phe Asp Met Phe Gly Val Cys Leu Val Asn Thr Leu
        115                 120                 125

Gly Ala Leu Pro Ile Ile His Ile Thr Leu Leu Cys His Pro Ile Thr
    130                 135                 140

Arg Gln Val Ala Met Leu Ala Tyr Leu Leu Ser Gly Tyr Gly Val
145                 150                 155                 160

His Cys Ala Leu Thr Ala Glu Ser Asn Ile His Arg Leu Gln Ser Phe
                165                 170                 175

Ile Trp Gln Ala Gly Phe Arg Phe Val Leu Phe Met Phe Arg Leu Ile
            180                 185                 190

Gly Pro Gly Arg Gly Ser Pro Ser Ser Leu Gln Leu Tyr Leu Thr Met
        195                 200                 205

Asp Ala Leu Ala Met Phe Gly Gly Leu Val Asn Val Ser Arg Phe Pro
    210                 215                 220

Glu Arg Phe Ser Pro Gly Arg Phe Asp Tyr Trp Leu Asn Ser His Gln
225                 230                 235                 240

Ile Met His Ile Met Val Val Leu Ser Ile Leu Tyr Leu His Trp Gly
                245                 250                 255

Met Leu Glu Asp Leu Arg Trp Leu Lys Gly Tyr His Cys Pro Asp Glu
            260                 265                 270

Tyr Gly Ile Tyr Asp Ile
            275
```

<210> SEQ ID NO 118
<211> LENGTH: 229
<212> TYPE: PRT
<213> ORGANISM: Homo sapiens

<400> SEQUENCE: 118

| Met | Asn | His | Arg | Val | Pro | Ala | His | Lys | Arg | Tyr | Gln | Pro | Thr | Glu | Tyr |
|-----|-----|-----|-----|-----|-----|-----|-----|-----|-----|-----|-----|-----|-----|-----|-----|
| 1 | | | | 5 | | | | | 10 | | | | | 15 | |

Glu His Ala Ala Asn Cys Ala Thr His Ala Phe Trp Ile Ile Pro Ser
                20                  25                  30

Ile Leu Gly Ser Ser Asn Leu Tyr Phe Leu Ser Asp Asp Asp Trp Glu
            35                  40                  45

Thr Ile Ser Ala Trp Ile Tyr Gly Leu Gly Leu Cys Gly Leu Phe Val
 50                      55                  60

Val Ser Thr Val Phe His Thr Ile Ser Trp Lys Lys Ser His Leu Arg
 65                  70                  75                  80

Met Val Glu His Cys Leu His Met Phe Asp Arg Met Val Ile Tyr Phe
                85                  90                  95

Phe Ile Ala Ala Ser Tyr Ala Pro Trp Leu Asn Leu Arg Glu Leu Gly
            100                 105                 110

Pro Trp Ala Ser His Met Arg Trp Leu Val Trp Ile Met Ala Ser Val
        115                 120                 125

Gly Thr Ile Tyr Val Phe Phe Phe His Glu Arg Tyr Lys Leu Val Glu
130                 135                 140

Leu Leu Cys Tyr Val Val Met Gly Phe Phe Pro Ala Leu Val Ile Leu
145                 150                 155                 160

Ser Met Pro Asn Thr Glu Gly Ile Trp Glu Leu Val Thr Gly Gly Val
                165                 170                 175

Phe Tyr Cys Leu Gly Met Val Phe Phe Lys Ser Asp Gly Arg Ile Pro
            180                 185                 190

Phe Ala His Ala Ile Trp His Leu Phe Val Ala Phe Gly Ala Gly Thr
        195                 200                 205

His Tyr Tyr Ala Ile Trp Arg Tyr Leu Tyr Leu Pro Ser Thr Leu Gln
210                 215                 220

Thr Lys Val Ser Lys
225

<210> SEQ ID NO 119
<211> LENGTH: 229
<212> TYPE: PRT
<213> ORGANISM: Danio rerio

<400> SEQUENCE: 119

Met Asn Asn Arg Val Pro Ser Ser Lys Arg Tyr Gln Pro Thr Glu Tyr
1               5                   10                  15

Glu His Ala Ala Asn Cys Ala Thr His Gly Phe Trp Ile Ile Pro Ser
                20                  25                  30

Ile Leu Gly Gly Ser Met Leu His Phe Leu Ser Asp Asp Gln Trp Glu
            35                  40                  45

Thr Ile Ser Ala Trp Met Tyr Gly Ile Gly Leu Ser Gly Leu Phe Ile
 50                  55                      60

Met Ser Thr Met Phe His Thr Val Ser Trp Lys Lys Ser His Leu Arg
 65                  70                  75                  80

Lys Val Glu Gln Arg Phe His Met Cys Asp Arg Met Val Ile Tyr Phe
                85                  90                  95

Phe Ile Ala Ala Ser Tyr Ala Pro Trp Leu Asn Leu Arg Glu Leu Gly
            100                 105                 110

Pro Trp Ala Val His Met Arg Trp Leu Val Trp Ile Met Ala Cys Ala
        115                 120                 125

```
Gly Ser Ala Tyr Val Phe Phe His Glu Lys Asn Lys Ile Leu Asp
            130                 135                 140

Leu Leu Cys Tyr Thr Ala Met Gly Ser Val Pro Ala Val Val Leu Leu
145                 150                 155                 160

Ser Met Pro Asn Arg Glu Gly Val Leu Glu Leu Ser Val Gly Gly Leu
                165                 170                 175

Phe Tyr Cys Leu Gly Val Val Phe Phe Lys Ser Asp Gly Leu Ile Pro
                180                 185                 190

Phe Ala His Ala Ile Trp His Val Phe Val Ala Val Gly Ala Ala Ile
                195                 200                 205

His Tyr Tyr Ala Ile Trp Lys Tyr Leu Tyr Ala Thr Gly Thr Cys Gln
            210                 215                 220

Ile Lys Ile Ser Arg
225

<210> SEQ ID NO 120
<211> LENGTH: 230
<212> TYPE: PRT
<213> ORGANISM: Danio rerio

<400> SEQUENCE: 120

Met Asn Asn Arg Ala Pro Tyr Asn Lys Arg Tyr Gln Pro Thr Glu Tyr
1               5                   10                  15

Glu His Ala Ala Asn Cys Ala Thr His Gly Leu Trp Ile Ile Pro Ser
                20                  25                  30

Ile Val Gly Gly Ile Leu Leu Tyr Phe Leu Ser Asp Asp His Trp Glu
            35                  40                  45

Glu Ile Ser Ala Trp Leu Tyr Gly Ala Gly Leu Ser Ser Leu Phe Ile
50                  55                  60

Ile Ser Thr Val Phe His Thr Val Ser Trp Lys Lys Ser His Leu Arg
65                  70                  75                  80

Arg Ser Val Glu His Cys Phe His Met Cys Asp Arg Met Val Ile Tyr
                85                  90                  95

Phe Phe Ile Ala Ala Ser Tyr Thr Pro Trp Leu Thr Leu Arg Asp Leu
            100                 105                 110

Gly Pro Trp Ala Ala His Met Arg Trp Val Val Trp Val Met Ala Ser
            115                 120                 125

Gly Gly Thr Ala Tyr Val Phe Phe His Glu Lys Phe Lys Val Val
            130                 135                 140

Glu Leu Ile Cys Tyr Ile Ala Met Gly Val Phe Pro Ala Leu Val Ile
145                 150                 155                 160

Leu Ser Met Ala Asp Arg Ser Gly Leu Cys Glu Leu Leu Gly Gly
                165                 170                 175

Gly Cys Tyr Val Leu Gly Met Ala Phe Phe Lys Ser Asp Gly Ile Val
            180                 185                 190

Pro Phe Ala His Ala Ile Trp His Leu Phe Val Ala Met Gly Ala Gly
            195                 200                 205

Ile His Tyr Tyr Ala Ile Trp Lys Tyr Leu Tyr Thr Pro Val Asn Gln
            210                 215                 220

Pro Thr Ser Thr Ala Arg
225                 230

<210> SEQ ID NO 121
<211> LENGTH: 228
<212> TYPE: PRT
```

<213> ORGANISM: Homo sapiens

<400> SEQUENCE: 121

Met Asn His Arg Ala Pro Ala Asn Gly Arg Tyr Lys Pro Thr Cys Tyr
1               5                   10                  15

Glu His Ala Ala Asn Cys Tyr Thr His Ala Phe Leu Ile Val Pro Ala
            20                  25                  30

Ile Val Gly Ser Ala Leu Leu His Arg Leu Ser Asp Asp Cys Trp Glu
        35                  40                  45

Lys Ile Thr Ala Trp Ile Tyr Gly Met Gly Leu Cys Ala Leu Phe Ile
    50                  55                  60

Ala Ser Thr Val Phe His Ile Val Ser Trp Lys Lys Ser His Leu Arg
65                  70                  75                  80

Thr Ala Glu His Cys Phe His Met Cys Asp Arg Met Val Ile Tyr Phe
                85                  90                  95

Phe Ile Ala Ala Ser Tyr Ala Pro Trp Leu Asn Leu Arg Glu Leu Gly
            100                 105                 110

Pro Leu Ala Ser His Met Arg Trp Phe Ile Trp Leu Met Ala Ala Gly
        115                 120                 125

Gly Thr Ile Tyr Val Phe Leu Tyr His Glu Lys Tyr Lys Val Val Glu
    130                 135                 140

Leu Phe Phe Tyr Leu Thr Met Gly Phe Ser Pro Ala Leu Val Val Thr
145                 150                 155                 160

Ser Met Asn Asn Thr Asp Gly Leu Gln Glu Leu Ala Cys Gly Gly Leu
                165                 170                 175

Ile Tyr Cys Leu Gly Val Val Phe Phe Lys Ser Asp Gly Ile Ile Pro
            180                 185                 190

Phe Ala His Ala Ile Trp His Leu Phe Val Ala Thr Ala Ala Val
        195                 200                 205

His Tyr Tyr Ala Ile Trp Lys Tyr Leu Tyr Arg Ser Pro Thr Asp Phe
    210                 215                 220

Met Arg His Leu
225

<210> SEQ ID NO 122
<211> LENGTH: 239
<212> TYPE: PRT
<213> ORGANISM: Danio rerio

<400> SEQUENCE: 122

Met Lys Arg Val Asn Ser Phe Gln Arg Phe Met Asn Thr Arg Ala Ala
1               5                   10                  15

Ala Asn Cys Arg Tyr Gln Pro Thr Cys Tyr Glu His Ala Ala Asn Cys
            20                  25                  30

Tyr Thr His Ala Leu Leu Ile Thr Pro Ala Phe Val Gly Met Ala Leu
        35                  40                  45

Leu His Arg Leu Ser Asp Asp Arg Trp Glu Arg Phe Thr Ala Trp Val
    50                  55                  60

Tyr Gly Met Gly Leu Ile Ala Leu Phe Leu Ser Thr Val Phe His
65                  70                  75                  80

Ile Ile Ser Trp Lys Lys Ser His Met Arg Thr Met Glu His Cys Phe
                85                  90                  95

His Met Cys Asp Arg Val Val Ile Tyr Phe Phe Ile Ala Ala Ser Tyr
            100                 105                 110

Thr Thr Trp Leu Asn Leu Arg Glu Leu Gly Pro Leu Ala Ala His Met

```
            115                 120                 125
Arg Trp Phe Val Trp Leu Met Ala Ala Ala Gly Thr Ile Tyr Val Phe
130                 135                 140

Asn Tyr His Glu Lys Tyr Lys Leu Val Glu Leu Met Phe Tyr Leu Thr
145                 150                 155                 160

Met Gly Phe Phe Pro Ala Leu Val Val Thr Ser Thr Thr Asn Thr Glu
                165                 170                 175

Gly Leu Ser Glu Leu Ala Phe Gly Gly Leu Val Tyr Cys Leu Gly Val
                180                 185                 190

Phe Phe Phe Lys Cys Asp Gly Val Ile Pro Phe Ala His Ala Ile Trp
                195                 200                 205

His Val Phe Val Ala Leu Ala Ala Ile His Tyr Ala Ile Trp
210                 215                 220

Lys Tyr Leu Tyr Arg Ser Pro Ala Leu Glu Asp Ile Arg Asp Ala
225                 230                 235

<210> SEQ ID NO 123
<211> LENGTH: 241
<212> TYPE: PRT
<213> ORGANISM: Entamoeba histolytica

<400> SEQUENCE: 123

Met Cys Phe Leu Cys Asp Ile Gln Thr Ala Arg Asn Gln Leu Thr Pro
1               5                   10                  15

His Asp Glu Arg Pro Gln Cys Leu Leu Glu Glu Gly Val Asn Val Leu
                20                  25                  30

Thr His Leu Phe Gly Ile Phe Tyr Ala Ile Phe Ile Lys Met Phe
            35                  40                  45

Arg Arg Tyr Ala Lys Lys His Asn Leu Asn Lys Met Asn Asn Leu Ala
50                  55                  60

Ile Leu Cys Phe Cys Leu Ala Ser Phe Thr Leu Tyr Phe Asn Ser Thr
65                  70                  75                  80

Thr Tyr His Leu Leu Asn Ile Leu Leu Pro Asn Ser Ile Cys Leu Arg
                85                  90                  95

Tyr Phe Phe Gln Arg Leu Asp His Ile Thr Ile Tyr Ile Met Ile Ser
                100                 105                 110

Gly Cys Tyr Leu Cys Phe Ile Phe Thr Arg Thr Phe Ala Lys Gly Tyr
            115                 120                 125

Phe Lys Thr Gly Cys Leu Ala Ile Phe Ile Val Val Ala Leu Ala Leu
130                 135                 140

Ile Gly Phe Ile Phe Thr Ile Phe Ala Pro Pro Thr Thr Arg Thr Asp
145                 150                 155                 160

Val Ile Met Tyr Leu Ala Met Gly Trp Ser Cys Val Leu Tyr Gly Pro
                165                 170                 175

Leu Val Phe Tyr Phe Cys Pro Leu Ser Leu Val Phe Tyr Leu Leu Thr
                180                 185                 190

Gly Gly Ile Ser Tyr Ala Ile Gly Thr Ile Phe Val Ala Trp Asp Gln
            195                 200                 205

Leu Phe Phe Asn His Gly Ile Trp His Leu Ile Val Trp Phe Ala Asn
210                 215                 220

Phe Gln His Ser Leu Gly Val Leu Met Gln Leu Met Thr Lys Arg Leu
225                 230                 235                 240

Lys
```

<210> SEQ ID NO 124
<211> LENGTH: 340
<212> TYPE: PRT
<213> ORGANISM: Ciona intestinalis

<400> SEQUENCE: 124

Met Gly Cys Cys Asn Ala Val Arg Ser Ser Lys Cys Asp Glu Tyr Pro
1               5                   10                  15

Val Gln Tyr Arg Thr Asp Phe Ile Arg Thr Gly Tyr Arg Pro Leu Pro
            20                  25                  30

Leu Ser Phe Lys Glu Cys Ile Lys Ser Ala Phe Tyr Ala Asn Asn Glu
        35                  40                  45

Thr Gly Asn Ile Trp Thr His Phe Ile Pro Phe Leu Phe Met Val His
    50                  55                  60

Arg Ala Tyr Asn Ile Ile Ser Lys Phe Glu Asp Leu Thr Asp Pro Ile
65                  70                  75                  80

Asn Phe Gly Tyr Tyr Val His Ser Ile Gly Val Thr Tyr Val Leu Ile
                85                  90                  95

Ala Ser Thr Ile Ala His Thr Phe Cys Thr His Ser Glu Leu Cys Phe
            100                 105                 110

Arg Lys Cys Tyr Ser Val Asp Arg Ala Ala Ile Ile Met Gln Gly Phe
        115                 120                 125

Ser Val Gln Leu Val Leu Glu Leu Phe Ile Cys Pro Pro Ser Cys Tyr
    130                 135                 140

Val Ala Glu Asp Ile Gly Arg Asn Ser His Val Ile Leu Thr Leu Tyr
145                 150                 155                 160

Cys Val Leu Ser Thr Ile Met Phe Cys Ser Ser Val His Pro Arg Leu
                165                 170                 175

Gly Arg Phe Gln Arg Phe Leu Ala Val Phe Pro Phe Gly Ile Gly Ser
            180                 185                 190

Ile Met Ile Asn Phe Ser Cys Ala Val Arg Tyr Leu Tyr Ser Ser Asn
        195                 200                 205

Ala Ile Glu Ser Thr Cys Phe Gly Thr Thr Lys Gly Asp His Val Leu
    210                 215                 220

Phe His Leu His Leu Ile Ala Val Cys Phe Ala Met Phe Phe Tyr Val
225                 230                 235                 240

Ala Lys Leu Pro Glu Arg Trp Tyr Pro Glu Lys Phe Asp Ile Val Gly
                245                 250                 255

Ser Ser His Gln Ile Phe His Ile Leu Val Ala Ile Ser Leu Tyr Phe
            260                 265                 270

Gln Asn Arg Leu Ile Glu His Val Thr Ala Glu Ala Lys Phe Lys Ile
        275                 280                 285

Glu Thr Gly Glu Leu Leu Arg Glu Pro Leu Ala Ser Ala Cys Thr Gln
    290                 295                 300

Thr Val Gly Val Phe Ile Leu Thr Phe Ile Thr Val His Ser Val Val
305                 310                 315                 320

Ala Leu Tyr Tyr Trp Lys Val Gln Pro Pro Ile Gln Ile Cys Lys Pro
                325                 330                 335

Pro Glu Lys Lys
            340

<210> SEQ ID NO 125
<211> LENGTH: 387
<212> TYPE: PRT
<213> ORGANISM: Ciona intestinalis

<400> SEQUENCE: 125

```
Met Leu Glu Ser Tyr Tyr Cys Val Phe Val Cys Lys Val Ser Ser Cys
1               5                   10                  15

Cys Val Asn Phe Asn Tyr Ser Ser Ser Leu Val Thr Arg Arg Ser
            20                  25                  30

Leu Trp Asp Thr Trp Leu Arg Ser Tyr Gly Leu Lys Pro Lys Ala Glu
            35                  40                  45

Thr Ala Glu Cys Tyr His Glu Ser Phe Ile Leu His Gly Tyr Arg Pro
        50                  55                  60

Thr Pro Ser Ser Val Leu Tyr Cys Val Lys Ser Leu Phe His Pro Thr
65                  70                  75                  80

Asn Glu Thr Leu Asn Val Trp Thr His Leu Ile Pro Phe Val Ile Ala
                85                  90                  95

Ala Thr Arg His Phe Lys Phe Ala Asn Glu Ile Met Thr Glu Arg Gly
            100                 105                 110

Tyr Thr Asp Pro Leu Phe Tyr Pro Tyr Trp Phe Phe Val Leu Gly Val
            115                 120                 125

Val Leu Thr Phe Phe Gly Ser Ser Leu Ala His Thr Phe Asn Cys Leu
130                 135                 140

Thr Pro Gly Ala Arg Glu Ala Cys Phe Cys Cys Asp Tyr Gly Cys Ile
145                 150                 155                 160

Ala Ile Gln Cys Ile Gly Leu Ala Thr Cys Phe Thr Phe Tyr Ile Cys
            165                 170                 175

Pro Tyr Thr Cys Val Ile Pro His Thr Gly Ser Tyr His Leu Ala Tyr
            180                 185                 190

Phe Ala Ile Ile Val Gly Ser Met Met Ala Val Pro Ile Val Cys Tyr
        195                 200                 205

Ser Arg Leu Pro Tyr Val Pro Tyr Arg Tyr Val Leu Arg Ile Ala Val
210                 215                 220

Tyr Val Val Leu Tyr Thr Ser Leu Cys Leu Pro Cys Phe Tyr Lys Tyr
225                 230                 235                 240

Leu Thr Phe Thr Pro Glu Pro Gln Phe Lys Thr Cys Gly Ile Ala Ile
            245                 250                 255

Gly Asp Glu Ser Arg Arg Asn Phe Phe Glu Leu Thr Cys Ile Met Ala
            260                 265                 270

Leu Ser Ala Thr Val Asn Gly Leu Arg Phe Pro Glu Arg Ile Leu Pro
        275                 280                 285

Gly Trp Phe Asp Ile Val Gly His Ser His Gln Ile Phe His Val Leu
        290                 295                 300

Ile Ala Gly Gly Leu Tyr Tyr Gln Asn Lys Phe Ile Glu Gly Ala Leu
305                 310                 315                 320

Arg Glu Ile Leu Gly Arg Leu Asp Glu Gly Thr Leu Ser Val Asp Asp
            325                 330                 335

Leu Asn Ile Thr Trp Tyr Ser Ala Phe Leu Phe Pro Ala Met Asn Gly
            340                 345                 350

Leu Ile Ser Met Val Leu Thr Phe Val Phe Ser Val Val Leu Cys Arg
            355                 360                 365

Arg Gln Asn Leu Gln Phe Gly Glu Asn Cys Gln Lys Asn Lys Ser Lys
            370                 375                 380

Lys Ala Gln
385
```

<210> SEQ ID NO 126

```
<211> LENGTH: 339
<212> TYPE: PRT
<213> ORGANISM: Ciona intestinalis

<400> SEQUENCE: 126

Met Pro Glu Tyr Glu Lys Tyr Val Cys Ser Arg Ala Gly Val Pro Ser
1               5                   10                  15

Cys Phe His Gln Asn Phe Val Asn Thr Gly Tyr Arg Arg Glu Ser Gly
            20                  25                  30

Ser Ile Leu Thr Cys Leu Gln Ser Ala Phe Trp Pro Thr Asn Glu Thr
        35                  40                  45

Phe Asn Phe Trp Thr His Phe Val Ala Ser Ile Met Leu Met Ser Arg
50                  55                  60

Thr Gly Arg Ile Ile Ser Glu Phe Thr Pro Phe Glu Ala Leu His
65                  70                  75                  80

Leu Pro Phe Tyr Ile His Ser Phe Gly Ser Cys Tyr Leu Leu Val Val
                85                  90                  95

Ser Ser Phe Ala His Leu Phe Cys Cys Tyr Ser Glu Arg Cys Cys His
            100                 105                 110

Arg Cys Phe Ala Val Asp Gln Ala Ala Val Val Leu Tyr Ala Leu Cys
        115                 120                 125

Val Leu Leu Gly Phe Glu His Leu Thr Cys Pro Met Ser Cys Tyr Gly
130                 135                 140

Pro Phe Asn Asp Leu Ser Arg Ala Val Tyr Met Gly Cys Val Val Ile
145                 150                 155                 160

Leu Thr Val Leu His Thr Met Phe Ser Val Gln Thr Ser His Ser Ser
                165                 170                 175

Tyr Ser Pro Ala Leu Arg Ser Leu Pro Cys Thr Leu Met Thr Leu Leu
            180                 185                 190

Ile Ile Leu Pro Cys Ile Val Arg Val Thr Met Asn Ile Asp Glu Pro
        195                 200                 205

Gly Cys Phe Pro Thr Thr Asn Lys Ser Tyr Asp Tyr Phe Ala Ala Val
210                 215                 220

Cys Phe Leu Ala Gln Thr Leu Phe Ile Ser Leu Gly Gly Phe Phe
225                 230                 235                 240

Ser Ser Cys Ile Pro Glu Arg Phe Tyr Pro Gly Lys Tyr Asp Ile Ile
                245                 250                 255

Gly Asn Ser His Gln Leu Phe His Ile Cys Ser Ala Leu Ala Met Tyr
            260                 265                 270

Phe Gln Ser Leu Leu Ile Glu Gly His Lys Leu Ile Tyr Leu Leu Val
        275                 280                 285

Thr Ile Arg Cys Phe Arg Tyr Ser Arg Asn Asn Leu Ser Val Thr Trp
290                 295                 300

Ala Cys Thr Val Gly Val Phe Ser Leu Val Phe Val Leu Thr His Thr
305                 310                 315                 320

Thr Val Leu Leu His Asp Arg Thr Arg Pro Asn Ile Val Lys Ile Thr
                325                 330                 335

Lys Ile Thr

<210> SEQ ID NO 127
<211> LENGTH: 343
<212> TYPE: PRT
<213> ORGANISM: Ciona intestinalis

<400> SEQUENCE: 127
```

Met Val Asp Pro Asp Tyr Phe His Ala Leu Lys Asn Ser Cys Asn
1               5                   10                  15

Asn Val Pro Gln Cys Cys Val Glu Pro Tyr Ile Leu Lys Gly Tyr Val
            20                  25                  30

Leu Pro His Met Pro Leu Arg Tyr Tyr Phe Lys Val Leu Trp Ile Pro
        35                  40                  45

Asn Asn Glu Leu Phe Asn Val Trp Thr His Leu Phe Pro Cys Leu Phe
50                  55                  60

Phe Ile Ser Met Leu Tyr Gln Phe Asn Gln Ser Leu Asn Leu Phe Glu
65                  70                  75                  80

Ser Trp Pro Val Leu Ile Val Thr Val Ser Ala Ile Leu Leu Thr Leu
                85                  90                  95

Cys Ser Ser Leu Ala His Leu Phe His Ser Arg Ser Ser Phe Gln His
            100                 105                 110

Cys Cys Trp Phe Met Val Asp Tyr Phe Gly Ile Thr Thr Phe Ala Tyr
            115                 120                 125

Ser Ser Thr Val Ser His Phe Phe Ala Ser Ser Gln Leu Ser Tyr Tyr
            130                 135                 140

Asn Arg Ile Gly Trp Leu Asn Leu Leu Val Phe Thr Leu Ile Ala Cys
145                 150                 155                 160

Cys Gly Phe Leu Cys Met Ser Phe Thr Gln Ala Gly Asn Arg Trp Gln
                165                 170                 175

Ser Val Glu Asn Ala Arg Lys Met Lys Leu Trp Ser Thr Val Phe Gly
            180                 185                 190

Tyr Leu Tyr Gly Met Leu Pro Ile Met His Arg Tyr Leu Ile Asn Ala
            195                 200                 205

Glu Asn Asp His Ala Leu Tyr Tyr His Lys Leu Gln Phe Ile Cys Met
210                 215                 220

Leu Leu Cys Pro Leu Phe Tyr Thr Ser Asp Leu Pro Gln Lys Leu Trp
225                 230                 235                 240

Pro Gly Lys Phe Asp Ile Val Gly His Ser His Gln Ile Phe His Val
                245                 250                 255

Phe Ala Ala Leu Ser Cys Tyr Phe Glu Ile Val Ala Ile His Met Asp
            260                 265                 270

Val Thr Asp Ile Asn Gly Pro Trp Asn Ala Leu Lys His Gln Asn Asp
            275                 280                 285

Phe Pro Thr Phe Glu Leu Phe Cys Thr Cys Ala Leu Ala Leu Ile Val
            290                 295                 300

Tyr Cys Ile Ile Leu Ala Ile Tyr Ile Ala Arg Ser Ile His Ala Asp
305                 310                 315                 320

Ser Ile Lys Lys Ile Pro Ala Cys Gln Cys Ser Asp Leu Asn Lys Asn
                325                 330                 335

His Gln Gln Lys Lys Val Asp
            340

<210> SEQ ID NO 128
<211> LENGTH: 355
<212> TYPE: PRT
<213> ORGANISM: Ciona intestinalis

<400> SEQUENCE: 128

Met Lys Pro Thr Asn Ser Asp Asp Glu Gln Asn Asn Asn Val Leu Lys
1               5                   10                  15

Gln Leu Pro Asp Glu Asn Asp Phe Leu His Ala Leu His Asn Asp His
            20                  25                  30

```
Thr Thr Val Pro Gln Cys Thr Val Ala Lys Tyr Ile Val Lys Gly Tyr
            35                  40                  45

Val Leu Pro His Met Pro Trp Arg Tyr Tyr Val Lys Ser Leu Phe Leu
 50                  55                  60

Pro Ser Asn Glu Leu Leu Asn Ile Trp Thr His Leu Ile Pro Gly Leu
 65                  70                  75                  80

Tyr Phe Ile Lys Met Leu Phe Arg Tyr Asn Glu Ala Ile Asp Leu Val
                 85                  90                  95

Glu Asn Trp Pro Leu Ser Leu Thr Ile Ile Ser Ser Ile Thr Val Met
                100                 105                 110

Met Cys Ser Ala Leu Met His Thr Phe His Ser Arg Ser Met Ser Asp
                115                 120                 125

His Ala Cys Trp Met Met Leu Asp Phe Phe Gly Ile Val Phe Tyr Ala
                130                 135                 140

Phe Gly Ser Thr Val Ser His Phe Tyr Gly Cys Ser Glu Leu His Tyr
145                 150                 155                 160

Tyr Gln Arg Ile Gly Trp Trp Asn Leu Leu Ile Phe Met Phe Asn Cys
                165                 170                 175

Thr Ser Val Phe Ala Cys Cys Asn Ser Lys Val Gly Gln Lys Asn
                180                 185                 190

Ser Asp Asp His Phe Thr Arg Phe Leu Arg Ile Ala Ser Val Gly Gly
                195                 200                 205

Gly Tyr Ile Tyr Gly His Leu Pro Leu Met His Arg Leu Phe Thr Ser
210                 215                 220

Gly Leu Asp Glu Ala Met Val Tyr His Ile Ile Ser Thr Val Cys Leu
225                 230                 235                 240

Thr Ile Ala Val Val Tyr Leu Ser Asp Phe Pro Gln Arg Trp Phe
                245                 250                 255

Ser Gly Thr Phe Asp Ile Ile Gly Gln Ser His Gln Leu Phe His Val
                260                 265                 270

Leu Ser Ala Leu Cys Cys Tyr Phe Asp Ile Leu Ala Val Glu Gln Asp
                275                 280                 285

Met Arg Ala Ser Asp Arg His Trp Ser Val Leu Ser Val Gln Pro Asp
                290                 295                 300

Thr Pro Ser Leu Leu His Val Ser Thr Ala Ala Ile Leu Leu Ile Ile
305                 310                 315                 320

Phe Ser Tyr Lys Phe Ala Ser Arg Cys Leu Gln Ser His Gly Gln Arg
                325                 330                 335

Ile Gly Ile Cys Pro Cys Leu Cys Cys Lys Gln Thr Asp Pro Lys Met
                340                 345                 350

Lys Tyr Gln
        355

<210> SEQ ID NO 129
<211> LENGTH: 340
<212> TYPE: PRT
<213> ORGANISM: Strongylocentrotus purpuratus

<400> SEQUENCE: 129

Met Trp Thr Ile Lys Leu Leu Arg Phe Asn Gln Val Pro Ser Asp Phe
 1               5                  10                  15

His Glu Pro Phe Ile Ile Ser Gly Tyr Arg Ser Cys Arg Ser Ser Ile
                20                  25                  30

Ser Ser Cys Leu Val Ser Ala Ile Gln Gly Ser Asn Glu Thr Ile Asn
```

```
            35                  40                  45
Phe Trp Thr His Phe Ile Pro Ala Met Trp Phe Gly Trp Thr Thr Leu
 50                  55                  60

Gln Gln Val Ala Asp Gly Ala Phe Ile Gln Asp Pro Phe Ser Trp Pro
 65                  70                  75                  80

Leu Ile Cys Phe Leu Leu Ser Cys Val Met Tyr Leu Phe Ala Ser Ala
                 85                  90                  95

Met Ala His Leu Phe Asn Cys Ile Ser Leu Pro Ala Arg Tyr Val Thr
            100                 105                 110

Phe Phe Phe Asp Tyr Gly Ala Ile Ser Ile Tyr Ser Phe Gly Ser Ser
        115                 120                 125

Ile Ala Tyr Cys Ala Tyr Thr Phe Pro Pro Glu Leu Leu His Thr Pro
130                 135                 140

Leu His Gln Val Phe Leu Val Met Ala Met Phe Thr Ala Met Leu Ser
145                 150                 155                 160

Thr Phe Leu Ala Cys Tyr Ser Arg Phe Ser Ser Asn His Phe Leu Cys
                165                 170                 175

His Ser Gly Arg Leu Pro Ala Ile Met Ile Pro Tyr Phe Trp Cys Ser
            180                 185                 190

Leu Pro Leu Leu Tyr Arg Val Ile Phe Cys Val Glu Pro Asp Pro Asn
        195                 200                 205

Ser Asp Ala Ala Leu Phe His Val Arg Gln Phe Cys Thr Ala Val
210                 215                 220

Thr Val Phe Phe Tyr Ala Ser Arg Phe Pro Glu Val Leu Ala Pro Gly
225                 230                 235                 240

Ile Phe Asp Phe Ile Gly His Ser His Gln Leu Phe His Ile Gly Gly
                245                 250                 255

Ala Phe Ser Thr Tyr Trp Gln Tyr His Ala Leu Leu Leu Asp Lys Ala
            260                 265                 270

Glu Arg Arg Gln Phe Leu Val Glu Ala Val Gly Leu Pro Thr Val Ala
        275                 280                 285

Gly Thr Ala Gly Ala Phe Val Val Leu Thr Val Asn Leu Leu Ile
290                 295                 300

Ile Trp Gly Phe Ser His Trp Val Ser Gln Pro Lys Ser Leu Glu Met
305                 310                 315                 320

Val Arg Gln Arg Leu Glu Glu Asp Lys Arg Lys Lys Gly Cys Gly
                325                 330                 335

Cys Lys Cys Asp
            340

<210> SEQ ID NO 130
<211> LENGTH: 368
<212> TYPE: PRT
<213> ORGANISM: Strongylocentrotus purpuratus

<400> SEQUENCE: 130

Met Ala Glu Arg Gly Ala Met Ser Ser Thr Lys Gly Asn Ala Thr Asp
  1               5                  10                  15

Asp Asp Arg Tyr Pro Thr Gly Thr Lys Gln His Ser Pro Arg Gln Ser
             20                  25                  30

Ser Ala Lys Ser Ser Gly Lys Cys Pro His Ser His Phe Leu Met Cys
         35                  40                  45

Ala Leu Thr Ala Gly Gln Val Pro Ser Asp Phe Arg Glu Pro Phe Ile
     50                  55                  60
```

```
Leu Ser Gly Tyr Arg Ser Tyr Arg Ser Ser Ala Ser Ser Cys Leu Ala
 65                  70                  75                  80

Ser Ala Leu Gln Arg Thr Asn Glu Thr Val Asn Phe Trp Thr His Phe
                 85                  90                  95

Ile Pro Ala Leu Ile Phe Ala Arg Leu Thr Trp Phe Val Ala Val Thr
            100                 105                 110

Asp His Gly Leu Ala Leu Asp Pro Phe Thr Trp Pro Val Ile Val Phe
            115                 120                 125

Leu Leu Gly Ala Cys Phe Tyr Met Thr Ala Ser Ser Val Ala His Met
            130                 135                 140

Phe Asn Ser Met Ser Gln Cys Ala Arg Tyr Ile Phe Phe Ile Asp
145                 150                 155                 160

Tyr Cys Gly Val Ser Leu Tyr Ser Leu Gly Thr Cys Ile Ala Tyr Tyr
                165                 170                 175

Ala Tyr Ala Phe Pro Pro Glu Leu Leu Asp Thr Pro Leu Tyr His Ala
            180                 185                 190

Tyr Leu Pro Val Ala Met Val Thr Ala Leu Cys Ser Tyr Leu Ala
            195                 200                 205

Cys Cys Ser Arg Phe Ser Ser Trp Pro Pro Phe Arg Asp Ala Gly Arg
210                 215                 220

Leu Pro Ala Phe Ala Ile Pro Tyr Ile Trp Cys Asn Val Pro Leu Val
225                 230                 235                 240

Tyr Arg Val Ile Tyr Cys Glu Ser Thr Gly Cys Gly Ser Glu Ala Leu
                245                 250                 255

Phe Phe His Ile Gln Gln Phe Tyr Trp Val Leu Gly Phe Ala Phe Phe
            260                 265                 270

Tyr Ala Thr Arg Val Pro Glu Val Ile Ala Pro Gly Thr Phe Asp Ile
            275                 280                 285

Ile Gly His Ser His Gln Phe Phe His Ile Gly Ser Ser Ile Ala Ser
            290                 295                 300

Tyr Cys Gln Tyr Leu Ala Leu Ile Ala Glu Leu Thr Glu Arg Ala His
305                 310                 315                 320

Tyr Leu Asp Asp Leu Arg Arg Pro Thr Phe Val Thr Thr Phe Gly Val
                325                 330                 335

Leu Leu Thr Val Leu Val Gly Asn Leu Val Ile Val Trp Ile Leu Ser
            340                 345                 350

Arg Arg Val Ile Gln Met Ser Arg Ser Lys Ala Thr Asn His Lys Asp
            355                 360                 365

<210> SEQ ID NO 131
<211> LENGTH: 344
<212> TYPE: PRT
<213> ORGANISM: Strongylocentrotus purpuratus

<400> SEQUENCE: 131

Met Gln Ile Asp Val Leu Ala Lys Asp Val Ile Leu Leu Cys Trp Asp
 1               5                  10                  15

Leu Asn Pro Val Pro Leu Ser Tyr Arg Glu Pro Phe Ile Leu Ser Arg
                 20                  25                  30

Tyr Arg Ser Cys Arg Ser Ser Leu Gly Thr Cys Leu Leu Ser Ala Leu
             35                  40                  45

His Ala Thr Asn Glu Thr Leu Asn Phe Trp Thr His Phe Val Pro Phe
         50                  55                  60

Leu Val Leu Gly Leu Val Thr Leu Gln His Val Leu Asp Pro Ser Phe
 65                  70                  75                  80
```

Arg Ser Asp Pro Phe Asn Trp Ala Phe Leu Val Phe Ala Leu Ser Gly
                85                  90                  95

Cys Val Tyr Leu Leu Gly Ser Ser Ile Ala His Met Phe Ser Cys Tyr
            100                 105                 110

Ser Glu Val Ala His Tyr Ile Cys Tyr Phe Ile Asp Tyr Ser Thr Val
        115                 120                 125

Ser Ile Tyr Ile Val Gly Leu Cys Val Ala Tyr Asn Glu Tyr Val Phe
    130                 135                 140

Pro Arg Tyr Ala Ile Asn Thr Val Met His Arg Val Tyr Leu Pro Met
145                 150                 155                 160

Val Phe Leu Leu Ser Leu Leu Phe Ser Ala Thr Ser Cys Ala Thr Lys
                165                 170                 175

Tyr Ser Lys His His Leu Leu Arg Ile His Gly Arg Lys Val Thr Phe
            180                 185                 190

Pro Ala Tyr Phe Leu Trp Cys Asn Leu Pro Leu Ala Tyr Arg Ala Phe
        195                 200                 205

Phe Gly Ser Ser Ser Ser Ser Ser Ser Thr Ala Asp Val Tyr His
    210                 215                 220

Ile Ala His Thr Ile Ala Ala Thr Leu Ala Gly Leu Ser Tyr Ala Ser
225                 230                 235                 240

His Leu Pro Glu Ala Leu Ala Pro Gly Arg Phe Asp Phe Ile Ala Gln
                245                 250                 255

Ser His Gln Leu Phe His Leu Cys Thr Ala Val Leu Thr Tyr Tyr Gln
            260                 265                 270

Tyr His Ala Leu Ser Ala Glu Met His Asp Arg Arg Glu Glu Leu Leu
        275                 280                 285

Thr Leu Cys Gly Thr Pro Thr Phe Val Gly Thr Phe Gly Val Leu Leu
    290                 295                 300

Ala Asn Ile Phe Leu His Gly Val Leu Ile Ala Gly Leu Ala Ile Trp
305                 310                 315                 320

Leu Arg Lys Pro Gly Gln Leu Ala Lys Ile His Lys Ser Leu Glu Met
                325                 330                 335

Pro Thr Ile Ser His Lys Glu Asp
            340

<210> SEQ ID NO 132
<211> LENGTH: 345
<212> TYPE: PRT
<213> ORGANISM: Strongylocentrotus purpuratus

<400> SEQUENCE: 132

Met Trp Glu Asn Val Asn Phe Arg Arg Leu Leu Gly Gly Ala Ser Lys
1               5                   10                  15

Asn Gly Tyr Arg Gly Ser Ala Asp Phe Asp Thr Arg Asp Val Asp Glu
            20                  25                  30

Val Pro Val Ile Phe Gln Glu Pro Phe Val Lys Tyr Gly Tyr Arg Glu
        35                  40                  45

Pro His His Gly Leu Thr Tyr Tyr Ala Lys Ser Phe Leu Glu Leu His
    50                  55                  60

Asn Glu Ser Leu Asn Val Trp Thr His Ala Ala Ala Phe Ser Ile Leu
65                  70                  75                  80

Leu Tyr Gln Ser Tyr Gln Phe Cys Ser Pro Leu Asp Val Met Asn Asp
                85                  90                  95

Pro Tyr Ala Leu Ile Phe Ala Ile Phe Cys Ala Cys Cys Cys Thr Phe

```
            100                 105                 110
Leu Leu Leu Ser Ala Ile Ala His Leu Phe His Ser His Ser Glu Leu
        115                 120                 125

Thr His Tyr Thr Cys Trp Phe Ile Asp Tyr Leu Gly Met Ser Ile Tyr
        130                 135                 140

Gly Phe Gly Gly Ser Leu Ala His Tyr Tyr Phe Ser Ala Leu Pro Ser
145                 150                 155                 160

Phe Met His Ser Val Ser Trp Phe Phe Ile Pro Leu Leu Val Leu
                165                 170                 175

Ser Tyr Gly Val Cys Phe Cys Cys Ser Phe Ala Lys Tyr Arg Tyr Lys
                180                 185                 190

Arg Pro Tyr Pro Phe Ala Arg Lys Leu Trp Gln Leu Gly Ser Val Gly
        195                 200                 205

Ala Gly Tyr Val Leu Ile Ile Thr Pro Ile Tyr His Arg Leu Leu Gly
        210                 215                 220

Cys Leu Phe Ser Asp Gln Pro Met Asp Gln Ala Leu Phe Phe His Phe
225                 230                 235                 240

Leu Gln Val Ser Phe Ile Leu Pro Ser Ile Phe Phe Ala Ala Pro
                245                 250                 255

Tyr Pro Gln Lys Leu Gln Pro Gly Lys Tyr Asp Ile Val Gly His Gly
                260                 265                 270

His Gln Met Phe His Val Ala Met Ala Phe Val Ser Tyr Tyr Gln Met
        275                 280                 285

Lys Ala Val His Leu Asp Phe Leu His Arg Arg Asp Glu Tyr Ser Thr
        290                 295                 300

His Thr Asp Pro Ser Met Ile Gln Ala Ile Leu Tyr Ile Thr Val Leu
305                 310                 315                 320

Val Ile Ala Asp Ile Ile Thr Leu Phe Val Phe Arg His Lys Val Trp
                325                 330                 335

Gln Asn Ile Ser Lys Val Asp Met Asp
                340                 345

<210> SEQ ID NO 133
<211> LENGTH: 357
<212> TYPE: PRT
<213> ORGANISM: Schistosoma japonicum

<400> SEQUENCE: 133

Met Lys Leu Val Phe Asn Gln Ser Phe Thr Gly Ser Asp Lys Asn Val
1               5                   10                  15

Gly Cys Arg Ala Pro Trp Ser Leu Gln Pro Ser Arg Lys Ser Arg Lys
            20                  25                  30

Asp Lys Leu Glu Ile Leu Leu Ala Ser Gln Ile Ser Ser Asp Phe His
        35                  40                  45

Glu Ile Gly Ile Leu Ser Gly Tyr Arg Lys Pro Ser Ala Ser Leu Ala
    50                  55                  60

Ala Gly Ile Leu Ser Ile Phe Gln Leu His Asn Glu Thr Leu Asn Ile
65                  70                  75                  80

Trp Thr Gln Ile Ile Pro Thr Val Tyr Phe Val Ile Glu Leu Ile Leu
                85                  90                  95

Asn Phe Phe His Ala Gly Glu Arg Phe Leu Leu Ile Tyr Leu Val Thr
            100                 105                 110

Ala Val Thr Phe Leu Phe Thr Ser Ser Cys Ala His Ser Leu Ser Cys
        115                 120                 125
```

-continued

Leu Ser Pro Arg Ala Arg His Val Cys Phe Phe Leu Asp Tyr Ile Gly
              130                 135                 140

Ile Thr Leu Tyr Ser Cys Gly Cys Ala Val Cys Tyr Tyr Ala Phe Ala
145                 150                 155                 160

Leu Pro Leu Asp Phe Leu Ser Leu Ser Pro Val Phe Tyr Leu Asn Leu
                165                 170                 175

Cys Asp Leu Phe Leu Phe Ile Ser Val Met Phe Cys Ile Cys Gly Ala
                180                 185                 190

Tyr Leu Ser Cys Gln Thr Arg Phe Trp Lys Pro Ser Leu Leu Arg Asn
                195                 200                 205

Val Val Arg Met Gly Ala Phe Ser Ile Asn Leu Leu Tyr Leu Ala Thr
            210                 215                 220

Pro Ile Leu Trp Arg Ser Tyr Ile Cys Arg Tyr Met Glu Arg Asp Tyr
225                 230                 235                 240

Asp Thr Tyr Glu Cys Cys Ser Leu Tyr Tyr Trp Asn Leu His Phe Met
                245                 250                 255

Ser Ala Phe Ala Ala Gly Leu Leu Tyr Val Ser His Phe Pro Glu Arg
                260                 265                 270

Leu Phe Leu Gly Lys Phe Asp Phe Phe Gly His Ser His Gln Ile Phe
            275                 280                 285

His Ile Leu Ser Ala Phe Gly Ser Val Thr Gln Tyr Tyr Ala Leu Arg
            290                 295                 300

Thr Asp Leu Lys Glu Arg Ser Ala Lys Leu Lys Val Leu His Ala
305                 310                 315                 320

Pro Ser Ile Pro Phe Ser Leu Leu Cys Leu Cys Leu Val Ile Leu Cys
                325                 330                 335

Asp Leu Ile Ile Phe Leu Lys Phe Tyr Lys Arg Leu Cys Ile Ile Ile
                340                 345                 350

Arg Ser Lys Arg Leu
            355

<210> SEQ ID NO 134
<211> LENGTH: 340
<212> TYPE: PRT
<213> ORGANISM: Branchiostoma floridae

<400> SEQUENCE: 134

Met Trp Ser Gly Leu Lys Val Trp Thr Thr Glu Leu Leu His Ile Asp
1               5                   10                  15

Asp Ile Pro His His Tyr Arg Glu His Cys Ile Val Arg Gly Tyr Arg
                20                  25                  30

Lys Pro Lys Ser Ser Ala Thr Asp Cys Val Leu Ser Val Phe Gln Leu
            35                  40                  45

Thr Asn Glu Thr Leu Asn Phe Trp Thr His Phe Leu Pro Phe Trp Tyr
        50                  55                  60

Phe Ile Trp Arg Leu Val Ala Val Ser Tyr Asp Phe Asp Phe Trp Val
65                  70                  75                  80

Asp Pro Tyr Thr Trp Pro Leu Leu Val Phe Met Leu Ser Cys Cys Ala
                85                  90                  95

Tyr Pro Ile Thr Ser Ser Met Ala His Cys Phe Asn Cys Met Ser Asp
                100                 105                 110

Arg Ala Gln His Ile Ser Tyr Phe Met Asp Tyr Gly Ala Leu Ser Leu
            115                 120                 125

Tyr Ser Leu Gly Ser Gly Ile Ala Tyr His Ala Tyr Val Phe Pro Asp
        130                 135                 140

-continued

```
Ser Phe Ile Gly Ser Trp Phe Asp Asp Val Phe Leu Arg Val Ala Thr
145                 150                 155                 160

Phe Leu Ala Val Gly Cys Thr Leu Leu Ser Cys Met Ser Arg Phe Glu
                165                 170                 175

Asp Arg Pro Arg Ile Arg Lys Ala Leu Arg Leu Leu Ser Phe Ser Leu
            180                 185                 190

Pro Tyr Phe Phe Asn Ser Val Pro Leu Cys Tyr Arg Val Phe Leu Cys
        195                 200                 205

His Gly Glu Gly Cys Ser His Asn Glu Ala Val Ile Ile Tyr Tyr Trp
    210                 215                 220

Met Leu Phe Phe Ser Phe Leu Thr Pro Phe Leu Tyr Ala Thr His Ile
225                 230                 235                 240

Pro Glu Val Leu Ala Pro Gly Lys Phe Asp Leu Ile Gly His Ser His
                245                 250                 255

Gln Leu Phe His Val Thr Gly Ile Ile Ala Thr Asn Phe Gln Ile Ser
            260                 265                 270

Gly Val Leu Thr Asp Leu Gln Met Arg Arg Glu Phe Leu Asp Val Val
        275                 280                 285

Arg Pro Gln Pro Met Glu Phe Trp Asp Asn Ile Gly Leu Met Ser Leu
    290                 295                 300

Val Leu Met Lys Asn Leu Leu Ile Ile Leu Phe Phe Thr Leu Ser Leu
305                 310                 315                 320

Tyr Val Glu Lys Pro Thr Trp Leu Lys Val Arg Gly His Gly Ile Lys
                325                 330                 335

Gly Lys Val Asp
            340

<210> SEQ ID NO 135
<211> LENGTH: 323
<212> TYPE: PRT
<213> ORGANISM: Branchiostoma floridae

<400> SEQUENCE: 135

Met Gln Leu Pro Arg Met Pro Cys Thr Lys Arg Ser Glu Asp Val Pro
1               5                   10                  15

Val Leu Phe Arg Glu Pro Tyr Val His Asp Gly Tyr Arg Pro Pro His
                20                  25                  30

Gln Pro Trp His Tyr Tyr Leu Leu Ser Leu Phe Gln Ile His Asn Glu
            35                  40                  45

Val Met Asn Ala Trp Thr His Leu Ile Pro Phe Ser Ile Leu Leu Tyr
50                  55                  60

Asn Val Phe Thr Arg Thr Gly Glu Leu Asp Phe Ser Ala Asp His Thr
65                  70                  75                  80

Ser Trp Ala Leu Leu Leu Gly Phe Gly Gly Cys Ser Phe Leu Phe
                85                  90                  95

Leu Ser Phe Ala Ala His Leu Phe Gln Ser His Ser Glu His Ala His
            100                 105                 110

Tyr Met Cys Phe Ile Leu Asp Tyr Val Gly Ile Ala Phe Tyr Gly Phe
        115                 120                 125

Thr Ala Gly Leu Ala Gln Phe Ser Ile Cys Ser Asp Pro Trp Phe Ser
    130                 135                 140

Arg Val Phe Lys Pro Val Phe Phe Pro Leu Leu Val Val Ser Gly Cys
145                 150                 155                 160

Tyr Thr Cys Ile Cys Cys Ser Tyr Gly Lys Val Arg Phe Asn Arg Pro
```

```
                         165                 170                 175
Tyr Pro Pro Met Arg Trp Val Leu Gln Ile Ser Ala Ile Gly Ser Met
                180                 185                 190
Tyr Val Leu Ser Met Ser Pro Val Leu His Arg Val Met Met Asp His
            195                 200                 205
Ala Arg Asn Ser Met Asp Thr Val Ser Trp Met His Val Ala His Thr
210                 215                 220
Ala Phe Phe Met Thr Gly Val Phe Phe Tyr Thr Ser Asn Val Pro His
225                 230                 235                 240
Arg Phe Gln Pro Gly Met Phe Asp Ile Val Gly His Gly His Gln Leu
                245                 250                 255
Phe His Val Ala Met Ala Thr Met Ala Ile Ile Gln Phe Glu Thr Val
            260                 265                 270
Phe Arg Asp Leu Gln Ser Gly Arg His Phe Leu Leu Ser Arg Pro Ser
        275                 280                 285
Val Thr Ser Ile Thr Val Gln Ala Thr Val Val Leu Leu Cys Cys Val
    290                 295                 300
Val Ser Thr Leu Ala Met Ala Ala Lys Val Arg Arg Lys Leu Lys Asn
305                 310                 315                 320
Lys Val Gln

<210> SEQ ID NO 136
<211> LENGTH: 315
<212> TYPE: PRT
<213> ORGANISM: Branchiostoma floridae

<400> SEQUENCE: 136

Met Pro Asp Met Lys Arg Ser Leu Thr Ile Asp Glu Val Pro Glu Val
1               5                   10                  15
His Lys Glu Pro Tyr Val Leu Thr Gly Tyr Arg Pro Gln Gln Pro
            20                  25                  30
Trp Arg Phe Tyr Leu Met Ser Ile Phe Ser Lys Asn Asn Glu Thr Met
        35                  40                  45
Asn Val Trp Thr His Leu Leu Pro Cys Phe Tyr Val Leu Trp Leu Leu
50                  55                  60
Lys Thr Tyr Ser Asp Glu Ala Gly Phe Thr Thr Ser Asp Pro Ser Ser
65                  70                  75                  80
Met Leu Leu Leu Leu Phe Gly Thr Ser Asn Phe Ala Phe His Leu Phe
                85                  90                  95
Ser Ala Phe Ala His Leu Leu His Ser Arg Ser Val Ala Val Tyr Tyr
            100                 105                 110
Val Ile Phe Ile Phe Asp Tyr Leu Gly Ile Ala Phe His Ala Phe Thr
        115                 120                 125
Ser Gly Thr Val Gln Tyr Phe Leu Ser Ser Glu Thr Ser Phe Phe His
    130                 135                 140
Ala Val His Pro Trp Tyr Pro Trp Ala Cys Val Leu Phe Thr Cys Cys
145                 150                 155                 160
Tyr Phe Ala Ala Asn Ala Tyr Ser His Val Thr Tyr Arg Arg Cys His
                165                 170                 175
Ser Glu Arg Ala Leu Thr Gln Val Val Ser Phe Ser Thr Thr Tyr Leu
            180                 185                 190
Trp Val Thr Leu Pro Val Ile His Arg Ile Tyr Ser Asp Ile Tyr Asn
        195                 200                 205
Gly Thr Val Asp Asp Val Thr Trp Met His Val Asn His Ile Leu Leu
```

```
                    210                 215                 220
Met Ile Ile Ala Gly Phe Phe Gly Ser Glu Met Pro Gln Arg Phe
225                 230                 235                 240

Phe Pro Gly Ala Cys Asp Val Ile Gly His Gly His Gln Ile Phe His
                    245                 250                 255

Val Ile Ile Thr Ala Ser Val Met Val Gln Leu Glu Ala Ser Phe Ala
                    260                 265                 270

Asp Leu Gln Asn Arg Arg His Leu Asp Leu Val Arg Ile Arg Pro Thr
                    275                 280                 285

Asp Met Ser Ile Thr Ala Tyr Leu Val Val Leu Phe Thr Ser Tyr Gly
                    290                 295                 300

Tyr Ile Thr Val Ile Phe Val Arg Lys Ala Leu
305                 310                 315

<210> SEQ ID NO 137
<211> LENGTH: 320
<212> TYPE: PRT
<213> ORGANISM: Branchiostoma floridae

<400> SEQUENCE: 137

Met Pro Asp Met Lys Arg Ser Leu Thr Ile Asp Glu Val Pro Asp Val
1               5                   10                  15

His Lys Glu Pro Tyr Val Leu Thr Gly Tyr Arg Pro Pro Gln Gln Pro
                20                  25                  30

Trp Arg Phe Tyr Leu Met Ser Ile Phe Ser Gln His Asn Glu Thr Met
            35                  40                  45

Asn Val Trp Thr His Leu Leu Pro Cys Phe Tyr Val Leu Trp Leu Leu
50                  55                  60

Lys Thr Tyr Ser Asp Asp Val Ser Phe Ala Ser Asp Asp Asp Ser Ser
65                  70                  75                  80

Met Leu Leu Leu Leu Phe Gly Thr Ser Asn Phe Thr Phe His Ile Phe
                85                  90                  95

Ser Ala Cys Ala His Leu Leu His Ser Arg Ser Val Ala Val Tyr Tyr
                100                 105                 110

Val Thr Phe Ile Phe Asp Tyr Leu Gly Ile Ala Phe His Ala Phe Thr
            115                 120                 125

Ser Gly Thr Val Gln Tyr Phe Leu Ser Ser Lys Ala Ser Phe Phe His
130                 135                 140

Ala Val His Pro Trp Phe Pro Trp Ala Cys Val Leu Phe Ser Cys Cys
145                 150                 155                 160

Tyr Phe Ala Ala Asn Ala Tyr Ser His Val Thr Tyr Arg Arg Cys His
                165                 170                 175

Ser Glu Arg Ala Leu Thr Gln Val Val Ser Phe Ser Thr Thr Tyr Leu
                180                 185                 190

Trp Ala Val Ser Pro Val Ile His Arg Ile Tyr Ser Asp Ile Tyr Asn
            195                 200                 205

Gly Thr Ala Asp Asp Val Thr Trp Met His Val Asn His Ile Leu Leu
210                 215                 220

Met Ile Ile Ala Gly Phe Phe Gly Ser Glu Ile Pro Gln Arg Phe
225                 230                 235                 240

Phe Pro Gly Ala Cys Asp Val Ile Gly His Gly His Gln Ile Phe His
                245                 250                 255

Val Ile Ile Thr Ala Ser Val Met Val Gln Leu Glu Ala Ser Phe Ala
                260                 265                 270
```

```
Asp Leu Gln Asn Arg Arg His Leu Asp Leu Val Arg Ile Arg Pro Thr
            275                 280                 285

Asp Met Ser Ile Thr Ala Tyr Leu Val Val Leu Leu Ser Tyr Gly Tyr
        290                 295                 300

Ile Thr Ala Ile Phe Val Arg Lys Ala Leu Ser Lys Ala Asn His Ile
305                 310                 315                 320

<210> SEQ ID NO 138
<211> LENGTH: 320
<212> TYPE: PRT
<213> ORGANISM: Branchiostoma floridae

<400> SEQUENCE: 138

Met Pro Asp Met Lys Arg Ser Leu Thr Ile Asp Glu Val Pro Asp Val
1               5                   10                  15

His Lys Glu Pro Tyr Val Leu Thr Gly Tyr Arg Pro Pro Gln Gln Pro
            20                  25                  30

Trp Arg Phe Tyr Leu Met Ser Ile Phe Ser Gln His Asn Glu Thr Met
        35                  40                  45

Asn Val Trp Thr His Phe Ile Pro Ser Phe Tyr Val Leu Trp Leu Leu
    50                  55                  60

Lys Ile Tyr Ser Glu Asp Val Ser Phe Ala Ser Asp Ala Ser Ser Met
65                  70                  75                  80

Leu Leu Leu Leu Phe Gly Thr Ser Ala Phe Thr Ser Gln Phe Leu Ser
                85                  90                  95

Ala Cys Ala His Leu Leu His Ser Arg Ser Val Ala Ala Tyr Tyr Val
            100                 105                 110

Thr Phe Ile Phe Asp Phe Leu Gly Ile Ala Phe His Val Phe Thr Ser
        115                 120                 125

Gly Thr Val Gln Tyr Phe Leu Ser Ser Glu Ala Ser Phe Phe His Ala
    130                 135                 140

Val Tyr Pro Trp Phe Pro Trp Ala Cys Val Leu Phe Ser Cys Cys Tyr
145                 150                 155                 160

Phe Ala Ala Thr Ala Tyr Ser His Val Arg Tyr Thr Arg Cys His Ser
                165                 170                 175

Glu Arg Val Met Thr Gln Val Val Ser Phe Ser Ile Ile Tyr Leu Gly
            180                 185                 190

Val Thr Ser Pro Val Ile His Arg Ile Tyr Ser Asp Ile Tyr Asn Gly
        195                 200                 205

Thr Val Asp Asp Val Thr Trp Met His Val Asn His Ile Leu Leu Val
    210                 215                 220

Ala Ile Ala Gly Phe Phe His Gly Ser Gly Ile Pro Gln Lys Phe Phe
225                 230                 235                 240

Pro Gly Ala Cys Asp Val Ile Gly His Gly His Gln Ile Phe His Val
                245                 250                 255

Val Ile Ser Thr Ser Leu Ile Phe Gln Leu Glu Ala Ser Phe Ala Asp
            260                 265                 270

Leu Gln Asn Arg Arg His Leu Asp Leu Val Arg Leu Arg Pro Pro Asp
        275                 280                 285

Met Ser Ile Thr Ala Tyr Leu Ile Val Leu Phe Thr Ser Tyr Gly Tyr
    290                 295                 300

Ile Thr Val Leu Phe Val Arg Lys Ala Leu Ser Lys Ala Asn His Ile
305                 310                 315                 320

<210> SEQ ID NO 139
```

```
<211> LENGTH: 320
<212> TYPE: PRT
<213> ORGANISM: Branchiostoma floridae

<400> SEQUENCE: 139

Met Pro Asp Met Lys Arg Ser Leu Thr Ile Asp Glu Val Pro Asp Val
1               5                   10                  15

His Lys Glu Pro Tyr Val Leu Thr Gly Tyr Arg Pro Pro Gln Gln Pro
            20                  25                  30

Trp Arg Phe Tyr Leu Met Ser Ile Phe Ser Gln His Asn Glu Thr Val
        35                  40                  45

Asn Val Trp Thr His Leu Leu Pro Cys Phe Tyr Val Leu Trp Leu Leu
    50                  55                  60

Lys Thr Tyr Ser Asp Glu Val Ser Phe Ala Ser Asp Ala Ser Ser Thr
65                  70                  75                  80

Leu Leu Leu Leu Val Gly Thr Ser Ile Phe Thr Ser Gln Phe Leu Ser
                85                  90                  95

Ala Cys Ala His Leu Leu His Ser Arg Ser Val Ala Ala Tyr Tyr Val
            100                 105                 110

Thr Phe Ile Phe Asp Phe Leu Gly Ile Ala Phe His Val Phe Thr Ser
        115                 120                 125

Gly Thr Val Asn Tyr Phe Leu Ser Ser Glu Ala Ser Phe Phe His Ala
    130                 135                 140

Val Tyr Pro Trp Phe Pro Trp Ala Cys Val Leu Phe Ser Cys Cys Tyr
145                 150                 155                 160

Phe Ala Ala Asn Ala Tyr Ser His Val Arg Tyr Thr Arg Cys His Ser
                165                 170                 175

Glu Arg Ala Met Ile Gln Val Val Ser Phe Gly Met Thr Tyr Leu Trp
            180                 185                 190

Ala Val Ser Pro Val Ile His Arg Ile Tyr Tyr Asp Val Tyr Asn Gly
        195                 200                 205

Asn Val Asp Asp Val Thr Trp Met His Val Asn His Ile Leu Leu Val
    210                 215                 220

Ala Ile Ala Gly Phe Phe His Gly Ser Gly Met Pro Gln Lys Phe Phe
225                 230                 235                 240

Pro Gly Ala Cys Asp Val Ile Gly His Gly His Gln Ile Phe His Val
                245                 250                 255

Val Ile Ser Thr Ser Leu Ile Phe Gln Leu Glu Ala Ser Phe Ala Asp
            260                 265                 270

Leu Gln Asn Gly Arg His Leu Asp Leu Ala Arg Ile Arg Pro Thr Asp
        275                 280                 285

Met Ser Ile Thr Ala Tyr Leu Val Val Leu Phe Thr Ser Tyr Gly Tyr
    290                 295                 300

Ile Thr Val Ile Phe Val Arg Lys Ala Leu Ser Lys Ala Asn Tyr Ser
305                 310                 315                 320

<210> SEQ ID NO 140
<211> LENGTH: 313
<212> TYPE: PRT
<213> ORGANISM: Branchiostoma floridae

<400> SEQUENCE: 140

Met Arg Arg Phe Leu Thr Val Asp Glu Val Pro Asp Ala His Lys Glu
1               5                   10                  15

Pro Phe Val Leu Thr Gly Tyr Arg Pro Pro His Arg Pro Trp Arg Tyr
            20                  25                  30
```

Tyr Leu Met Ser Met Phe Ser Met His Asn Glu Thr Met Ser Val Trp
         35                  40                  45

Thr His Leu Ile Pro Ser Ile Tyr Val Leu Tyr Val Leu Lys Thr Tyr
     50                  55                  60

Phe Asp Asp Leu Asp Tyr Thr Gly Asp Val Ser Ala Arg Leu Phe Leu
 65                  70                  75                  80

Tyr Tyr Gly Thr Ser Asn Phe Thr Leu Gln Phe Leu Ser Ala Cys Ala
                 85                  90                  95

His Leu Leu Cys Ser Arg Ser Val Ala Ala His His Val Ala Phe Thr
            100                 105                 110

Ile Asp Tyr Met Gly Ile Ala Phe Tyr Met Tyr Ser Val Thr Leu Ala
        115                 120                 125

Gln Gly Tyr Ile Ser Ser Glu Pro Ser Phe Thr Tyr Ala Val His Pro
    130                 135                 140

Trp Phe Pro Trp Val Ala Leu Leu Ile Asn Cys Leu Tyr Phe Ala Ala
145                 150                 155                 160

Asn Ala His Ser His Val Arg Tyr Arg Arg Gly Asp Pro Glu Arg Ala
                165                 170                 175

Met Leu Gln Leu Cys Ser Phe Ile Met Met Tyr Leu Phe Gly Thr Leu
            180                 185                 190

Pro Ile Ile His Arg Ile Leu Ser Asp Ala Tyr Asn Gly Ser Val Asp
        195                 200                 205

Asp Val Thr Trp Met Tyr Val Arg His Ile Leu Leu Leu Ala Thr Gly
    210                 215                 220

Gly Phe Phe His Ala Ser Glu Val Pro Gln Arg Phe Leu Pro Gly Met
225                 230                 235                 240

Cys Asp Val Ile Gly His Gly His Gln Ile Phe His Val Leu Gly Ser
                245                 250                 255

Val Ser Val Leu Thr Glu Met Lys Ala Val Phe Ala Asp Leu Gln Asn
            260                 265                 270

Arg Arg His Leu Asp Pro Ile Leu Pro Thr Asp Leu Ser Val Thr Thr
        275                 280                 285

Tyr Phe Ile Val Leu Phe Ala Ser Tyr Val Tyr Ile Ala Tyr Val Phe
    290                 295                 300

Val Arg Lys Ala Leu Ser Gln Gly Ser
305                 310

<210> SEQ ID NO 141
<211> LENGTH: 313
<212> TYPE: PRT
<213> ORGANISM: Branchiostoma floridae

<400> SEQUENCE: 141

Met Arg Arg Phe Leu Thr Val Asp Glu Val Pro Asp Val His Lys Glu
 1               5                  10                  15

Pro Phe Val Leu Thr Gly Tyr Arg Pro Pro His Arg Pro Trp Arg Tyr
             20                  25                  30

Tyr Leu Thr Ser Ile Phe Ser Leu His Asn Glu Thr Val Asn Val Trp
         35                  40                  45

Thr Asn Ile Ile Pro Cys Ile Tyr Leu Leu Tyr Leu Arg Ser Ile Tyr
     50                  55                  60

Ser Asp Glu Val Lys Phe Thr Gly Gly Val Ser Ala Arg Leu Phe Leu
 65                  70                  75                  80

Tyr Ala Ala Ile Ser Asn Phe Thr Leu His Phe Leu Ser Thr Cys Ala

```
                85                  90                  95
His Leu Leu Tyr Ser Arg Ser Val Ala Ala Tyr His Ile Gly Phe Met
            100                 105                 110

Phe Asp Phe Met Gly Ile Ala Phe Tyr Leu Phe Ser Phe Thr Leu Ala
            115                 120                 125

His Cys Tyr Ile Ser Ser Glu Pro Ser Tyr Ala Tyr Ala Val His Pro
            130                 135                 140

Trp Phe Pro Trp Val Val Leu Leu Asn Cys Leu Tyr Met Val Ala
145                 150                 155                 160

Asn Ala His Ala His Phe Glu Tyr Gly Arg Gly Asp Pro Lys Arg Ser
                165                 170                 175

Met Ile Gln Leu Cys Ser Phe Ser Met Thr Tyr Leu Phe Gly Thr Leu
                180                 185                 190

Pro Ile Ile His Arg Ile Leu Ser Asp Val Tyr Asn Gly Ser Val Asp
                195                 200                 205

Asp Val Thr Trp Met His Val Arg His Ile Leu Leu Ala Thr Gly
210                 215                 220

Gly Phe Phe His Ala Ser Glu Val Pro Gln Arg Phe Leu Pro Gly Met
225                 230                 235                 240

Cys Asp Val Ile Gly His Gly His Gln Ile Phe His Val Ile Cys Ser
                245                 250                 255

Thr Ser Leu Thr His Leu Lys Ala Ile Phe Ala Asp Leu Lys Ser
                260                 265                 270

Gly Arg His Gln Asp Leu Val Arg Pro Thr Glu Leu Ser Ile Thr Thr
                275                 280                 285

Cys Tyr Ala Val Leu Phe Ala Ala Tyr Gly Tyr Ile Ala Phe Ile Phe
290                 295                 300

Ala Arg Lys Ala Leu Ser Gln Gly Lys
305                 310
```

<210> SEQ ID NO 142
<211> LENGTH: 341
<212> TYPE: PRT
<213> ORGANISM: Lottia gigantea

<400> SEQUENCE: 142

```
Met Ile Thr Arg His Gln Gly Tyr His Lys Arg Thr Pro Ser Cys Ser
1               5                   10                  15

Leu Gly Ile Cys Gly Pro Ile Tyr Ala Val Asp Gln Val Pro Glu Gln
            20                  25                  30

Phe His Glu Met Phe Ile Leu His Gly Tyr Arg His Pro Lys Ser Ser
        35                  40                  45

Phe Thr Gln Cys Val Leu Ser Leu Phe Asp Ala Thr Asn Glu Thr Leu
    50                  55                  60

Asn Ala Trp Thr His Phe Leu Pro Ala Phe Tyr Phe Ile Trp Val Phe
65                  70                  75                  80

Phe Gly Leu Ser Gln Ser Leu Asn Phe Trp Ser Asp Ser Tyr Thr Trp
                85                  90                  95

Pro Leu Leu Val Tyr Met Leu Val Cys Cys Val Phe Pro Phe Met Ser
            100                 105                 110

Ala Ile Ala His Thr Phe Asn Thr Met Ser Glu Arg Ala Arg His Ile
        115                 120                 125

Cys Phe Phe Leu Asp Tyr Thr Ala Leu Ser Leu Leu Ser Leu Gly Val
    130                 135                 140
```

```
Ala Ile Ala Tyr Arg Ala Tyr Ala Phe Pro Gln Ala Leu Arg Asn Thr
145                 150                 155                 160

Ile Tyr Gly Asp Leu Phe Val Thr Gly Ala Val Ile Asn Ser Leu Leu
            165                 170                 175

Cys Val Leu Val Ser Cys Glu Thr Arg Phe Met Lys Pro Ser Gly Leu
            180                 185                 190

Arg Lys Val Leu Arg Leu Gly Ser Phe Ala Leu Pro Tyr Val Tyr Asp
            195                 200                 205

Ser Ile Pro Ile Val Tyr Arg Leu Leu Phe Cys Ser Lys Thr Glu Cys
210                 215                 220

Ala Leu Thr Ser His Pro Leu Leu Ala Arg Gln Phe Ile Phe Ala Phe
225                 230                 235                 240

Phe Ser Ala Phe Leu Tyr Ala Thr His Leu Pro Glu Arg Leu Arg Pro
            245                 250                 255

Gly Gln Phe Asp Ile Ile Gly His Ser His Gln Leu Phe His Ile Ser
            260                 265                 270

Ser Ile Leu Ala Thr Met Asp Gln Ile Gln Ala Met Leu Gly Asp Met
            275                 280                 285

Arg Glu Arg Ala Glu Glu Leu Lys Ala Ser Trp Glu Phe Thr Ser Pro
290                 295                 300

Asn Ser Ser Leu Asn Ile Leu Ala Ala Val Leu Ile Leu Asn Thr Ile
305                 310                 315                 320

Ile Ile Phe Ile Phe Ser Ile Arg Arg Leu Pro Leu Ala Thr Lys Ser
                325                 330                 335

Glu Gly Arg Cys Cys
            340

<210> SEQ ID NO 143
<211> LENGTH: 328
<212> TYPE: PRT
<213> ORGANISM: Lottia gigantea

<400> SEQUENCE: 143

Met Ala Thr Lys Ser His Tyr Gln Thr Leu Thr Leu Asn His Ile Pro
1               5                   10                  15

Tyr Pro Met Arg His Ala Phe Ile Glu Thr Gly Tyr Arg Gln Leu His
            20                  25                  30

Lys Pro Trp Ser Tyr Tyr Leu Ser Val Ala Lys Trp His Asn Glu
            35                  40                  45

Thr Leu Asn Val Trp Thr His Val Ile Ala Ser Ile Ile Pro Tyr
50                  55                  60

Tyr Gly Val Gln Phe His Gln Lys His Asp Leu Leu Tyr Ser Glu
65                  70                  75                  80

Gly Asn Lys Met Leu Val Cys Phe Leu Gly Cys Leu Thr Leu Thr Val
            85                  90                  95

Leu Ser Ser Ile Ala His Trp Phe Gly Ser Arg Ser Val Lys Ser His
                100                 105                 110

Val Ile Phe Phe Leu Met Asp Tyr Ser Gly Ile Ala Leu Tyr Val Tyr
            115                 120                 125

Thr Thr Ser Val Val Ala Leu Tyr Ile Cys Gly Asp Ile His Ser Phe
130                 135                 140

Glu Thr Leu Arg Pro Phe Tyr Val Gln Val Gly Val Val Leu Ala Thr
145                 150                 155                 160

Ile Cys Phe Ala Ile Asn Cys Ala Ala Lys Val Trp Ile Glu Asn Lys
                165                 170                 175
```

```
Ser Phe Ser Ser Met Lys Lys Phe Gly Met Ile Ala Pro Tyr Ile Leu
            180                 185                 190

Phe Ala Leu Tyr Val Ser Cys Pro Leu Phe Pro Arg Tyr Trp His Cys
            195                 200                 205

Tyr Leu Asp Ser Lys Cys Ala Leu Tyr Ser Leu Asn Asn Ile Thr Leu
    210                 215                 220

Cys Tyr Ala Leu Phe Val Leu Glu Ala Ile Val Tyr Ala Leu His Ile
225                 230                 235                 240

Pro Glu Arg Trp Lys Ala Lys Ser Phe Asp His Cys Gly Gln Ser His
                245                 250                 255

Gln Ile Phe His Ile Ser Val Leu Val Thr Met Val Val Gln Ile Tyr
                260                 265                 270

Thr Leu Asp Asn Glu Ile Ala Ser Gly His Ser Ser Gln Phe Glu Phe
        275                 280                 285

Asp Phe Glu Lys Asn Val Ala Gly Phe Val Cys Leu Val Ile Ser Leu
        290                 295                 300

Thr Met Val Ile Leu Phe Tyr Leu Pro Ser Ile Asp Lys Leu Ser His
305                 310                 315                 320

Lys Phe Lys Ser Ser Lys Ser Glu
                325

<210> SEQ ID NO 144
<211> LENGTH: 336
<212> TYPE: PRT
<213> ORGANISM: Lottia gigantea

<400> SEQUENCE: 144

Met Ser Leu Val Ser Ser Thr Ile Gly Leu Ile Lys His Tyr Leu Cys
1               5                   10                  15

Ile Gln Lys Thr Val Asn Ser Lys Ser Ile Pro Ala Pro Phe Arg Glu
            20                  25                  30

Pro Tyr Ile Leu Thr Gly Tyr Arg Leu Pro Lys Lys Ser Trp Ser Tyr
        35                  40                  45

Tyr Ile Val Ser Leu Phe Gln Trp His Asn Glu Thr Ile Asn Val Trp
    50                  55                  60

Thr His Leu Val Ala Cys Leu Phe Val Leu Gly Glu Leu Ala Arg Phe
65                  70                  75                  80

Gly Leu Lys Tyr Asp Leu Phe Ser Asp Lys Asp Gly Ala Leu Leu
                85                  90                  95

Ala Phe Gly Leu Ser Cys Leu Thr Met Phe Phe Ser Ser Met Ser
            100                 105                 110

His Leu Leu His Leu Lys Ser Ile Lys Val His Tyr Ile Leu Ser Leu
        115                 120                 125

Ala Asp Tyr Ala Gly Ile Ser Leu Tyr Gly Ser Gly Ala Gly Ile Ala
    130                 135                 140

Thr Phe Tyr Ser Cys Cys Gln Pro Asn Val Tyr Asp Val Met Ala Pro
145                 150                 155                 160

Phe Tyr Ile Ile Gly Asn Val Ile Val Gly Trp Phe Val Tyr Ala Thr
                165                 170                 175

Cys Val Ile Ala Lys Leu Thr Phe Val Gly Pro His Ala Ala Gln Arg
            180                 185                 190

Lys Leu Met Cys Val Phe Ala Phe Thr Ile Gln Gly Thr Trp Ile Val
        195                 200                 205

Thr Pro Leu Leu Ser Asn Tyr Tyr Thr Tyr Phe Phe Asp Pro Glu Cys
```

```
            210                 215                 220

Ser Ile Trp Asn Leu Asn His Ile Thr Ile Ser Cys Leu Leu Cys Val
225                 230                 235                 240

Leu Glu Gly Ile Ala Phe Ala Ala His Ile Pro Glu Arg Tyr Arg Pro
                245                 250                 255

Lys Met Phe Asp Tyr Val Gly His Gly His Gln Ile Phe His Leu Leu
                260                 265                 270

Cys Ile Phe Ser Val Ile Tyr Gln Met Arg Ala Val Asp Arg Asn Val
                275                 280                 285

Asp Met Gly Leu Ala Ala His Thr Gly Met Asn Ile Asn Asp Val Leu
            290                 295                 300

Ile Gly Phe Thr Ala Leu Ile Met Ser Gln Ile Ile Thr Thr Phe Phe
305                 310                 315                 320

Val Leu Gly Leu Val Asp Lys Lys Val Asn Glu Ile Val Lys Ala Ser
                325                 330                 335

<210> SEQ ID NO 145
<211> LENGTH: 341
<212> TYPE: PRT
<213> ORGANISM: Lottia gigantea

<400> SEQUENCE: 145

Met Pro Ile Gln Lys Ile Val Lys Ser Phe Pro Ser Thr Thr Ser Lys
1               5                   10                  15

Asp Gln Val Pro Lys Leu Phe His Glu Pro His Val Glu Thr Gly Phe
                20                  25                  30

Arg His Leu His Gln Pro Trp Ser Tyr Tyr Phe Phe Ser Val Phe Gln
            35                  40                  45

Val His Asn Glu Cys Met Asn Thr Trp Thr His Leu Ile Ala Leu Trp
50                  55                  60

Leu Ile Leu Tyr Arg Thr Tyr Arg Leu Ala Leu Glu Phe Asp Phe Ile
65                  70                  75                  80

Asn Asp Pro Tyr Met Trp Pro Leu Leu Ala Ser Leu Leu Thr Met Ile
                85                  90                  95

Ile Leu Tyr Ile Cys Ser Ser Cys Ala His Cys Phe Ser Asn Lys Ser
            100                 105                 110

Glu Ser Ile His Tyr Thr Cys Phe Met Ile Asp Tyr Ala Gly Ile Gly
            115                 120                 125

Leu Tyr Gly Met Gly Ser Thr Met Leu His Tyr Ala Tyr Cys Leu His
            130                 135                 140

Thr Asp Met Val Asp Thr Trp Ala His His Trp Asp Val Glu Leu Gly
145                 150                 155                 160

Val Cys Leu Gly Val Leu Val Thr Val Cys Cys Ser Ile Ser Lys Thr
                165                 170                 175

Arg Tyr Ser Arg Pro Tyr Pro Phe Val Arg Arg Ile Trp Gln Leu Ser
                180                 185                 190

Ser Thr Leu Ala Val Tyr Val Trp Leu Ile Tyr Pro Ile Ala Tyr Arg
            195                 200                 205

Val Ala Leu Tyr Leu Phe His His Gln Trp Asp Ser Gly Leu Ser His
            210                 215                 220

His Ile Gln Gln Met Ile Trp Phe Phe Ala Gly Gly Phe Phe Phe Gly
225                 230                 235                 240

Ser Asp Val Pro Gln Arg Phe Cys Pro Gly Lys Phe Asp Phe Ile Gly
                245                 250                 255
```

```
His Ser His Gln Ile Phe His Ile Cys Ile Leu Met Thr Ser Tyr Lys
            260                 265                 270

Gln Leu Asp Ala Val Tyr Glu Asp Ile Lys Asn Asn Trp Ala Glu Ile
            275                 280                 285

His Arg Leu Pro Glu Pro Thr Leu Ile Asn Ser Phe Gly Ala Val Leu
            290                 295                 300

Leu Thr Ile Val Leu Asn Met Ile Ala Val Met Tyr Phe Arg Ser Val
305                 310                 315                 320

Ala Cys Arg Lys Ile His Asp Asn Asn Gln Gln Asn Asn Asn Ile Asn
            325                 330                 335

His Asn Lys Thr Asp
            340

<210> SEQ ID NO 146
<211> LENGTH: 340
<212> TYPE: PRT
<213> ORGANISM: Lottia gigantea

<400> SEQUENCE: 146

Met Asp Gly Leu Leu Arg Asn Lys Leu Pro Lys Gln Phe Gln Pro Leu
1               5                   10                  15

Phe Lys Ala Gln Arg Thr Gln Phe Gln Glu Lys Val Leu Val Thr Phe
            20                  25                  30

Arg Glu Pro Tyr Ile Leu Arg Gly Tyr Arg Leu Thr Asn Lys Pro Trp
            35                  40                  45

His Tyr Tyr Leu Val Ser Leu Phe Asn Trp His Asn Glu Thr Ile Asn
            50                  55                  60

Ile Trp Thr His Leu Leu Ser Phe Ile Tyr Ile Val Leu His Ile Ile
65                  70                  75                  80

Asn Leu Cys Glu Lys Tyr Asp Val Met Asn Thr Ser Glu Gly Ala Val
            85                  90                  95

Val Leu Gly Tyr Ser Phe Gly Ala Leu Ser Leu Thr Ser Phe Ser Thr
            100                 105                 110

Ile Ala His Leu Phe His Ser Lys Ser Leu Arg His His Tyr Glu Phe
            115                 120                 125

Phe Met Leu Asp Tyr Phe Gly Val Ser Leu Tyr Ser Leu Gly Cys Gly
            130                 135                 140

Ile Leu Thr Ile Tyr Arg Phe Cys Pro Glu Asn Ser Phe Gln Ile Leu
145                 150                 155                 160

Gln Thr Phe Tyr Leu Pro Leu His Leu Ile Leu Cys Tyr Asn Asn Phe
            165                 170                 175

Leu Ser Ile Ser Thr Ala Lys Leu Tyr Phe Phe Gly Val Ile Arg Lys
            180                 185                 190

Cys Leu Thr Val Ser Ala Cys Leu Ser Thr Ile Ser Met Leu Tyr
            195                 200                 205

Pro Leu Leu Cys Thr Tyr Tyr Glu Cys Phe Asn Asp Thr Ala Cys His
            210                 215                 220

Ile Ser Ser Leu Asn His Leu Gly Leu Met Tyr Val Phe Leu Phe Leu
225                 230                 235                 240

Ser Thr Val Ala Tyr Leu Ala His Gln Pro Glu Met Ser Asn Leu Gly
            245                 250                 255

Met Cys Asp Ile Val Gly His Ser His Gln Trp Phe His Val Phe Val
            260                 265                 270

Phe Cys Thr Ile Leu Ala Gln Tyr Asn Ala Met Glu Lys Glu Ile Asp
            275                 280                 285
```

Leu Asn Lys Gly Val Ile Ser Glu Val Gln Leu Ser Thr Val Ile
            290                 295                 300

Tyr Phe Leu Leu Leu Leu Ser Leu Asn Ser Val Thr Phe Leu Phe Leu
305                 310                 315                 320

Gln Pro Ala Leu Lys Arg Lys Val Val Asp Ile Glu Asn Thr Asn His
                325                 330                 335

Ile Lys Gln Lys
            340

<210> SEQ ID NO 147
<211> LENGTH: 363
<212> TYPE: PRT
<213> ORGANISM: Capitella sp.

<400> SEQUENCE: 147

Met Ala Thr Thr Leu Gln Leu Tyr His Val Ser Glu Ile Pro Ser Phe
1               5                   10                  15

Phe His Glu Leu Tyr Ile His Arg Gly Tyr Arg His Pro Arg Ser Ser
            20                  25                  30

Val Arg Ser Cys Leu Arg Ser Cys Phe Tyr Leu His Asn Glu Thr Val
        35                  40                  45

Asn Phe Trp Thr His Phe Ile Pro Ala Val Phe Tyr Leu Phe Val Leu
    50                  55                  60

Val Thr Asp Cys Tyr Gln Tyr Asn Leu Leu Leu Asp Ala Tyr Gly Leu
65                  70                  75                  80

Pro Met Leu Ala Tyr Leu Ile Ser Met Thr Leu Phe Pro Thr Ala Ser
                85                  90                  95

Ala Leu Ala His Leu Phe Asn Thr Ile Ser Glu Lys Ala Arg His Met
            100                 105                 110

Cys Phe Phe Leu Asp Tyr Phe Ala Leu Ser Ile Phe Gly Ile Gly Thr
        115                 120                 125

Ala Ile Ala Tyr His Ala Tyr Ser Phe Pro Val Ala Leu Ile Ser Thr
    130                 135                 140

Trp Trp Gln His Leu Tyr Leu Leu Val Ala Val Val Asn Ala Leu Leu
145                 150                 155                 160

Ser Phe Val Leu Ser Cys Arg Thr Arg Phe Leu Asp His Gly Leu Arg
                165                 170                 175

Lys Lys Met Phe Arg Ile Leu Ser Phe Ala Val Pro Tyr Leu Phe Asp
            180                 185                 190

Val Leu Pro Val Cys Tyr Arg Ala Ile His Gly Asp Val Val Asp Phe
        195                 200                 205

Ser Leu Gly Gly Met His Tyr His Val Arg Gln Ser Val Phe Ala Phe
    210                 215                 220

Leu Ser Ala Leu Ile Tyr Ser Ser His Leu Pro Glu Arg Leu Ser Pro
225                 230                 235                 240

Gly Arg Phe Asp Ile Ile Gly Gln Ser His Gln Leu Phe His Val Val
                245                 250                 255

Ser Val Met Gly Thr His Asp Leu Met Thr Gly Met Arg Met Asp Met
            260                 265                 270

Leu Gln Arg Arg Gln Leu Met Asp Ala His Gln Pro Ser Tyr Ser Ile
        275                 280                 285

Leu Leu Met Val Ala Val Val Gly Phe Asn Leu Val Ile Leu Tyr Tyr
    290                 295                 300

Phe Trp Met Gln Leu Asp Gly Val Ile Leu Lys Ser Thr Ser Ser Glu

```
                305                 310                 315                 320
Asp Leu Thr Lys Leu Asn Asn Leu Cys Asn Gly Ala Gly Leu Thr Asn
                    325                 330                 335

Gly Lys Ser Gly His His Leu Ile Asp Arg Gln Leu Thr Asn Asp Val
                    340                 345                 350

Ser Arg Arg Ser Lys Leu Arg Pro His Val Glu
                    355                 360

<210> SEQ ID NO 148
<211> LENGTH: 352
<212> TYPE: PRT
<213> ORGANISM: Capitella sp.

<400> SEQUENCE: 148

Met Glu Thr Leu Lys Ser Phe Thr Asp Arg Met Val Ala Ser Ser Asn
1               5                   10                  15

Gly Leu Val Pro Trp His Glu Val Pro Glu Asp Ser Arg Glu Lys Tyr
                20                  25                  30

Ile Leu Thr Gly Tyr Arg Arg Pro Asn Glu Gly Gln Trp Leu Ser Cys
            35                  40                  45

Ile Gly Ser Ala Phe Gln Trp His Asn Glu Thr Ile Asn Ile Trp Thr
        50                  55                  60

His Leu Leu Pro Ala Phe Tyr Phe Ile Tyr Phe Ala Leu Met Ala Leu
65                  70                  75                  80

Arg Cys Glu His Val Pro Asn Asn Ser Leu Phe Ala Phe Tyr Gly Tyr
                85                  90                  95

Leu Leu Ala Val Cys Ser Leu Phe Val Ser Ser Ala Ala His Leu
                100                 105                 110

Cys Thr His Cys His Phe Leu Lys Asp Ile Phe Phe Met Met Asp Tyr
            115                 120                 125

Ser Ala Ile Ser Phe Tyr Gly Val Gly Ala Ser Ile Ala Val Phe Ala
        130                 135                 140

Tyr Ser Arg Pro Lys His Gln Ile Leu Val Asp Thr Glu Glu Ala Phe
145                 150                 155                 160

Leu Ile Gly Ile Val Ile Leu Ala Ile Ala Ala Ser Trp Thr Ser Cys
                165                 170                 175

Trp Thr Arg Ile Ser Gln Ser Ser Leu Gly His Leu Ile Arg Thr Ser
            180                 185                 190

Ala Tyr Ala Ala Pro Phe Val Tyr Gly Ser Met Pro Ala Val Ala Arg
        195                 200                 205

Cys Phe His Asp Ile Ser Leu Pro Pro Thr Asn Ile Thr Thr Gly His
    210                 215                 220

Asn Thr Gly Asp Glu Ala Leu Pro Val Ile Asp Lys Tyr Ser Phe Ile
225                 230                 235                 240

Gln Met Tyr Ile Trp His Phe Val Leu Met Ala Ser Ala Gly Leu Val
                245                 250                 255

Asn Ile Ser Arg Val Pro Glu Cys Trp Phe Pro Gly Thr Phe Asp Leu
            260                 265                 270

Ile Gly Ser Ser His Gln Trp Phe His Val Leu Ile Phe Leu Ser Ile
        275                 280                 285

Arg Gln Gln Phe Trp Phe Thr Val Ser Asp Ile Cys Val Pro Asn Arg
    290                 295                 300

His Ile Ser Ala Ser Met Tyr Gly His Tyr Phe Asn Gly Trp Tyr Leu
305                 310                 315                 320
```

```
Leu Ser Ala Phe Ala Val Thr Leu Ile Ala Leu Ala Phe Ile Ile Thr
                325                 330                 335
Phe Ser Phe Lys Asn Ile His Glu Glu Lys Pro Val Val Lys Gln Glu
            340                 345                 350
```

<210> SEQ ID NO 149
<211> LENGTH: 348
<212> TYPE: PRT
<213> ORGANISM: Capitella sp.

<400> SEQUENCE: 149

```
Met Ser Arg Val Gln Ser Thr Pro Ile Phe Gly Thr Thr Lys Thr Arg
1               5                   10                  15

Phe Arg Ser Leu Pro Arg Val Pro Ser Leu Pro Val Phe Val Pro Thr
            20                  25                  30

Arg Ser Lys Ala Gln Val Pro Leu Leu Phe Arg Glu Ala Tyr Val Asp
        35                  40                  45

His Gly Phe Arg Glu Leu His Arg Pro Trp Trp Ser Tyr Leu Leu Ser
    50                  55                  60

Val Leu Gln Leu His Asn Glu Ser Met Asn Val Trp Thr His Leu Val
65                  70                  75                  80

Ala Leu Val Leu Met Leu Lys His Leu His Thr Phe Asn Gln His Leu
                85                  90                  95

Asp Phe Leu Thr Asp Pro Tyr Ser Trp Pro Leu Leu Ala Gly Phe Val
            100                 105                 110

Cys Gly Leu Leu Leu Tyr Ser Phe Ser Ser Met Ala His Cys Phe His
        115                 120                 125

Ser Lys Ser Glu Leu Val His Tyr Leu Ala Phe Met Val Asp Tyr Ala
    130                 135                 140

Gly Ile Gly Leu Tyr Gly Leu Gly Ser Thr Ile Ile His Phe Tyr Tyr
145                 150                 155                 160

Cys Thr Glu Leu Glu Leu His Leu Phe Thr Gln Asn Phe Phe Val Pro
                165                 170                 175

Val Gly Cys Ala Leu Ala Phe Leu Val Phe Phe Cys Cys Ser Tyr Ala
            180                 185                 190

Lys Val Ser Tyr Ser Arg Pro Tyr Pro Phe Val Arg Lys Val Trp Gln
        195                 200                 205

Met Val Pro Val Leu Gly Val Tyr Phe His Leu Ser Ile Pro Leu Val
    210                 215                 220

His Arg Phe Ile Leu Cys Leu Thr Ser Ser Ala Cys Pro Ser
225                 230                 235                 240

Ile Gln His His Ala Gln Gln Met Val Trp Phe Ile Leu Ser Gly Ile
                245                 250                 255

Phe Tyr Ala Ser Asp Leu Pro Gln Arg Phe His Pro Gly Arg Phe Asp
            260                 265                 270

His Phe Phe His Ser His Gln Leu Phe His Ile Cys Ile Met Met Ser
        275                 280                 285

Thr Ser Lys Gln Met Asp Ala Val Leu Leu Asp Tyr Gln Met Arg Leu
    290                 295                 300

Ala Ala Ile Leu Ala Gln Pro Glu Pro Ser Leu Phe Ser Ala Phe Gly
305                 310                 315                 320

Pro Val Ala Val Val Leu Ala Ala Gln Ile Ile Ser Phe Cys Phe Phe
                325                 330                 335

Arg Ser Ile Val Lys Arg Lys Leu Ala Lys Arg Asp
            340                 345
```

```
<210> SEQ ID NO 150
<211> LENGTH: 336
<212> TYPE: PRT
<213> ORGANISM: Capitella sp.

<400> SEQUENCE: 150
```

| | | | | | | | | | | | | | | | |
|---|---|---|---|---|---|---|---|---|---|---|---|---|---|---|---|
| Met | Asp | Phe | Val | Phe | Gln | Lys | Thr | Leu | Pro | Asp | Ser | Asp | Val | Gly | Leu |
| 1 | | | | 5 | | | | | 10 | | | | | 15 | |

| | | | | | | | | | | | | | | | |
|---|---|---|---|---|---|---|---|---|---|---|---|---|---|---|---|
| Leu | Phe | Arg | Glu | Pro | Phe | Ile | Lys | Thr | Gly | Tyr | Arg | Gln | Pro | Tyr | Arg |
| | | | 20 | | | | | 25 | | | | | 30 | | |

| | | | | | | | | | | | | | | | |
|---|---|---|---|---|---|---|---|---|---|---|---|---|---|---|---|
| Pro | Trp | Ser | Tyr | Tyr | Ile | Gly | Ser | Leu | Phe | Arg | Val | His | Asn | Glu | Thr |
| | | 35 | | | | | 40 | | | | | 45 | | | |

| | | | | | | | | | | | | | | | |
|---|---|---|---|---|---|---|---|---|---|---|---|---|---|---|---|
| Leu | Asn | Val | Trp | Ser | His | Leu | Ala | Tyr | Leu | Ala | Ile | Phe | Leu | Arg | His |
| | 50 | | | | | 55 | | | | | 60 | | | | |

| | | | | | | | | | | | | | | | |
|---|---|---|---|---|---|---|---|---|---|---|---|---|---|---|---|
| Val | Tyr | Val | Leu | Arg | Ala | Glu | Leu | Asp | Tyr | Ser | Ala | Asp | Pro | Leu | Ala |
| 65 | | | | | 70 | | | | | 75 | | | | | 80 |

| | | | | | | | | | | | | | | | |
|---|---|---|---|---|---|---|---|---|---|---|---|---|---|---|---|
| Trp | Pro | Met | Leu | Gly | Phe | Ala | Ala | Gly | Thr | Ile | Ala | Tyr | Thr | Ala | Leu |
| | | | | 85 | | | | | 90 | | | | | 95 | |

| | | | | | | | | | | | | | | | |
|---|---|---|---|---|---|---|---|---|---|---|---|---|---|---|---|
| Ser | Ala | Met | Ala | His | Leu | Leu | Gln | Ser | Arg | Ser | Glu | Met | Ser | His | Tyr |
| | | | 100 | | | | | 105 | | | | | 110 | | |

| | | | | | | | | | | | | | | | |
|---|---|---|---|---|---|---|---|---|---|---|---|---|---|---|---|
| Val | Cys | Tyr | Gln | Leu | Asp | Tyr | Ala | Gly | Ile | Gly | Leu | Asn | Ala | Val | Gly |
| | | 115 | | | | | 120 | | | | | 125 | | | |

| | | | | | | | | | | | | | | | |
|---|---|---|---|---|---|---|---|---|---|---|---|---|---|---|---|
| Asn | Gly | Leu | Leu | Val | Tyr | Tyr | Met | Val | Ala | Thr | Glu | Thr | Phe | Tyr | Arg |
| | 130 | | | | | 135 | | | | | 140 | | | | |

| | | | | | | | | | | | | | | | |
|---|---|---|---|---|---|---|---|---|---|---|---|---|---|---|---|
| Trp | Phe | Gly | Trp | Phe | Phe | Ile | Pro | Val | Asn | Phe | Leu | Gly | Phe | Phe |  |
| 145 | | | | | 150 | | | | | 155 | | | | | 160 |

| | | | | | | | | | | | | | | | |
|---|---|---|---|---|---|---|---|---|---|---|---|---|---|---|---|
| Asp | Cys | Ala | Cys | Met | Gly | Val | Ala | Met | Leu | Trp | Phe | Pro | Lys | Pro | Tyr |
| | | | | 165 | | | | | 170 | | | | | 175 | |

| | | | | | | | | | | | | | | | |
|---|---|---|---|---|---|---|---|---|---|---|---|---|---|---|---|
| Pro | Tyr | Gln | Arg | Lys | Ile | Trp | Gln | Met | Gly | Ser | Thr | Gly | Phe | His | Val |
| | | | 180 | | | | | 185 | | | | | 190 | | |

| | | | | | | | | | | | | | | | |
|---|---|---|---|---|---|---|---|---|---|---|---|---|---|---|---|
| Leu | Phe | Ala | Met | Trp | Pro | Leu | Ala | His | Lys | Ile | Val | Glu | Thr | Leu | Tyr |
| | | 195 | | | | | 200 | | | | | 205 | | | |

| | | | | | | | | | | | | | | | |
|---|---|---|---|---|---|---|---|---|---|---|---|---|---|---|---|
| Ser | Gln | Gly | Thr | Met | Ser | Pro | Ser | Val | Val | Leu | Pro | His | Ala | His | Tyr |
| | 210 | | | | | 215 | | | | | 220 | | | | |

| | | | | | | | | | | | | | | | |
|---|---|---|---|---|---|---|---|---|---|---|---|---|---|---|---|
| Ser | Ala | Trp | Phe | Leu | Phe | Ser | Val | Ser | Phe | Phe | Ala | Ser | His | Val | Pro |
| 225 | | | | | 230 | | | | | 235 | | | | | 240 |

| | | | | | | | | | | | | | | | |
|---|---|---|---|---|---|---|---|---|---|---|---|---|---|---|---|
| Glu | Arg | Leu | Leu | Pro | Gly | Ala | Phe | Asp | Met | Val | Gly | His | Gly | His | Gln |
| | | | | 245 | | | | | 250 | | | | | 255 | |

| | | | | | | | | | | | | | | | |
|---|---|---|---|---|---|---|---|---|---|---|---|---|---|---|---|
| Ile | Phe | His | Leu | Ala | Val | Gly | Tyr | Cys | Ser | Trp | Leu | Gln | Tyr | Glu | Val |
| | | | 260 | | | | | 265 | | | | | 270 | | |

| | | | | | | | | | | | | | | | |
|---|---|---|---|---|---|---|---|---|---|---|---|---|---|---|---|
| Gly | Leu | Leu | Glu | Met | Lys | Thr | Arg | Pro | Arg | His | Leu | Val | Ala | Met | Ala |
| | | 275 | | | | | 280 | | | | | 285 | | | |

| | | | | | | | | | | | | | | | |
|---|---|---|---|---|---|---|---|---|---|---|---|---|---|---|---|
| Asn | Pro | Asn | Gly | Thr | Thr | Ile | Phe | Gly | Gly | Ile | Leu | Ala | Val | Val | Leu |
| | 290 | | | | | 295 | | | | | 300 | | | | |

| | | | | | | | | | | | | | | | |
|---|---|---|---|---|---|---|---|---|---|---|---|---|---|---|---|
| Gly | Asp | Leu | Ile | Phe | Leu | Val | Cys | Thr | His | Asn | Trp | Arg | Lys | Lys | Ile |
| 305 | | | | | 310 | | | | | 315 | | | | | 320 |

| | | | | | | | | | | | | | | |
|---|---|---|---|---|---|---|---|---|---|---|---|---|---|---|
| Cys | Ala | Glu | Asp | Val | Lys | Arg | Arg | Leu | Arg | Arg | Lys | Arg | Leu | Glu |
| | | | | 325 | | | | | 330 | | | | | 335 |

```
<210> SEQ ID NO 151
<211> LENGTH: 349
<212> TYPE: PRT
<213> ORGANISM: Nematostella vectensis

<400> SEQUENCE: 151
```

Met Lys Tyr Leu Tyr Asn Trp Arg Leu Gly Gly Leu Ala Arg Asn Gln
1               5                   10                  15

Gln Arg Thr Pro Gly Ala Ser Glu His Leu Gly Leu Val Gln Lys Glu
            20                  25                  30

Ser Gly Arg Asp Gly Lys Gly His Gly Lys Met Val Tyr Arg Arg Leu
        35                  40                  45

Val Pro Val Glu Ile Pro Asp Asn Asn Asn Glu Asn Glu Leu Lys Val
50                  55                  60

Leu Arg Ala Leu Glu Lys Asp Glu Glu Thr Lys Glu Asn Ala Cys Asp
65                  70                  75                  80

Leu Pro Pro Lys Leu Cys Ser Leu Gln Cys Cys Pro Ser Trp Leu Gln
                85                  90                  95

Phe Asn Lys Phe Val Leu Thr Gly Tyr Arg Cys Asp Tyr Thr Val Ser
            100                 105                 110

Glu Cys Leu Asp Ser Leu Leu Tyr Val His Asn Glu Ser Val Asn Ile
        115                 120                 125

Tyr Ser His Gly Ile Pro Cys Val Leu Met Met Ile Leu Ile Pro Leu
    130                 135                 140

Thr Ala Ser Gln Ala Cys Leu Glu Ser Ser Phe Trp Phe Ser Leu His
145                 150                 155                 160

Tyr Phe Ala Cys Phe Ala Pro Phe Phe Ser Ser Pro Ile Tyr His Leu
                165                 170                 175

Phe Met Cys His Lys Gln Gly Ser Thr Ala Tyr Asn Gly Leu Leu Thr
            180                 185                 190

Phe Asp Met Cys Gly Ile Trp Ala Val Asn Thr Phe Gly Ala Leu Cys
        195                 200                 205

Gly Ile Arg Ala Thr Leu Phe Cys Phe Pro Ile Trp Arg Met Thr Ala
    210                 215                 220

Leu Ile Thr Tyr Ile Leu Ile Ser Phe Ile Ser Leu Tyr Phe Ile Leu
225                 230                 235                 240

Gly Ala Arg Thr Pro Lys Glu Arg Phe Val Pro Leu Thr Val Phe Gly
                245                 250                 255

Val Met Arg Tyr Leu Phe Ile Gly Val Arg Leu Phe Leu Arg Tyr Leu
            260                 265                 270

Gly Tyr Gly Cys Gly Ser Asp Gly Ala Leu Pro Tyr Cys Val Leu Met
        275                 280                 285

Asp Leu Phe Ala Cys Val Gly Gly Val Ile Asn Ile Ala Arg Val Pro
    290                 295                 300

Glu Lys Trp Phe Pro Gly Gln Phe Asp Ile Ile Gly Asn Ser His Gln
305                 310                 315                 320

Ile Met His Val Leu Ser Val Ile Ser Val Ile Phe Leu His Leu Gly
                325                 330                 335

Ser Ser Lys Glu Phe Glu Trp Met Ala Glu Tyr Lys Cys
            340                 345

<210> SEQ ID NO 152
<211> LENGTH: 342
<212> TYPE: PRT
<213> ORGANISM: Nematostella vectensis

<400> SEQUENCE: 152

Met Ile Asn Asn Asn Asn Asn Leu Lys Gln His Thr Glu Val Leu Glu
1               5                   10                  15

Lys Thr Leu Leu Gly Asp Arg Ala Val Asp Phe Glu Phe Arg Glu Pro

```
            20                  25                  30
Phe Ile Val Ser Gly Tyr Arg Arg Pro Gly Phe Ser Phe Lys Gln Cys
            35                  40                  45

Ile His Ser Ala Phe Tyr Ala His Asn Glu Thr Ile Asn Val Trp Ser
 50                  55                  60

His Ile Leu Ala Leu Val Gly Phe Leu Tyr His Cys Leu Pro Val Phe
 65                  70                  75                  80

Cys Leu Arg Ser Asn Pro Phe Thr Asp Pro Val Tyr Pro Leu Leu
                 85                  90                  95

Ser Phe Ser Leu Gly Ile Ser Ala Met Phe Leu Met Ser Ser Ser Ala
                100                 105                 110

His Leu Phe Asn Cys Met Ser Ala Lys Val Arg His Ile Cys Phe Phe
                115                 120                 125

Phe Asp Tyr Ala Ala Ile Ser Thr Tyr Thr Phe Thr Ala Gly Leu Val
        130                 135                 140

Phe Tyr Tyr Tyr Ser Arg Pro Thr Asn Thr Asp Leu Lys Leu Met Asn
145                 150                 155                 160

Ser Asn Cys Leu Phe Leu Cys Ile Ser Ala Ala Ile Ser Leu Ala Thr
                165                 170                 175

Thr Tyr Leu Cys Cys Ala Ser Arg His Lys Trp Val Gln His Lys Phe
                180                 185                 190

Leu Leu Arg Thr Gly Thr Phe Val Ile Ser Trp Leu Phe Asn Thr Leu
            195                 200                 205

Pro Phe Thr Thr Arg Ala Ile Tyr Cys Asp Ser Lys Leu Glu Cys Asn
        210                 215                 220

Thr Val Ala Phe Ala Tyr Phe Lys Arg Gln Val Phe Tyr Phe Phe Leu
225                 230                 235                 240

Ala Ala Leu Ser Asn Val Ile Arg Ile Pro Glu Arg Phe Ile Pro Gly
                245                 250                 255

Leu Phe Asp Phe Phe Gly Gln Ser His His Phe Leu His Ile Leu Cys
                260                 265                 270

Ser Leu Gly Ala Ile Asp Asp Phe Val Ala Val Glu Leu Asp Met Asn
            275                 280                 285

Ile Arg Arg Glu Ile Leu His Ala Ser Ser Thr Val Leu Pro Thr Phe
        290                 295                 300

Gly Asn Ser Leu Gly Leu Met Ile Ala Val Leu Leu Gly Asn Ile Ala
305                 310                 315                 320

Ile Val Ile Trp Phe Ala Val His Cys Pro Val Ser Leu Gln Ile Asp
                325                 330                 335

Lys Gln Leu Lys Thr Lys
                340

<210> SEQ ID NO 153
<211> LENGTH: 382
<212> TYPE: PRT
<213> ORGANISM: Nematostella vectensis

<400> SEQUENCE: 153

Met Ser Cys Lys Glu Ser Asn Gly Asp Ala His Gln Asn Gly Lys His
 1               5                  10                  15

His Asp Val Asn Arg Asn Gln Gln Trp Pro Phe Asp Asp Thr Lys Gly
                20                  25                  30

Ala Leu Ser Gly Arg Lys Gly Leu Arg Phe Val His Glu Leu Pro Pro
            35                  40                  45
```

Ser Tyr His Glu Pro Phe Ile Leu Ser Gly Tyr Arg Asn Pro Gly Asn
 50                 55                  60

Phe Ser Leu Arg Gln Cys Leu Val Thr Ala Phe Ser Leu His Asn Glu
 65                 70                  75                  80

Thr Ile Asn Ile Trp Ser His Leu Ile Ala Phe Ile Ala Phe Ala Val
                 85                  90                  95

Tyr Phe Tyr Tyr Lys Phe Gln Ala Leu Gly Val Gly Phe Thr Phe Gly
                100                 105                 110

Pro Thr Gly Tyr Pro Leu Met Cys Phe Ala Phe Gly Ile Cys Leu Val
                115                 120                 125

Phe Ile Ser Ser Ala Gly Ala His Leu Phe Cys Cys Leu Ser Glu Glu
130                 135                 140

Cys Arg His Ile Cys Phe Tyr Leu Asp Tyr Ala Ala Ile Ser Val Phe
145                 150                 155                 160

Thr Leu Thr Ala Ala Gln Ala Phe Tyr Phe Tyr Ser Arg Pro Ser Gly
                165                 170                 175

Lys Thr Leu Phe Ile Phe Asp Ser Pro His Leu Tyr Leu Gly Ile Ser
                180                 185                 190

Ala Phe Leu Ser Val Val Asn Val Ala Leu Ser Cys Leu Ser Arg His
                195                 200                 205

Tyr Leu Arg Asp Phe Arg Phe Leu Leu Arg Ala Gly Pro Asn Leu Ile
210                 215                 220

Lys Ile Leu Tyr Asp Thr Trp Pro Phe Val Ala Arg Ile Asn His Cys
225                 230                 235                 240

Thr Met Ala Thr Asp Cys Asn Ala Ile Ala Val Thr Leu Phe Tyr Arg
                245                 250                 255

His Trp Leu Cys Tyr Gly Ile Ser Gly Ile Thr Tyr Ala Ala Lys Ile
                260                 265                 270

Pro Glu Arg Trp Met Pro Gly Val Phe Asp Phe Phe Gly His Ser His
                275                 280                 285

His Phe Leu His Ile Val Thr Ile Phe Gly Asn Tyr Tyr Ala Phe Leu
                290                 295                 300

Ala Val Ser Leu Asp Met Thr Asn Arg Ala Glu Leu Leu Ser Lys Leu
305                 310                 315                 320

Pro Val Gln Pro Thr Val Phe Thr Thr Phe Gly Met Leu Leu Ile Val
                325                 330                 335

Leu Leu Ser Gly Gly Ile Ile Thr Trp Val Phe Ile Tyr Arg Phe Leu
                340                 345                 350

Gln Gln Asp Arg Gly Ala Asp Glu Tyr Val Gly Gly Thr Gln Tyr Thr
                355                 360                 365

Val Ile Tyr Arg Arg Lys Gly Asn Tyr Glu Lys Lys Thr Ser
                370                 375                 380

<210> SEQ ID NO 154
<211> LENGTH: 342
<212> TYPE: PRT
<213> ORGANISM: Nematostella vectensis

<400> SEQUENCE: 154

Met Ile Cys Asn Glu Lys Ser Thr Ala Ala Ile Gly Asn Asn Asn Leu
1                5                  10                  15

Ser Lys Leu Ser Ala Val Leu Gln Ser Pro Leu Glu Leu Val Phe Asp
                20                  25                  30

Cys Asp Ile Pro Glu Gly Phe Arg Thr Pro Phe Ile Lys Thr Gly Tyr
                35                  40                  45

```
Arg Lys Pro Gly Leu Thr Met Trp Gly Cys Phe Lys Ser Leu Ile Glu
         50                  55                  60

Pro Thr Asn Glu Thr Val Asn Val Trp Thr His Val Leu Ala Leu Val
 65                  70                  75                  80

Leu Phe Leu Leu Arg Phe Ser Asn Val Phe Ser Asn Ser Asp Phe Asp
                 85                  90                  95

Pro Trp Cys Tyr Gly Leu Val Cys Phe Ala Ile Gly Ile Ala Ser Leu
                100                 105                 110

Met Ala Met Ser Ser Ser Ala His Leu Ile Asn Cys Met Ser Leu Ser
                115                 120                 125

Ala His His Ile Gly Phe Tyr Leu Asp Tyr Ala Ala Ile Cys Val Tyr
            130                 135                 140

Ser Phe Ser Gly Ser Gln Ala Phe Phe Tyr Ser Arg Pro Ser Gln
145                 150                 155                 160

Thr Asp Phe Val Leu Leu Ser Ser Pro Thr Val Phe Leu Thr Val Ser
                165                 170                 175

Ala Ile Met Ser Cys Leu Cys Thr Ala Val Cys Cys Ala Ser Arg His
                180                 185                 190

Arg Trp Leu Arg Ser Lys Tyr Val Ile Arg Thr Ser Met Phe Met Leu
            195                 200                 205

Tyr Phe Ile Ile Val Thr Ser Pro Phe Thr Tyr Arg Leu Ala Tyr Ser
            210                 215                 220

Thr Ala Glu Ser Glu Thr Ser Arg Ala Val His Tyr Phe Asn Arg His
225                 230                 235                 240

Ile Ile Asn Tyr Ile Leu Ser Ala Phe Val Asn Val Thr Lys Leu Pro
                245                 250                 255

Glu Arg Tyr Phe Pro Arg Leu Asp Phe Leu Gly Gln Ser His His
                260                 265                 270

Phe Leu His Ile Leu Ala Ala Leu Gly Ala Ala Asp Ala Phe Thr Ala
            275                 280                 285

Thr Asn Leu Asp Met Lys Thr Arg Gln Asp Leu Leu Ala Gly Leu Pro
            290                 295                 300

Gly Pro Asn Leu Trp Asn Thr Phe Gly Val Phe Phe Thr Val Ala Phe
305                 310                 315                 320

Thr Asn Leu Phe Ile Val Tyr Leu Phe Ser Lys Ala Leu Leu Lys Gln
                325                 330                 335

Glu Lys Glu Lys Ser Asn
            340

<210> SEQ ID NO 155
<211> LENGTH: 315
<212> TYPE: PRT
<213> ORGANISM: Nematostella vectensis

<400> SEQUENCE: 155

Met Ser Leu Ser Ala Glu Glu Val Pro Leu Gln Phe Arg Glu Gln Phe
 1               5                  10                  15

Ile Ile Ser Gly Tyr Arg Arg Pro Tyr Ala Ser Ala Arg Asp Cys Ile
            20                  25                  30

Lys Ser Ala Phe Gly Pro Tyr Asn Glu Thr Leu Asn Phe Trp Thr His
                35                  40                  45

Phe Val Pro Phe Leu Leu Phe Ser Ala Arg Phe Val Trp Thr Phe His
 50                  55                  60

Arg Asp Gly Ile Asp Leu Tyr Arg Leu Pro Leu Val Ser Phe Ala Leu
```

```
                65                  70                  75                  80
Gly Ile Cys Gly Phe Leu Leu Met Ser Ser Cys Ala His Leu Phe Asn
                85                  90                  95

Ser Met Ser Pro Arg Ile Arg His Cys Cys Phe Phe Cys Asp Tyr Ser
            100                 105                 110

Ala Ile Ser Val Tyr Ser Val Gly Ala Gly Leu Ser Phe Tyr Phe Tyr
            115                 120                 125

Ser Arg Pro Ile Gly Val Gly Val Phe Pro Pro Lys Val Tyr Ile
            130                 135                 140

Thr Gly Ser Ile Leu Ile Ser Leu Leu Ser Thr Thr Leu Cys Cys Ala
145                 150                 155                 160

Ser Arg His Arg Trp Ala Asn Tyr Lys Tyr Ala Ile Arg Thr Gly Ser
                165                 170                 175

Phe Val Leu Ala Phe Leu Tyr Asn Cys Leu Pro His Tyr Arg Phe
                180                 185                 190

Ile Ile Glu Gly Ala Asp Lys Leu Asp Pro Val Ala Met Ser Tyr Phe
                195                 200                 205

Lys Arg His Thr Val Phe Tyr Leu Leu Ala Ala Val Ala Asn Thr Thr
                210                 215                 220

Arg Ile Pro Glu Arg Leu Ile Pro Gly Val Phe Asp Val Ile Gly His
225                 230                 235                 240

Ser His Asn Phe Leu His Ile Phe Thr Ala Leu Gly Val Ala Asp Gln
                245                 250                 255

Tyr Thr Ala Met Glu Leu Glu Met Ile His Arg Glu Pro Ile Leu Lys
                260                 265                 270

His Leu His Val Asp Val Tyr Ser Lys Ser Leu Asn Leu Met Ile Cys
                275                 280                 285

Ala Leu Leu Ala Asn Ile Gly Ile Val Val Leu Phe Gly Val Arg Leu
                290                 295                 300

Lys Ser Asn Lys Glu Glu Glu His Lys Ile Leu
305                 310                 315

<210> SEQ ID NO 156
<211> LENGTH: 301
<212> TYPE: PRT
<213> ORGANISM: Nematostella vectensis

<400> SEQUENCE: 156

Ile Pro Pro Glu Tyr Arg Asp Arg Tyr Ile Arg Ser Gly Tyr Arg Lys
1               5                   10                  15

Pro Gly Leu Thr Phe Leu Glu Cys Leu Gln Ser Leu Phe His Trp Asn
            20                  25                  30

Asn Glu Val Leu Asn Val Trp Thr His Tyr Ile Thr Leu Leu Phe Phe
            35                  40                  45

Thr Trp Lys Phe Cys Asn Leu Gly Arg Asp Leu Ser Gln Pro Glu Tyr
50                  55                  60

Tyr Pro Leu Leu Ala Tyr Ala Ile Gly Ala Cys Met Phe Pro Leu Leu
65                  70                  75                  80

Ser Cys Ile Ala His Thr Phe Ser Ser Met Ser Ile Ser Val Arg His
                85                  90                  95

Ile Cys Phe Phe Cys Asp Tyr Ala Gly Ile Ser Leu Tyr Ser Ile Gly
                100                 105                 110

Ser Ser Val Ala Tyr Phe Phe Tyr Thr Ile Pro Pro Asp Val Lys Ser
                115                 120                 125
```

```
Thr Trp Leu Gly Trp Ala Tyr Pro Pro Leu Asn Val Leu Met Ala Ala
        130                 135                 140

Ser Cys Cys Tyr Val Cys Cys Ile Ser Arg Ala Lys Gln Trp Ser Lys
145                 150                 155                 160

Tyr Gln Thr Val Met Arg Ala Cys Ser Phe Ala Val Pro Tyr Val Phe
                165                 170                 175

Cys Ser Ser Phe Ile Leu His Lys Leu Leu Ile Ser Arg Asn Ser Pro
                180                 185                 190

Ser Ser Ser Trp Phe His Cys Ser Gln Phe Phe Trp Cys Thr Leu Met
            195                 200                 205

Ala Ile Ala Met Thr Thr Lys Val Pro Glu Lys Tyr Phe Met Glu Tyr
        210                 215                 220

Phe Asp Ile Val Gly His Ser His Gln Trp Phe His Ile Phe Val Ser
225                 230                 235                 240

Val Gly Thr Asn Gln Gln Ile Asn Ala Val Leu Leu Asp Met Ile Asp
                245                 250                 255

Leu Glu Asn Thr Gly Gln Leu Pro Leu Val Ser Phe Leu Ser Ser Val
                260                 265                 270

Gly Leu Val Leu Leu Val Ala Leu Val Asp Thr Ala Ile Val Val Tyr
            275                 280                 285

Phe Ser Arg Lys Ile Leu Gln Lys Lys Ile Lys Pro Ser
290                 295                 300

<210> SEQ ID NO 157
<211> LENGTH: 356
<212> TYPE: PRT
<213> ORGANISM: Trichoplax adhaerens

<400> SEQUENCE: 157

Met Phe Asp Leu Lys Gln Asn Gly Asn Glu Asn Ile Thr Glu Thr Asn
1               5                   10                  15

Ala Lys Ala Ala Val Glu Ala Ser Leu Glu Lys Gly Asn Asn Asp Glu
                20                  25                  30

Ser Ser Lys Ile Pro Glu Val Arg Tyr Ser Thr Tyr Tyr Asn Gly Lys
            35                  40                  45

Lys Val Asn Val Tyr Arg Val Val Gln Pro Pro Asn Asp Trp Lys
50                  55                  60

Thr Leu Pro Phe Asn Lys Leu Pro Asp Trp Leu Gln Asp Asn Glu Phe
65                  70                  75                  80

Leu Val Lys Gly Tyr Arg Pro Gln Leu Pro Ser Val Ser Leu Cys Leu
                85                  90                  95

Arg Ser Ile Phe Arg Ile His Thr Glu Thr Gly Asn Ile Trp Thr His
                100                 105                 110

Leu Leu Gly Phe Ile Gly Leu Leu Ile Phe Ala Ile Tyr Cys Phe Ser
            115                 120                 125

Val Pro Leu Ser Gln Lys Thr Trp Gln Glu Gln Ala Val Phe Gly Ala
        130                 135                 140

Phe Phe Ala Gly Ala Ile Thr Cys Leu Leu Phe Ser Ser Phe Phe His
145                 150                 155                 160

Thr Ile Tyr Cys Tyr Ser Phe Arg Val Met Lys Ser Ser Ala Lys Leu
                165                 170                 175

Asp Tyr Leu Gly Ile Ala Thr Leu Val Val Gly Ser Asn Val Ser Leu
                180                 185                 190

Ile Tyr Tyr Ala Phe Tyr Cys Tyr Thr Ile Pro Leu Ile Ile Tyr Glu
            195                 200                 205
```

```
Thr Val Ala Ile Val Leu Gly Thr Ala Ala Ile Val Ser Leu Phe
    210                 215                 220

Asp Lys Phe Ser Glu Ser Lys Tyr Arg Thr Phe Arg Ala Ala Leu Phe
225                 230                 235                 240

Gly Gly Val Gly Gly Ser Gly Val Val Pro Leu Leu His Tyr Cys Gly
                245                 250                 255

Ile Thr Gly Phe Tyr Arg Ala Ile Glu Ile Gly Gly Ile Pro Trp Phe
                260                 265                 270

Leu Ala Ser Gly Leu Ser Tyr Leu Val Gly Val Thr Leu Tyr Ala Thr
                275                 280                 285

Arg Thr Pro Glu Arg Phe Phe Pro Gly Arg Cys Asp Ile Val Phe Gln
    290                 295                 300

Ser His Gln Leu Phe His Val Phe Val Val Gly Ala Ile Leu Thr
305                 310                 315                 320

Tyr Cys Ser Leu Asn Ser Tyr Ala Asp Tyr His Gln Leu Val Gly His
                325                 330                 335

Asn Cys Ser Val Val His Ser Ile Phe Lys Asn Gly Phe Val Thr Gln
                340                 345                 350

Leu Arg Arg Ser
        355
```

<210> SEQ ID NO 158
<211> LENGTH: 315
<212> TYPE: PRT
<213> ORGANISM: Trichoplax adhaerens

<400> SEQUENCE: 158

```
Met Thr Thr Phe Val Phe Arg Arg Ser Arg Ile Arg Ser Arg Phe Arg
1               5                   10                  15

Ser Ile Ser Gly Asp Gln Lys Lys Glu Cys His Gly Ser Ile Gln Leu
                20                  25                  30

Tyr Asn Ile Ser Gln Val Pro Pro Phe Leu Lys Phe Asn Pro His Ile
                35                  40                  45

Tyr Ser Gly Tyr Arg Val Asn Leu Ser Tyr Gln Ser Cys Leu Lys Ser
50                  55                  60

Leu Phe Val Leu Ser Asn Glu Ser Ile Asn Ile Trp Ser His Phe Leu
65                  70                  75                  80

Gly Phe Phe Ile Phe Val Tyr Leu Leu Val Phe Asp Asn Val Tyr Val
                85                  90                  95

Val Pro Trp Thr Leu Gln Ser Met Pro Asp Arg Ile Val Ile Ser Ser
                100                 105                 110

Ala Cys Leu Phe Tyr Met Ser Thr Leu Leu Leu Ser Thr Leu Tyr His
                115                 120                 125

Leu Phe His Cys His Ser Glu Arg Met Asn Gln Leu Trp Leu Lys Met
130                 135                 140

Asp Ile Gly Gly Ile Gly Ile Gly Ile Ile Gly Gly Phe Val Ser Gly
145                 150                 155                 160

Leu Tyr Val Ala Tyr Tyr Cys His Arg Tyr Trp Leu Leu Ile Tyr Val
                165                 170                 175

Ile Val Ser Thr Leu Leu Ile Ser Thr Ser Val Tyr Asn Leu Ala Cys
                180                 185                 190

Ser Asp Ala Lys Gly Ile Gln Phe Gln Ile Ser Asn Leu Asn Phe Arg
                195                 200                 205

Met Asn Arg Thr Val Val Phe Val Ile Ile Val Ala Phe Ser Leu Val
```

```
            210                 215                 220
Pro Ile Phe His Phe Ile Tyr Leu His Asp Gly Ile Ser Ser Thr Phe
225                 230                 235                 240

Val Arg Gln Phe Thr Ile Gly Ala Ser Tyr Met Leu Phe Tyr Gly Leu
                245                 250                 255

Met Gly Cys Leu Phe Leu Val Thr Lys Phe Pro Glu Arg Leu Phe Pro
            260                 265                 270

Gly Lys Phe Asp Tyr Val Ala Ser Ser His Gln Phe Trp His Leu Phe
        275                 280                 285

Val Phe Leu Leu Phe Tyr Ser Trp His Gln Ser Cys Leu Asp Ala Val
    290                 295                 300

Gln Tyr Arg Ile Lys Asn Gln Cys Glu Ile Ile
305                 310                 315

<210> SEQ ID NO 159
<211> LENGTH: 320
<212> TYPE: PRT
<213> ORGANISM: Trichoplax adhaerens

<400> SEQUENCE: 159

Met Ala Ala Gln Asn Gln Leu Leu Asp Ala Asp Gln Ile Pro Ala Ile
1               5                   10                  15

Phe Arg Asp Asp His Ile Ile Arg Gly Tyr Arg Lys Pro Gly Leu Thr
                20                  25                  30

Val Ile Gln Cys Ile Lys Ser Met Leu Gln Met Asn Asn Glu Thr Val
            35                  40                  45

Asn Phe Trp Thr His Met Ile Pro Phe Leu Tyr Phe Leu Ile Arg Phe
50                  55                  60

Tyr Thr Ile Asp Gln Gln Tyr Gln Leu Val Glu Asp Pro Phe Tyr Trp
65                  70                  75                  80

Pro Leu Leu Cys Tyr Ile Val Gly Ser Ser Tyr Pro Leu Phe Ser Cys
                85                  90                  95

Ile Ala His Ala Leu Asn Cys Met Ser Glu Ser Ala Arg His Ile Cys
            100                 105                 110

Phe Phe Leu Asp Tyr Ala Ser Ile Ser Leu Tyr Ser Phe Thr Cys Ala
        115                 120                 125

Ile Ala Tyr Phe Tyr Leu Arg Pro Val Thr Phe Phe Thr Met Asp
    130                 135                 140

Trp Tyr Ile Thr Leu Ser Ser Met Met Ala Ile Cys Cys Cys Leu Thr
145                 150                 155                 160

Ser Cys Ile Ser Arg Leu Tyr Ala His Thr Ser Arg Pro Tyr Ile Tyr
                165                 170                 175

Arg Thr Leu Ala Phe Ala Leu Gln Trp Val Tyr Val Asn Ser Met Leu
            180                 185                 190

Ala Tyr Arg Ile Phe Ser Cys His His Gln Cys Arg Leu Thr Ser
        195                 200                 205

Asp Tyr Tyr His Thr Met Gln Phe Val Met Ala Ile Leu Val Ala Ile
    210                 215                 220

Phe Met Thr Ser Lys Phe Pro Glu Cys Val Trp Pro Thr Ser Phe Asp
225                 230                 235                 240

Ile Cys Gly Gln Ser His His Trp Phe His Ile Phe Val Cys Val Gly
                245                 250                 255

His Arg Tyr Gln Leu Asp Gly Ile Leu Asn Asp Ile Gln Gln Arg Gln
            260                 265                 270
```

```
His Val Ile Arg Leu Ile Lys Pro Thr Phe Ser Ser Thr Leu Gly Val
            275                 280                 285

Leu Phe Val Ile Ala Cys Asn Ser Ile Ile Val Ile Tyr Phe Ser
    290                 295                 300

Tyr Leu Ile Ile Arg Arg Ser Asn Arg Ala Lys Gln Val Lys Ser Thr
305                 310                 315                 320

<210> SEQ ID NO 160
<211> LENGTH: 310
<212> TYPE: PRT
<213> ORGANISM: Trichoplax adhaerens

<400> SEQUENCE: 160

Lys Leu Leu Thr Ala Lys Gln Ile Pro Ser Phe Tyr Arg Glu Pro Tyr
1               5                   10                  15

Ile Leu Ser Gly Tyr Arg Pro Leu Phe Ser Asp Leu Ser Val Cys Phe
                20                  25                  30

Arg Ser Leu Phe Gln Arg Thr Asn Glu Thr Leu Asn Val Trp Thr His
            35                  40                  45

Leu Ile Pro Cys Leu Tyr Phe Ala Phe Asn Tyr Val Gln Phe Phe Leu
    50                  55                  60

Lys Asn Asp Ile Ser Asp Pro Tyr Val Arg Gly Ile Ile Thr Ala
65                  70                  75                  80

Ile Gly Ser Cys Gly Phe Leu Gly Phe Ser Ser Val Ala His Leu Phe
                85                  90                  95

Cys Cys Leu Ser Ala Asn Val Arg His Thr Cys Tyr Tyr Ile Asp Tyr
            100                 105                 110

Ala Gly Ile Cys Leu Tyr Ser Ile Cys Gly Gly Phe Ser Phe Leu Phe
    115                 120                 125

Tyr Ala Arg Pro Ala Leu Glu Ala Asp Ser Asp Trp Phe Tyr Arg His
            130                 135                 140

Arg Ile Leu Phe Leu Ser Ile Ser Val Val Ile Ser Asn Val Ile Cys
145                 150                 155                 160

Leu Leu Thr Cys Ile Ser Arg His Lys Trp Leu Arg Phe Arg Tyr Leu
                165                 170                 175

Ile Arg Thr Leu Ala Phe Thr Val Pro Tyr Phe Tyr Asn Ala Leu Pro
            180                 185                 190

Leu Phe Tyr Arg Ile Ser Ser Cys Pro Val Asp Ala Cys Asn Pro Glu
    195                 200                 205

Ala Leu Arg Tyr Tyr Leu Asn Trp Phe Trp Tyr Ala Met Ser Phe
            210                 215                 220

Val Ser Asn Ile Ala Arg Leu Pro Glu Arg Leu Ala Pro Gly Gln Phe
225                 230                 235                 240

Asp Ile Ile Gly His Ser His Gln Trp Leu His Ile Phe Leu Ala Phe
                245                 250                 255

Gly Asn Asp Ala Phe Ile Lys Gly Ile Met Ser Asp Phe Thr His Arg
            260                 265                 270

Arg Asn Gln Leu Leu Leu Thr Ser Lys Val Thr Asp Leu Ser Tyr Glu
    275                 280                 285

Phe Thr Ile Val Ile Val Gly Ile Leu Asn Leu Met Val Ile Ile Ala
            290                 295                 300

Val Tyr Asn Ala Leu Leu
305                 310

<210> SEQ ID NO 161
```

```
<211> LENGTH: 322
<212> TYPE: PRT
<213> ORGANISM: Trichoplax adhaerens

<400> SEQUENCE: 161

Met Thr Glu Met Arg Lys Ser Asn Ser Ile Ser Tyr Leu Pro Val His
1               5                   10                  15

Gln Met Pro Thr Gln Tyr Arg Glu Pro Tyr Ile Leu Thr Gly Tyr Arg
            20                  25                  30

Glu Pro Cys Ser Thr Cys Lys Ser Cys Leu Arg Ser Leu Ile Arg Ala
        35                  40                  45

Ser Asn Glu Thr Leu Asn Val Trp Thr His Phe Leu Pro Ile Ile Tyr
50                  55                  60

Phe Leu Asn Arg Ala Ile Gln Phe Tyr Ser Asn Asn Asp Ser Gly Cys
65                  70                  75                  80

Phe Glu Phe Gln Tyr Tyr Pro Phe Met Pro Asn Tyr Ile Gly Ile Ile
            85                  90                  95

Phe Tyr His Leu Ala Ser Ser Ile Ala His Leu Phe Cys Ser Met Ser
        100                 105                 110

Ile Lys Tyr Arg His Thr Cys Phe Tyr Ile Asp Tyr Ser Gly Ile Cys
    115                 120                 125

Ile Tyr Ala Met Gly Ala Gly Ile Thr Tyr Tyr Asn Leu Tyr Val Leu
130                 135                 140

Pro Asn Ala Pro Thr Asn Asn Tyr Pro Leu Ser Gln Ile Ala Phe Thr
145                 150                 155                 160

Ile Leu Ser Phe Gly Val Ser Leu Ser Val Cys Leu Val Ser Cys Ile
            165                 170                 175

Ser Arg His Tyr Trp Arg Ser Thr Gly Ala Val Ile Arg Thr Gly Ala
        180                 185                 190

Phe Ala Ile Asn Leu Ile Phe Asn Thr Ser Pro Ser Leu Trp Leu Phe
    195                 200                 205

Trp Gln Asn Gln Leu Pro Ser Ala Thr His Leu Val Arg Gln Trp Ser
210                 215                 220

Trp Tyr Val Ala Ala Ile Thr Ala Tyr Val Phe Lys Ile Pro Glu Lys
225                 230                 235                 240

Phe Ala Pro Gly Lys Phe Asp Val Ile Gly His Ser His Gln Trp Phe
            245                 250                 255

His Val Phe Leu Ser Leu Gly Thr Val Glu Gln Ile Asn Ser Leu Glu
        260                 265                 270

Phe Asp Val Asn Ala Cys Arg Pro Lys Tyr Met Pro Ser Asp Ala Pro
    275                 280                 285

Ser Phe Phe Ile Thr Ile Gly Ser Met Met Leu Ala Ile Leu Leu Asn
290                 295                 300

Ala Leu Ile Val Ser Ile Cys Ser Tyr Lys Leu Ala Arg His Ala Lys
305                 310                 315                 320

Met Asp

<210> SEQ ID NO 162
<211> LENGTH: 207
<212> TYPE: PRT
<213> ORGANISM: Trichoplax adhaerens

<400> SEQUENCE: 162

Met Gly Pro Thr Val Thr Val Lys Arg Leu Arg Phe Met Asn Ala Pro
1               5                   10                  15
```

Val Thr Gly Cys Gln Cys His Tyr Gln Ala Thr Thr Ile Glu Gln Thr
            20                  25                  30

Ala Asn Ile Leu Thr His Gly Val Trp Ile Ile Pro Ala Ile Tyr Ala
        35                  40                  45

Leu Leu Lys Met Leu Thr Leu Ser Thr Thr Gln Asn Gln Tyr Trp Ile
50                  55                  60

Ala Trp Cys Met Ile Ser Arg Phe Leu His Phe Trp Asp Arg Ser Thr
65                  70                  75                  80

Ile Phe Thr Phe Ile Ala Ser Cys Phe Met Pro Trp Phe Val Leu Thr
                85                  90                  95

Glu Thr Leu Ser Asn Thr Tyr Val Met Lys Trp Leu Val Cys Ile Trp
            100                 105                 110

Leu Met Ala Met Leu Gly Ile Thr Phe Thr Tyr Leu Phe Leu Asp Arg
        115                 120                 125

Tyr Lys Leu Leu Glu Thr Leu Leu Tyr Val Ile Leu Gly Val Val Pro
130                 135                 140

Ser Ile Pro Ile Leu Tyr Ala Asn Gln Asn Ser Gly Ala Trp Glu Leu
145                 150                 155                 160

Thr Ala Gly Gly Gly Ile Tyr Val Met Gly Ile Leu Phe Phe Lys Cys
                165                 170                 175

Asp Gly Arg Ile Pro Phe Ala His Ala Ile Trp His Thr Phe Val Ala
            180                 185                 190

Cys Gly Ala Leu Ile His Tyr Ser Ala Val Ile Arg Tyr Lys Tyr
        195                 200                 205

<210> SEQ ID NO 163
<211> LENGTH: 431
<212> TYPE: PRT
<213> ORGANISM: Saccharomyces cerevisiae
<220> FEATURE:
<221> NAME/KEY: MISC_FEATURE
<223> OTHER INFORMATION: alpha-factor receptor

<400> SEQUENCE: 163

Met Ser Asp Ala Ala Pro Ser Leu Ser Asn Leu Phe Tyr Asp Pro Thr
1               5                   10                  15

Tyr Asn Pro Gly Gln Ser Thr Ile Asn Tyr Thr Ser Ile Tyr Gly Asn
            20                  25                  30

Gly Ser Thr Ile Thr Phe Asp Glu Leu Gln Gly Leu Val Asn Ser Thr
        35                  40                  45

Val Thr Gln Ala Ile Met Phe Gly Val Arg Cys Gly Ala Ala Ala Leu
50                  55                  60

Thr Leu Ile Val Met Trp Met Thr Ser Arg Ser Arg Lys Thr Pro Ile
65                  70                  75                  80

Phe Ile Ile Asn Gln Val Ser Leu Phe Leu Ile Ile Leu His Ser Ala
                85                  90                  95

Leu Tyr Phe Lys Tyr Leu Leu Ser Asn Tyr Ser Ser Val Thr Tyr Ala
            100                 105                 110

Leu Thr Gly Phe Pro Gln Phe Ile Ser Arg Gly Asp Val His Val Tyr
        115                 120                 125

Gly Ala Thr Asn Ile Ile Gln Val Leu Leu Val Ala Ser Ile Glu Thr
130                 135                 140

Ser Leu Val Phe Gln Ile Lys Val Ile Phe Thr Gly Asp Asn Phe Lys
145                 150                 155                 160

Arg Ile Gly Leu Met Leu Thr Ser Ile Ser Phe Thr Leu Gly Ile Ala
                165                 170                 175

```
Thr Val Thr Met Tyr Phe Val Ser Ala Val Lys Gly Met Ile Val Thr
            180                 185                 190

Tyr Asn Asp Val Ser Ala Thr Gln Asp Lys Tyr Phe Asn Ala Ser Thr
            195                 200                 205

Ile Leu Leu Ala Ser Ser Ile Asn Phe Met Ser Phe Val Leu Val Val
210                 215                 220

Lys Leu Ile Leu Ala Ile Arg Ser Arg Arg Phe Leu Gly Leu Lys Gln
225                 230                 235                 240

Phe Asp Ser Phe His Ile Leu Leu Ile Met Ser Cys Gln Ser Leu Leu
            245                 250                 255

Val Pro Ser Ile Ile Phe Ile Leu Ala Tyr Ser Leu Lys Pro Asn Gln
            260                 265                 270

Gly Thr Asp Val Leu Thr Thr Val Ala Thr Leu Leu Ala Val Leu Ser
            275                 280                 285

Leu Pro Leu Ser Ser Met Trp Ala Thr Ala Ala Asn Asn Ala Ser Lys
            290                 295                 300

Thr Asn Thr Ile Thr Ser Asp Phe Thr Ser Thr Asp Arg Phe Tyr
305                 310                 315                 320

Pro Gly Thr Leu Ser Ser Phe Gln Thr Asp Ser Ile Asn Asn Asp Ala
            325                 330                 335

Lys Ser Ser Leu Arg Ser Arg Leu Tyr Asp Leu Tyr Pro Arg Arg Lys
            340                 345                 350

Glu Thr Thr Ser Asp Lys His Ser Glu Arg Thr Phe Val Ser Glu Thr
            355                 360                 365

Ala Asp Asp Ile Glu Lys Asn Gln Phe Tyr Gln Leu Pro Thr Pro Thr
            370                 375                 380

Ser Ser Lys Asn Thr Arg Ile Gly Pro Phe Ala Asp Ala Ser Tyr Lys
385                 390                 395                 400

Glu Gly Glu Val Glu Pro Val Asp Met Tyr Thr Pro Asp Thr Ala Ala
            405                 410                 415

Asp Glu Glu Ala Arg Lys Phe Trp Thr Glu Asp Asn Asn Leu
            420                 425                 430

<210> SEQ ID NO 164
<211> LENGTH: 382
<212> TYPE: PRT
<213> ORGANISM: Homo sapiens
<220> FEATURE:
<221> NAME/KEY: MISC_FEATURE
<223> OTHER INFORMATION: sphingosine-1-phosphate receptor

<400> SEQUENCE: 164

Met Gly Pro Thr Ser Val Pro Leu Val Lys Ala His Arg Ser Ser Val
1               5                   10                  15

Ser Asp Tyr Val Asn Tyr Asp Ile Ile Val Arg His Tyr Asn Tyr Thr
            20                  25                  30

Gly Lys Leu Asn Ile Ser Ala Asp Lys Glu Asn Ser Ile Lys Leu Thr
            35                  40                  45

Ser Val Val Phe Ile Leu Ile Cys Cys Phe Ile Ile Leu Glu Asn Ile
            50                  55                  60

Phe Val Leu Leu Thr Ile Trp Lys Thr Lys Lys Phe His Arg Pro Met
65                  70                  75                  80

Tyr Tyr Phe Ile Gly Asn Leu Ala Leu Ser Asp Leu Leu Ala Gly Val
            85                  90                  95

Ala Tyr Thr Ala Asn Leu Leu Leu Ser Gly Ala Thr Thr Tyr Lys Leu
```

```
            100                 105                 110
Thr Pro Ala Gln Trp Phe Leu Arg Glu Gly Ser Met Phe Val Ala Leu
        115                 120                 125

Ser Ala Ser Val Phe Ser Leu Leu Ala Ile Ala Ile Glu Arg Tyr Ile
    130                 135                 140

Thr Met Leu Lys Met Lys Leu His Asn Gly Ser Asn Asn Phe Arg Leu
145                 150                 155                 160

Phe Leu Leu Ile Ser Ala Cys Trp Val Ile Ser Leu Ile Leu Gly Gly
                165                 170                 175

Leu Pro Ile Met Gly Trp Asn Cys Ile Ser Ala Leu Ser Ser Cys Ser
            180                 185                 190

Thr Val Leu Pro Leu Tyr His Lys His Tyr Ile Leu Phe Cys Thr Thr
        195                 200                 205

Val Phe Thr Leu Leu Leu Ser Ile Val Ile Leu Tyr Cys Arg Ile
    210                 215                 220

Tyr Ser Leu Val Arg Thr Arg Ser Arg Arg Leu Thr Phe Arg Lys Asn
225                 230                 235                 240

Ile Ser Lys Ala Ser Arg Ser Ser Glu Lys Ser Leu Ala Leu Leu Lys
                245                 250                 255

Thr Val Ile Ile Val Leu Ser Val Phe Ile Ala Cys Trp Ala Pro Leu
            260                 265                 270

Phe Ile Leu Leu Leu Leu Asp Val Gly Cys Lys Val Lys Thr Cys Asp
        275                 280                 285

Ile Leu Phe Arg Ala Glu Tyr Phe Leu Val Leu Ala Val Leu Asn Ser
    290                 295                 300

Gly Thr Asn Pro Ile Ile Tyr Thr Leu Thr Asn Lys Glu Met Arg Arg
305                 310                 315                 320

Ala Phe Ile Arg Ile Met Ser Cys Cys Lys Cys Pro Ser Gly Asp Ser
                325                 330                 335

Ala Gly Lys Phe Lys Arg Pro Ile Ile Ala Gly Met Glu Phe Ser Arg
            340                 345                 350

Ser Lys Ser Asp Asn Ser Ser His Pro Gln Lys Asp Glu Gly Asp Asn
        355                 360                 365

Pro Glu Thr Ile Met Ser Ser Gly Asn Val Asn Ser Ser
    370                 375                 380

<210> SEQ ID NO 165
<211> LENGTH: 593
<212> TYPE: PRT
<213> ORGANISM: Homo sapiens
<220> FEATURE:
<221> NAME/KEY: MISC_FEATURE
<223> OTHER INFORMATION: parathyroid hormone receptor

<400> SEQUENCE: 165

Met Gly Thr Ala Arg Ile Ala Pro Gly Leu Ala Leu Leu Leu Cys Cys
1               5                   10                  15

Pro Val Leu Ser Ser Ala Tyr Ala Leu Val Asp Ala Asp Asp Val Met
            20                  25                  30

Thr Lys Glu Glu Gln Ile Phe Leu Leu His Arg Ala Gln Ala Gln Cys
        35                  40                  45

Glu Lys Arg Leu Lys Glu Val Leu Gln Arg Pro Ala Ser Ile Met Glu
    50                  55                  60

Ser Asp Lys Gly Trp Thr Ser Ala Ser Thr Ser Gly Lys Pro Arg Lys
65                  70                  75                  80
```

```
Asp Lys Ala Ser Gly Lys Leu Tyr Pro Glu Ser Glu Asp Lys Glu
             85                  90                  95
Ala Pro Thr Gly Ser Arg Tyr Arg Gly Arg Pro Cys Leu Pro Glu Trp
            100                 105                 110
Asp His Ile Leu Cys Trp Pro Leu Gly Ala Pro Gly Glu Val Val Ala
            115                 120                 125
Val Pro Cys Pro Asp Tyr Ile Tyr Asp Phe Asn His Lys Gly His Ala
130                 135                 140
Tyr Arg Arg Cys Asp Arg Asn Gly Ser Trp Glu Leu Val Pro Gly His
145                 150                 155                 160
Asn Arg Thr Trp Ala Asn Tyr Ser Glu Cys Val Lys Phe Leu Thr Asn
            165                 170                 175
Glu Thr Arg Glu Arg Glu Val Phe Asp Arg Leu Gly Met Ile Tyr Thr
            180                 185                 190
Val Gly Tyr Ser Val Ser Leu Ala Ser Leu Thr Val Ala Val Leu Ile
            195                 200                 205
Leu Ala Tyr Phe Arg Arg Leu His Cys Thr Arg Asn Tyr Ile His Met
210                 215                 220
His Leu Phe Leu Ser Phe Met Leu Arg Ala Val Ser Ile Phe Val Lys
225                 230                 235                 240
Asp Ala Val Leu Tyr Ser Gly Ala Thr Leu Asp Glu Ala Glu Arg Leu
            245                 250                 255
Thr Glu Glu Glu Leu Arg Ala Ile Ala Gln Ala Pro Pro Pro Pro Ala
            260                 265                 270
Thr Ala Ala Ala Gly Tyr Ala Gly Cys Arg Val Ala Val Thr Phe Phe
            275                 280                 285
Leu Tyr Phe Leu Ala Thr Asn Tyr Tyr Trp Ile Leu Val Glu Gly Leu
            290                 295                 300
Tyr Leu His Ser Leu Ile Phe Met Ala Phe Phe Ser Glu Lys Lys Tyr
305                 310                 315                 320
Leu Trp Gly Phe Thr Val Phe Gly Trp Gly Leu Pro Ala Val Phe Val
            325                 330                 335
Ala Val Trp Val Ser Val Arg Ala Thr Leu Ala Asn Thr Gly Cys Trp
            340                 345                 350
Asp Leu Ser Ser Gly Asn Lys Lys Trp Ile Ile Gln Val Pro Ile Leu
            355                 360                 365
Ala Ser Ile Val Leu Asn Phe Ile Leu Phe Ile Asn Ile Val Arg Val
            370                 375                 380
Leu Ala Thr Lys Leu Arg Glu Thr Asn Ala Gly Arg Cys Asp Thr Arg
385                 390                 395                 400
Gln Gln Tyr Arg Lys Leu Leu Lys Ser Thr Leu Val Leu Met Pro Leu
            405                 410                 415
Phe Gly Val His Tyr Ile Val Phe Met Ala Thr Pro Tyr Thr Glu Val
            420                 425                 430
Ser Gly Thr Leu Trp Gln Val Gln Met His Tyr Glu Met Leu Phe Asn
            435                 440                 445
Ser Phe Gln Gly Phe Phe Val Ala Ile Ile Tyr Cys Phe Cys Asn Gly
            450                 455                 460
Glu Val Gln Ala Glu Ile Lys Lys Ser Trp Ser Arg Trp Thr Leu Ala
465                 470                 475                 480
Leu Asp Phe Lys Arg Lys Ala Arg Ser Gly Ser Ser Ser Tyr Ser Tyr
            485                 490                 495
Gly Pro Met Val Ser His Thr Ser Val Thr Asn Val Gly Pro Arg Val
```

```
                    500                 505                 510
Gly Leu Gly Leu Pro Leu Ser Pro Arg Leu Leu Pro Thr Ala Thr
            515                 520                 525

Asn Gly His Pro Gln Leu Pro Gly His Ala Lys Pro Gly Thr Pro Ala
            530                 535                 540

Leu Glu Thr Leu Glu Thr Thr Pro Pro Ala Met Ala Ala Pro Lys Asp
545                 550                 555                 560

Asp Gly Phe Leu Asn Gly Ser Cys Ser Gly Leu Asp Glu Glu Ala Ser
                565                 570                 575

Gly Pro Glu Arg Pro Pro Ala Leu Leu Gln Glu Glu Trp Glu Thr Val
            580                 585                 590

Met

<210> SEQ ID NO 166
<211> LENGTH: 348
<212> TYPE: PRT
<213> ORGANISM: Homo sapiens

<400> SEQUENCE: 166

Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
            20                  25                  30

Glu Pro Trp Gln Phe Ser Met Leu Ala Ala Tyr Met Phe Leu Leu Ile
        35                  40                  45

Val Leu Gly Phe Pro Ile Asn Phe Leu Thr Leu Tyr Val Thr Val Gln
    50                  55                  60

His Lys Lys Leu Arg Thr Pro Leu Asn Tyr Ile Leu Leu Asn Leu Ala
65                  70                  75                  80

Val Ala Asp Leu Phe Met Val Leu Gly Gly Phe Thr Ser Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Val Cys Lys Pro Met Ser
    130                 135                 140

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Ala Gly Trp Ser
                165                 170                 175

Arg Tyr Ile Pro Glu Gly Leu Gln Cys Ser Cys Gly Ile Asp Tyr Tyr
            180                 185                 190

Thr Leu Lys Pro Glu Val Asn Asn Glu Ser Phe Val Ile Tyr Met Phe
        195                 200                 205

Val Val His Phe Thr Ile Pro Met Ile Ile Ile Phe Phe Cys Tyr Gly
    210                 215                 220

Gln Leu Val Phe Thr Val Lys Glu Ala Ala Ala Gln Gln Glu Ser
225                 230                 235                 240

Ala Thr Thr Gln Lys Ala Glu Lys Glu Val Thr Arg Met Val Ile Ile
                245                 250                 255

Met Val Ile Ala Phe Leu Ile Cys Trp Val Pro Tyr Ala Ser Val Ala
            260                 265                 270

Phe Tyr Ile Phe Thr His Gln Gly Ser Asn Phe Gly Pro Ile Phe Met
```

|   |   |   | 275 |   |   |   | 280 |   |   |   | 285 |
|---|---|---|---|---|---|---|---|---|---|---|---|

Thr Ile Pro Ala Phe Phe Ala Lys Ser Ala Ala Ile Tyr Asn Pro Val
            290                 295                 300

Ile Tyr Ile Met Met Asn Lys Gln Phe Arg Asn Cys Met Leu Thr Thr
305                 310                 315                 320

Ile Cys Cys Gly Lys Asn Pro Leu Gly Asp Asp Glu Ala Ser Ala Thr
                325                 330                 335

Val Ser Lys Thr Glu Thr Ser Gln Val Ala Pro Ala
                340                 345

<210> SEQ ID NO 167
<211> LENGTH: 375
<212> TYPE: PRT
<213> ORGANISM: Homo sapiens
<220> FEATURE:
<221> NAME/KEY: MISC_FEATURE
<223> OTHER INFORMATION: estrogen receptor

<400> SEQUENCE: 167

Met Asp Val Thr Ser Gln Ala Arg Gly Val Gly Leu Glu Met Tyr Pro
1               5                   10                  15

Gly Thr Ala Gln Pro Ala Ala Pro Asn Thr Thr Ser Pro Glu Leu Asn
            20                  25                  30

Leu Ser His Pro Leu Leu Gly Thr Ala Leu Ala Asn Gly Thr Gly Glu
        35                  40                  45

Leu Ser Glu His Gln Gln Tyr Val Ile Gly Leu Phe Leu Ser Cys Leu
    50                  55                  60

Tyr Thr Ile Phe Leu Phe Pro Ile Gly Phe Val Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Val Ala Asp Leu Ile Leu Val Ala Asp Ser
            100                 105                 110

Leu Ile Glu Val Phe Asn Leu His Glu Arg Tyr Tyr Asp Ile Ala Val
        115                 120                 125

Leu Cys Thr Phe Met Ser Leu Phe Leu Gln Val Asn Met Tyr Ser Ser
    130                 135                 140

Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Gln His Thr Asp Glu Ala Cys Phe Cys Phe
        195                 200                 205

Ala Asp Val Arg Glu Val Gln Trp Leu Glu Val Thr Leu Gly Phe Ile
    210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
                245                 250                 255

Ala Leu Arg Met Ile Leu Ala Val Val Leu Val Phe Phe Val Cys Trp
            260                 265                 270

Leu Pro Glu Asn Val Phe Ile Ser Val His Leu Leu Gln Arg Thr Gln
        275                 280                 285

```
Pro Gly Ala Ala Pro Cys Lys Gln Ser Phe Arg His Ala His Pro Leu
    290                 295                 300
Thr Gly His Ile Val Asn Leu Ala Ala Phe Ser Asn Ser Cys Leu Asn
305                 310                 315                 320
Pro Leu Ile Tyr Ser Phe Leu Gly Glu Thr Phe Arg Asp Lys Leu Arg
                325                 330                 335
Leu Tyr Ile Glu Gln Lys Thr Asn Leu Pro Ala Leu Asn Arg Phe Cys
                340                 345                 350
His Ala Ala Leu Lys Ala Val Ile Pro Asp Ser Thr Glu Gln Ser Asp
                355                 360                 365
Val Arg Phe Ser Ser Ala Val
                370                 375

<210> SEQ ID NO 168
<211> LENGTH: 264
<212> TYPE: PRT
<213> ORGANISM: Homo sapiens

<400> SEQUENCE: 168

Met Pro Ser Ile Phe Ala Tyr Gln Ser Ser Glu Val Asp Trp Cys Glu
1               5                   10                  15
Ser Asn Phe Gln Tyr Ser Glu Leu Val Ala Glu Phe Tyr Asn Thr Phe
                20                  25                  30
Ser Asn Ile Pro Phe Phe Ile Phe Gly Pro Leu Met Met Leu Leu Met
                35                  40                  45
His Pro Tyr Ala Gln Lys Arg Ser Arg Tyr Ile Tyr Val Val Trp Val
            50                  55                  60
Leu Phe Met Ile Ile Gly Leu Phe Ser Met Tyr Phe His Met Thr Leu
65                  70                  75                  80
Ser Phe Leu Gly Gln Leu Leu Asp Glu Ile Ala Ile Leu Trp Leu Leu
                85                  90                  95
Gly Ser Gly Tyr Ser Ile Trp Met Pro Arg Cys Tyr Phe Pro Ser Phe
                100                 105                 110
Leu Gly Gly Asn Arg Ser Gln Phe Ile Arg Leu Val Phe Ile Thr Thr
            115                 120                 125
Val Val Ser Thr Leu Leu Ser Phe Leu Arg Pro Thr Val Asn Ala Tyr
    130                 135                 140
Ala Leu Asn Ser Ile Ala Leu His Ile Leu Tyr Ile Val Cys Gln Glu
145                 150                 155                 160
Tyr Arg Lys Thr Ser Asn Lys Glu Leu Arg His Leu Ile Glu Val Ser
                165                 170                 175
Val Val Leu Trp Ala Val Ala Leu Thr Ser Trp Ile Ser Asp Arg Leu
                180                 185                 190
Leu Cys Ser Phe Trp Gln Arg Ile His Phe Phe Tyr Leu His Ser Ile
            195                 200                 205
Trp His Val Leu Ile Ser Ile Thr Phe Pro Tyr Gly Met Val Thr Met
    210                 215                 220
Ala Leu Val Asp Ala Asn Tyr Glu Met Pro Gly Glu Thr Leu Lys Val
225                 230                 235                 240
Arg Tyr Trp Pro Arg Asp Ser Trp Pro Val Gly Leu Pro Tyr Val Glu
                245                 250                 255
Ile Arg Gly Asp Asp Lys Asp Cys
                260

<210> SEQ ID NO 169
```

```
<211> LENGTH: 275
<212> TYPE: PRT
<213> ORGANISM: Homo sapiens

<400> SEQUENCE: 169

Met Gly Ala Pro His Trp Trp Asp Gln Leu Gln Ala Gly Ser Ser Glu
1               5                   10                  15

Val Asp Trp Cys Glu Asp Asn Tyr Thr Ile Val Pro Ala Ile Ala Glu
            20                  25                  30

Phe Tyr Asn Thr Ile Ser Asn Val Leu Phe Phe Ile Leu Pro Pro Ile
        35                  40                  45

Cys Met Cys Leu Phe Arg Gln Tyr Ala Thr Cys Phe Asn Ser Gly Ile
    50                  55                  60

Tyr Leu Ile Trp Thr Leu Leu Val Val Gly Ile Gly Ser Val Tyr
65                  70                  75                  80

Phe His Ala Thr Leu Ser Phe Leu Gly Gln Met Leu Asp Glu Leu Ala
                85                  90                  95

Val Leu Trp Val Leu Met Cys Ala Leu Ala Met Trp Phe Pro Arg Arg
            100                 105                 110

Tyr Leu Pro Lys Ile Phe Arg Asn Asp Arg Gly Arg Phe Lys Val Val
        115                 120                 125

Val Ser Val Leu Ser Ala Val Thr Thr Cys Leu Ala Phe Val Lys Pro
    130                 135                 140

Ala Ile Asn Asn Ile Ser Leu Met Thr Leu Gly Val Pro Cys Thr Ala
145                 150                 155                 160

Leu Leu Ile Ala Glu Leu Lys Arg Cys Asp Asn Met Arg Val Phe Lys
                165                 170                 175

Leu Gly Leu Phe Ser Gly Leu Trp Trp Thr Leu Ala Leu Phe Cys Trp
            180                 185                 190

Ile Ser Asp Arg Ala Phe Cys Glu Leu Leu Ser Ser Phe Asn Phe Pro
        195                 200                 205

Tyr Leu His Cys Met Trp His Ile Leu Ile Cys Leu Ala Ala Tyr Leu
    210                 215                 220

Gly Cys Val Cys Phe Ala Tyr Phe Asp Ala Ala Ser Glu Ile Pro Glu
225                 230                 235                 240

Gln Gly Pro Val Ile Lys Phe Trp Pro Ser Glu Lys Trp Ala Phe Ile
                245                 250                 255

Gly Val Pro Tyr Val Ser Leu Leu Cys Ala Asn Lys Lys Ser Ser Val
            260                 265                 270

Lys Thr Thr
        275

<210> SEQ ID NO 170
<211> LENGTH: 251
<212> TYPE: PRT
<213> ORGANISM: Homo sapiens

<400> SEQUENCE: 170

Met Ala Pro Ala Val Asp Arg Lys Gly Tyr Trp Gly Pro Thr Thr Ser
1               5                   10                  15

Thr Leu Asp Trp Cys Glu Glu Asn Tyr Ser Val Thr Tyr Ile Ala
            20                  25                  30

Glu Phe Trp Asn Thr Val Ser Asn Leu Ile Met Ile Pro Pro Met
        35                  40                  45

Phe Gly Ala Ile Gln Ser Val Arg Asp Gly Leu Glu Lys Arg Tyr Ile
    50                  55                  60
```

```
Ala Ser Tyr Leu Ala Leu Thr Val Val Gly Met Gly Ser Trp Cys Phe
 65                  70                  75                  80

His Met Thr Leu Lys Tyr Glu Met Gln Leu Leu Asp Glu Leu Pro Met
                 85                  90                  95

Ile Tyr Ser Cys Cys Ile Phe Val Tyr Cys Met Phe Glu Cys Phe Lys
            100                 105                 110

Ile Lys Asn Ser Val Asn Tyr His Leu Leu Phe Thr Leu Val Leu Phe
            115                 120                 125

Ser Leu Ile Val Thr Thr Val Tyr Leu Lys Val Lys Glu Pro Ile Phe
130                 135                 140

His Gln Val Met Tyr Gly Met Leu Val Phe Thr Leu Val Leu Arg Ser
145                 150                 155                 160

Ile Tyr Ile Val Thr Trp Val Tyr Pro Trp Leu Arg Gly Leu Gly Tyr
                165                 170                 175

Thr Ser Leu Gly Ile Phe Leu Leu Gly Phe Leu Phe Trp Asn Ile Asp
            180                 185                 190

Asn Ile Phe Cys Glu Ser Leu Arg Asn Phe Arg Lys Lys Val Pro Pro
            195                 200                 205

Ile Ile Gly Ile Thr Thr Gln Phe His Ala Trp His Ile Leu Thr
210                 215                 220

Gly Leu Gly Ser Tyr Leu His Ile Leu Phe Ser Leu Tyr Thr Arg Thr
225                 230                 235                 240

Leu Tyr Leu Arg Tyr Arg Pro Lys Val Lys Phe
                245                 250

<210> SEQ ID NO 171
<211> LENGTH: 275
<212> TYPE: PRT
<213> ORGANISM: Saccharomyces cerevisiae

<400> SEQUENCE: 171

Met Leu Phe Ser Trp Pro Tyr Pro Glu Ala Pro Ile Glu Gly Tyr Trp
 1               5                  10                  15

Gly Lys Pro Thr Ser Leu Ile Asp Trp Cys Glu Glu Asn Tyr Val Val
                 20                  25                  30

Ser Pro Tyr Ile Ala Glu Trp Ser Asn Thr Ile Thr Asn Ser Ile Phe
             35                  40                  45

Leu Met Thr Ala Phe Tyr Ser Thr Ser Ala Trp Arg Asn Lys Leu
 50                  55                  60

Glu Thr Arg Tyr Ile Leu Ile Gly Met Gly Phe Ser Leu Val Gly Ile
 65                  70                  75                  80

Gly Ser Trp Leu Phe His Met Thr Leu Gln Tyr Arg Tyr Gln Leu Leu
                 85                  90                  95

Asp Glu Leu Pro Met Leu Tyr Ala Thr Ile Ile Pro Ser Trp Ser Ile
                100                 105                 110

Phe Ala Glu Thr Gln Gly Ile Leu Ile Lys Asp Glu Lys Lys Arg Lys
            115                 120                 125

Glu Ser Ser Phe Arg Ile Gln Met Val Ile Ser Phe Ile Met Cys Gly
130                 135                 140

Ile Val Thr Ile Leu Thr Trp Ile Tyr Val Val Val Gln Lys Pro Ala
145                 150                 155                 160

Ile Phe Gln Val Leu Tyr Gly Ile Leu Thr Leu Leu Val Val Leu
                165                 170                 175

Ser Gly Trp Leu Thr Tyr Tyr His Val His Asp Ser Phe Ala Lys Lys
```

```
            180                 185                 190
Asn Leu Phe Ile Thr Met Val Met Gly Met Ile Pro Phe Val Ile Gly
            195                 200                 205

Phe Ile Cys Trp Gln Leu Asp Ile His Leu Cys Ser Phe Trp Ile Tyr
            210                 215                 220

Ile Arg Arg Thr Tyr Leu Ala Leu Pro Leu Gly Val Leu Leu Glu Leu
225                 230                 235                 240

His Ala Trp Trp His Leu Leu Thr Gly Thr Gly Val Tyr Ile Phe Val
                245                 250                 255

Val Tyr Leu Gln Tyr Leu Arg Ile Leu Thr His Gly Asn Pro Asn Asp
            260                 265                 270

Phe Leu Phe
        275

<210> SEQ ID NO 172
<211> LENGTH: 275
<212> TYPE: PRT
<213> ORGANISM: Saccharomyces cerevisiae

<400> SEQUENCE: 172

Met Gly Ile Phe Arg Trp Asn Tyr Pro Glu Ser Ser Val Pro Gly Val
1               5                   10                  15

Trp Gly Glu Thr Thr Ser Thr Ile Asp Trp Cys Glu Glu Asn Tyr Val
            20                  25                  30

Val Ser Pro Tyr Ile Ala Glu Trp Ser Asn Thr Leu Thr Asn Ser Val
        35                  40                  45

Phe Ile Leu Ser Ala Ile Tyr Thr Thr Tyr Ser Ala Tyr Lys Asn Lys
    50                  55                  60

Leu Glu Lys Arg Phe Leu Leu Ile Gly Phe Gly Tyr Gly Leu Val Gly
65                  70                  75                  80

Val Gly Ser Trp Leu Phe His Met Thr Leu Lys Tyr Arg Phe Gln Leu
                85                  90                  95

Leu Asp Glu Leu Pro Met Ile Tyr Ala Met Cys Ile Pro Thr Trp Ser
            100                 105                 110

Leu Val Cys Glu Ala Lys Glu Ala Leu Leu Asn Gly Asp Asn His Lys
        115                 120                 125

Lys Val Pro Leu Phe Glu Gln Ile Phe Ile Gly Val Ile Gly Leu
    130                 135                 140

Ala Val Thr Thr Ala Ser Ile Leu Tyr Val Ile Tyr Lys Asn Val Asp
145                 150                 155                 160

Ile His Gln Ile Leu Phe Gly Val Gln Ile Val Val Ala Ala Thr
                165                 170                 175

Ala Gly Ser Leu Thr Tyr Arg Tyr Val His Asp Pro Leu Ala Lys Arg
            180                 185                 190

Asn Leu Lys Ala Ser Met Ala Leu Gly Ala Ile Leu Phe Leu Ser Gly
            195                 200                 205

Tyr Ile Ser Trp Leu Leu Asp Ile His Tyr Cys Ser Phe Trp Val His
            210                 215                 220

Val Arg Arg Ser Ile Leu Ala Leu Pro Leu Gly Val Leu Leu Glu Pro
225                 230                 235                 240

His Gly Trp Trp His Ile Leu Thr Gly Met Gly Ile Tyr Phe Tyr Ile
                245                 250                 255

Val Ser Leu Glu His Leu Arg Val Ile Thr Leu Asn Val Ser Cys Asn
            260                 265                 270
```

Tyr Gln Phe
    275

<210> SEQ ID NO 173
<211> LENGTH: 60
<212> TYPE: DNA
<213> ORGANISM: Artificial Sequence
<220> FEATURE:
<223> OTHER INFORMATION: Primer

<400> SEQUENCE: 173
tttcccagtc acgacgttgt aaaacgacgg ccagtgaatt attgctatca gcgatactaa    60

<210> SEQ ID NO 174
<211> LENGTH: 60
<212> TYPE: DNA
<213> ORGANISM: Artificial Sequence
<220> FEATURE:
<223> OTHER INFORMATION: Primer

<400> SEQUENCE: 174
gtcataggga tagcccgcat agtcaggaac atcgtatggg taggagacaa tcccgttctc    60

<210> SEQ ID NO 175
<211> LENGTH: 60
<212> TYPE: DNA
<213> ORGANISM: Artificial Sequence
<220> FEATURE:
<223> OTHER INFORMATION: Primer

<400> SEQUENCE: 175
tttcccagtc acgacgttgt aaaacgacgg ccagtgaatt gaattcgaca ggttatcagc    60

<210> SEQ ID NO 176
<211> LENGTH: 57
<212> TYPE: DNA
<213> ORGANISM: Artificial Sequence
<220> FEATURE:
<223> OTHER INFORMATION: Primer

<400> SEQUENCE: 176
gctcttgcac actcttagtc ctttctaata aagttgacat gtcgacctcg agcggga       57

<210> SEQ ID NO 177
<211> LENGTH: 62
<212> TYPE: DNA
<213> ORGANISM: Artificial Sequence
<220> FEATURE:
<223> OTHER INFORMATION: Primer

<400> SEQUENCE: 177
ggtggtggcg accatcacga gaatctttat tttcagggcg acatgtcttc ccacaaagga    60
tc                                                                   62

<210> SEQ ID NO 178
<211> LENGTH: 69
<212> TYPE: DNA
<213> ORGANISM: Artificial Sequence
<220> FEATURE:
<223> OTHER INFORMATION: Primer

<400> SEQUENCE: 178
atatctgcag aattccagca cactggcggc cgttactagt ggatcctcag agaagggtgt    60
catcagtac                                                            69

<210> SEQ ID NO 179
<211> LENGTH: 62
<212> TYPE: DNA
<213> ORGANISM: Artificial Sequence
<220> FEATURE:
<223> OTHER INFORMATION: Primer

<400> SEQUENCE: 179

```
ggtggtggcg accatcacga gaatctttat tttcagggcg ccatgggcat gtccctctc    60 tt                                                                  62
```

<210> SEQ ID NO 180
<211> LENGTH: 69
<212> TYPE: DNA
<213> ORGANISM: Artificial Sequence
<220> FEATURE:
<223> OTHER INFORMATION: Primer

<400> SEQUENCE: 180

```
atatctgcag aattccagca cactggcggc cgttactagt ggatcttcac agtgcatcct    60
cttcactgc                                                            69
```

<210> SEQ ID NO 181
<211> LENGTH: 3111
<212> TYPE: DNA
<213> ORGANISM: Saccharomyces cerevisiae
<220> FEATURE:
<221> NAME/KEY: misc_feature
<222> LOCATION: (102)..(603)
<223> OTHER INFORMATION: truncated FET3 promoter sequence
<220> FEATURE:
<221> NAME/KEY: misc_feature
<222> LOCATION: (202)..(603)
<223> OTHER INFORMATION: truncated FET3 promoter sequence
<220> FEATURE:
<221> NAME/KEY: misc_feature
<222> LOCATION: (601)..(603)
<223> OTHER INFORMATION: ATG start codon

<400> SEQUENCE: 181

```
gtctgtgttt ctgtgtgaga cattactgct gtaaaaagga aaaatagaaa agaataacag    60
atacgagaat ctgtgctgcc ttctttgcga taatgccttg gcttgcctat ttcacggtta   120
caggaataat aacatgttca taccgtttca ggaccaataa atggtcttct gcgagagaaa   180
aaggacactc tccgtccgac agaaataagc tttacttttcc gggtgcgaat cagcccgttg   240
cgcctggggt ggtccctaca gtacgctgag tcgccgataa agaccctccg cctagagcta   300
ggcgaggctg acttaggcag gcccaacagg caaggcccat cttcaaaagt gcacccattt   360
gcaggtgctc ttattctcgc caattgcgac agaaaatgaa ggatgcactc aaacagtcga   420
tccttcgagg gagtatgcca aggcctcgtg catgtagtgc gattatatat atatatatat   480
atatatatat atgtatgtaa gcaggccatg ccctatagct cttgttctat aagcgatgga   540
taggcatagg aaacgaagag gaccccagtg taaggaagag tagcaaaaaa ttagaactag   600
atgactaacg ctttgctctc tatagccgtt ttgcttttct cgatgctctc gctagcacaa   660
gcggagacgc acacgtttaa ttggaccact ggctgggact acaggaacgt tgatgggcta   720
aagagccgtc ccgtgatcac ctgtaatggc cagttcccat ggccagatat aacggtcaac   780
aaaggtgacc gtgtgcagat ttacttgacc aacggaatga acaacaccaa tacttctatg   840
catttccacg gtctcttcca aaacggaacc gcctctatgg acggtgtgcc cttcttgacg   900
caatgtccaa ttgcgccagg cagtactatg ctttacaatt tcacggtgga ctacaatgta   960
```

-continued

```
ggcacctact ggtaccattc acacacggac ggtcaatatg aagacgggat gaaaggtctt    1020
ttcatcatca aggatgatag cttccsctac gattacgatg aggaactttc tttatcgctt    1080
agtgagtggt accacgactt ggtcacggac ttgacgaagt cgttcatgag tgtttataat    1140
ccgacaggtg ctgagcccat cccacagaac ttgattgtta acaacacgat gaatctgaca    1200
tgggaagtcc agcccgatac gacgtatctt ttgagaattg tcaacgtggg tgggttcgtt    1260
tcgcagtact tttggatcga ggaccacgaa atgaccgtgg tcgaaatcga cggtatcact    1320
accgagaaga acgtaacgga tatgctttac atcactgtcg ctcagagata tacagtcctg    1380
gttcacacta aaacgacac ggacaaaaat tcgccatca tgcagaaatt tgatgacacc    1440
atgttggatg tcattccaag tgatttacag ctgaatgcaa cctcttatat ggtctacaac    1500
aaaaccgctg cgctgcccac acaaaattac gtggattcaa ttgataactt cttggacgat    1560
ttctacttgc aaccgtacga gaaagaagcc atctatggcg agccagatca tgtgattacc    1620
gttgacgttg ttatggataa cttgaaaaac ggtgtgaatt acgccttctt caataatatc    1680
acctatactg caccaaaagt tcctactttg atgaccgttt tgtcttcagg tgatcaagca    1740
aacaactccg aaatctacgg ttcaaacacg cacactttca tcctagagaa ggatgaaatc    1800
gtggagattg tgctaaataa ccaggacaca ggtacccatc ctttccattt acatggtcac    1860
gctttccaaa ccatccagag agatcgtaca tatgatgatg ccctaggtga agttcctcac    1920
agtttcgatc cggacaacca ccctgccttc ccagaatacc caatgagaag agatacttta    1980
tacgttagac acaatccaa tttcgtcatc aggtttaaag ccgataaccc aggtgtttgg    2040
ttcttccatt gtcatatcga atggcatttg ttgcaaggtt tgggtcttgt tctcgtggag    2100 gatcctttg gtatccaaga tgctcattct caacaactca gtgaaaacca cttagaagtt    2160
tgccagagtt gctctgtggc cactgaaggt aacgccgctg ccaatacact ggatttaact    2220
gatttaactg gtgaaaatgt tcagcatgcc ttcattccta ccggttttac caaaaaaggt    2280
attattgcca tgacattctc ctgctttgcc ggtattcttg gtattatcac aattgcaatt    2340
tatggtatga tggatatgga agatgcgacc gaaaaggtta ttcgagactt gcacgtggac    2400
cctgaagtct tgctaaatga ggttgatgaa aatgaagagc gtcaggtaaa cgaagatcgt    2460
cattccactg aaaagcatca attttaact aaagccaaac ggttcttcta ataaaggaag    2520
atcatgtatt ttgcggttaa cctgtttttt ttttttcggt caagggttcc aaatgcattt    2580
gcatgtaaag tgaatgccct tgtcttactt aatattacat agacatatac ttaataatct    2640
accacgtttc aaattcaata atgcatgctt cttggcggtt tttgacatga atcctcatc    2700 tgtcacgagg ctgatgtgca tacttttact tttaatcgat gacatgatca gtttcttttg    2760
aacaaaaagc cgttatgggt tgaaaaaaag tgaaatgaa aaagtcatca gaaatatatg    2820
aaagatataa taaattgtcg aagagaaatt acgtcgagga ggttgaggaa ataagaatg    2880 gcaacgacag atatcatatc tctagtaaaa aataatttac tctatttcca aatgtggacg    2940
gaagtggaaa ttttcaagaa cgattttatca tggaagggaa atagcctgag attactgaga    3000
ggtcgtccgc ctcacaagct gagcaacgat gtagacacag agcatgaaaa tagcttgtca    3060
tcgccacgcc cgctagagtt catattaccc atcaatatgt cacagtacaa a            3111
```